(12) United States Patent
Frey, II et al.

(10) Patent No.: US 9,556,260 B2
(45) Date of Patent: Jan. 31, 2017

(54) TREATMENT OF CENTRAL NERVOUS SYSTEM DISORDERS BY INTRANASAL ADMINISTRATION OF IMMUNOGLOBULIN G

(71) Applicants: Baxalta Incorporated, Bannockburn, IL (US); Baxalta GmbH, Glattpark (Opfikon) (CH)

(72) Inventors: William H. Frey, II, White Bear Lake, MN (US); Leah Ranae Bresin Hanson, Vadnais Heights, MN (US); Sharon Pokropinski, Schaumburg, IL (US); Francisco M. Rausa, III, Vernon Hills, IL (US)

(73) Assignees: Baxalta Incorporated, Bannockburn, IL (US); Balxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 14/189,981

(22) Filed: Feb. 25, 2014

(65) Prior Publication Data
US 2014/0242067 A1    Aug. 28, 2014

Related U.S. Application Data

(60) Provisional application No. 61/769,673, filed on Feb. 26, 2013, provisional application No. 61/862,814, filed on Aug. 6, 2013.

(51) Int. Cl.
| | |
|---|---|
| C07K 16/06 | (2006.01) |
| C07K 16/18 | (2006.01) |
| A61K 9/12 | (2006.01) |
| A61P 25/28 | (2006.01) |
| A61K 31/198 | (2006.01) |
| A61K 31/4172 | (2006.01) |
| A61K 31/401 | (2006.01) |
| A61K 9/00 | (2006.01) |
| A61K 39/00 | (2006.01) |
| A61K 9/08 | (2006.01) |

(52) U.S. Cl.
CPC ............ *C07K 16/18* (2013.01); *A61K 9/0043* (2013.01); *A61K 31/198* (2013.01); *A61K 31/401* (2013.01); *A61K 31/4172* (2013.01); *C07K 16/06* (2013.01); *A61K 9/08* (2013.01); *A61K 2039/505* (2013.01); *A61K 2039/543* (2013.01); *C07K 2317/55* (2013.01)

(58) Field of Classification Search
None
See application file for complete search history.

(56) References Cited

U.S. PATENT DOCUMENTS

| 5,624,898 A | 4/1997 | Frey, II |
| 6,715,485 B1 | 4/2004 | Djupesland |
| 2004/0101909 A1 | 5/2004 | Lemieux et al. |
| 2007/0254889 A1 | 11/2007 | Jin et al. |
| 2008/0305077 A1 | 12/2008 | Frey, II et al. |
| 2011/0151393 A1 | 6/2011 | Frey, II et al. |

FOREIGN PATENT DOCUMENTS

| WO | WO 96/22802 A1 | 8/1996 |
| WO | WO 01/60420 A1 | 8/2001 |
| WO | WO 03/028668 A2 | 4/2003 |
| WO | WO 2006/091332 A2 | 8/2006 |
| WO | WO 2007/095616 A2 | 8/2007 |
| WO | WO 2007/106617 A2 | 9/2007 |
| WO | WO 2009/058957 A2 | 5/2009 |
| WO | WO 2009/111240 A1 | 9/2009 |
| WO | WO 2011/095543 A1 | 8/2011 |

OTHER PUBLICATIONS

Weltzin et al., Clinical Microbiology Reviews, Jul. 1999, p. 383-393 (particularly, Table 2 IVIG administration for RSV).*
Bohmwald et al., Rev Med Virol. 24:407-419, Oct. 2014 (evidence that RSV presents with CNS conditions such as fever, seizure and central apnea).*
Cattepoel et al. PLoS One, vol. 6, Issue 4: e18296, Apr. 2011.*
Chu LW, Hong Kong Med J., 18(3) Jun. 2012.*
Kelly et al., J Appl Physiol., 89:323-337, 2000.*
Magga et al. J Neuroinflam., 7:90, 2010.*
Widiapradja et al. J Neuroschem., 122:321-332, 2012.*
Kolobov et al. Bulletin of Exp. Biol. Med., 154(4): 425-427, Feb. 2013 [abstract only].*
Xiao et al., Program No. 853.14. 2012 Neuroscience Meeting Planner. New Orleans, LA: Society for Neuroscience, 2012. Online.*
Xiao et al., Journal of Alzheimer's Disease, vol. 35, No. 4, pp. 777-788, Jul. 24, 2013.*
Chauhan et al., Alzhiemer's & Dementia, vol. 8, issue S4, poster p. 1-261, Jul. 14-19, 2012.*
Akassoglou, K. et al., "Oligodendrocyte Apoptosis and Primary Demyelination Induced by Local TNF/p55TNF Receptor Signaling in the Central Nervous System of Transgenic Mice," *American Journal of Pathology*, Sep. 1998, vol. 153, No. 3, pp. 801-813.
Athwal, G.S., "The Emergence of Antibody Fragments and Derivatives," *Innovations in Pharmaceutical Technology*, Jul. 2009, pp. 46-48.
Awad, A. et al., "Idiopathic Transverse Myelitis and Neuromyelitis Optica: Clinical Profiles, Pathophysiology and Therapeutic Choices," *Current Neuropharmacology*, 2011, vol. 9, pp. 417-428.
Bohmwald, K. et al., "Central nervous system alterations caused by infection with the human respiratory syncytial virus," *Rev. Med. Virol.*, 2014, 13 pages.
Bolli, R. et al., "$_L$-Proline reduces IgG dimer content and enhances the stability of intravenous immunoglobulin (IVIG) solutions," *Biologicals*, 2010, vol. 38, pp. 150-157.

(Continued)

*Primary Examiner* — Kimberly A. Ballard
*Assistant Examiner* — Stacey N MacFarlane
(74) *Attorney, Agent, or Firm* — Morgan, Lewis & Bockius LLP

(57) ABSTRACT

The present invention provides, among other aspects, methods and compositions for treating a central nervous system (CNS) disorder by delivering a therapeutically effective amount of a composition of pooled human immunoglobulin G (IgG) to the brain via intranasal administration of the composition directly to the olfactory epithelium of the nasal cavity. In particular, methods and compositions for treating Alzheimer's disease are provided.

31 Claims, 28 Drawing Sheets
(9 of 28 Drawing Sheet(s) Filed in Color)

(56) References Cited

OTHER PUBLICATIONS

Cattepoel, S. et al., "Chronic Intranasal Treatment with an Anti Aβ$_{30-42}$ scFv Antibody Ameliorates Amyloid Pathology in a Transgenic Mouse Model of Alzheimer's Disease," *PLoS One*, Apr. 2011, vol. 6, No. 4, pp. 1-13.
Dodel, R.C. et al., "Intravenous immunoglobulins containing antibodies against β-amyloid for the treatment of Alzheimer's disease," *J Neurol Neurosurg Psychiatry*, 2004, vol. 75, pp. 1472-1474.
Dodel, R. et al., "Intravenous immunoglobulin for treatment of mild-to-moderate Alzheimer's disease: a phase 2, randomised, double-blind, placebo-controlled, dose-finding trial," *Lancet Neurol*, 2013, vol. 12, pp. 233-243.
Elovaara, I. et al., "Intravenous Immunoglobulins Are a Therapeutic Option in the Treatment of Multiple Sclerosis Relapse," *Clinical Neuropharmacology*, Mar./Apr. 2011, vol. 34, No. 2, pp. 84-89.
Ertekin-Taner, N., "Genetics of Alzheimer's Disease: A Centennial Review," *Neurol Clin.*, Aug. 2007, vol. 25, No. 3, 43 pages.
Fillit, H. et al., "IV immunoglobulin is associated with a reduced risk of Alzheimer disease and related disorders," *Neurology*, 2009, vol. 3, pp. 180-185.
Fu, H.J. et al., "Amyloid-β Immunotherapy for Alzheimer's' Disease," *CNS Neurol Disord Drug Targets*, Apr. 2010, vol. 9, No. 2, pp. 197-206.
Haley, M. et al., "The Role for Intravenous Immunoglobulin in the Treatment of West Nile Virus Encephalitis," *Clinical Infectious Disease*, Sep. 15, 2003, vol. 37, pp. e-88-90.
Harmsen, M.M. et al., "Properties, production, and applications of camelid single-domain antibody fragments," *Appl Microbiol Biotechnol*, 2007, vol. 77, pp. 13-22.
Imbach, P. et al., "High-Dose Intravenous Gammaglobulin for Idiopathic Thrombocytopenic Purpura in Childhood," *The Lancet*, Jun. 6, 1981, pp. 1228-1231.
International Search Report mailed Jun. 17, 2014, for International Patent Application No. PCT/US2014/018426, 5 pages.
Johnson, N.J. et al., "Trigeminal pathways deliver a low molecular weight drug from the nose to the brain and orofacial structures," *Mol Pharm.*, Jun. 7, 2010, vol. 7, No. 3, pp. 884-893.
Kraus, D. et al., "Schilder's disease: Non-invasive diagnosis and successful treatment with human immunoglobulins," *Official Journal of the European Paediatric Neurology Society*, 2012, vol. 16, pp. 206-207.
Magga, J. et al., "Human intravenous immunoglobulin provides protection against Aβ toxicity by multiple mechanisms in a mouse model of Alzheimer's disease," *Journal of Neuroinflammation*, 2010, vol. 7, No. 90, pp. 1-15.
Mirra, S.S. et al., "Making the Diagnosis of Alzheimer's Disease, A Primer for Practicing Pathologists," *Diagnosing Alzheimer's Disease*, Feb. 1993, vol. 117, No. 2, pp. 132-144.
Orange, J.S. et al., "Use of intravenous immunoglobulin in human disease: A review of evidence by members of the Primary Immunodeficiency Committee of the American Academy of Allergy, Asthma and Immunology," *J Allergy Clin Immunol*, 2006, vol. 117, pp. S525-S553.
Orbach, H. et al., "Intravenous Immunoglobulin, Adverse Effects and Safe Administration," *Clinical Reviews in Allergy and Immunology*, 2005, vol. 29, pp. 173-184.
Pardridge, W.M., "Drug and Gene Targeting to the Brain with Molecular Trojan Horses," *Nature Reviews*, Feb. 2002, vol. 1, pp. 131-139.
Pardridge, W.M., "Blood-Brain Barrier Drug Targeting: The Future Development of Brain Drug Development," *Molecular Interventions*, Mar. 2003, vol. 3, No. 2, pp. 90-105.
Patrias, L.M. et al., "Specific antibodies to soluble alpha-synuclein conformation in intravenous immunoglobulin preparations," *Clinical and Experimental Immunology*, 2010, vol. 161, pp. 527-535.
Perl, D.P., "Neuropathology of Alzheimer's Disease and Related Disorders," *Dementia*, Nov. 2000, vol. 18, No. 4, pp. 847-864.
Perlmutter, S.J. et al., "Therapeutic plasma exchange and intravenous immunoglobulin for obsessive-compulsive disorder and tic disorders in childhood," *The Lancet*, Oct. 2, 1999, vol. 354, pp. 1153-1158.
Pohl, D. et al., "Treatment of Acute Disseminated Encephalomyelitis," *Current Treatment Options in Neurology*, 2012, vol. 14, pp. 264-275.
Puli, L. et al., "Effects of human intravenous immunoglobulin on amyloid pathology and neuroinflammation in a mouse model of Alzheimer's disease," *Journal of Neuroinflammation*, 2012, vol. 9, No. 105, pp. 1-19.
Relkin, N.R. et al., "18-Month study of intravenous immunoglobulin for treatment of mild Alzheimer's disease," *Neurobiology of Aging*, 2009, vol. 30, pp. 1728-1736.
Smith, L.M. et al., "Effects of intravenous immunoglobulin on alpha synuclein aggregation and neurotoxicity," *International Immunopharmacology*, 2012, vol. 14, pp. 550-557.
Snider, L.A. et al., "Childhood-Onset Obsessive-Compulsive Disorder and Tic Disorders: Case Report and Literature Report," *Journal of Child and Adolescent Psychopharmacology*, 2003, vol. 13, Suppl 1, pp. S81-S88.
Stangel, M., "New advances in the treatment of neurological diseases using high dose intravenous immunoglobulins," *Therapeutic Advances in Neurological Disorders*, 2008, vol. 1, No. 2, pp. 115-124.
Stevenson, B.R. et al., "The epithelial tight junction: Structure, function and preliminary biochemical characterization," *Molecular and Cellular Biochemistry*, 1988, vol. 83, pp. 129-145.
Stiehm, E.R., "Lessons From Kawasaki Disease: All Brands of IVIG Are Not Equal," *The Journal of Pediatrics*, Jan. 2006, Editorials, pp. 6-8.
Vo, A.A. et al., "Safety and Adverse Events Profiles of Intravenous Gammaglobulin Products Used for Immunomodulation: A Single-Center Experience," *Clin J Am Soc Nephrol*, 2006, vol. 1, pp. 844-852.
Weltzin, R. et al., "Intranasal Antibody Prophylaxis for Protection against Viral Disease," *Clinical Microbiology Reviews*, Jul. 1999, vol. 12, No. 3, pp. 383-393.
Xiao, C. et al., "Brain Transit and Ameliorative Effects of Intranasally Delivered Anti-Amyloid-β Oligomer Antibody in 5XFAD Mice," *J Alzheimers Dis.*, 2013, vol. 35, No. 4, pp. 777-778.

* cited by examiner

TREATMENT OF CENTRAL NERVOUS SYSTEM DISORDERS BY INTRANASAL ADMINISTRATION OF IMMUNOGLOBULIN G

CROSS REFERENCES TO APPLICATIONS

This application claims priority to U.S. Provisional Patent Application Ser. Nos. 61/769,673 filed Feb. 26, 2013, and 61/862,814 filed Aug. 6, 2013, the disclosures of which are hereby incorporated herein by reference in their entireties for all purposes.

BACKGROUND OF THE INVENTION

The central nervous system (CNS) is the processing center for the nervous system. CNS disorders can affect the brain, the spinal cord, and nerve endings, resulting in neurological and/or psychiatric disorders. CNS disorders can be caused by genetic inheritance, trauma, infection, autoimmune disorders, structural defects, tumors, and stroke. Certain CNS disorders are characterized as neurodegenerative disease, many of which are inherited genetic diseases. Examples of neurodegenerative diseases include Huntington's disease, ALS, hereditary spastic hemiplegia, primary lateral sclerosis, spinal muscular atrophy, Kennedy's disease, Alzheimer's disease, a polyglutamine repeat disease, or Parkinson's disease. Treatment of CNS disorders, e.g., genetic diseases of the brain such as Parkinson's disease, Huntington's disease, and Alzheimer's disease, remain an ongoing problem.

Alzheimer's disease is a common form of age-related dementia that causes gradual loss of cognitive function, including memory and critical thinking abilities. Alzheimer's disease is diagnosed clinically by through a finding of progressive memory loss and decrease in cognitive abilities. However, confirmation of Alzheimer's disease does not occur until after death.

Alzheimer's disease is becoming more prevalent in developed nations, where an increase in the population of elder persons has occurred due in part to improved healthcare. While less than 1% of the population under the age of 60 is affected by Alzheimer's, it is estimated that 25% to 33% of persons develop some form of Alzheimer's by the age of 85. As of 2012, 5.4 million Americans were diagnosed with Alzheimer's. As life expectancy continues to increase worldwide, the prevalence of Alzheimer's and other age-related dementia should continue to grow as well.

Alzheimer's disease is typically classified as either "early onset," referring to cases that begin to manifest at between 30 and 60 years of age in affected individuals, and the more common "late onset" Alzheimer's, in which symptoms first become apparent after the age of 60. Although only about 10% of all Alzheimer's cases are familial, early onset Alzheimer's disease has been linked to mutations in the amyloid precursor protein (app), presenilin 1 (psen1), and presenilin 2 (psen2) genes, while late onset Alzheimer's disease has been linked to mutations in the apolipoprotein E (apoE) gene (Ertekin-Taner N., *Neurol Clin.*, 25:611-667 (2007)).

Histopathologically, this neurodegenerative disease is characterized by the formation of amyloid plaques, neurofibrillary tangles, amyloid angiopathy, and granolovacuolar degeneration in the cerebral cortex (Mirra et al., *Arch Pathol Lab Med.*, 117:132-144 (1993); Perl D P, *Neurol Clin.*, 18:847-864 (2000)). The characteristic amyloid plaques, used to confirm Alzheimer's disease post-mortem, are formed largely by deposition of a small amyloid-beta (Aβ) peptide derived from the amyloid precursor protein (APP).

To date, the U.S. Food and Drug Administration (FDA) has approved two types of medications for the management of Alzheimer's disease: cholinesterase inhibitors, including donepezil (e.g., ARICEPT®), rivastigmine (e.g., EXELON®), galantamine (e.g., RAZADYNE®), and tacrine (e.g., COGNEX®); and the NMDA-type glutamate receptor inhibitor memantine (marketed under a number of different brands). Although a cure for Alzheimer's disease has not been identified, these therapies serve to alleviate cognitive symptoms such as memory loss, confusion, and loss of critical thinking abilities in subjects diagnosed with age-related dementia (e.g., Alzheimer's disease). In all, it is estimated that healthcare spending on Alzheimer's disease and related age-related dementias in 2012 will be $200 billion in the United States alone (*Factsheet*, Alzheimer's Association, March 2012).

In addition to these approved therapies, several studies have suggested that pooled intravenous immunoglobulin (IVIG) is effective in slowing the progression of symptoms in Alzheimer's patients (Dodel R C et al., *J Neurol Neurosurg Psychiatry*, Oct; 75(10):1472-4 (2004); Magga J. et al., *J Neuroinflammation*, December 7; 7:90 (1997); Relkin N R et al., *Neurobiol Aging*, 30(11):1728-36 (2008); Puli L. et al., *J Neuroinflammation* May 29; 9:105 (2012)).

Immune globulin products from human plasma were first used in 1952 to treat immune deficiency. Initially, intramuscular or subcutaneous administration of immunoglobulin isotype G (IgG) isolated from plasma were the methods of choice. However, IgG products that could be administered intravenously, referred to as intravenous immunoglobulin (IVIG), were later developed to allow for the administration of larger amounts of IgG necessary for effective treatment of various diseases. Usually, IVIG contains the pooled immunoglobulin G (IgG) immunoglobulins from the plasma of multiple donors, e.g., more than a hundred or more than a thousand blood donors. These purified IgG products are primarily used in treating three main categories of medical conditions: (1) immune deficiencies: X-linked agammaglobulinemia, hypogammaglobulinemia (primary immune deficiencies), and acquired compromised immunity conditions (secondary immune deficiencies), featuring low antibody levels; (2) inflammatory and autoimmune diseases; and (3) acute infections.

Specifically, many people with primary immunodeficiency disorders lack antibodies needed to resist infection. In certain cases these deficiencies can be supplemented by the infusion of purified IgG, commonly through intravenous administration (i.e., IVIG therapy). Several primary immunodeficiency disorders are commonly treated in the fashion, including X-linked agammaglobulinemia (XLA), Common Variable Immunodeficiency (CVID), Hyper-IgM Syndrome (HIM), Severe Combined Immunodeficiency (SCID), and some IgG subclass deficiencies (Blaese and Winkelstein, *J. Patient & Family Handbook for Primary Immunodeficiency Diseases*. Towson, M D: Immune Deficiency Foundation; 2007).

While IgG treatment can be very effective for managing primary immunodeficiency disorders, this therapy is only a temporary replacement for antibodies that are not being produced in the body, rather than a cure for the disease. Accordingly, patients depend upon repeated doses of IgG therapy, typically about once a month for life. This therapy places a great demand on the continued production of IgG compositions. However, unlike other biologics that are produced via in vitro expression of recombinant DNA vectors, IgG is fractionated from human blood and plasma donations. Thus, the level of commercially available IgG is limited by the available supply of blood and plasma donations.

Several factors drive the demand for IgG, including the acceptance of IgG treatments, the identification of additional indications for which IgG therapy is effective, and increasing patient diagnosis and IgG prescription. Notably, the global demand for IgG more than quadrupled between 1990 and 2009, and continues to increase at an annual rate between about 7% and 10% (Robert P., Pharmaceutical Policy and Law, 11 (2009) 359-367). For example, the Australian National Blood Authority reported that the demand for IgG in Australia grew by 11.1% for the 2010-2011 fiscal year (National Blood Authority Australia Annual Report 2010-2011).

It has been reported that in 2007, 26.5 million liters of plasma were fractionated, generating 75.2 metric tons of IgG, with an average production yield of 2.8 grams per liter (Robert P., supra). This same report estimated that global IgG yields are expected to increase to about 3.43 grams per liter by 2012. However, due to the continued growth in global demand for IgG, projected at between about 7% and 14% annually between now and 2015, further improvement of the overall IgG yield will be needed to meet global demand. One of the factors that may drive increased demand for pooled human immunoglobulins (e.g., IVIG) over the next decade is whether or not IgG is approved for the treatment of Alzheimer's disease. It is estimated that if these treatments are approved by major regulatory agencies, an additional 5% increase in demand for IVIG will be seen (Robert P., supra).

Due in part to the increasing global demand and fluctuations in the available supply of immunoglobulin products, several countries, including Australia and England, have implemented demand management programs to protect supplies of these products for the highest demand patients during times of product shortages. Thus, the development of methodologies that reduce the amount of pooled immunoglobulin G needed to treat various indications will be critical as the increase in demand for pooled immunoglobulin begins to outpace the increase in global manufacturing output.

Pooled human immunoglobulin G (IgG) is manufactured according to different processes depending upon the specific manufacturer. However, the origin of most manufacturing processes is found in the fourth installment of a series of seminal papers published on the preparation and properties of serum and plasma proteins, Cohn et al. (J. Am. Chem. Soc., 1946, 68(3): 459-475). This paper first described a method for the alcohol fractionation of plasma proteins (method 6), which allows for the isolation of a fraction enriched in IgG from human plasma.

The Cohn procedures were initially developed to obtain albumin at relatively high (95%) purity by fractional precipitation with alcohol. However, it was realized by Oncley et al. (J. Am. Chem. Soc., 1949, 71(2): 541-550), Deutsch et al. (J. Biol. Chem., 1946, 164, 109-118), and Kistler and Nitschmann (Vox Sang., 1962, 7, 414-424), that particular protein precipitates (Fraction II and Fraction II+III) from the Cohn method could be used as a starting material for the purification of highly enriched immunoglobulin compositions. In order to achieve the higher purity and safety required for the intravenous administration of IgG compositions, several purification and polishing steps (e.g. adsorption in general or all different chromatographic techniques, Cross-flow-filtration, etc.) have been added to IgG manufacturing processes after the alcohol fractionation steps.

Current IgG manufactures typically rely on either a Cohn method 6 Fraction II+III precipitate or a Kistler-Nitschmann precipitate A as the starting material for downstream processing. Both fractions are formed by a two step process in which proteins such as fibrinogen and Factor XIII are removed by an initial precipitation step (Fraction I precipitation) performed at high pH (7.2) with low ethanol concentration (8-10% v/v), followed by a second precipitation step in which IgG is precipitated from the Fraction I supernatant at pH 6.8 with 20-25% (v/v) ethanol (Fraction II+III) or at pH 5.85 with 19% ethanol (v/v) ethanol (precipitate A), while albumin and a significant portion of A1PI remain in the supernatant.

These methods, while laying the foundation for an entire industry of plasma derived blood proteins, were unable to provide IgG preparations having sufficiently high purity for the chronic treatment of several immune-related diseases, including Kawasaki syndrome, immune thrombocytopenic purpura, and primary immune deficiencies, without an undue occurrence of serious side effects. As such, additional methodologies employing various techniques, such as ion exchange chromatography, were developed to provide higher purity IgG formulations. Hoppe et al. (Munch Med Wochenschr 1967 (34): 1749-1752), Falksveden (Swedish Patent No. 348942), and Falksveden and Lundblad (Methods of Plasma Protein Fractionation 1980) were among the first to employ ion exchange chromatography for this purpose.

It is common practice to administer IgG by intravenous (IV) injection (Imbach et al., *Lancet* 1(8232): 1228-31 (1981)). Intravenous IgG (IVIG) may be administered alone or in combination with other compositions. IVIG is often administered over a 2 to 5 hour period, once a day for 2 to 7 days, with follow-up doses every 10 to 21 days or every 3 to 4 weeks. Such an administration regime is time consuming and inconvenient for many patients. This inconvenience may be aggravated in the case of Alzheimer's patients, who may have difficulty sitting quietly during the infusion period, and may have to rely on their caregiver to bring them to an infusion center or supervise their infusion.

Systemic IVIG administration may cause adverse side effects. For example, IVIG may cause backache, headache, migraine, joint or muscle pain, general feeling of discomfort, leg cramps, rash, pain at the injection site, hives, dizziness, unusual fatigue or tiredness or weakness, chills, fever, sweating, increased heart rate, increased blood pressure, cough, redness of the face, upset stomach, upper abdominal pain, and vomiting. Immediate adverse effects post-IVIG administration which have been observed include headache, flushing, malaise, chest tightness, fever, chills, myalgia, fatigue, dyspnea, back pain, nausea, vomiting, diarrhea, blood pressure changes, tachycardia, and anaphylactic reactions. Orbach et al., *Clin. Rev. Allergy Immunol.*, 29(3): 173-84 (2005).

Furthermore, the adverse side effects may vary based on the IVIG manufacturer. Most manufactures preparations contain between 90% and 99% purified IgG in combination with stabilizers and liquid(s) for reconstitution. Orange et al. 2006 (J. Allergy Clin. Immunol. 117(4 Suppl.): S525); Vo et al. 2006 (Clin. J. Am. Soc. Nephrol. 1(4): 844; Stiehm et al. 2006 (J. Pediatr. 148(1): 6). For example, some manufacturers use maltose as a stabilizer while others use sucrose or amino acids.

The sodium and sugar content in WIG, along with varying amounts of IgA and additional chemicals used in the IVIG production can affect the tolerability and efficacy of the brand of IVIG in patients. Specifically, older patients often suffer from co-morbid conditions that increase the risk of IVIG adverse side effects. For example, subjects with renal disorders, vascular disorders, or diabetes also have a heightened risk of renal insufficiency and thrombotic events following IVIG administration because IVIG compositions are commonly hyper-viscous and contain high concentrations of sugar and salt.

IVIG also carries the risk of catheter-related infection, i.e., an infection where the catheter or needle enters a subject's vein or skin. Examples of catheter-related infection are tenderness, warmth, irritation, drainage, redness, swelling, and pain at the catheter site. Accordingly, alternate modes of administration would be beneficial from the standpoint of time, convenience, and adverse side effects.

In addition to adverse side effects of systemic administration of IVIG, penetration of IVIG across the blood-brain barrier has been shown to be unpredictable and intraventricular or intrathecal IgG may be necessary. For example, Haley et al. administered IVIG in the treatment of meningeal inflammation caused by West Nile virus encephalitis. Haley et al. found that penetration of IVIG was unpredictable and posited that intrathecal or intraventricular administration may be required. Haley et al. 2003 (Clin. Inf. Diseases 37: e88-90).

It is difficult to target the CNS with IV administration therapeutic compositions because of the blood-brain barrier (BBB). The BBB provides an efficient barrier, preventing and/or limiting access to the CNS of therapeutic compositions administered intravenously into the peripheral circulation. Specifically, the BBB prevents diffusion of most therapeutic compositions, especially polar compositions, into the brain from the circulating blood.

At least three methods for increasing the passage of molecules through the BBB have been developed. First, lipophilic compounds such as lipid-soluble drugs and polar drugs encased in a lipid membrane have been developed. Lipophilic compounds with a molecular weight of less than 600 Da can diffuse through the BBB. Second, therapeutic compounds can be bound to transporter molecules which can cross the BBB through a saturable transporter system. Examples of saturable transporter molecules are transferrin, insulin, IGF-1, and leptin. Third, therapeutic compounds can cross the BBB by binding the therapeutic compounds to polycationic molecules such as positively-charged proteins that preferentially bind to the negatively-charged endothelial surface of the BBB. Patridge et al. 2003 (Mol. Interv. 3(2): 90-105); Patridge et al. 2002 (Nature Reviews-Drug Discovery 1:131-139). However, each of the above-described approaches for increasing the delivery of therapeutics through BBB to gain access to the CNS are limited. One such limitation is that the above-described approaches rely on systemic delivery systems, e.g., administration directly or indirectly to the blood stream, which results in non-specific delivery of the therapeutic agent to other parts in the body, increasing the chance of adverse side effects.

Intranasal administration of therapeutics has become an increasingly explored method for delivering therapeutic agents to the brain because it circumvents the BBB and is a localized, non-invasive method for delivery. Furthermore, intranasal administration offers the advantages, over more traditional methods of delivery (e.g., intravenous, subcutaneous, oral transmucosal, oral or rectal administration), of being simple to administer, providing rapid onset of action, and avoiding first-pass metabolism. Unfortunately, intranasal administration has only been shown effective for the transport of small molecules, and to a certain extent smaller Fc fusion proteins, to the brain. The delivery of larger molecules, such as intact antibodies, has not yet been demonstrated. The difficulty in transporting larger proteins is believed to be due to the limited permeability of tight junctions present in the olfactory epithelia, which likely excludes globular molecules having a hydrodynamic radius of more than 3.6 Å (Stevenson B R, et al., Mol Cell Biochem., 1988 October; 83(2):129-45).

U.S. Pat. No. 5,624,898 to Frey describes compositions and methods for transporting neurologic agents, which promote nerve cell growth and survival or augment the activity of functioning cells, to the brain by means of the olfactory neural pathway. The neurological agents of the '898 patent are transported to the brain by means of the nervous system, rather than the circulatory system, so that potentially therapeutic agents that are unable to cross the blood-brain barrier may be delivered to damaged neurons in the brain. The compositions described in the '898 patent include a neurologic agent in combination with a pharmaceutical carrier and/or additive which promote the transfer of the agent within the olfactory system. The '898 patent does not teach intranasal administration of pooled human immunoglobulins.

PCT publications WO 2006/091332 and WO 2009/058957, both by Bentz et al., describe methods for the delivery of therapeutic polypeptides to the brain by fusing the polypeptide to an antibody or antibody fragment and administering the resulting fusion protein intranasally. Although the examples of the '332 and '957 PCT publications suggest that Fc-fusion "mimetibodies" may be administered intranasally, neither publication demonstrates delivery of larger, intact antibodies. In fact, the '957 PCT publication, published three years after the '332 PCT publication, states that "[i]n published delivery studies to date, intranasal delivery efficiency to the CNS has been very low and the delivery of large globular macromolecules, such as antibodies and their fragments, has not been demonstrated." The '957 PCT publication purports to solve this problem through the use of a permeability enhancer (e.g., membrane fluidizers, tight junction modulators, and medium chain length fatty acids and salts and esters thereof, as described below), which enhances intranasal administration to the central nervous system. Neither PCT publication teaches intranasal administration of pooled human immunoglobulins.

PCT publication WO 2003/028668 by Barstow et al., describes the treatment of immune-mediated diseases by alimentary administration (i.e., administration to the digestive tract) of pooled immunoglobulins. Although the '668 PCT publication discloses nasal administration of a composition of pooled immunoglobulins, it is in the context of delivering the composition to the digestive tract. The '668 PCT publication does not teach the delivery of pooled human immunoglobulins to the brain via intranasal administration.

PCT publication WO 2001/60420 by Adjei et al., describes aerosol formulations of therapeutic polypeptides, including immunoglobulins, for pulmonary delivery. These aerosolizable compositions are formulated such that after oral or nasal inhalation, the therapeutic agent is effectively delivered to the patient's lungs. The '420 PCT publication does not teach the delivery of therapeutic agents to the brain via intranasal administration.

Accordingly, there is a need in the art for methods of treating central nervous system disorders, such as Alzheimer's disease, using pooled human immunoglobulin G that provide specific targeting to the CNS (e.g., administration primarily to the brain), reduce systemic distribution of the pooled immunoglobulins, and lower the therapeutically effected dose needed for administration.

BRIEF SUMMARY OF INVENTION

The present disclosure provides solutions to these and other problems by providing methods and compositions for the treatment of central nervous system disorders via intranasal administration of pooled human immunoglobulin G. Advantageously, intranasal administration provides directed delivery of pooled IgG to the brain, bypassing the requirement that it pass through the blood brain barrier (BBB). As shown herein, intranasal administration allows the delivery of intact IgG to the brain. This results in greater efficiency for the treatment and reduces the necessary IgG dose that must be administered to achieve the desired effect. As pooled human IgG is isolated from donated human plasma, pooled IgG is a limited resource. The reduction in the effective dose of IgG provided by the present disclosure effectively increases the therapeutic potential provided by the world's supply of pooled human IgG. Furthermore, as demonstrated herein, intranasal administration of IgG nearly eliminates the systemic exposure caused by intravenous administration, improving the overall safety profile of the treatment. Finally, it was surprisingly found that IgG is efficiently transported to the brain when intranasally administered in the absence of permeability enhancers, some of which have neurostimulatory effects themselves.

In one aspect, the disclosure provides a method for treating a central nervous system (CNS) disorder in a subject in need thereof, the method including delivering a therapeutically effective amount of a composition comprising pooled human immunoglobulin G (IgG) to the brain of the subject, where delivering the composition to the brain includes intranasally administering the composition directly to the olfactory epithelium of the nasal cavity of the subject.

In another aspect, the disclosure provides a method for treating a central nervous system (CNS) disorder in a subject in need thereof, the method including delivering a therapeutically effective amount of a composition comprising pooled human immunoglobulin G (IgG) to the brain of the subject, where delivering the composition to the brain includes intranasally administering the composition to a nasal epithelium of the subject associated with trigeminal nerve endings.

In another aspect, the disclosure provides a method for treating a central nervous system (CNS) disorder in a subject in need thereof, the method including delivering a therapeutically effective amount of a composition comprising pooled human immunoglobulin G (IgG) to the brain of the subject, where delivering the composition to the brain includes intranasally administering the composition to the upper third of the nasal cavity of the subject.

In another aspect, the disclosure provides a method for treating a central nervous system (CNS) disorder in a subject in need thereof, the method including delivering a therapeutically effective amount of a composition comprising pooled human immunoglobulin G (IgG) to the brain of the subject, where delivering the composition to the brain includes intranasally administering the composition to one or both maxillary sinus of the subject.

In one embodiment of the methods described above, the CNS disorder is selected from the group consisting of a neurodegenerative disorder of the central nervous system, a systemic atrophy primarily affecting the central nervous system, an extrapyramidal and movement disorder, a demyelinating disorder of the central nervous system, an episodic or paroxysmal disorder of the central nervous system, a paralytic syndrome of the central nervous system, a nerve, nerve root, or plexus disorder of the central nervous system, an organic mental disorder, a mental or behavioral disorder caused by psychoactive substance use, a schizophrenia, schizotypal, or delusional disorder, a mood (affective) disorder, neurotic, stress-related, or somatoform disorder, a behavioral syndrome, an adult personality or behavior disorder, a psychological development disorder, and a child onset behavioral or emotional disorder.

In one embodiment of the methods described above, the CNS disorder is selected from the group consisting of Alzheimer's disease, Parkinson's disease, multiple sclerosis, amyotrophic lateral sclerosis (ALS), Huntington's disease, cerebral palsy, bipolar disorder, schizophrenia, and Pediatric acute-onset neuropyschiatric syndrome (PANS).

In one embodiment of the methods described above, the CNS disorder is selected from the group consisting of Alzheimer's disease, Parkinson's disease, multiple sclerosis, Pediatric Autoimmune Neuropsychiatric Disorders Associated with Streptococcal infections (PANDAS), and Pediatric acute-onset neuropyschiatric syndrome (PANS).

In one embodiment of the methods described above, the CNS disorder is selected from the group consisting of Alzheimer's disease, multiple sclerosis, and Parkinson's disease.

In one embodiment of the methods described above, the CNS disorder is Alzheimer's disease.

In one embodiment of the methods described above, intranasal administration of the composition includes the use of a non-invasive intranasal delivery device.

In one embodiment of the methods described above, intranasal administration of the composition includes administration of a liquid drop of the composition directly onto the nasal epithelium, the nasal epithelium of the subject associated with trigeminal nerve endings, or the upper third of the nasal cavity of the subject.

In one embodiment of the methods described above, intranasal administration of the composition includes directed administration of an aerosol of the composition to the nasal epithelium, the nasal epithelium of the subject associated with trigeminal nerve endings, or the upper third of the nasal cavity of the subject.

In one embodiment of the methods described above, the aerosol of the composition is a liquid aerosol.

In one embodiment of the methods described above, the aerosol of the composition is a powder aerosol.

In one embodiment of the methods described above, at least 40% of the pooled human IgG administered to the subject contacts the nasal epithelium of the subject, the olfactory epithelium of the nasal cavity of the subject, a nasal epithelium of the subject associated with trigeminal nerve endings, the upper third of the nasal cavity of the subject, or one or both maxillary sinus of the subject.

In one embodiment of the methods described above, at least 50% of the pooled human IgG administered to the subject contacts the olfactory epithelium of the nasal cavity of the subject, the nasal epithelium of the subject associated with trigeminal nerve endings, the upper third of the nasal cavity of the subject, or one or both maxillary sinus of the subject.

In one embodiment of the methods described above, at least 60% of the pooled human IgG administered to the subject contacts the olfactory epithelium of the nasal cavity of the subject, the nasal epithelium of the subject associated with trigeminal nerve endings, the upper third of the nasal cavity of the subject, or one or both maxillary sinus of the subject.

In one embodiment of the methods described above, the pooled human IgG composition does not contain a permeability enhancer.

In one embodiment of the methods described above, the pooled human IgG composition consists essentially of pooled human IgG and an amino acid.

In one embodiment of the methods described above, the amino acid is selected from the group consisting of glycine, histidine, and proline. In a specific embodiment of the methods provided above, the amino acid is glycine.

In one embodiment of the methods described above, the pooled human IgG composition is an aqueous composition.

In one embodiment of the methods described above, the pooled human IgG composition includes from 10 mg/mL to 250 mg/mL pooled human IgG and from 50 mM to 500 mM glycine.

In one embodiment of the methods described above, the pH of the composition is from 4.0 to 6.0. In another embodiment of the methods provided above, the pH of the composition is from 4.0 to 7.5. In another embodiment of the methods provided above, the pH of the composition is from 6.0 to 7.5.

In one embodiment of the methods described above, the pooled human IgG composition is a dry powder composition.

In one embodiment of the methods described above, the dry powder composition is prepared from an aqueous solution including from 10 mg/mL to 250 mg/mL pooled human IgG and from 50 mM to 500 mM glycine.

In one embodiment of the methods described above, the dry powder composition is prepared from an aqueous solution having a pH of from 4.0 to 6.0. In another embodiment of the methods provided above, the pH of the composition is from 4.0 to 7.5 In another embodiment of the methods provided above, the pH of the composition is from 6.0 to 7.5

In one embodiment of the methods described above, the method includes intranasally administering to the subject a dose of from 0.08 mg to 100 mg pooled human IgG per kg body weight of the subject (mg IgG/kg). In a specific embodiment of the methods provided above, the method includes intranasally administering to the subject a dose of from 0.2 mg to 40 mg pooled human IgG per kg body weight of the subject (mg IgG/kg). In a specific embodiment of the methods provided above, the method includes intranasally administering to the subject a dose of from 5 mg to 20 mg pooled human IgG per kg body weight of the subject (mg IgG/kg). In a specific embodiment of the methods provided above, the method includes intranasally administering to the subject a dose of from 5 mg to 10 mg pooled human IgG per kg body weight of the subject (mg IgG/kg). In a specific embodiment of the methods provided above, the method includes intranasally administering to the subject a dose of from 1 mg to 5 mg pooled human IgG per kg body weight of the subject (mg IgG/kg).

In one embodiment of the methods described above, the method includes intranasally administering to the subject a fixed dose of from 50 mg to 10 g pooled human IgG. In a specific embodiment of the methods provided above, the method includes intranasally administering to the subject a fixed dose of from 100 mg to 5.0 g pooled human IgG. In a specific embodiment of the methods provided above, the method includes intranasally administering to the subject a fixed dose of from 500 mg to 2.5 g pooled human IgG.

In one embodiment of the methods described above, the method includes intranasally administering to the subject a dose of pooled human IgG at least twice monthly. In a specific embodiment of the methods described above, the method includes intranasally administering to the subject a dose of pooled human IgG at least once weekly. In a specific embodiment of the methods described above, the method includes intranasally administering to the subject a dose of pooled human IgG at least twice weekly. In a specific embodiment of the methods described above, the method includes intranasally administering to the subject a dose of pooled human IgG at least once daily. In a specific embodiment of the methods described above, the method includes intranasally administering to the subject a dose of pooled human IgG at least twice daily.

In one embodiment of the methods described above, the pooled human IgG composition includes at least 0.1% anti-amyloid β IgG.

In one embodiment of the methods described above, the method further includes administering a second therapy for the CNS disorder to the subject in need thereof.

In one embodiment of the methods described above, the second therapy for the CNS disorder is a cholinesterase inhibitor. In a specific embodiment of the methods described above, the cholinesterase inhibitor is selected from the group consisting of donepezil (e.g., ARICEPT®), rivastigmine (e.g., EXELON®), galantamine (e.g., RAZADYNE®), and tacrine (e.g., COGNEX®).

In one embodiment of the methods described above, the second therapy for the CNS disorder is an inhibitor of NMDA-type glutamate receptor. In a specific embodiment of the methods described above, the inhibitor of NMDA-type glutamate receptor is memantine.

In another aspect, the disclosure provides the use of a composition comprising pooled human immunoglobulin G (IgG) for the treatment of a central nervous system (CNS) disorder in a subject in need thereof by intranasal administration.

In some embodiments of the uses described above, intranasal administration includes administration to the nasal epithelium of the subject. In other embodiments of the uses described above, intranasal administration comprises administration to the olfactory epithelium of the nasal cavity of the subject. In other embodiments of the uses described above, intranasal administration includes administration to a nasal epithelium of the subject associated with trigeminal nerve endings. In other embodiments of the uses described above, intranasal administration includes administration to the upper third of the nasal epithelium of the nasal cavity of the subject. In yet other embodiments, of the uses described above, intranasal administration includes administration to one or both maxillary sinus of the subject.

In one embodiment of the uses described above, the CNS disorder is selected from the group consisting of a neurodegenerative disorder of the central nervous system, a systemic atrophy primarily affecting the central nervous system, an extrapyramidal and movement disorder, a demyelinating disorder of the central nervous system, an episodic or paroxysmal disorder of the central nervous system, a paralytic syndrome of the central nervous system, a nerve, nerve root, or plexus disorder of the central nervous system, an organic mental disorder, a mental or behavioral disorder caused by psychoactive substance use, a schizophrenia, schizotypal, or delusional disorder, a mood (affective) disorder, neurotic, stress-related, or somatoform disorder, a behavioral syndrome, an adult personality or behavior disorder, a psychological development disorder, and a child onset behavioral or emotional disorder.

In one embodiment of the uses described above, the CNS disorder is selected from the group consisting of Alzheimer's disease, Parkinson's disease, multiple sclerosis, amyotrophic lateral sclerosis (ALS), Huntington's disease, cerebral palsy, bipolar disorder, schizophrenia, and Pediatric acute-onset neuropyschiatric syndrome (PANS).

In one embodiment of the uses described above, the CNS disorder is selected from the group consisting of Alzheimer's disease, Parkinson's disease, multiple sclerosis, Pediatric Autoimmune Neuropsychiatric Disorders Associated with Streptococcal infections (PANDAS), and Pediatric acute-onset neuropyschiatric syndrome (PANS).

In one embodiment of the uses described above, the CNS disorder is selected from the group consisting of Alzheimer's disease, multiple sclerosis, and Parkinson's disease.

In one embodiment of the uses described above, the CNS disorder is Alzheimer's disease.

In one embodiment of the uses described above, intranasal administration of the composition includes the use of a non-invasive intranasal delivery device.

In one embodiment of the uses described above, intranasal administration of the composition includes administration of a liquid drop of the composition directly onto the nasal epithelium, the nasal epithelium of the subject associated with trigeminal nerve endings, or the upper third of the nasal cavity of the subject.

In one embodiment of the uses described above, intranasal administration of the composition includes directed administration of an aerosol of the composition to the nasal epithelium, the nasal epithelium of the subject associated with trigeminal nerve endings, or the upper third of the nasal cavity of the subject.

In one embodiment of the uses described above, the aerosol of the composition is a liquid aerosol.

In one embodiment of the uses described above, the aerosol of the composition is a powder aerosol.

In one embodiment of the uses described above, at least 40% of the pooled human IgG administered to the subject contacts the nasal epithelium of the subject, the olfactory epithelium of the nasal cavity of the subject, a nasal epithelium of the subject associated with trigeminal nerve endings, the upper third of the nasal cavity of the subject, or one or both maxillary sinus of the subject.

In one embodiment of the uses described above, at least 50% of the pooled human IgG administered to the subject contacts the nasal epithelium of the subject, the olfactory epithelium of the nasal cavity of the subject, a nasal epithelium of the subject associated with trigeminal nerve endings, the upper third of the nasal cavity of the subject, or one or both maxillary sinus of the subject.

In one embodiment of the uses described above, at least 60% of the pooled human IgG administered to the subject contacts the nasal epithelium of the subject, the olfactory epithelium of the nasal cavity of the subject, a nasal epithelium of the subject associated with trigeminal nerve endings, the upper third of the nasal cavity of the subject, or one or both maxillary sinus of the subject.

In one embodiment of the uses described above, the pooled human IgG composition does not contain a permeability enhancer.

In one embodiment of the uses described above, the pooled human IgG composition consists essentially of pooled human IgG and an amino acid.

In one embodiment of the uses described above, the amino acid is selected from the group consisting of glycine, histidine, and proline. In a specific embodiment of the methods provided above, the amino acid is glycine.

In one embodiment of the uses described above, the pooled human IgG composition is an aqueous composition.

In one embodiment of the uses described above, the pooled human IgG composition includes from 10 mg/mL to 250 mg/mL pooled human IgG and from 50 mM to 500 mM glycine.

In one embodiment of the uses described above, the pH of the composition is from 4.0 to 6.0. In another embodiment of the uses described above, the pH of the composition is from 4.0 to 7.5. In another embodiment of the methods provided above, the pH of the composition is from 6.0 to 7.5.

In one embodiment of the uses described above, the pooled human IgG composition is a dry powder composition.

In one embodiment of the uses described above, the dry powder composition is prepared from an aqueous solution including from 10 mg/mL to 250 mg/mL pooled human IgG and from 50 mM to 500 mM glycine.

In one embodiment of the uses described above, the dry powder composition is prepared from an aqueous solution having a pH of from 4.0 to 6.0. In another embodiment of the uses described above, the pH of the composition is from 4.0 to 7.5 In another embodiment of the uses described above, the pH of the composition is from 6.0 to 7.5

In one embodiment of the uses described above, the use includes intranasally administering to the subject a dose of from 0.08 mg to 100 mg pooled human IgG per kg body weight of the subject (mg IgG/kg). In a specific embodiment of the uses described above, the use includes intranasally administering to the subject a dose of from 0.2 mg to 40 mg pooled human IgG per kg body weight of the subject (mg IgG/kg). In a specific embodiment of the uses described above, the use includes intranasally administering to the subject a dose of from 5 mg to 20 mg pooled human IgG per kg body weight of the subject (mg IgG/kg). In a specific embodiment of the uses described above, the use includes intranasally administering to the subject a dose of from 5 mg to 10 mg pooled human IgG per kg body weight of the subject (mg IgG/kg). In a specific embodiment of the uses described above, the use includes intranasally administering to the subject a dose of from 1 mg to 5 mg pooled human IgG per kg body weight of the subject (mg IgG/kg).

In one embodiment of the uses described above, the use includes intranasally administering to the subject a fixed dose of from 50 mg to 10 g pooled human IgG. In a specific embodiment of the uses provided above, the use includes intranasally administering to the subject a fixed dose of from 100 mg to 5.0 g pooled human IgG. In a specific embodiment of the uses provided above, the use includes intranasally administering to the subject a fixed dose of from 500 mg to 2.5 g pooled human IgG.

In one embodiment of the uses described above, the method includes intranasally administering to the subject a dose of pooled human IgG at least twice monthly. In a specific embodiment of the uses described above, the method includes intranasally administering to the subject a dose of pooled human IgG at least once weekly. In a specific embodiment of the uses described above, the method includes intranasally administering to the subject a dose of pooled human IgG at least twice weekly. In a specific embodiment of the uses described above, the method includes intranasally administering to the subject a dose of pooled human IgG at least once daily. In a specific embodiment of the uses described above, the method includes intranasally administering to the subject a dose of pooled human IgG at least twice daily.

In one embodiment of the uses described above, the pooled human IgG composition includes at least 0.1% anti-amyloid β IgG.

In one embodiment of the uses described above, the method further includes administering a second therapy for the CNS disorder to the subject in need thereof.

In one embodiment of the uses described above, the second therapy for the CNS disorder is a cholinesterase inhibitor. In a specific embodiment of the uses described above, the cholinesterase inhibitor is selected from the group consisting of donepezil (e.g., ARICEPT®), rivastigmine (e.g., EXELON®), galantamine (e.g., RAZADYNE®), or tacrine (e.g., COGNEX®).

In one embodiment of the uses described above, the second therapy for the CNS disorder is an inhibitor of NMDA-type glutamate receptor. In a specific embodiment of the uses described above, the inhibitor of NMDA-type glutamate receptor is memantine.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2A illustrates results of brain tissue $^{125}$I IgG concentrations (nM) 30 (n=8) and 90 (n=6) minutes after administration of a liquid protein IgG preparation, normalized to a 6.0 mg dose. FIG. 2B illustrates results of brain tissue $^{125}$I IgG concentrations (nM) 30 (n=12) and 90 (n=6) minutes after administration of a solid microsphere IgG preparation, normalized to a 6.0 mg dose.

FIG. 3A shows the percent area covered by beta-amyloid plaques. Four slides from the cortex of each mouse were analyzed using ImageJ software. The data is distributed in the given range by plaque radius size (in micrometers). Significant differences between transgenic treatment groups are marked in the graph with the p-value. FIG. 3B shows the average number of beta-amyloid plaques. Four slides from the cortex of each mouse were analyzed using ImageJ software. The data is distributed in the given range by plaque radius size (in micrometers). Significant differences between transgenic treatment groups are marked in the graph with the p-value. FIG. 3C shows the average number of beta-amyloid plaques. Four slides from the hippocampus of each mouse were analyzed using ImageJ software. The data is distributed in the given range by plaque radius size (in micrometers). FIG. 3D shows the percent area covered by beta-amyloid plaques. Four slides from the hippocampus of each mouse were analyzed using ImageJ software. The data is distributed in the given range by plaque radius size (in micrometers). FIG. 3E shows immunofluorescent staining of amyloid plaques in the hippocampus and cortex of aged TG2576 transgenic mice (field of view=5.3 mm). For the immunofluorescent staining, mice were intranasally administered saline, low dose IgG, or high dose IgG three times weekly over a period of 8 months. Each value is reported as the mean value for the cohorts±standard error.

FIG. 6A shows a Coomassie stained, non-reducing gel of sprayed and non-sprayed (control) IgG. FIG. 6B shows a Western blot of a reducing gel probed with an anti-IgG antibody.

FIG. 8A shows the total amyloid area (plaque and vasculature). FIG. 8B shows the number (#) of amyloid deposits (plaque and vasculature). FIG. 8C shows the total intensity of all amyloid deposits (i.e., the Sum Intensity).

FIG. 9A shows the total amyloid area (plaque and vasculature). FIG. 9B shows the number (#) of amyloid deposits (plaque and vasculature). FIG. 9C shows the total intensity of all amyloid deposits (i.e., the Sum Intensity).

FIG. 10A shows the vascular amyloid area. FIG. 10B shows the number (#) of vascular deposits. FIG. 10C shows the total intensity of vascular deposits (i.e., the Sum Intensity).

FIG. 11A shows the relative plaque contribution to total amyloid. FIG. 11B shows the relative vascular contribution to total amyloid.

FIG. 12A shows a z-stack max intensity projection image created from five individual images at 10× with a 512×512 resolution. FIGS. 12B-12F show single images created from thirty of z-stacks projections as shown in FIG. 12A, encompassing the whole tissue section that were tiled (6×5, 5% overlap). Representative images from the groups: Tg-Saline with Thresholding, Full-Resolution, Portion of the cortex and hippocampus (FIG. 12A); Tg-Low without Thresholding (FIG. 12B); WT-Saline with thresholding (FIG. 12C); Tg-Saline with thresholding (FIG. 12D); Tg-Low with thresholding (FIG. 12E); and Tg-High with thresholding (FIG. 12F).

DETAILED DESCRIPTION OF INVENTION

Introduction

Figure 1A:
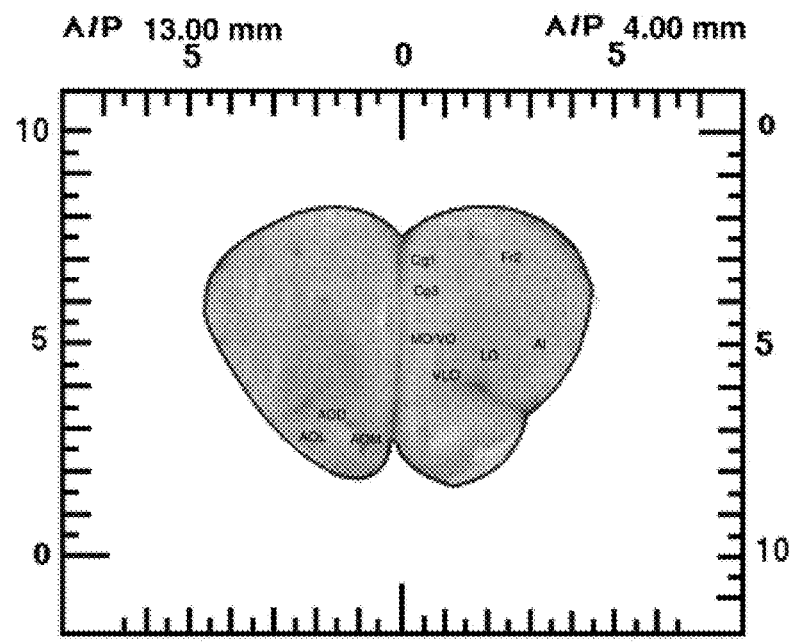
FIGS. 1A-1F show brain slices from rats used to assess the biodistribution of intranasally administered IgG in Example 2. Six 2 mm slices (3 rostral to the optic chiasm and 3 caudal) were acquired.
Figure 1B:
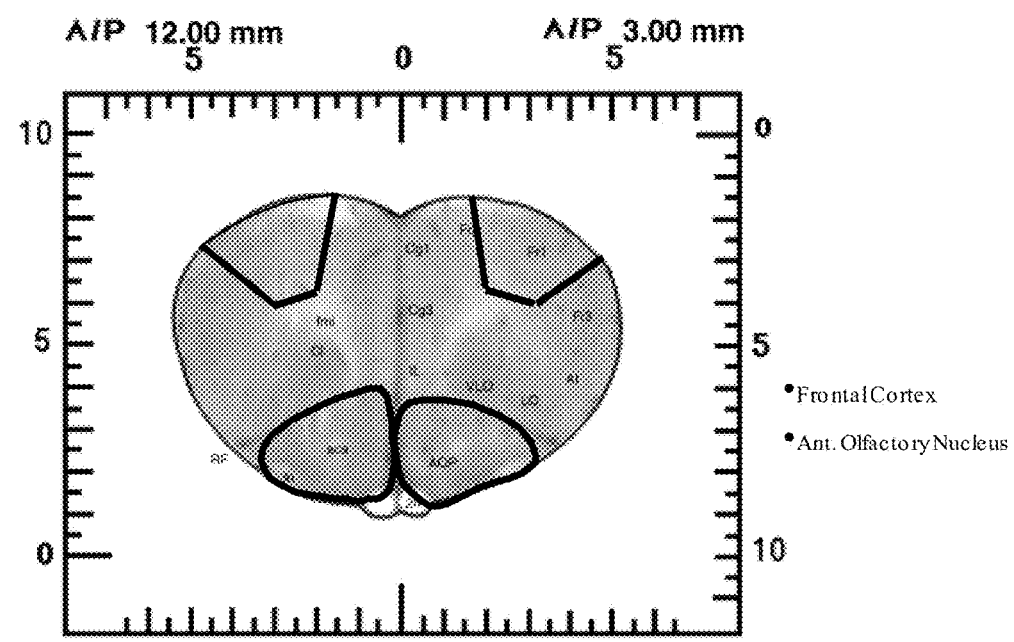
Figure 1C:
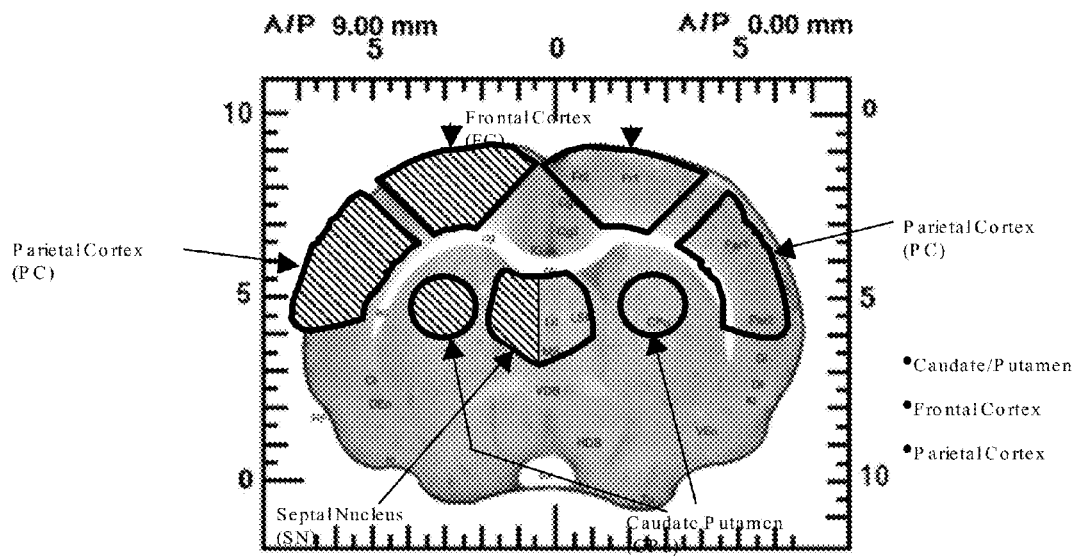
Figure 1D:
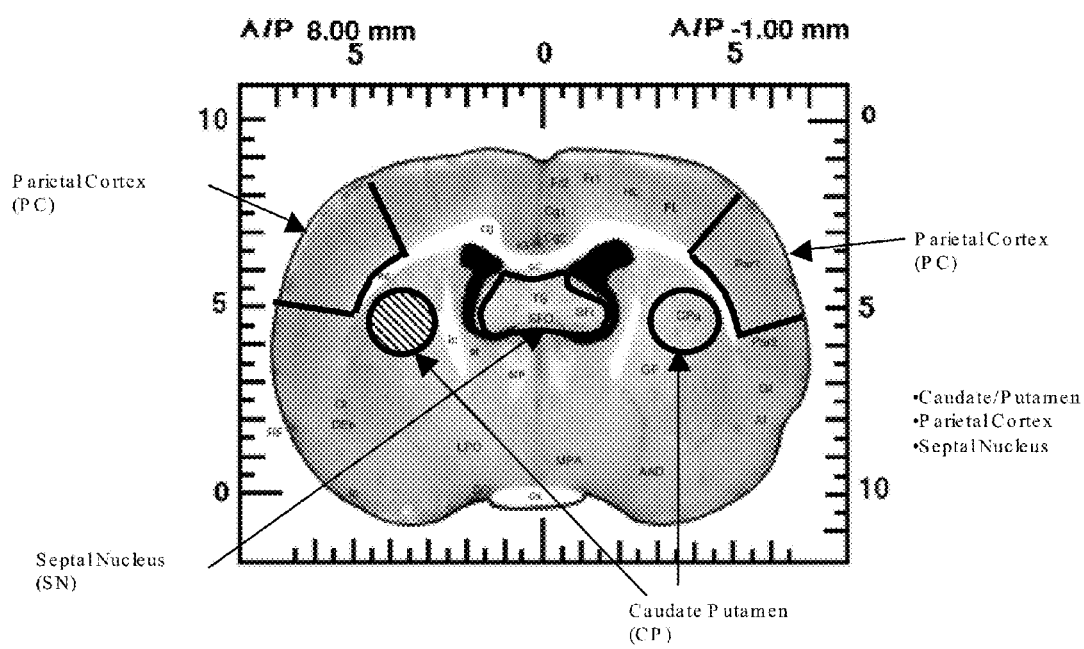
Figure 1E:
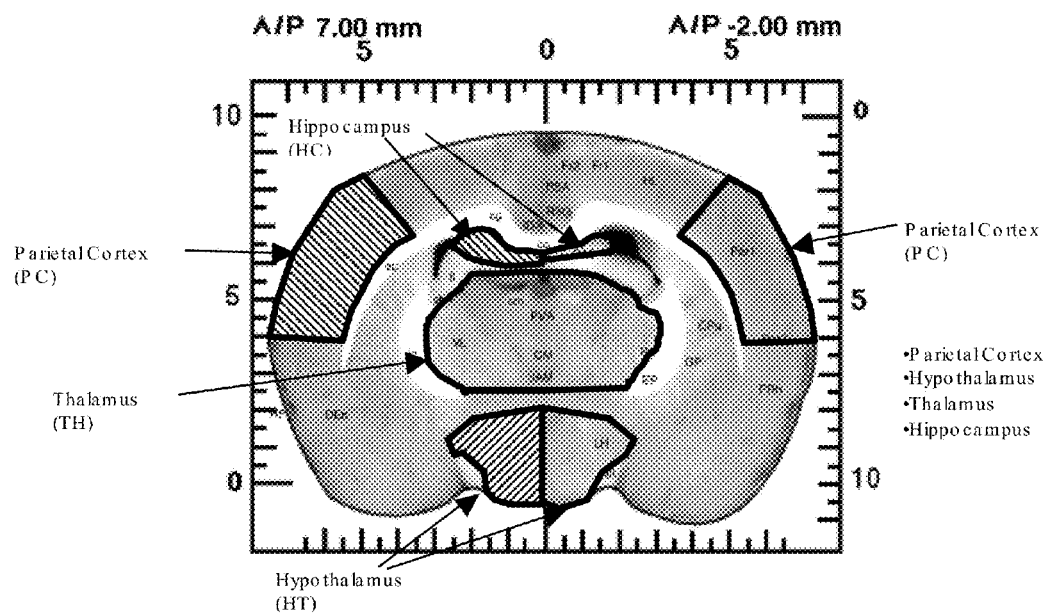
Figure 1F:
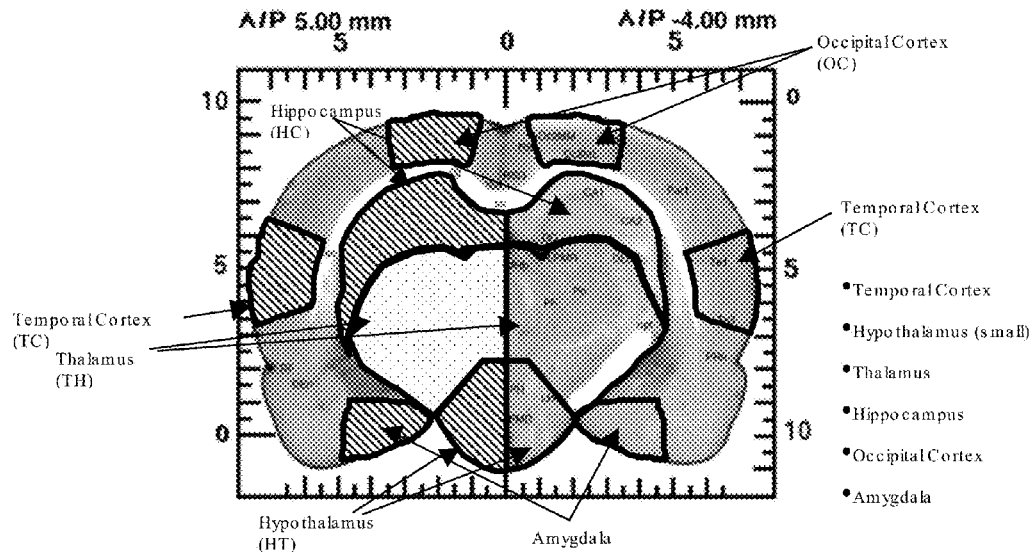

The present disclosure provides methods and compositions for treating a central nervous system (CNS) disorder in a subject by intranasal delivery of a therapeutically effective amount of pooled human immunoglobulin G (IgG) directly to the epithelium of the nasal cavity of the subject. In a specific embodiment, pooled human IgG is administered directly to the olfactory epithelium of the nasal cavity. In some embodiments, pooled IgG is delivered to the upper third of the nasal cavity, e.g., above the lower turbinates. In some embodiments, pooled IgG is delivered to the brain via the trigeminal nerve after intranasal administration to the nasal respiratory epithelium. In a specific embodiment, pooled IgG is delivered to the brain via the maxillary nerve after intranasal administration to the nasal respiratory epithelium. In other embodiments, pooled IgG is delivered to the brain after administration to the maxillary sinus.

In some embodiments, methods and compositions for the treatment of Alzheimer's disease, multiple sclerosis, and Parkinson's disease via intranasal administration of pooled human IgG are provided herein. In other embodiments, the methods and compositions provided herein are useful for the treatment of CNS disorder known to one of skill in the art including, without limitation, a neurodegenerative disorder of the central nervous system, a systemic atrophy primarily affecting the central nervous system, an extrapyramidal and movement disorder, a demyelinating disorder of the central nervous system, an episodic or paroxysmal disorder of the central nervous system, a paralytic syndrome of the central nervous system, a nerve, nerve root, or plexus disorder of the central nervous system, an organic mental disorder, a mental or behavioral disorder caused by psychoactive substance use, a schizophrenia, schizotypal, or delusional disorder, a mood (affective) disorder, neurotic, stress-related, or somatoform disorder, a behavioral syndrome, an adult personality or behavior disorder, a psychological development disorder, or a child onset behavioral or emotional disorder. In some embodiments, the CNS disorder is selected from the group consisting of Alzheimer's disease, Parkinson's disease, multiple sclerosis, amyotrophic lateral sclerosis (ALS), Huntington's disease, cerebral palsy, bipolar disorder, schizophrenia, or Pediatric acute-onset neuropyschiatric syndrome (PANS). In some embodiments, the CNS disorder is selected from the group consisting of Alzheimer's disease, Parkinson's disease, multiple sclerosis, Pediatric Autoimmune Neuropsychiatric Disorders Associated with Streptococcal infections (PANDAS), or Pediatric acute-onset neuropyschiatric syndrome (PANS).

Advantageously, it is shown herein that intranasal administration of IgG increased weight and survival time of Alzheimer's disease mice models. For example, it is shown in Example 6 that intranasal administration of IgG, at either high (0.8 g/kg once every two weeks) or low (0.4 g/k once every two weeks) doses, prolonged the lifespan of TG2576 mice. This result shows that intranasal administration of IgG is capable of increasing lifespan in the Alzheimer's mouse model, indicating efficacy in Alzheimer's treatment.

Moreover, intranasal administration of IgG significantly reduced plaques in the cerebral cortex of in the Alzheimer's mouse model. It is shown in Example 4 that treatment with pooled human IgG reduced the percent area covered by plaques in the Alzheimer's mouse model by about 25%, when administered intranasally at either low (0.4 mg/kg/2 wk; p=0.014) or high (0.8 mg/kg/2 wk; p=0.037) dosage. This is further indication of the efficacy of intranasal administration of IgG in the treatment of Alzheimer's disease.

As further demonstrated herein, intranasal administration results in a much more discriminate delivery of pooled human IgG to the brain, as compared to intravenous administration. For example, it is shown in Example 9 that intranasal administration of pooled human immunoglobulin G resulted in a 6-fold lower blood exposure as compared to intravenous administration. The lower system exposure of IgG provided by intranasal administration advantageously reduces the risk of side effects associated with the systemic exposure of IgG.

Advantageously, it was also found that pooled human immunoglobulin G was efficiently delivered to the brain following intranasal administration in the absence of a permeability enhancer (e.g., membrane fluidizers, tight junction modulators, and medium chain length fatty acids and salts and esters thereof, as described below). Previous reports have suggested that in order to achieve efficient transport of biotherapeutics (e.g., mimetibodies and Fc fusions) through the olfactory epithelium, a permeability enhancer is required (WO 2009/058957). However, as shown in the examples provided herein, pooled human IgG is efficiently delivered to the brain when intranasally administered as a liquid or dry powder formulated with only an amino acid (e.g., glycine).

Advantageously, it is also shown herein that the dose of pooled human IgG can be significantly reduced when administered intranasally, as compared to intravenous administration. For example, it is shown in Example 9 that administration of a low dose of pooled human IgG (0.002 g/kg IgG) intranasally delivered directly to the olfactory epithelium results in substantially the same amount of IgG being delivered to the right and left hemispheres of the brain as for intravenous administration of a ten-fold higher dose of pooled human IgG (0.02 g/kg IgG; compare corrected AUC values for right and left hemisphere IgG delivery in Table 71 and Table 72). A ten-fold reduction in the amount of pooled human IgG required for administration is significant because of the limited supply of pooled human IgG and the high cost associated therewith.

The results described above, which taken together suggest that low doses of intranasally administered pooled human IgG is effective for the treatment of Alzheimer's disease, are surprising given the difficulty of delivering full-length immunoglobulins to the brain via intranasal administration. First, although antibody fragments (e.g., Fabs) have previously been administered intranasally, the inventors are unaware of any reports demonstrating delivery of full-length antibodies to the brain via intranasal administration. In fact, it has been reported that the delivery of full-length antibodies poses a great difficulty in the field of medicine (Harmsen M M et al., Appl Microbiol Biotechnol., 2007, 77(1): 13-22; Athwal G S, Innovations in Pharmaceutical Technology, July 2009; WO 2006/091332; and WO 2009/058957). Consistent with these reports, Applicants found that antibody fragments are delivered much more readily to the brain, as compared to full-length immunoglobulins, after intranasal administration. For example, it is shown in Example 2 that, on average, the concentration of Fabs in brain tissue post-intranasal administration is 19-times higher than the concentration of full-length immunoglobulins post-intranasal administration. Given the significantly lower delivery of full-length immunoglobulins to the brain, it is surprising that intranasal administration of pooled immunoglobulins provides the effective results shown herein.

Advantageously, intranasal delivery of the pooled human IgG composition disclosed herein can be accomplished by a non-invasive means, as compared to intravenous, subcutaneous, and intramuscular administration, all of which require puncture of the skin of the subject. For example, it is shown in Example 3 that pooled human IgG can be efficiently delivered to the brain using nasal drops or a nasal spray.

Another benefit provided by the methods and compositions provided herein for intranasal administration of pooled human IgG is improved patient compliance. Treatment with intravenous IgG (IVIG) requires a lengthy administration period under medical supervision, generally taking place at hospitals and medical facilities. For example, initial administration of IVIG occurs over a 2 to 5 hour period, once a day for 2 to 7 consecutive days. Follow-up doses, also typically administered at a hospital over a period of 2 to 5 hours, are required every 1 to 4 weeks depending on the indication being treated and dosing regimen. Such an administration regime is time consuming and inconvenient for many patients. In comparison, intranasal administration can be administered at home without medical supervision. Also, intranasal administration can be performed quickly, over several minutes depending on the number of drops/sprays required, rather than several hours as required for intravenous administration. Thus, treatment can be prescribed more frequently at lower doses to maintain an effective level of IgG in the CNS with minimal inconvenience because administration occurs at home in a shorter period of time.

Furthermore, IVIG therapy requires catheterization which can cause discomfort and infection at the site of the catheter. IVIG solutions are often high in sodium and glucose to create isotonicity, causing increased risk to the elderly population, which already have increased rates of diabetes and high blood pressure. On the other hand, intranasal administration is non-invasive, i.e. there is no catheterization and does not carry invasive-procedure related risks such as infection and discomfort at the site of the catheter. Intranasal administration of pooled human IgG compositions is an improved procedure for elderly persons because it does not require IV perfusion and thus does not create a systemic increase in concentrations of salt or glucose in the blood.

Thus, as compared to currently utilized modes of administering pooled human IgG (e.g., intravenous, subcutaneous, and intramuscular) intranasal administration increases the ease of administration, decreases overall administration time, decreases the number of hospital visits required, and eliminates the risks associated with catheter-based administration (e.g., IV administration). Thus, implementation of intranasal administration of pooled human IgG will result in improved patient compliance.

Definitions

As used herein, the terms "disorder of the central nervous system," "central nervous system disorder," "CNS disorder," and the like refer to a disorder affecting either the spinal cord (e.g., a myelopathy) or brain (e.g., an encephalopathy) of a subject, which commonly presents with neurological and/or psychiatric symptoms. CNS disorders include many neurodegenerative diseases (e.g., Huntington's disease, Amyotrophic lateral sclerosis (ALS), hereditary spastic hemiplegia, primary lateral sclerosis, spinal muscular atrophy, Kennedy's disease, Alzheimer's disease, ataxias, Huntington's disease, Lewy body disease, a polyglutamine repeat disease, and Parkinson's disease) and psychiatric disorders (e.g., mood disorders, schizophrenias, and autism). Non-limiting examples of ataxia include Friedreich's ataxia and the spinocerebellar ataxias. Specifically for this application, CNS disorders do not include disorders resulting from acute viral and bacterial infections.

Non-limiting examples of CNS disorders include neurodegenerative disorders of the central nervous system, systemic atrophies primarily affecting the central nervous system, extrapyramidal and movement disorders, demyelinating disorders of the central nervous system, episodic or paroxysmal disorders of the central nervous system, paralytic syndromes of the central nervous system, nerve, nerve root, or plexus disorders of the central nervous system, organic mental disorders, mental or behavioral disorders caused by psychoactive substance use, schizophrenic, schizotypal, or delusional disorders, mood (affective) disorders, neurotic, stress-related, or somatoform disorders, behavioral syndromes, adult personality or behavior disorders, psychological development disorders, and child onset behavioral or emotional disorders. (Diagnostic and Statistical Manual of Mental Disorders, 4th Edition (DSM-IV); The World Health Organization, The International Classification of Diseases, 10th revision (ICD-10), Chapter V. Further exemplary CNS disorders are provided herein below.

Neurodegenerative CNS disorders are typically characterized by progressive dysfunction and/or cell death in the central nervous system. The hallmark of many neurodegenerative CNS disorders is the accumulation of misfolded proteins, such as beta-amyloid, tau, alpha-synuclein, and TDP-43, both intracellularly and extracellularly. Many neurodegenerative diseases are also associated with gross mitochondrial dysfunction. Common examples of neurodegenerative CNS disorders include Alzheimer's disease (AD), Parkinson's disease (PD), Huntington's disease, and Amyotrophic lateral sclerosis (ALS).

Psychiatric disorders (also referred to as mental illnesses) commonly present with cognitive deficits and mood dysregulation. Psychiatric disorders are generally defined by a combination of how a person feels, acts, thinks or perceives. Well established systems for the classification of psychiatric disorders include the International Statistical Classification of Diseases and Related Health Problems, 10th Revision (World Health Organization, tenth revision (2010), the content of which is hereby expressly incorporated by reference in its entirety for all purposes) and the Diagnostic and Statistical Manual of Mental Disorders (DSM-IV; American Psychiatric Association, DS-IV-TR (2000), the content of which is hereby expressly incorporated by reference in its entirety for all purposes). Common examples of psychiatric disorders include mood disorders, schizophrenia, and autism.

As used herein, the terms "pooled human immunoglobulin G" and "pooled human IgG" refer to a composition containing polyvalent immunoglobulin G (IgG) purified from the blood/plasma of multiple donors, e.g., more than a hundred or more than a thousand blood donors. Typically, the composition will be at least 80% IgG (w/w, e.g., weight IgG per weight total protein), preferably at least 85%, 86%, 87%, 88%, 89%, 90%, 91%, 92%, 93%, 94%, 95%, 96%, 97%, 98%, or 99% IgG (w/w). In certain embodiments, the pooled human IgG composition contains intact IgG immunoglobulins. In other embodiments, the pooled human IgG composition contains IgG fragments, for example those prepared by treatment of intact antibodies with trypsin. In certain embodiments, the pooled human IgG compositions used in the treatments disclosed herein contain natural or synthetic modifications, e.g., post-translational modifications and/or chemical modifications.

As used herein, the terms "high titer anti-amyloid β pooled immunoglobulin G" and "high titer anti-amyloid β pooled IgG" refer to a composition containing polyvalent immunoglobulin G (IgG) purified from the blood/plasma of multiple donors, e.g., more than a hundred or more than a thousand blood donors, having a relative titer of anti-amyloid β immunoglobulin G that is greater than the expected titer of anti-amyloid β immunoglobulins in a pooled IgG composition prepared from the blood/plasma of more than a thousand random individuals. Commercially available intravenous immunoglobulin G (IVIG) preparations contain IgGs that specifically recognize epitopes of various conformers of amyloid β, e.g., amyloid β monomers, amyloid β fibrils, and cross-linked amyloid β protein species (CAPS). It has been reported that a commercial preparation of GAMMAGARD LIQUID® (10% Immune Globulin Infusion (Human); Baxter International Inc., Deerfield, Ill.) contains 0.1% anti-amyloid β fibril IgG, 0.04% anti-CAPS IgG, and 0.02% anti-amyloid β monomer IgG, having $EC_{50}$ affinities of 40 nM, 40 nM, and 350 nM for their target amyloid β conformer, respectively (O'Nuallain B. et al., *Biochemistry*, 2008 Nov. 25; 47(47):12254-6, the content of which is hereby incorporated by reference in its entirety for all purposes). In some embodiments, a high titer anti-amyloid β pooled immunoglobulin G composition contains a high titer of IgG specific for one or more conformer of amyloid β. In other embodiments, a high titer anti-amyloid β pooled immunoglobulin G composition contains a high titer of IgG specific for amyloid β monomers, amyloid β fibrils, and cross-linked amyloid β protein species (CAPS).

Accordingly, in one embodiment, a high titer anti-amyloid β pooled immunoglobulin G composition contains at least 0.1% anti-amyloid β IgG (e.g., 0.1% IgG with specific affinity for any amyloid β conformer). In another embodiment, a high titer anti-amyloid β pooled immunoglobulin G composition contains at least 0.2% anti-amyloid β IgG. In yet other embodiments, a high titer anti-amyloid β pooled immunoglobulin G composition contains at least 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.5%, 2.0%, 2.5%, 3.0%, 3.5%, 4.0%, 4.5%, 5.0% or more anti-amyloid β IgG.

In one embodiment, a high titer anti-amyloid β pooled immunoglobulin G composition contains at least 0.1% anti-amyloid β fibril IgG. In another embodiment, a high titer anti-amyloid β pooled immunoglobulin G composition contains at least 0.2% anti-amyloid β fibril IgG. In yet other embodiments, a high titer anti-amyloid β pooled immunoglobulin G composition contains at least 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.5%, 2.0%, 2.5%, 3.0%, 3.5%, 4.0%, 4.5%, 5.0% or more anti-amyloid β fibril IgG.

In one embodiment, a high titer anti-amyloid β pooled immunoglobulin G composition contains at least 0.04% anti-CAPS IgG. In another embodiment, a high titer anti-amyloid β pooled immunoglobulin G composition contains at least 0.08% anti-CAPS IgG. In yet other embodiments, a high titer anti-amyloid β pooled immunoglobulin G composition contains at least 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.5%, 2.0%, 2.5%, 3.0%, 3.5%, 4.0%, 4.5%, 5.0% or more anti-CAPS IgG.

In one embodiment, a high titer anti-amyloid β pooled immunoglobulin G composition contains at least 0.02% anti-amyloid β monomer IgG. In another embodiment, a high titer anti-amyloid β pooled immunoglobulin G composition contains at least 0.04% anti-amyloid β monomer IgG. In yet other embodiments, a high titer anti-amyloid β pooled immunoglobulin G composition contains at least 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.5%, 2.0%, 2.5%, 3.0%, 3.5%, 4.0%, 4.5%, 5.0% or more anti-amyloid β monomer IgG.

High titer anti-amyloid β pooled IgG can be prepared according to standard methods for the manufacture of pooled IgG starting with a standard pool of blood/plasma of multiple donors, e.g., more than a hundred or more than a thousand blood donors, and subsequently enriched for anti-amyloid β immunoglobulin G. Methods for the enrichment of target-specific immunoglobulin G molecules are well known in the art (for example, see U.S. Patent Application Publication No. 2004/0101909, the content of which is hereby expressly incorporated by reference herein in its entirety for all purposes). Alternatively, high titer anti-amyloid β pooled IgG can be prepared according to standard methods for the manufacture of pooled IgG starting with an enriched pool of blood/plasma from at least fifty, one hundred, two hundred, five hundred, or one thousand donors having a high relative titer of anti-amyloid β immunoglobulin G. As compared to the manufacture of standard IgG for intravenous administration, hyperimmune IgG preparations are commonly prepared from smaller donor pools. These enriched pools of blood/plasma can be formed, for example, by selectively pooling blood/plasma donations or donors with a high relative titer of anti-amyloid β immunoglobulin G, e.g., by selection of high titer blood/plasma donations or donors. Alternatively, an enriched pool of blood/plasma can be formed by screening for blood/plasma donations or donors with a low relative titer of anti-amyloid β immunoglobulin G and excluding these donations or donors from the starting blood/plasma pool, e.g., screening for low titer blood/plasma donations or donors.

As used herein, the term "intactness" refers to a percentage of therapeutic agent that has not been at least partially degraded at a particular point in time following administration. In one embodiment, intactness is a measure of the total administered dose of the therapeutic agent that has not been at least partially degraded at the particular point in time (i.e., systemic intactness). In another embodiment, intactness is a measure of the therapeutic agent present at a particular site of the subject, e.g., brain or bloodstream, which has not been at least partially degraded (i.e., local intactness). In one embodiment, the intactness of administered immunoglobulin (e.g., pooled human IgG) is measured by mass spectroscopy. For example, the intactness of the administered immunoglobulins is determined by analyzing a biological sample from the subject, or proteins extracted from the biological sample, by mass spectroscopy. In some embodiments, the intactness of the administered immunoglobulins is determined by separating proteins present in a biological sample from the subject by molecular weight, size, or shape (e.g., by electrophoresis or size exclusion chromatography) and determining the size distribution of administered immunoglobulins in the sample.

In one embodiment, the intactness of immunoglobulin (e.g., pooled human IgG) in the brain of a subject following intranasal administration is at least 40%. In preferred embodiments, the intactness of immunoglobulin (e.g., pooled human IgG) in the brain of a subject following intranasal administration is at least 50%, preferably at least 60%. In certain embodiments, the intactness of immunoglobulin (e.g., pooled human IgG) in the brain of a subject following intranasal administration is at least 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, or higher.

As used herein, the terms "intranasal administration" and "nasal administration" refer to administration of a therapeutic composition to the nasal cavity of a subject such that a therapeutic agent in the composition is delivered directly to one or more epithelium located in the nose. In certain embodiments, intranasal administration is achieved using a liquid preparation (e.g., an aqueous preparation), an aerosolized preparation, or a dry powder preparation, each of which can be administered via an externally propelled or self-propelled (e.g., via inhalation) non-invasive nasal delivery device, or via a gel, cream, ointment, lotion, or paste directly applied to one or more nasal epithelium (e.g., olfactory epithelium or nasal respiratory epithelium).

As used herein, the term "nasal epithelium" refers to the tissues lining the internal structure of the nasal cavity. The term nasal epithelium includes both the nasal respiratory epithelium, located in the lower two-thirds of the nasal cavity in humans, and the olfactory epithelium, located in the upper third of the nasal cavity of humans.

As used herein, the term "olfactory epithelium" refers to a specialized epithelial tissue inside the nasal cavity involved in smell. In humans, the olfactory epithelium is located in the upper third of the nasal cavity.

As used herein, the term "directed administration" refers to a process of preferentially delivering a therapeutic agent to a first location in a subject as compared a second location or systemic distribution of the agent. For example, in one embodiment, directed administration of a therapeutic agent results in at least a two-fold increase in the ratio of therapeutic agent delivered to a targeted site to therapeutic agent delivered to a non-targeted site, as compared to the ratio following systemic or non-directed administration. In other embodiments, directed administration of a therapeutic agent results in at least a 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 60-fold, 70-fold, 80-fold, 90-fold, 100-fold, 200-fold, 300-fold, 400-fold, 500-fold, 750-fold, 1000-fold, or greater increase in the ratio of therapeutic agent delivered to a targeted site to therapeutic agent delivered to a non-targeted site, as compared to the ratio following systemic or non-directed administration. In a particular embodiment, directed administration of an agent is contrasted to intravenous administration of the agent. For example, in one embodiment, the ratio of therapeutic agent present at a targeted site to therapeutic agent present in the blood stream is increased at least two-fold when the agent is subject to directed administration (e.g., by delivery to the brain via intranasal administration), as compared to when the therapeutic agent is administered intravenously.

As used herein, the term "non-invasive nasal delivery device" refers an instrument that is capable of delivering a therapeutic composition (e.g., pooled human IgG) to the nasal cavity without piercing the epithelium of the subject. Non-limiting examples of non-invasive nasal delivery devices include propellant (e.g., a pressurized inhaler) and non-propellant (e.g., a pump-type inhaler) types of aerosol or atomizer devices, particle dispersion devices, nebulizers, and pressurized olfactory delivery devices for delivery of liquid or powder formulations.

The term "treatment" or "therapy" generally means obtaining a desired physiologic effect. The effect may be prophylactic in terms of completely or partially preventing a disease or condition or symptom thereof and/or may be therapeutic in terms of a partial or complete cure for an injury, disease or condition and/or amelioration of an adverse effect attributable to the injury, disease or condition and includes arresting the development or causing regression of a disease or condition. Treatment can also refer to any delay in onset, amelioration of symptoms, improvement in patient survival, increase in survival time or rate, improvement in cognitive function, etc. The effect of treatment can be compared to an individual or pool of individuals not receiving the treatment.

As used herein, a "therapeutically effective amount or dose" or "sufficient/effective amount or dose," refers to a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used here, the terms "dose" and "dosage" are used interchangeably and refer to the amount of active ingredient given to an individual at each administration. The dose will vary depending on a number of factors, including frequency of administration; size and tolerance of the individual; severity of the condition; risk of side effects; and the route of administration. One of skill in the art will recognize that the dose can be modified depending on the above factors or based on therapeutic progress. The term "dosage form" refers to the particular format of the pharmaceutical, and depends on the route of administration. For example, a dosage form can be a liquid or dry powder, formulated for intranasal administration.

As used herein, a therapeutic composition "consisting essentially of a buffering agent and pooled human IgG" may also contain residual levels of chemical agents used during the manufacturing process, e.g., surfactants, buffers, salts, and stabilizing agents, as well as chemical agents used to pH the final composition, for example, counter ions contributed by an acid (e.g., hydrochloric acid or acetic acid) or base (e.g., sodium or potassium hydroxide), and/or trace amounts of contaminating proteins.

As used herein, the term "permeability enhancer" refers to a component of a therapeutic composition formulated for intranasal administration which promotes the passage of biotherapeutics (e.g., mimetibodies and Fc-fusion polypeptides) through the nasal epithelium. Non-limiting examples of permeability enhancers include membrane fluidizers, tight junction modulators, and medium chain length fatty acids and salts and esters thereof. Non-limiting examples of medium chain length fatty acids and salts and esters thereof included mono-, di-, and triglycerides (such as sodium caprylate, sodium caprate, glycerides (CAPMUL, GELUCIRE 44/14 PEG32 glyceryl laurate EP); lipids; pegylated peptides; and liposomes. Surfactants and similarly acting compounds can also be used as permeability enhancers. Non-limiting examples of surfactants and similarly acting compounds include polysorbate-80, phosphatidylcholine, N-methylpiperazine, sodium salicylate, melittin, and palmitoyl carnitine chloride (PCC). Generally, the pooled human immunoglobulin G compositions described herein are formulated for intranasal administration in the absence of permeability enhancers.

As used herein, the term "dry powder composition" refers to a lyophilized or spray dried form of a therapeutic pooled human IgG formulation. In one embodiment, a dry powder composition contains less than 10%, 9%, 8%, 7%, 6%, 5%, 4%, 3%, 2%, 1%, or less residual water content.

A "control" is used herein, refers to a reference, usually a known reference, for comparison to an experimental group. One of skill in the art will understand which controls are valuable in a given situation and be able to analyze data based on comparisons to control values. Controls are also valuable for determining the significance of data. For example, if values for a given parameter vary widely in controls, variation in test samples will not be considered as significant.

Before the present disclosure is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Administration

Intranasal (IN) administration is an advantageous mode of delivering a drug to the brain because it is non-invasive and there is a direct connection between the olfactory system and the brain. Intranasal administration of IgG (INIG) to treat neurological diseases is particularly advantageous because the direct connection between the olfactory system and the brain obviates delivery concerns associated with the blood-brain barrier (BBB) and minimizes systemic exposure to the drug, thereby minimizing side effects of the drug. Furthermore, IN delivery allows compositions such as powders, granules, solutions, ointments, and creams, thereby obviating the need for intravenous and intramuscular administration. For example, when a drug is administered intranasally, it is transported through the nasal mucosa and along the olfactory neural pathway. The drug can be administered alone or can be combined with a carrier molecule(s) to promote transport through the nasal mucosa and along the olfactory neural pathway. The drug can also be administered in combination with an absorption enhancer. Absorption enhancers promote the absorption of the drug through the nasal mucosa and along the olfactory neural pathway. Furthermore, additional molecules can be added to facilitate drug transport across the olfactory neural pathway.

IN administration can also be used to deliver therapeutic drugs to the brain via the trigeminal pathway. Specifically, IN administration can be used to deliver IgG via the trigeminal pathway. The olfactory and trigeminal nerves receive high concentrations of a drug with IN administration because the absorbent respiratory and olfactory pseudoepithelium are innervated by the trigeminal nerve. These nerves can then transport the drug into the brain and other connected structures. For example, the trigeminal nerve branches directly or indirectly reach the maxillary sinus, brainstem, hindbrain, cribriform plate, forebrain (e.g., cortex and diencephalon), orofacial structures (e.g., teeth, masseter muscle, and the temporomandibular joint), midbrain, cerebellum, cervical spinal cord, thoracic spinal cord, and lumbar spinal cord. Accordingly, INIG can be carried across the trigeminal pathway to reach and treat neurological diseases.

In certain embodiments, methods are provided for the treatment of CNS disorders by administration of pooled human immunoglobulins to tissue innervated by the olfactory and/or trigeminal nerves. Surprisingly, it was found that therapeutically effective amounts of pooled human immunoglobulin are delivered to the CNS when administered intranasally. For example, it is shown herein that intranasal administration of pooled human immunoglobulins is effective to reduce total amyloid plaque load in a rodent model of Alzheimer's disease. Moreover, by specifically targeting the nasal epithelium, as opposed to the respiratory system (lung, pharynx, etc.), systemic exposure of the pooled human immunoglobulins is reduced.

Many types of intranasal delivery devices can be used to practice the methods provided herein. In some embodiments, the delivery device is an intranasal device for the administration of liquids. Non-limiting examples of devices useful for the administration of liquid compositions (e.g., liquid pooled IgG compositions) include vapor devices (e.g., vapor inhalers), drop devices (e.g., catheters, single-dose droppers, multi-dose droppers, and unit-dose pipettes), mechanical spray pump devices (e.g., squeeze bottles, multi-dose metered-dose spray pumps, and single/duo-dose spray pumps), bi-directional spray pumps (e.g., breath-actuated nasal delivery devices), gas-driven spray systems/atomizers (e.g., single- or multi-dose HFA or nitrogen propellant-driven metered-dose inhalers, including traditional and circumferential velocity inhalers), and electrically powered nebulizers/atomizers (e.g., pulsation membrane nebulizers, vibrating mechanical nebulizers, and hand-held mechanical nebulizers). In some embodiments, the delivery device is an intranasal device for the administration of powders or gels. Non-limiting examples of devices useful for the administration of powder compositions (e.g., lyophilized or otherwise dried pooled IgG compositions) include mechanical powder sprayers (e.g., hand-actuated capsule-based powder spray devices and hand-actuated powder spray devices, hand actuated gel delivery devices), breath-actuated inhalers (e.g., single- or multi-dose nasal inhalers and capsule-based single- or multi-dose nasal inhalers), and insufflators (e.g., breath-actuated nasal delivery devices). In some embodiments, the pooled human immunoglobulins are preferentially administered to the olfactory area, located in the upper third of the nasal cavity, and particularly to the olfactory epithelium. Fibers of the olfactory nerve are unmyelinated axons of olfactory receptor cells, which are located in the superior one-third of the nasal cavity. The olfactory receptor cells are bipolar neurons with swellings covered by hair-like cilia that project into the nasal cavity. At the other end, axons from these cells collect into aggregates and enter the cranial cavity at the roof of the nose. Surrounded by a thin tube of pia, the olfactory nerves cross the subarachnoid space containing CSF and enter the inferior aspects of the olfactory bulbs. Once the pooled human immunoglobulin is dispensed into the nasal cavity, the immunoglobulin can undergo transport through the nasal mucosa and into the olfactory bulb and interconnected areas of the brain, such as the hippocampal formation, amygdaloid nuclei, nucleus basalis of Meynert, locus ceruleus, the brain stem, and the like (e.g., Johnson et al., Molecular Pharmaceutics (2010) 7(3):884-893).

In certain embodiments, pooled human immunoglobulin is administered to tissue innervated by the trigeminal nerve. The trigeminal nerve innervates tissues of a mammal's (e.g., human) head including skin of the face and scalp, oral tissues, and tissues surrounding the eye. The trigeminal nerve has three major branches, the ophthalmic nerve, the maxillary nerve, and the mandibular nerve. In some embodiments, the methods provided herein include targeted administration of pooled human immunoglobulin to one or more of these trigeminal branches, i.e. the trigeminal pathway. In some embodiments, the methods provided herein include targeted administration of pooled human immunoglobulin to the maxillary sinus, thereby reaching the brainstem, hindbrain, cribriform plate, forebrain (e.g., cortex and diencephalon), midbrain, cerebellum, cervical spinal cord, thoracic spinal cord, and lumbar spinal cord through the trigeminal pathway. In certain embodiments, methods provided herein include targeted administration of pooled human immunoglobulin for treatment of a disorder of the CNS (e.g., Alzheimer's disease).

In some embodiments, the pooled human immunoglobulin is administered to nasal tissues innervated by the trigeminal nerve, for example, to nasal tissues including the sinuses, the inferior two-thirds of the nasal cavity and the nasal septum. In certain embodiments, the pooled human immunoglobulin is targeted to the inferior two-thirds of the nasal cavity and/or the nasal septum.

In some embodiments, the pooled human immunoglobulin is administered to one or both maxillary sinus of the individual. Methods and devices for administration to the maxillary sinus are known in the art, for example, see United States Patent Application Publication Number 2011/0151393, the contents of which are hereby incorporated by reference in their entirety for all purposes.

The maxillary sinus is in fluid communication with the patient's nasal cavity and comprises right and left maxillary sinuses. Each maxillary sinus communicates with the corresponding nasal passage via the orifice of the maxillary sinus. The maximum volume of the maxillary sinus in adults is approximately 4 to 15 ml, though individual sinuses may comprise volumes outside of this range.

The pathway from the nasal passages to the corresponding orifice of maxillary sinus, and ultimately to the corresponding maxillary sinus, allows for a device to be inserted into the nasal passage to the orifice of the maxillary sinus, whereupon at least one effective amount or dose of pooled human immunoglobulins may be administered and delivered into the maxillary sinus. The pathway to the maxillary sinus is tortuous and requires: traversing the nostril, moving through the region between the lower and middle concha, navigating over and into the semilunar hiatus, traveling superiorly into the maxillary sinus opening, resisting the ciliated action of the ostium/tube passing into the maxillary sinus and ultimately moving into the sinus itself.

Since the trigeminal nerve passes through the maxillary sinus, the pooled human immunoglobulins in the maxillary sinus after delivery therein will be moved along the trigeminal nerve to structures innervated by the trigeminal nerve. In this fashion, pooled human IgG administered to one or both of the maxillary sinus is delivered to the brain via the trigeminal nerve.

In one embodiment, the pooled human IgG compositions provided herein for the treatment of a CNS disorder (e.g., Alzheimer's disease) are intranasally administered as a liquid preparation, e.g., an aqueous based preparation. For example, in one embodiment, nasal drops are instilled in the nasal cavity by tilting the head back sufficiently and apply the drops into the nares. In another embodiment, the drops are snorted up the nose. In another embodiment, nasal drops are applied with an applicator or tube onto the upper third of the nasal mucosa. In another embodiment, nasal drops are applied with an applicator or tube into one or both of maxillary sinus of the subject. In another embodiment, the liquid preparation may be placed into an appropriate device so that it may be aerosolized for inhalation through the nasal cavity. For example, in one embodiment, the therapeutic agent is placed into a plastic bottle atomizer. In a specific embodiment, the atomizer is advantageously configured to allow a substantial amount of the spray to be directed to the upper one-third region or portion of the nasal cavity (e.g., the olfactory epithelium). In another embodiment, the liquid preparation is aerosolized and applied via an inhaler, such as a metered-dose inhaler (for example, see, U.S. Pat. No. 6,715,485). In a specific embodiment, the inhaler is advantageously configured to allow a substantial amount of the aerosol to be directed to the upper one-third region or portion of the nasal cavity (e.g., the olfactory epithelium). In certain embodiments, a substantial amount of the pooled human immunoglobulin refers to at least 25%, 30%, 35%, 40%, 45%, 50%, 55%, 60%, 65%, 70%, 75%, 80%, 85%, 90%, 95%, or 100% of the composition, which is administered to the upper one-third region of the nasal cavity (e.g., administered to the upper one-third of the nasal epithelium).

In one embodiment, the pooled human IgG compositions provided herein for the treatment of a CNS disorder (e.g., Alzheimer's disease) are intranasally administered as a dry powder. Dry powder nasal delivery devices are well known in the art, for example, see PCT publication No. WO 1996/222802. In one embodiment, following intranasal administration, pooled human IgG is absorbed across the olfactory epithelium, which is found in the upper third of the nasal cavity. In another embodiment, following intranasal administration, pooled human IgG is absorbed across the nasal respiratory epithelium, which is innervated with trigeminal nerves, in the lower two-thirds of the nasal cavity. The trigeminal nerves also innervate the conjunctive, oral mucosa, and certain areas of the dermis of the face and head, and absorption after intranasal administration of the IgG from these regions may also occur. In other embodiments, following intranasal administration, pooled human IgG is absorbed across the maxillary sinus epithelium. In yet other embodiments, pooled human IgG may be absorbed across more than one of these nasal epitheliums and subsequently delivered to the brain of the subject.

Although administration is referred to herein as a single event that may occur according to some regular or irregular frequency of the course of a treatment, a single administration even may include multiple administrations. In this regard, a single dosage of pooled human IgG may be partitioned into two or more physical compositions for administration. For example, a 200 mg dose of pooled human IgG in a liquid composition formulated at 200 g/L IgG may be administered to a 50 kg subject (4 mg/kg IgG) in four drops having a volume of 250 µL each. Likewise, a dry powder composition containing a single dosage of pooled human IgG may be administered, for example, in two or more distinct puffs. In some embodiments, pooled human IgG is administered in one or more puffs or sprays into each nare of the individual (e.g., one or more puff into the right nare and one or more puffs into the left nare).

In certain embodiments, the methods described herein for treating a CNS disorder include intranasal administration of pooled human IgG via a non-invasive intranasal delivery device. In one embodiment, the non-invasive intranasal delivery device is a non-propellant type aerosol or atomizer device, a propellant type aerosol or atomizer device, a non-propellant pump-type device, a particle dispersion device, a nebulizer device, or a pressurized olfactory delivery device.

In one embodiment the non-invasive intranasal delivery device delivers a liquid drop of a pooled human IgG composition to the nasal cavity of a subject. In a particular embodiment, the non-invasive intranasal delivery device delivers a liquid drop of pooled human IgG directly to a nasal epithelium of the subject. In a more specific embodiment, the non-invasive intranasal delivery device delivers a liquid drop of pooled human IgG directly to the olfactory epithelium of the subject. In one embodiment, the liquid drop is administered by tilting the head of the subject back and administering the drop into a nare of the subject. In another embodiment, the liquid drop is administered by inserting the tip of a non-invasive intranasal delivery device into a nare of the subject and squirting or spraying the drop into the nasal cavity of the subject.

In another embodiment, the non-invasive intranasal delivery device delivers a liquid or a powder aerosol of a pooled human IgG composition to the nasal cavity of a subject. In a particular embodiment, the non-invasive intranasal delivery device delivers a liquid or a powder aerosol of pooled human IgG directly to a nasal epithelium of the subject. In a more specific embodiment, the non-invasive intranasal delivery device delivers a liquid or a powder aerosol of pooled human IgG directly to the olfactory epithelium of the subject.

In another embodiment, the non-invasive intranasal delivery device delivers a dry powder composition of pooled human IgG composition to the nasal cavity of a subject. In a particular embodiment, the non-invasive intranasal delivery device delivers a dry powder composition of pooled human IgG directly to a nasal epithelium of the subject. In a more specific embodiment, the non-invasive intranasal delivery device delivers a dry powder composition of pooled human IgG directly to the olfactory epithelium of the subject.

In another embodiment, the non-invasive intranasal delivery device delivers a sustained release or controlled release composition of pooled human IgG composition to the nasal cavity of a subject. In a specific embodiment the sustained release composition comprises a dry powder composition of pooled human IgG. In some embodiments, the sustained release composition is a gel, paste, hydrogel, cream, lotion, film, or similar form that coats at least a portion of the nasal epithelium (e.g., all or a portion of the olfactory epithelium, all or a portion of a nasal epithelium associated with trigeminal nerve endings, all or a portion of the upper third of the nasal epithelium, all or a portion of the lower third of the nasal epithelium, or all or a portion of the nasal maxillary epithelium.

In one embodiment, the intranasal device is a single-use, disposable device. In another embodiment, the intranasal device is a multi- or repeat-use device. In certain embodiments, the single-use or multi-use device is pre-metered. In a specific embodiment, the single-use or multi-use device is pre-filled. In certain embodiments, the multi- or repeat-use device is refillable. In certain embodiments, the device is refilled by inserting a pooled human IgG composition into a chamber of the device. In other embodiments, a chamber of the multi- or repeat-use device designed to hold the pooled human IgG composition is replaced with a new, pre-filled chamber.

In certain embodiments, the pooled human immunoglobulin compositions are administered by a pressurized nasal delivery (PND) device. In one embodiment, the PND device can be used to deliver a liquid IgG composition to the nasal cavity. In one embodiment, the PND device can be used to deliver a powder IgG composition to the nasal cavity. In one embodiment, the PND device administers an IgG composition into one nostril. In one embodiment, the Impel device administers an IgG composition into both nostrils.

In some embodiments, the PND device is configured to deliver the liquid or powder IgG compositions to a particular epithelium, location, and/or structure of the nasal cavity. For example, in one embodiment, the PND device is configured to deliver the IgG composition to the upper nasal cavity. In one embodiment, the PND device is configured to deliver the IgG composition to the olfactory epithelium of the nasal cavity. In one embodiment, the PND device is configured to deliver the IgG composition to the lower two thirds of the nasal epithelium. In one embodiment, the PND device is configured to deliver the IgG composition to a nasal epithelium associated with trigeminal nerve endings. In one embodiment, the PND device is configured to deliver the IgG composition to the nasal maxillary sinus epithelium.

Methods for configuring pressurized delivery devices to achieve a particular delivery profile are known in the field. For example, in one embodiment, a pressurized nasal delivery device is configured to produce a stream, spray, puff, etc., have a particular characteristic. For example, in one embodiment, to achieve administration to the upper third of the nasal epithelium, the device is configured to produce a strong, focused stream, spray, puff, etc. In one embodiment, the strong focused spray is created by imparting circumferential and/or axial velocity onto the stream of the therapeutic composition (e.g., pooled human IgG) being administered into the nose. In another embodiment, to achieve administration to a greater portion of the nasal epithelium (e.g., the entire or the lower two thirds of the nasal epithelium), the device is configured to produce a diffuse and/or weaker stream, spray, puff, etc. In some embodiments, the tip of the delivery device is configured to physically direct the stream, spray, puff, etc., to the desired intranasal location when inserted into the subject's nare. For example, a kink or bend may be introduced into the tip of the delivery device to "point" the stream, spray, puff, etc., at a targeted epithelium. In some embodiments, the delivery pattern of the device is adjustable, such that the device can be differentially configured to target the therapeutic agent (e.g., pooled human IgG) to a particular epithelium, structure, or location within the nose. In certain embodiments, the pooled human immunoglobulin compositions are administered by a breath-powered technology device. In certain embodiments, the breath-powered technology provides positive pressure during administration. In certain embodiments, the positive pressure expands narrow nasal passages. In certain embodiments, the expansion of the nasal passages allows reliable delivery of liquid or powder pooled human immunoglobulin compositions described herein to the CNS. In some embodiments, exhalation into the device propels the therapeutic (e.g., pooled human IgG) into the nose, while at the same time closing the soft-palette, thereby reducing deposition of the therapeutic into the throat and/or lungs. In one embodiment, the breath-powered technology device administers an IgG composition described herein into one nostril. In one embodiment, the breath-powered technology device administers an IgG composition described herein into two nostrils.

Non-limiting examples of commercial intranasal delivery devices include the EQUADEL® nasal spray pump (Aptar Pharma), the Solovent dry powder device (BD Technologies), the Unidose nasal drug delivery device (Consort Medical PLC), the NasoNeb® Nasal Nebulizer (MedInvent, LLC), the VeriDoser® nasal delivery device (Mystic Pharmaceuticals), the VRx2™ nasal delivery device (Mystic Pharmaceuticals), the DirectHaler™ Nasal device (DirectHaler A/S), the TriViar™ single-use unit-dose dry powder inhaler (Trimel Pharmaceuticals), the SinuStar™ Aerosol Delivery System (Pari USA), the Aero Pump (Aero Pump GmbH), the Fit-Lizer™ nasal delivery device (Shin Nippon Biomedical Laboratories), the LMA MAD Nasal™ device (LMA North America, Inc.), the Compleo intranasal bioadhesive gel delivery system (Trimel Pharmaceuticals), Impel's Pressurized Olfactory Delivery (POD) device (Impel Neuropharma), the ViaNase™ electronic atomizer (Kurve Technology, Inc.), the OptiNose powder delivery device (OptiNose US Inc.), and the Optinose liquid delivery device (OptiNose US Inc.)

In one embodiment, an intranasal device described herein can deliver 10%-20% of the metered IgG dose to the olfactory region. In one embodiment, an intranasal device described herein can deliver 20%-30% of the metered IgG dose to the olfactory region. In one embodiment, an intranasal device described herein can deliver 5%-20% of the metered IgG dose to the olfactory region. In one embodiment, an intranasal device described herein can deliver 30%-40% of the metered IgG dose to the olfactory region. In one embodiment, an intranasal device described herein can deliver 40%-50% of the metered IgG dose to the olfactory region. In one embodiment, an intranasal device described herein can deliver 60%-70% of the metered IgG dose to the olfactory region. In one embodiment, an intranasal device described herein can deliver 60%-80% of the metered IgG dose to the olfactory region. In one embodiment, an intranasal device described herein can deliver 70%-80% of the metered IgG dose to the olfactory region. In one embodiment, an intranasal device described herein can deliver 80%-90% of the metered IgG dose to the olfactory region. In one embodiment, an intranasal device described herein can deliver 60%-80% of the metered IgG dose to the olfactory region.

In certain embodiments, the pooled human immunoglobulin compositions are administered by an intranasal device described above in one or more doses. In one embodiment the more than one dose is administer by the intranasal device in alternating nostrils. In one embodiment, the more than one does is administered by the intranasal device at different time points throughout the day. In certain embodiments the more than one dose is two, three, four, five, six, seven, eight, nine, ten, eleven, twelve, thirteen, fourteen, fifteen, sixteen, seventeen, eighteen, nineteen, or twenty or more doses. In certain embodiments the more than one dose is administered by the intranasal device one, two, three, four, five, six, seven, eight, nine, or ten or more time points throughout the day.

In certain embodiments, the pooled human immunoglobulin compositions are administered by an intranasal device described above in an initial dose or set of doses followed by repeat maintenance doses. In certain embodiments the initial dose is one, two, three, four, five, six, seven, eight, nine, ten, eleven, twelve, thirteen, fourteen, fifteen, sixteen, seventeen, eighteen, nineteen, or twenty or more doses.

In another embodiment, a gel, cream, ointment, lotion, or paste containing pooled human IgG is applied onto the nasal epithelium, for example, by use of an application stick or swab. In a particular embodiment, a gel, cream, ointment, lotion, or paste containing pooled human IgG is applied directly onto a nasal epithelium of the subject. In a more specific embodiment, a gel, cream, ointment, lotion, or paste containing pooled human IgG is applied directly onto the olfactory epithelium of the subject.

In certain embodiments, a substantial fraction of the therapeutic agent present in the composition is delivered directly to one or more nasal epithelium. In certain embodiments, at least 25%, 30%, 35%, 40%, 45%, 50%, 55%, 60%, 65%, 70%, 75%, 80%, 85%, 90%, 95%, or 100% of the therapeutic agent present in the composition is delivered directly to a nasal epithelium. In a specific embodiment, a substantial fraction of the therapeutic agent present in the composition is delivered directly to the olfactory epithelium. In a more specific embodiment, at least 25%, 30%, 35%, 40%, 45%, 50%, 55%, 60%, 65%, 70%, 75%, 80%, 85%, 90%, 95%, or 100% of the therapeutic agent present in the composition is delivered directly to the olfactory epithelium. In another specific embodiment, a substantial fraction of the therapeutic agent present in the composition is delivered directly to nasal epithelium innervated with trigeminal nerves. In a more specific embodiment, at least 25%, 30%, 35%, 40%, 45%, 50%, 55%, 60%, 65%, 70%, 75%, 80%, 85%, 90%, 95%, or 100% of the therapeutic agent present in the composition is delivered directly to nasal epithelium innervated with trigeminal nerves.

In some embodiments, pooled human IgG can be administered to a subject as a combination therapy with another treatment, e.g., another treatment for a disorder of the central nervous system (e.g., Alzheimer's disease, age-related dementia, Parkinson's disease, or multiple sclerosis). For example, the combination therapy can include administering to the subject (e.g., a human patient) one or more additional agents that provide a therapeutic benefit to the subject who has, or is at risk of developing, a disorder of the central nervous system, e.g., Alzheimer's disease. In some embodiments, the pooled human IgG and the one or more additional agents are administered at the same time. In other embodiments, the pooled human IgG is administered first in time and the one or more additional agents are administered second in time. In some embodiments, the one or more additional agents are administered first in time and the pooled human IgG is administered second in time.

The pooled human IgG can replace or augment a previously or currently administered therapy. For example, upon treating with pooled human IgG, administration of the one or more additional agents can cease or diminish, e.g., be administered at lower levels. In other embodiments, administration of the previous therapy is maintained. In some embodiments, a previous therapy will be maintained until the level of polyclonal IgG reaches a level sufficient to provide a therapeutic effect. The two therapies can be administered in combination.

In one embodiment, a human receiving a first therapy for a disorder of the central nervous system, e.g., Alzheimer's disease, who is then treated with pooled human IgG, continues to receive the first therapy at the same or a reduced amount. In another embodiment, treatment with the first therapy overlaps for a time with treatment with pooled human IgG, but treatment with the first therapy is subsequently halted.

In a particular embodiment, pooled human IgG may be administered in combination with a treatment for an age-related dementia, e.g., Alzheimer's disease. In certain embodiments, the treatment for an age-related dementia co-administered with pooled human IgG is administration of a cholinesterase inhibitor (e.g., ARICEPT (donepezil), EXELON (rivastigmine), RAZADYNE (galantamine), or COGNEX (tacrine), or an inhibitor of the NMDA-type glutamate receptor (e.g., memantine).

In further embodiments the second therapy is levodopa (L-DOPA). The second therapy can also be a dopamine agonist. Non-limiting examples of dopamine agonists include bromocriptine, pergolide, pramipexole, ropinirole, piribedil, cabergoline, apomorphine and lisuride. The second therapy can be a MAO-B inhibitor. Non-limiting examples of MAO-B inhibitors are selegiline and rasgiline. Addition second therapies can include amantaine, anticholinergic compositions, clozapine, modafinil, and non-steroidal anti-inflammatory drugs.

In further embodiments the second therapy is CAMPATH (alemtuzumab), ZENAPX (daclizumab), rituximab, dirucotide, BHT-3009, cladribine, dimethyl fumarate, estriol, laquinimod, pegylated interferon-β-1a, minocycline, statins, temsirolimus, teriflunomide, and low dose naltexone.

In certain embodiments the second therapy is psychotherapy. Non-limiting examples of psychotherapy are psychosocial intervention, behavioral intervention, reminiscence therapy, validation therapy, supportive psychotherapy, sensory integration, simulated presence therapy, cognitive retraining, and stimulation-oriented therapies such as art, music, pet, exercise, and recreational activities.

Furthermore, two or more second therapies can be combined with therapeutic intranasal IgG. For example, therapeutic intranasal IgG can be combined with memantine and donepezil.

Dosing

The use of intravenous immunoglobulin G (IVIG) for the treatment of disorders of the central nervous system (CNS) is currently under investigation (Awad et al. 2011 (Current Neuropharmacology, 9:417428); Pohl et al. 2012 (Current Treatment Options in Neurology, 14:264-275); Krause et al. 2012 (European J. of Paediatric Neurology, 16:206-208); Elovaara et al. 2011 (Clinical Neuropharmacology, 34(2): 84-89); Perlmutter, et al. 1999 (The Lancet, 354:1153-1158); Snider et al. 2003 (J. of Child and Adolescent Psychopharmacology, 13(supp 1): S81-S88). In these trials, subjects are administered between 0.4 g/kg body weight and 2.0 g/kg body weight IVIG per dosage. Specifically, the treatment regimes of CNS disorders with IVIG range from 0.4 g/kg body weight IVIG administered once daily for 5 consecutive days to 2.0 g/kg body weight IVIG administered once daily for 2 consecutive days. There are several variations of these IVIG treatment regimes. For example, IVIG treatment regimes may be 1.0 g/kg body weight IVIG administered twice a day (total 2.0 g/kg body weight IVIG per day). The initial 2 to 5 day IVIG dosages can also be followed with maintenance doses ranging from 0.4 g/kg to 0.5 g /kg body weight IVIG. Due to the limited supply of pooled human IgG, and high cost associated therewith, large-scale implementation of these treatments may prove problematic if they are approved by major regulatory bodies.

Typical intravenous dosing of IgG in human Alzheimer's trials ranges from 200 mg/kg to 400 mg/kg every two weeks. Advantageously, the inventors have found that levels of pooled human IgG seen in the brain after intravenous administration can also be achieved by intranasal administration. For example, it is shown in Example 3 that administration of pooled human IgG (0.02 g/kg IgG) intranasally as drops (IN1) or a liquid spray delivered directly to the olfactory epithelium (IN3) results in substantially the same amount of IgG being delivered to the right and left hemispheres of the brain as for intravenous administration of pooled human IgG (0.02 g/kg IgG; compare corrected AUC values for right and left hemisphere IgG delivery in Table 69, Table 71, and Table 72). Significantly, intranasal administration of IgG liquid drops at concentrations ten-fold lower (0.002 g/kg IgG) also resulted in the delivery of intact IgG to the cerebral cortex (see, Table 70). Any reduction in the amount of pooled human IgG required for administration is significant because of the limited supply of pooled human IgG and the high cost associated therewith.

Accordingly, in certain embodiments, the methods for treating a CNS disorder provided herein include intranasally administering from about 0.05 mg of pooled human IgG per kg body weight (mg/kg IgG) to about 500 mg/kg IgG in a single dosage.

In certain embodiments, the methods for treating a CNS disorder provided herein include intranasally administering a low dose of pooled human IgG. In one embodiment, a low dose of pooled human IgG is from about 0.05 mg/kg IgG to about 10 mg/kg IgG. In specific embodiments, a low dose of pooled human IgG is about 0.05 mg/kg, 0.06 mg/kg, 0.07 mg/kg, 0.08 mg/kg, 0.09 mg/kg, 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 6.0 mg/kg, 7.0 mg/kg, 8.0 mg/kg, 9.0 mg/kg, or 10.0 mg/kg IgG. In yet other embodiments, a low dose of pooled human IgG is from 0.1 mg/kg to 5 mg/kg, 0.5 mg/kg to 5 mg/kg, 1 mg/kg to 5 mg/kg, 2 mg/kg to 5 mg/kg, 0.5 mg/kg to 10 mg/kg, 1 mg/kg to 10 mg/kg, 2 mg/kg to 10 mg/kg, 1 mg/kg to 8 mg/kg, 2 mg/kg to 8 mg/kg, 3 mg/kg to 8 mg/kg, 4 mg/kg to 8 mg/kg, 5 mg/kg to 8 mg/kg, 1 mg/kg to 6 mg/kg, 2 mg/kg to 6 mg/kg, 3 mg/kg to 6 mg/kg, 4 mg/kg to 6 mg/kg, 5 mg/kg to 6 mg/kg, 1 mg/kg to 4 mg/kg, 2 mg/kg to 4 mg/kg, or 3 mg/kg to 4 mg/kg IgG.

In certain embodiments, the methods for treating a CNS disorder provided herein include intranasally administering a medium dose of pooled human IgG. In one embodiment, a medium dose of pooled human IgG is from about 10 mg/kg IgG to about 100 mg/kg IgG. In specific embodiments, a medium dose of pooled human IgG is about 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 55, 60, 65, 70, 75, 80, 85, 90, 95, or 100 mg/kg IgG. In yet other embodiments, a medium dose of pooled human IgG is from 10 mg/kg to 100 mg/kg, 25 mg/kg to 100 mg/kg, 50 mg/kg to 100 mg/kg, 75 mg/kg to 100 mg/kg, 10 mg/kg to 75 mg/kg, 25 mg/kg to 75 mg/kg, 50 mg/kg to 75 mg/kg, 10 mg/kg to 50 mg/kg, 25 mg/kg to 50 mg/kg, or 10 mg/kg to 25 mg/kg IgG.

In some embodiments, the methods for treating a CNS disorder provided herein include intranasally administering a high dose of pooled human IgG. In one embodiment, a high dose of pooled human IgG is from about 100 mg/kg IgG to about 400 mg/kg IgG. In specific embodiments, a high dose of pooled human IgG is about 100 mg/kg, 110, 120 mg/kg, 130 mg/kg, 140 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, or higher. In yet other embodiments, a high dose of pooled human IgG is from 100 mg/kg to 400 mg/kg, 150 mg/kg to 400 mg/kg, 200 mg/kg to 400 mg/kg, 250 mg/kg to 400 mg/kg, 300 mg/kg to 400 mg/kg, 350 mg/kg to 400 mg/kg, 100 mg/kg to 300 mg/kg, 150 mg/kg to 300 mg/kg, 200 mg/kg to 300 mg/kg, 250 mg/kg to 300 mg/kg, 100 mg/kg to 200 mg/kg, 150 mg/kg to 200 mg/kg, or 100 mg/kg to 150 mg/kg IgG.

In some embodiments, pooled human IgG is administered at a set dosage, regardless of the weight of the subject. Without being bound by theory, unlike intravenous administration, the final concentration of IgG in the brain should be independent of total body weight when administered intranasally since the therapeutic will travel directly from the nose to the brain. Accordingly, a standard dose of intranasal pooled human IgG, which is independent of body weight, may simplify the process of dosing individual subjects.

Accordingly, in one embodiment, the methods described herein include intranasal administration of a fixed dose of pooled human IgG of from about 50 mg to about 10 g. In some embodiments, the fixed dose of IgG is about 50 mg, 75 mg, 100 mg, 125 mg, 150 mg, 175 mg, 200 mg, 225 mg, 250 mg, 275 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1.0 g, 1.25 g, 1.5 g, 1.75 g, 2.0 g, 2.5 g, 3.0 g, 3.5 g, 4.0 g, 4.5 g, 5.0 g, 5.5 g, 6.0 g, 6.5 g, 7.0 g, 7.5 g, 8.0 g, 8.5 g, 9.0 g, 9.5 g, 10.0 g, or more IgG. In other embodiments, the methods described herein include intranasal administration of from 50 mg to 5 g, 100 mg to 5 g, 250 mg to 5 g, 500 mg to 5 g, 750 mg to 5 g, 1 g to 5 g, 2.5 g to 5 g, 50 mg to 2.5 g, 100 mg to 2.5 g, 250 mg to 2.5 g, 500 mg to 2.5 g, 750 mg to 2.5 g, 1 g to 2.5 g, 50 mg to 1 g, 100 mg to 1 g, 250 mg to 1 g, 500 mg to 1 g, 750 mg to 1 g, 50 mg to 500 mg, 100 mg to 500 mg, 250 mg to 500 mg, 50 mg to 250 mg, 100 mg to 250 mg, or 50 mg to 100 mg pooled human IgG.

Depending upon the CNS disorder being treated and the progression of the disorder in the subject, the pooled human IgG compositions described herein are intranasally administered to a subject anywhere from several times daily to monthly. For example, a subject diagnosed with a CNS disorder in an early stage of progression may require only a low dosage and/or low dosage frequency, while a subject diagnosed with a CNS disorder in a late stage of progression may require a high dose and/or high dosage frequency. In yet another embodiment, a subject having a high likelihood of developing a CNS disorder may also be prescribed a low dose and/or low dosing frequency as a prophylactic treatment or to delay onset of symptoms associated with a CNS disorder. For example, a subject with a familial history of an age-related dementia (e.g., Alzheimer's disease) may be intranasally administered pooled human IgG at a low dosage and/or low frequency to delay the onset of symptoms associated with the age-related dementia. A skilled physician will readily be able to determine an appropriate dosage and dosing frequency for a subject diagnosed with or having a high likelihood of developing a CNS disorder.

In one embodiment, where the progression of a particular CNS disorder in a subject requires frequent dosing, the methods provided herein for treating a disorder of the central nervous system include administering a composition comprising pooled human immunoglobulin G (IgG) to the subject at least once a week. In other embodiments, the method includes administering a composition comprising pooled human immunoglobulin G (IgG) to the subject at least two, three, four, five, or six times a week. In yet another embodiment, the method includes administering a composition comprising pooled human immunoglobulin G (IgG) to the subject at least once daily. In other embodiments, the method includes administering a composition comprising pooled human immunoglobulin G (IgG) to the subject at least two, three, four, five, or more times daily. In a specific embodiment, the CNS disorder is an age-related dementia, Parkinson's disease, or multiple sclerosis. In a more specific embodiment, the CNS disorder is Alzheimer's disease.

In another embodiment, where the progression of a particular CNS disorder in a subject requires less frequent dosing, the methods provided herein for treating a disorder of the central nervous system include administering a composition comprising pooled human immunoglobulin G (IgG) to the subject at least once a month. In other embodiments, the method includes administering a composition comprising pooled human immunoglobulin G (IgG) to the subject at least two, three, four, five, six, or more times a month. In yet another embodiment, the method includes administering a composition comprising pooled human immunoglobulin G (IgG) to the subject at least once daily. In other embodiments, the method includes administering a composition comprising pooled human immunoglobulin G (IgG) to the subject at least two, three, four, five, or more times daily. In a specific embodiment, the CNS disorder is an age-related dementia, Parkinson's disease, or multiple sclerosis. In a more specific embodiment, the CNS disorder is Alzheimer's disease.

In certain embodiments, the composition can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 times a month. The composition can be administered between equally spaced days of the month, for example, on the $1^{st}$ and the $15^{th}$ of each month. Alternatively, the composition can be administered in block dosing at the beginning, end, or middle of the month. For example, the composition can be administered only on the $1^{st}$, $1^{st}$-$2^{nd}$, $1^{st}$-$3^{rd}$, $1^{st}$-$4^{th}$, $1^{st}$-$5^{th}$, $1^{st}$-$6^{th}$, $6^{th}$, or $1^{st}$-$7^{th}$ days of the month. Similar dosing schemes can be administered toward the middle or end of the month.

In certain embodiments the dosing can change between dosing days. For example, on the first day of dosing a subject can receive 10 mg/kg IgG and on the second day of dosing the subject can receive 20 mg/kg IgG. Similarly, a subject who is administered two or more doses per day of intranasal IgG can receive two different doses. For example, the first dose of the day can be 10 mg/kg IgG and the second dose of the day can be 5 mg/kg IgG.

In certain embodiments, the methods provided herein for the treatment of a CNS disorder include intranasally administering from 0.05 mg/kg to 50 mg/kg pooled human immunoglobulin to a subject in need thereof daily. In other embodiments, the methods provided herein for the treatment of a CNS disorder include intranasally administering pooled human IgG in a dosage/frequency combination selected from variations 1 to 816 found in Table 1 and Table 2.

TABLE 1

Exemplary combinations of dosage and frequency for methods of treating a CNS disorder by intranasal administration of pooled human IgG.

| | One Time Monthly | Two Times Monthly | Three Times Monthly | Four Times Monthly | One Time Weekly | Two Times Weekly | Three Times Weekly | Every Other Day |
|---|---|---|---|---|---|---|---|---|
| 0.05 mg/kg | Var. 1 | Var. 52 | Var. 103 | Var. 154 | Var. 205 | Var. 256 | Var. 307 | Var. 358 |
| 0.1 mg/kg | Var. 2 | Var. 53 | Var. 104 | Var. 155 | Var. 206 | Var. 257 | Var. 308 | Var. 359 |
| 0.25 mg/kg | Var. 3 | Var. 54 | Var. 105 | Var. 156 | Var. 207 | Var. 258 | Var. 309 | Var. 360 |
| 0.5 mg/kg | Var. 4 | Var. 55 | Var. 106 | Var. 157 | Var. 208 | Var. 259 | Var. 310 | Var. 361 |
| 0.75 mg/kg | Var. 5 | Var. 56 | Var. 107 | Var. 158 | Var. 209 | Var. 260 | Var. 311 | Var. 362 |
| 1.0 mg/kg | Var. 6 | Var. 57 | Var. 108 | Var. 159 | Var. 210 | Var. 261 | Var. 312 | Var. 363 |
| 1.5 mg/kg | Var. 7 | Var. 58 | Var. 109 | Var. 160 | Var. 211 | Var. 262 | Var. 313 | Var. 364 |
| 2.0 mg/kg | Var. 8 | Var. 59 | Var. 110 | Var. 161 | Var. 212 | Var. 263 | Var. 314 | Var. 365 |
| 2.5 mg/kg | Var. 9 | Var. 60 | Var. 111 | Var. 162 | Var. 213 | Var. 264 | Var. 315 | Var. 366 |
| 3.0 mg/kg | Var. 10 | Var. 61 | Var. 112 | Var. 163 | Var. 214 | Var. 265 | Var. 316 | Var. 367 |
| 3.5 mg/kg | Var. 11 | Var. 62 | Var. 113 | Var. 164 | Var. 215 | Var. 266 | Var. 317 | Var. 368 |
| 4.0 mg/kg | Var. 12 | Var. 63 | Var. 114 | Var. 165 | Var. 216 | Var. 267 | Var. 318 | Var. 369 |
| 4.5 mg/kg | Var. 13 | Var. 64 | Var. 115 | Var. 166 | Var. 217 | Var. 268 | Var. 319 | Var. 370 |
| 5.0 mg/kg | Var. 14 | Var. 65 | Var. 116 | Var. 167 | Var. 218 | Var. 269 | Var. 320 | Var. 371 |
| 6.0 mg/kg | Var. 15 | Var. 66 | Var. 117 | Var. 168 | Var. 219 | Var. 270 | Var. 321 | Var. 372 |
| 7.0 mg/kg | Var. 16 | Var. 67 | Var. 118 | Var. 169 | Var. 220 | Var. 271 | Var. 322 | Var. 373 |
| 8.0 mg/kg | Var. 17 | Var. 68 | Var. 119 | Var. 170 | Var. 221 | Var. 272 | Var. 323 | Var. 374 |
| 9.0 mg/kg | Var. 18 | Var. 69 | Var. 120 | Var. 171 | Var. 222 | Var. 273 | Var. 324 | Var. 375 |
| 10 mg/kg | Var. 19 | Var. 70 | Var. 121 | Var. 172 | Var. 223 | Var. 274 | Var. 325 | Var. 376 |
| 11 mg/kg | Var. 20 | Var. 71 | Var. 122 | Var. 173 | Var. 224 | Var. 275 | Var. 326 | Var. 377 |
| 12 mg/kg | Var. 21 | Var. 72 | Var. 123 | Var. 174 | Var. 225 | Var. 276 | Var. 327 | Var. 378 |
| 13 mg/kg | Var. 22 | Var. 73 | Var. 124 | Var. 175 | Var. 226 | Var. 277 | Var. 328 | Var. 379 |
| 14 mg/kg | Var. 23 | Var. 74 | Var. 125 | Var. 176 | Var. 227 | Var. 278 | Var. 329 | Var. 380 |
| 15 mg/kg | Var. 24 | Var. 75 | Var. 126 | Var. 177 | Var. 228 | Var. 279 | Var. 330 | Var. 381 |
| 16 mg/kg | Var. 25 | Var. 76 | Var. 127 | Var. 178 | Var. 229 | Var. 280 | Var. 331 | Var. 382 |
| 17 mg/kg | Var. 26 | Var. 77 | Var. 128 | Var. 179 | Var. 230 | Var. 281 | Var. 332 | Var. 383 |
| 18 mg/kg | Var. 27 | Var. 78 | Var. 129 | Var. 180 | Var. 231 | Var. 282 | Var. 333 | Var. 384 |
| 19 mg/kg | Var. 28 | Var. 79 | Var. 130 | Var. 181 | Var. 232 | Var. 283 | Var. 334 | Var. 385 |
| 20 mg/kg | Var. 29 | Var. 80 | Var. 131 | Var. 182 | Var. 233 | Var. 284 | Var. 335 | Var. 386 |
| 22.5 mg/kg | Var. 30 | Var. 81 | Var. 132 | Var. 183 | Var. 234 | Var. 285 | Var. 336 | Var. 387 |
| 25 mg/kg | Var. 31 | Var. 82 | Var. 133 | Var. 184 | Var. 235 | Var. 286 | Var. 337 | Var. 388 |

TABLE 1-continued

Exemplary combinations of dosage and frequency for methods of treating a CNS disorder by intranasal administration of pooled human IgG.

| | One Time Monthly | Two Times Monthly | Three Times Monthly | Four Times Monthly | One Time Weekly | Two Times Weekly | Three Times Weekly | Every Other Day |
|---|---|---|---|---|---|---|---|---|
| 27.5 mg/kg | Var. 32 | Var. 83 | Var. 134 | Var. 185 | Var. 236 | Var. 287 | Var. 338 | Var. 389 |
| 30 mg/kg | Var. 33 | Var. 84 | Var. 135 | Var. 186 | Var. 237 | Var. 288 | Var. 339 | Var. 390 |
| 32.5 mg/kg | Var. 34 | Var. 85 | Var. 136 | Var. 187 | Var. 238 | Var. 289 | Var. 340 | Var. 391 |
| 35 mg/kg | Var. 35 | Var. 86 | Var. 137 | Var. 188 | Var. 239 | Var. 290 | Var. 341 | Var. 392 |
| 37.5 mg/kg | Var. 36 | Var. 87 | Var. 138 | Var. 189 | Var. 240 | Var. 291 | Var. 342 | Var. 393 |
| 40 mg/kg | Var. 37 | Var. 88 | Var. 139 | Var. 190 | Var. 241 | Var. 292 | Var. 343 | Var. 394 |
| 45 mg/kg | Var. 38 | Var. 89 | Var. 140 | Var. 191 | Var. 242 | Var. 293 | Var. 344 | Var. 395 |
| 50 mg/kg | Var. 39 | Var. 90 | Var. 141 | Var. 192 | Var. 243 | Var. 294 | Var. 345 | Var. 396 |
| 0.5-40 mg/kg | Var. 40 | Var. 91 | Var. 142 | Var. 193 | Var. 244 | Var. 295 | Var. 346 | Var. 397 |
| 0.5-30 mg/kg | Var. 41 | Var. 92 | Var. 143 | Var. 194 | Var. 245 | Var. 296 | Var. 347 | Var. 398 |
| 0.5-20 mg/kg | Var. 42 | Var. 93 | Var. 144 | Var. 195 | Var. 246 | Var. 297 | Var. 348 | Var. 399 |
| 0.5-20 mg/kg | Var. 43 | Var. 94 | Var. 145 | Var. 196 | Var. 247 | Var. 298 | Var. 349 | Var. 400 |
| 0.5-10 mg/kg | Var. 44 | Var. 95 | Var. 146 | Var. 197 | Var. 248 | Var. 299 | Var. 350 | Var. 401 |
| 0.5-5 mg/kg | Var. 45 | Var. 96 | Var. 147 | Var. 198 | Var. 249 | Var. 300 | Var. 351 | Var. 402 |
| 1-20 mg/kg | Var. 46 | Var. 97 | Var. 148 | Var. 199 | Var. 250 | Var. 301 | Var. 352 | Var. 403 |
| 1-15 mg/kg | Var. 47 | Var. 98 | Var. 149 | Var. 200 | Var. 251 | Var. 302 | Var. 353 | Var. 404 |
| 1-10 mg/kg | Var. 48 | Var. 99 | Var. 150 | Var. 201 | Var. 252 | Var. 303 | Var. 354 | Var. 405 |
| 1-5 mg/kg | Var. 49 | Var. 100 | Var. 151 | Var. 202 | Var. 253 | Var. 304 | Var. 355 | Var. 406 |
| 2-10 mg/kg | Var. 50 | Var. 101 | Var. 152 | Var. 203 | Var. 254 | Var. 305 | Var. 356 | Var. 407 |
| 2-5 mg/kg | Var. 51 | Var. 102 | Var. 153 | Var. 204 | Var. 255 | Var. 306 | Var. 357 | Var. 408 |

\* Var. = variation

TABLE 2

Exemplary combinations of dosage and frequency for methods of treating a CNS disorder by intranasal administration of pooled human IgG.

| | Four Times Weekly | Five Times Weekly | Six Times Weekly | One Time Daily | Two Times Daily | Three Times Daily | Four Times Daily | Five Times Daily |
|---|---|---|---|---|---|---|---|---|
| 0.05 mg/kg | Var. 409 | Var. 460 | Var. 511 | Var. 562 | Var. 613 | Var. 664 | Var. 715 | Var. 766 |
| 0.1 mg/kg | Var. 410 | Var. 461 | Var. 512 | Var. 563 | Var. 614 | Var. 665 | Var. 716 | Var. 767 |
| 0.25 mg/kg | Var. 411 | Var. 462 | Var. 513 | Var. 564 | Var. 615 | Var. 666 | Var. 717 | Var. 768 |
| 0.5 mg/kg | Var. 412 | Var. 463 | Var. 514 | Var. 565 | Var. 616 | Var. 667 | Var. 718 | Var. 769 |
| 0.75 mg/kg | Var. 413 | Var. 464 | Var. 515 | Var. 566 | Var. 617 | Var. 668 | Var. 719 | Var. 770 |
| 1.0 mg/kg | Var. 414 | Var. 465 | Var. 516 | Var. 567 | Var. 618 | Var. 669 | Var. 720 | Var. 771 |
| 1.5 mg/kg | Var. 415 | Var. 466 | Var. 517 | Var. 568 | Var. 619 | Var. 670 | Var. 721 | Var. 772 |
| 2.0 mg/kg | Var. 416 | Var. 467 | Var. 518 | Var. 569 | Var. 620 | Var. 671 | Var. 722 | Var. 773 |
| 2.5 mg/kg | Var. 417 | Var. 468 | Var. 519 | Var. 570 | Var. 621 | Var. 672 | Var. 723 | Var. 774 |

TABLE 2-continued

Exemplary combinations of dosage and frequency for methods of treating a CNS disorder by intranasal administration of pooled human IgG.

| | Four Times Weekly | Five Times Weekly | Six Times Weekly | One Time Daily | Two Times Daily | Three Times Daily | Four Times Daily | Five Times Daily |
|---|---|---|---|---|---|---|---|---|
| 3.0 mg/kg | Var. 418 | Var. 469 | Var. 520 | Var. 571 | Var. 622 | Var. 673 | Var. 724 | Var. 775 |
| 3.5 mg/kg | Var. 419 | Var. 470 | Var. 521 | Var. 572 | Var. 623 | Var. 674 | Var. 725 | Var. 776 |
| 4.0 mg/kg | Var. 420 | Var. 471 | Var. 522 | Var. 573 | Var. 624 | Var. 675 | Var. 726 | Var. 777 |
| 4.5 mg/kg | Var. 421 | Var. 472 | Var. 523 | Var. 574 | Var. 625 | Var. 676 | Var. 727 | Var. 778 |
| 5.0 mg/kg | Var. 422 | Var. 473 | Var. 524 | Var. 575 | Var. 626 | Var. 677 | Var. 728 | Var. 779 |
| 6.0 mg/kg | Var. 423 | Var. 474 | Var. 525 | Var. 576 | Var. 627 | Var. 678 | Var. 729 | Var. 780 |
| 7.0 mg/kg | Var. 424 | Var. 475 | Var. 526 | Var. 577 | Var. 628 | Var. 679 | Var. 730 | Var. 781 |
| 8.0 mg/kg | Var. 425 | Var. 476 | Var. 527 | Var. 578 | Var. 629 | Var. 680 | Var. 731 | Var. 782 |
| 9.0 mg/kg | Var. 426 | Var. 477 | Var. 528 | Var. 579 | Var. 630 | Var. 681 | Var. 732 | Var. 783 |
| 10 mg/kg | Var. 427 | Var. 478 | Var. 529 | Var. 580 | Var. 631 | Var. 682 | Var. 733 | Var. 784 |
| 11 mg/kg | Var. 428 | Var. 479 | Var. 530 | Var. 581 | Var. 632 | Var. 683 | Var. 734 | Var. 785 |
| 12 mg/kg | Var. 429 | Var. 480 | Var. 531 | Var. 582 | Var. 633 | Var. 684 | Var. 735 | Var. 786 |
| 13 mg/kg | Var. 430 | Var. 481 | Var. 532 | Var. 583 | Var. 634 | Var. 685 | Var. 736 | Var. 787 |
| 14 mg/kg | Var. 431 | Var. 482 | Var. 533 | Var. 584 | Var. 635 | Var. 686 | Var. 737 | Var. 788 |
| 15 mg/kg | Var. 432 | Var. 483 | Var. 534 | Var. 585 | Var. 636 | Var. 687 | Var. 738 | Var. 789 |
| 16 mg/kg | Var. 433 | Var. 484 | Var. 535 | Var. 586 | Var. 637 | Var. 688 | Var. 739 | Var. 790 |
| 17 mg/kg | Var. 434 | Var. 485 | Var. 536 | Var. 587 | Var. 638 | Var. 689 | Var. 740 | Var. 791 |
| 18 mg/kg | Var. 435 | Var. 486 | Var. 537 | Var. 588 | Var. 639 | Var. 690 | Var. 741 | Var. 792 |
| 19 mg/kg | Var. 436 | Var. 487 | Var. 538 | Var. 589 | Var. 640 | Var. 691 | Var. 742 | Var. 793 |
| 20 mg/kg | Var. 437 | Var. 488 | Var. 539 | Var. 590 | Var. 641 | Var. 692 | Var. 743 | Var. 794 |
| 22.5 mg/kg | Var. 438 | Var. 489 | Var. 540 | Var. 591 | Var. 642 | Var. 693 | Var. 744 | Var. 795 |
| 25 mg/kg | Var. 439 | Var. 490 | Var. 541 | Var. 592 | Var. 643 | Var. 694 | Var. 745 | Var. 796 |
| 27.5 mg/kg | Var. 440 | Var. 491 | Var. 542 | Var. 593 | Var. 644 | Var. 695 | Var. 746 | Var. 797 |
| 30 mg/kg | Var. 441 | Var. 492 | Var. 543 | Var. 594 | Var. 645 | Var. 696 | Var. 747 | Var. 798 |
| 32.5 mg/kg | Var. 442 | Var. 493 | Var. 544 | Var. 595 | Var. 646 | Var. 697 | Var. 748 | Var. 799 |
| 35 mg/kg | Var. 443 | Var. 494 | Var. 545 | Var. 596 | Var. 647 | Var. 698 | Var. 749 | Var. 800 |
| 37.5 mg/kg | Var. 444 | Var. 495 | Var. 546 | Var. 597 | Var. 648 | Var. 699 | Var. 750 | Var. 801 |
| 40 mg/kg | Var. 445 | Var. 496 | Var. 547 | Var. 598 | Var. 649 | Var. 700 | Var. 751 | Var. 802 |
| 45 mg/kg | Var. 446 | Var. 497 | Var. 548 | Var. 599 | Var. 650 | Var. 701 | Var. 752 | Var. 803 |
| 50 mg/kg | Var. 447 | Var. 498 | Var. 549 | Var. 600 | Var. 651 | Var. 702 | Var. 753 | Var. 804 |
| 0.5-40 mg/kg | Var. 448 | Var. 499 | Var. 550 | Var. 601 | Var. 652 | Var. 703 | Var. 754 | Var. 805 |
| 0.5-30 mg/kg | Var. 449 | Var. 500 | Var. 551 | Var. 602 | Var. 653 | Var. 704 | Var. 755 | Var. 806 |
| 0.5-20 mg/kg | Var. 450 | Var. 501 | Var. 552 | Var. 603 | Var. 654 | Var. 705 | Var. 756 | Var. 807 |
| 0.5-20 mg/kg | Var. 451 | Var. 502 | Var. 553 | Var. 604 | Var. 655 | Var. 706 | Var. 757 | Var. 808 |
| 0.5-10 mg/kg | Var. 452 | Var. 503 | Var. 554 | Var. 605 | Var. 656 | Var. 707 | Var. 758 | Var. 809 |
| 0.5-5 mg/kg | Var. 453 | Var. 504 | Var. 555 | Var. 606 | Var. 657 | Var. 708 | Var. 759 | Var. 810 |

TABLE 2-continued

Exemplary combinations of dosage and frequency for methods of treating a CNS disorder by intranasal administration of pooled human IgG.

| | Four Times Weekly | Five Times Weekly | Six Times Weekly | One Time Daily | Two Times Daily | Three Times Daily | Four Times Daily | Five Times Daily |
|---|---|---|---|---|---|---|---|---|
| 1-20 mg/kg | Var. 454 | Var. 505 | Var. 556 | Var. 607 | Var. 658 | Var. 709 | Var. 760 | Var. 811 |
| 1-15 mg/kg | Var. 455 | Var. 506 | Var. 557 | Var. 608 | Var. 659 | Var. 710 | Var. 761 | Var. 812 |
| 1-10 mg/kg | Var. 456 | Var. 507 | Var. 558 | Var. 609 | Var. 660 | Var. 711 | Var. 762 | Var. 813 |
| 1-5 mg/kg | Var. 457 | Var. 508 | Var. 559 | Var. 610 | Var. 661 | Var. 712 | Var. 763 | Var. 814 |
| 2-10 mg/kg | Var. 458 | Var. 509 | Var. 560 | Var. 611 | Var. 662 | Var. 713 | Var. 764 | Var. 815 |
| 2-5 mg/kg | Var. 459 | Var. 510 | Var. 561 | Var. 612 | Var. 663 | Var. 714 | Var. 765 | Var. 816 |

\* Var. = variation

Formulation

Pharmaceutical compositions of pooled human immunoglobulin G described herein can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the pooled human IgG preparation is employed in the pharmaceutical compositions described herein. The pharmaceutical composition can be formulated into dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels can be varied so as to obtain an amount of the active ingredient which is effective to achieve the desired therapeutic response for a particular patient without being toxic to the patient. A physician can start doses of the pharmaceutical composition at levels lower than that required to achieve the desired therapeutic effect and gradually increase the dosage until the desired effect is achieved. In general, effective doses vary depending upon many different factors, including the specific disease or condition to be treated, its severity, physiological state of the patient, other medications administered, and whether treatment is prophylactic or therapeutic.

In one embodiment, a therapeutic composition of pooled human IgG formulated for intranasal administration does not contain a permeability enhancer. Permeability enhancers facilitate the transport of molecules through the mucosa, including the mucous, and the nasal epithelium. Non-limiting examples of absorption enhancers include mucoadhesives, ciliary beat inhibitors, mucous fluidizers, membrane fluidizers, and tight junction modulators. Specific non-limiting examples include bile salts, phospholipids, sodium glycyrrhetinate, sodium caprate, ammonium tartrate, gamma. aminolevulinic acid, oxalic acid, malonic acid, succinic acid, maleic acid, and oxaloacetic acid.

In addition to pooled human IgG, the pharmaceutical compositions provided herein include one or more stabilizing agents. In a specific embodiment, the stabilizing agent is a buffering agent suitable for intranasal administration. Non-limiting examples of buffering agents suitable for formulating the pooled human IgG compositions provided herein include an amino acid (e.g., glycine, histidine, or proline) a salt (e.g., citrate, phosphate, acetate, glutamate, tartrate, benzoate, lactate, gluconate, malate, succinate, formate, propionate, or carbonate), or any combination thereof adjusted to an appropriate pH. Generally, the buffering agent will be sufficient to maintain a suitable pH in the formulation for an extended period of time. In a particular embodiment, the buffering agent is sufficient to maintain a pH of 4 to 7.5. In a specific embodiment, the buffering agent is sufficient to maintain a pH of approximately 4.0, or approximately 4.5, or approximately 5.0, or approximately 5.5, or approximately 6.0, or approximately 6.5, or approximately 7.0, or approximately 7.5.

In a particular embodiment, a pooled human IgG composition described herein for the treatment of a CNS disorder via intranasal administration contains a stabilizing amount of an amino acid. In certain embodiments, a stabilizing amount of an amino acid is from about 25 mM to about 500 mM In a particular embodiment, the stabilizing agent employed in the pooled human IgG compositions provided herein is an amino acid. Non-limiting examples of amino acids include isoleucine, alanine, leucine, asparagine, lysine, aspartic acid, methionine, cysteine, phenylalanine, glutamic acid, threonine, glutamine, tryptophan, glycine, valine, proline, selenocysteine, serine, tyrosine, arginine, histidine, ornithine, taurine, combinations thereof, and the like. In one embodiment, the stabilizing amino acids include arginine, histidine, lysine, serine, proline, glycine, alanine, threonine, and a combination thereof. In a preferred embodiment, the amino acid is glycine. In another preferred embodiment, the amino acid is proline. In yet another preferred embodiment, the amino acid is histidine.

For purposes of stabilizing the compositions provided herein, the buffering agent (e.g., glycine, histidine, or proline) will typically be added to the formulation (or to a solution from which a dry powder composition is to be prepared) at a concentration from 5 mM to 0.75 M. In one embodiment, at least 100 mM of the buffering agent is added to the formulation. In another embodiment, at least 200 mM of the buffering agent is added to the formulation. In yet another embodiment, at least 250 mM of the buffering agent is added to the formulation. In yet other embodiments, the formulations provided herein contains at least 25 mM, 50 mM, 75 mM, 100 mM, 150 mM, 200 mM, 250 mM, 300 mM, 350 mM, 400 mM, 450 mM, 500 mM, 550 mM, 600 mM, 650 mM, 700 mM, 750 mM, or more of the buffering agent. In a specific embodiment, the buffering agent is glycine.

In one embodiment, the concentration of buffering agent (e.g., glycine, histidine, or proline) in the formulation (or in the solution from which a dry powder composition is to be prepared) is at or about from 5 mM to 500 mM. In certain embodiments, the concentration of the buffering agent in the formulation will be at or about 5 mM, 10 mM, 15 mM, 20 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM or higher. In a specific embodiment, the buffering agent is glycine.

In yet other embodiments, the concentration of the buffering agent (e.g., glycine, histidine, or proline) in formulation (or in the solution from which a dry powder composition is to be prepared) is from 50 mM to 500 mM, 100 mM to 500 mM, 200 mM to 500 mM, 250 mM to 500 mM, 300 mM to 500 mM, 50 mM to 300 mM, 100 mM to 300 mM, 200 mM to 300 mM, or 225 mM to 275 mM. In yet other specific embodiments, the concentration of the buffering agent (e.g., glycine, histidine, or proline) in formulations provided herein is 250±50 mM, 250±40 mM, 250±30 mM, 250±25 mM, 250±20 mM, 250±15 mM, 250±10 mM, 250±5 mM, or 250 mM.

In some embodiments, the pooled human immunoglobulins are formulated with between 100 mM and 400 mM histidine; no more than 10 mM of an alkali metal cation; and a pH between 5.0 and 7.0.

In some embodiments of the pooled human immunoglobulin histidine formulation, the concentration of histidine is between 5 mM and 500 mM. In another embodiment, the concentration of histidine in the formulation will be between 100 mM and 400 mM. In another embodiment, the concentration of histidine in the formulation will be between 200 mM and 300 mM. In another embodiment, the concentration of histidine in the formulation will be between 225 mM and 275 mM. In another embodiment, the concentration of histidine in the formulation will be between 240 mM and 260 mM. In a particular embodiment, the concentration of histidine will be 250 mM. In certain other embodiments, the concentration of histidine in the formulation will be 5±0.5 mM, 10±1 mM, 15±1.5 mM, 20±2 mM, 25±2.5 mM, 50±5 mM, 75±7.5 mM, 100±10 mM, 125±12.5 mM, 150±15 mM, 175±17.5 mM, 200±20 mM, 225±22.5 mM, 250±25 mM, 275±27.5 mM, 300±30 mM, 325±32.5 mM, 350±35 mM, 375±37.5 mM, 400±40 mM, 425±42.5 mM, 450±45 mM, 475±47.5 mM, 500±50 mM or higher. In yet other embodiments, the concentration of histidine in the formulation will be 5 mM, 10 mM, 15 mM, 20 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM or higher.

In some embodiments of the pooled human immunoglobulin histidine formulation, the pH of the histidine formulation is from 4.0 to 7.5. In some embodiments, the pH of the histidine formulation is from 4.0 to 6.0. In some embodiments, the pH of the histidine formulation is from 4.0 to 4.5. In some embodiments, the pH of the histidine formulation is from 4.5 to 5.0. In some embodiments, the pH of the histidine formulation is from 4.0 to 5.5. In some embodiments, the pH of the histidine formulation is from 4.0 to 6.5. In some embodiments, the pH of the histidine formulation is from 4.0 to 7.0. In some embodiments, the pH of the histidine formulation is from 4.5 to 6.0. In some embodiments, the pH of the histidine formulation is from 4.5 to 6.5. In some embodiments, the pH of the histidine formulation is from 4.5 to 7.0. In some embodiments, the pH of the histidine formulation is from 4.5 to 7.5. In some embodiments, the pH of the histidine formulation is from 5.5 to 7.0. In some embodiments, the pH of the histidine formulation is from 6.0 to 7.0. In some embodiments, the pH of the histidine formulation is from 6.5 to 7.0. In some embodiments, the pH of the histidine formulation is from 5.0 to 6.5. In some embodiments, the pH of the histidine formulation is from 5.0 to 7.0. In some embodiments, the pH of the histidine formulation is from 5.5 to 6.5. In some embodiments, the pH of the histidine formulation is from 6.0 to 6.5. In some embodiments, the pH of the histidine formulation is from 5.0 to 6.0. In some embodiments, the pH of the histidine formulation is from 5.5 to 6.0. In some embodiments, the pH of the histidine formulation is from 5.0 to 5.5. In some embodiments, the pH of the histidine formulation is from 7.0 to 7.5. In some embodiments, the pH of the histidine formulation is from 6.0 to 7.5. In some embodiments, the pH of the histidine formulation is from 5.5 to 7.5. In some embodiments, the pH of the histidine formulation is from 5.0 to 7.5. In some embodiments, the pH of the histidine formulation is 5.0±0.2, 5.1±0.2, 5.2±0.2, 5.3±0.2, 5.4±0.2, 5.5±0.2, 5.6±0.2, 5.7±0.2, 5.8±0.2, 5.9±0.2, 6.0±0.2, 6.1±0.2, 6.2±0.2, 6.3±0.2, 6.4±0.2, 6.5±0.2, 6.6±0.2, 6.7±0.2, 6.8±0.2, 6.9±0.2, or 7.0±0.2. In some embodiments, the pH of the histidine formulation is 5.0±0.1, 5.1±0.1, 5.2±0.1, 5.3±0.1, 5.4±0.1, 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, or 7.0±0.1.

In one embodiment, the pooled human IgG compositions described herein for the treatment of a CNS disorder via intranasal administration is formulated at a pH from about 4.0 to about 7.0. In particular embodiments, a pooled human IgG compositions is formulated at a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.7, 6.8, 6.9, or 7.0. In other embodiments, a pooled human IgG composition is formulated at a pH from 4.0 to 6.5, 4.0 to 6.0, 4.0 to 5.5, 4.0 to 5.0, 4.0 to 4.5, 4.5 to 6.5, 4.5 to 6.0, 4.5 to 5.5, 4.5 to 5.0. In yet other embodiments, a pooled human IgG composition is formulated at a pH of 4.8±0.5, 4.8±0.4, 4.8±0.3, 4.8±0.2, 4.8±0.1, or about 4.8.

In one embodiment, liquid compositions of pooled human IgG formulated for intranasal administration are provided for the treatment of CNS disorders (e.g., Alzheimer's disease, Parkinson's disease, and multiple sclerosis). In a specific embodiment, the liquid composition is an aqueous composition. In a particular embodiment, an aqueous therapeutic composition formulated for intranasal administration provided herein consists essentially of a buffering agent and pooled human IgG.

In one embodiment, a liquid composition formulated for intranasal administration contains from about 1.0 g pooled human IgG per liter (g/L IgG) to about 250 g/L IgG. In other embodiments, the liquid composition formulated for intranasal administration contains about 1 g/L, 2 g/L, 3 g/L, 4 g/L, 5 g/L, 6 g/L, 7 g/L, 8 g/L, 9 g/L, 10 g/L, 12.5 g/L, 15 g/L, 17.5 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, or higher concentration of pooled human IgG. In certain embodiments, the liquid composition formulated for intranasal administration contains from 5.0 g/L to 250 g/L, 10 g/L to 250 g/L, 20 g/L to 250 g/L, 30 g/L to 250 g/L, 40 g/L to 250 g/L, 50 g/L to 250 g/L, 60 g/L to 250 g/L, 70 g/L to 250 g/L, 80 g/L to 250 g/L, 90 g/L to 250 g/L, 100 g/L to 250 g/L, 125 g/L to 250 g/L, 150 g to 250 g/L, 175 g/L to 250 g/L, 200 g/L to 250 g/L IgG.

In certain embodiments, the methods for treating a CNS disorder provided herein include intranasally administering a liquid composition containing a low concentration of pooled human IgG. In one embodiment, a low concentration of pooled human IgG contains from 1.0 g/L to 100 g/L, 5.0 g/L to 100 g/L, 10 g/L to 100 g/L, 20 g/L to 100 g/L, 30 g/L to 100 g/L, 40 g/L to 100 g/L, 50 g/L to 100 g/L, 60 g/L to 100 g/L, 70 g/L to 100 g/L, 75 g/L to 100 g/L, 80 g/L to 50 g/L, 1.0 g/L to 50 g/L, 5.0 g/L to 50 g/L, 10 g/L to 50 g/L, 20 g/L to 50 g/L, 30 g/L to 50 g/L, or 40 g/L to 50 g/L IgG.

In certain embodiments, the methods for treating a CNS disorder provided herein include intranasally administering a liquid composition containing an intermediate concentration of pooled human IgG. In one embodiment, an intermediate concentration of pooled human IgG contains from 75 g/L to 200 g/L, 100 g/L to 200 g/L, 110 g/L to 200 g/L, 120 g/L to 200 g/L, 130 g/L to 200 g/L, 140 g/L to 200 g/L, 150 g/L to 200 g/L, 160 g/L to 200 g/L, 170 g/L to 200 g/L, 175 g/L to 200 g/L, 180 g/L to 200 g/L, 75 g/L to 150 g/L, 100 g/L to 150 g/L, 110 g/L to 150 g/L, 120 g/L to 150 g/L, 130 g/L to 150 g/L, or 140 g/L to 150 g/L IgG.

In certain embodiments, the methods for treating a CNS disorder provided herein include intranasally administering a liquid composition containing a high concentration of pooled human IgG. In one embodiment, a high concentration of pooled human IgG contains from 175 g/L to 250 g/L, 200 g/L to 250 g/L, 210 g/L to 250 g/L, 220 g/L to 250 g/L, 230 g/L to 250 g/L, or 240 g/L to 250 g/L IgG.

In a particular embodiment, a liquid compositions of pooled human IgG formulated for intranasal administration consists essentially of from 100 g/L to 250 g/L pooled human IgG and from 150 mM to 350 mM glycine.

In another particular embodiment, a liquid compositions of pooled human IgG formulated for intranasal administration consists essentially of from 150 g/L to 250 g/L pooled human IgG and from 200 mM to 300 mM glycine.

In yet another particular embodiment, a liquid compositions of pooled human IgG formulated for intranasal administration consists essentially of from 200 g/L to 250 g/L pooled human IgG and 250±25 mM glycine.

In certain embodiments, the liquid compositions of pooled human IgG formulated for intranasal administration provided herein further include a humectant. Non-limiting examples of humectants include glycerin, polysaccharides, and polyethylene glycols.

In certain embodiments, the liquid compositions of pooled human IgG formulated for intranasal administration provided herein further include an agent that increases the flow properties of the composition. Non-limiting examples of agents that increase to flow properties of an aqueous composition include sodium carboxymethyl cellulose, hyaluronic acid, gelatin, algin, carageenans, carbomers, galactomannans, polyethylene glycols, polyvinyl alcohol, polyvinylpyrrolidone, sodium carboxymethyl dextran, and xantham.

In one embodiment, dry powder compositions of pooled human IgG formulated for intranasal administration are provided for the treatment of CNS disorders (e.g., Alzheimer's disease, Parkinson's disease, and multiple sclerosis). In a specific embodiment, a dry powder therapeutic composition formulated for intranasal administration provided herein consists essentially of a buffering agent and pooled human IgG.

In one embodiment, a dry powder composition of pooled human IgG formulated for intranasal administration further comprises a bulking agent. Non-limiting examples of bulking agents include oxyethylene maleic anhydride copolymer, polyvinylether, polyvinylpyrrolidone polyvinyl alcohol, polyacrylates, including sodium, potassium or ammonium polyacrylate, polylactic acid, polyglycolic acid, polyvinyl alcohol, polyvinyl acetate, carboxyvinyl polymer, polyvinylpyrrolidone, polyethylene glycol, celluloses (including cellulose, microcrystalline cellulose, and alpha-cellulose), cellulose derivatives (including methyl cellulose, ethyl cellulose, hydroxyethyl cellulose, hydroxypropyl cellulose, hydroxypropyl methyl cellulose, sodium carboxymethyl cellulose and ethylhydroxy ethyl cellulose), dextrins (including alpha-, beta-, or gamma-cyclodexthn, and dimethyl-beta-cyclodexthn), starches (including hydroxyethyl starch, hydroxypropyl starch, carboxymethyl starch), polysaccharides (including dextran, dextrin and alginic acid, hyaluronic acid, and pectic acid), carbohydrates (such as mannitol, glucose, lactose, fructose, sucrose, and amylose), proteins (including casein, gelatin, chitin, and chitosan), gums (such as gum arabic, xanthan gum, tragacanth gum, and glucomannan), phospholipids, and combinations thereof.

In certain embodiments, a dry powder composition of pooled human IgG formulated for intranasal administration further comprises a mucosal penetration enhancer. Non-limiting examples of mucosal penetration enhancers are bile salts, fatty acids, surfactants and alcohols. Specific non-limiting examples of mucosal penetration enhancers are sodium cholate, sodium dodecyl sulphate, sodium deoxycholate, taurodeoxycholate, sodium glycocholate, dimethylsulfoxide or ethanol.

In certain embodiments, a dry powder composition of pooled human IgG formulated for intranasal administration further comprises a dispersant. A dispersant is an agent that assists aerosolization of the IgG or the absorption of the IgG in intranasal mucosal tissue, or both. Non-limiting examples of dispersants are a mucosal penetration enhancers and surfactants.

In certain embodiments, a dry powder composition of pooled human IgG formulated for intranasal administration further comprises a bioadhesive agent. Non-limiting examples of bioadhesive agents include chitosan or cyclodextrin. In certain embodiments, a dry powder composition of pooled human IgG formulated for intranasal administration further comprises a filler. Non-limiting examples of fillers include sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate.

The particle size a dry powder composition of pooled human IgG can be determined by standard methods in the art. For example, the particles can be screened or filtered through a mesh sieve. In certain embodiments, the dry particles have an average diameter from about 0.1 μm to about 250 μm. In some embodiments, the dry particles have an average diameter between from 1 μm to about 25 μm. In some embodiments, the dry particles have an average diameter between from 10 μm to about 100 μm. In yet other embodiments, the dray particles have an average diameter of about 0.1 μm±10%, 0.2 μm±10%, 0.3 μm±10%, 0.4 μm±10%, 0.5 μm±10%, 0.6 μm±10%, 0.7 μm±10%, 0.8 μm±10%, 0.9 μm±10%, 1.0 μm±10%, 2 μm±10%, 3 μm±10%, 4 μm±10%, 5 μm±10%, 6 μm±10%, 7 μm±10%, 8 μm±10%, 9 μm±10%, 10 μm±10%, 11 μm±10%, 12 μm±10%, 13 μm±10%, 14 μm±10%, 15 μm±10%, 16 μm±10%, 17 μm±10%, 18 μm±10%, 19 μm±10%, 20 μm±10%, 25 μm±10%, 30 μm±10%, 35 μm±10%, 40 μm±10%, 45 μm±10%, 50 μm±10%, 60 μm±10%, 65 μm±10%, 70 μm±10%, 75 μm±10%, 80 μm±10%, 85 μm±10%, 90 μm±10%, 95 μm±10%, 100 μm±10%, 110 μm±10%, 120 μm±10%, 130 μm±10%, 140 μm±10%, 150 μm±10%, 160 μm±10%, 170 μm±10%, 180 μm±10%, 190 μm±10%, 200 μm±10%, 225 μm±10%, 250 μm±10%, 275 μm±10%, 300 μm±10%, 350 μm±10%, 400 μm±10%, 450 μm±10%, 500 μm±10%, or greater.

In one embodiment, gel, cream, or ointment compositions of pooled human IgG formulated for intranasal administration are provided for the treatment of CNS disorders (e.g., Alzheimer's disease, Parkinson's disease, and multiple sclerosis). In a specific embodiment, a gel, cream, or ointment therapeutic composition formulated for intranasal administration provided herein consists essentially of a buffering agent and pooled human IgG.

In one embodiment, a gel, cream, or ointment composition of pooled human IgG formulated for intranasal administration further comprises a carrier agent. Non-limiting examples of carrier agents for gel and ointment compositions include natural or synthetic polymers such as hyaluronic acid, sodium alginate, gelatin, corn starch, gum tragacanth, methylcellulose, hydroxyethylcellulose, carboxymethylcellulose, xanthan gum, dextrin, carboxymethylstarch, polyvinyl alcohol, sodium polyacrylate, methoxyethylene maleic anhydride copolymer, polyvinylether, polyvinylpyrrolidone, fats and oils such as beeswax, olive oil, cacao butter, sesame oil, soybean oil, camellia oil, peanut oil, beef fat, lard, and lanolin, white petrolatum, paraffins, hydrocabon gel ointments, fatty acids such as stearic acid, alcohols such as cetyl alcohol and stearyl alcohol, polyethylene glycol, water, and combinations thereof.

In certain embodiments, the pooled human immunoglobulins are co-formulated with one or more vasoconstrictor agents. When present, the vasoconstrictor agent reduces non-target exposure (e.g., systemic exposure) of the pooled human immunoglobulin, by reducing absorption of the immunoglobulins into the blood, effectively increasing the targeting of the immunoglobulin to the CNS (e.g., to the brain). Methods for the co-formulation of other pharmaceuticals and vasoconstrictors can be found in U.S. Patent Application Publication No. 2008/0305077, the content of which is expressly incorporated herein by reference in its entirety for all purposes. Non-limiting examples of vasoconstrictors that may be co-formulated with pooled human immunoglobulins in this fashion include tetrahydrozoline, methoxamine, phenylephrine, ephedrine, norepinephrine, oxymetazoline, tetrahydrozoline, xylometazoline, clonidine, guanabenz, guanfacine, α-methyldopa, arginine vasopressin, and pseudoephedrine.

Disorders of the Central Nervous System—

IVIG treatment has been used in the treatment of CNS disorders. Specifically, IVIG has been studied or used in the treatment of Multiple Sclerosis (MS), stiff-person syndrome, Alzheimer's disease (AD), postpolio syndrome, narcolepsy, stroke, and fibromyalgia and other pain syndromes. Stangle 2008 (Therapeutic Advances in Neurological Disorders, 1(2):115-124).

IVIG has also been used to treat neuromyelitis optica (NMO). NMO, also known as Devic's disease or Devic's syndrome, is an autoimmune, inflammatory disorder of the optic nerves and spinal cord. For example, a 2 g/kg induction dose of IVIG followed by 0.4-0.5 g/kg monthly maintenance doses of IVIG has been used to treat NMO. Awad et al. 2011 (Current Neuropharmacology, 9:417428).

IVIG has also been used and studied for the treatment of acute disseminated encephalomyelitis (ADEM). ADEM is an immune mediated disease of the brain. Specifically, ADEM involves autoimmune demyelination and is classified as a MS borderline disease. For example, a standard dose of 2 g/kg IVIG given over 2-5 days can be used to treat ADEM. Pohl et al. 2012 (Current Treatment Options in Neurology, 14:264-275).

IVIG has also studied and used in the treatment of Parkinson's disease (PD). For example, studies have shown that IVIG may reduce α-synuclein neurotoxicity, a possible contributing factor to the pathogenesis of PD, through an unknown mechanism. Smith et al. 2012 (International Immunopharmacology, 14:550-557) and Patrias et al. (Clinical and Experimental Immunology, 161:527-535).

IVIG has also been used and studied for the treatment of MS. For example, IVIG has been used successfully in the treatment of Schilder's disease (SD), a rare variant of MS. Krause et al. 2012 (European J. of Paediatric Neurology, 16:206-208). IVIG has also been suggested to be beneficial in the treatment of acute relapses in MS patients. Elovaara et al. 2011 (Clinical Neuropharmacology, 34(2):84-89).

IVIG has also been used and studied for the treatment of obsessive-compulsive disorders (OCD) and tic disorders. For example, IVIG was shown to lessen the severity of symptoms of OCD and tic disorders in children with infection-triggered OCD and tic disorders. Perlmutter, et al. 1999 (The Lancet, 354:1153-1158). Similarly, it has been shown that IVIG is effective in reducing neuropsychiatric symptom severity in a subgroup OCD and tic disorder patients with childhood-onset OCD and tic disorders. Snider et al. 2003 (J. of Child and Adolescent Psychopharmacology, 13(supp 1): S81-S88).

In one aspect, the present invention provides a method for treating a central nervous system (CNS) disorder in a subject in need thereof by delivering a therapeutically effective amount of a composition comprising pooled human immunoglobulin G (IgG) to the brain of the subject, wherein delivering the composition to the brain comprises intranasally administering the composition directly to an epithelium of the nasal cavity of the subject. In a specific embodiment, the composition is administered directly to the olfactory epithelium of the nasal cavity. In certain embodiments, the CNS disorder is selected from the group consisting of a systemic atrophy primarily affecting the central nervous system, an extrapyramidal and movement disorder, a neurodegenerative disorder of the central nervous system, a demyelinating disorder of the central nervous system, an episodic or paroxysmal disorder of the central nervous system, a paralytic syndrome of the central nervous system, a nerve, nerve root, or plexus disorder of the central nervous system, an organic mental disorder, a mental or behavioral disorder caused by psychoactive substance use, a schizophrenia, schizotypal, or delusional disorder, a mood (affective) disorder, neurotic, stress-related, or somatoform disorder, a behavioral syndrome, an adult personality or behavior disorder, a psychological development disorder, or a child onset behavioral or emotional disorder. In some embodiments, the CNS disorder is selected from the group consisting of Alzheimer's disease, Parkinson's disease, multiple sclerosis, amyotrophic lateral sclerosis (ALS), Huntington's disease, cerebral palsy, bipolar disorder, schizophrenia, or Pediatric acute-onset neuropyschiatric syndrome (PANS). In some embodiments, the CNS disorder is selected from the group consisting of Alzheimer's disease, Parkinson's disease, multiple sclerosis, Pediatric Autoimmune Neuropsychiatric Disorders Associated with Streptococcal infections (PANDAS), or Pediatric acute-onset neuropyschiatric syndrome (PANS).

In one embodiment, the CNS disorder is a systemic atrophy primarily affecting the central nervous system. Non-limiting examples of systemic atrophies that primarily affect the central nervous system include: Huntington's disease; hereditary ataxias (e.g., congenital non-progressive ataxia, early-onset cerebellar ataxias—such as early-onset cerebellar ataxia with essential tremor, Hunt's ataxia, early-onset cerebellar ataxia with retained tendon reflexes, Friedreich's ataxia, and X-linked recessive spinocerebellar ataxia—late-onset cerebellar ataxia, ataxia telangiectasia (Louis-Bar syndrome), or hereditary spastic paraplegia); a spinal muscular atrophy or related disorder thereof (e.g., Werdnig-Hoffman disease (Type 1), progressive bulbar palsy of childhood (Fazio-Londe syndrome), Kugelberg-Welander disease (Type 3), or a motor neuron disease—such as familial motor neuron disease, amyotrophic lateral sclerosis (ALS), primary lateral sclerosis, progressive bulbar palsy, and progressive spinal muscular atrophy); paraneoplastic neuromyopathy and neuropathy; systemic atrophy primarily affecting the central nervous system in neoplastic disease; paraneoplastic limbic encephalopathy; and systemic atrophy primarily affecting the central nervous system in myxoedema.

In one embodiment, the CNS disorder is an extrapyramidal and movement disorder. Non-limiting examples of extrapyramidal and movement disorders that affect the central nervous system include: Parkinson's disease; a secondary parkinsonism (e.g., malignant neuroleptic syndrome or postencephalitic parkinsonism); a degenerative disease of the basal ganglia (e.g., Hallervorden-Spatz disease, progressive supranuclear ophthalmoplegia (Steele-Richardson-Olszewski disease), or striatonigral degeneration), a dystonia (e.g., drug-induced dystonia, idiopathic familial dystonia, idiopathic non-familial dystonia, spasmodic torticollis, idiopathic orofacial dystonia—such as orofacial dyskinesia—or blepharospasm); an essential tremor; a drug-induced tremor, myoclonus, drug-induced chorea, drug-induced tics; restless legs syndrome; and stiff-man syndrome.

In one embodiment, the CNS disorder is a neurodegenerative disorder of the central nervous system. Non-limiting examples of neurodegenerative disorders that affect the central nervous system include: Alzheimer's disease; a circumscribed brain atrophy (e.g., Pick's disease); senile degeneration of brain; a degeneration of nervous system due to alcohol; grey-matter degeneration (e.g., Alpers' disease); Lewy body dementia, subacute necrotizing encephalopathy (e.g., Leigh's disease); and subacute combined degeneration of spinal cord. In certain embodiments, the CNS disorder is disorder characterized by dementia. In certain embodiments, the dementia is a cortical dementia (associated, for example, with Alzheimer's) arising from a disorder affecting the cerebral cortex. In certain embodiments, the dementia is a subcortical dementia (associated, for example, with Parkinson's disease and Huntington's disease) resulting from dysfunction in the parts of the brain that are beneath the cortex. In certain embodiments, the dementia is a side effect of drug administration. In specific embodiments, the dementia is a side effect of the administration of a chemotherapeutic agent. In specific embodiments, the dementia is a result of undergoing cardiac bypass. In specific embodiments, the dementia is a result of a vascular disorder (e.g., myocardial infarction, stroke, high blood pressure). In specific embodiments, the dementia is a result of depression.

In one embodiment, the CNS disorder is a demyelinating disorder of the central nervous system. Non-limiting examples of demyelinating disorders that affect the central nervous system include: multiple sclerosis; an acute disseminated demyelination disorder (e.g., neuromyelitis optica (Devic's syndrome) or acute and subacute hemorrhagic leukoencephalitis (Hurst's disease)); diffuse sclerosis; central demyelination of corpus callosum; central pontine myelinolysis; acute transverse myelitis in demyelinating disease of central nervous system; subacute necrotizing myelitis; and concentric sclerosis (Baló disease).

In one embodiment, the CNS disorder is an episodic or paroxysmal disorder of the central nervous system. Non-limiting examples of episodic and paroxysmal disorders that affect the central nervous system include: epilepsy (e.g., localization-related (focal)(partial) idiopathic epilepsy and epileptic syndromes with seizures of localized onset, localization-related (focal)(partial) symptomatic epilepsy and epileptic syndromes with simple partial seizures; localization-related (focal)(partial) symptomatic epilepsy and epileptic syndromes with complex partial seizures; a benign epileptic syndrome—such as myoclonic epilepsy in infancy and neonatal convulsions (familial)—childhood absence epilepsy (e.g., pyknolepsy), epilepsy with grand mal seizures on awakening, a juvenile epilepsy—such as absence epilepsy or myoclonic epilepsy (impulsive petit mal)—a nonspecific epileptic seizure—such as an atonic, clonic, myoclonic, tonic, or tonic-clonic epileptic seizure, epilepsy with myoclonic absences or myoclonic-astatic seizures, infantile spasms, Lennox-Gastaut syndrome, Salaam attacks, symptomatic early myoclonic encephalopathy, West's syndrome, epilepsia partialis continua (Kozhevnikov epilepsy), grand mal seizures, or petit mal); headaches (e.g., a migraine—such as a migraine without aura (common migraine), a migraine with aura (classical migraine), status migrainosus, and complicated migraine—cluster headache syndrome, a vascular headache, a tension-type headache, a chronic post-traumatic headache, or a drug-induced headache); a cerebrovascular episodic or paroxysmal disorder (e.g., a transient cerebral ischaemic attacks or related syndrome—such as vertebrobasilar artery syndrome, carotid artery syndrome (hemispheric), a multiple and bilateral precerebral artery syndrome, amaurosis fugax, and transient global amnesia—a vascular syndrome of the brain—such as middle cerebral artery syndrome, anterior cerebral artery syndrome, posterior cerebral artery syndrome, a brain stem stroke syndrome (e.g., Benedikt syndrome, Claude syndrome, Foville syndrome, Millard-Gubler syndrome, Wallenberg syndrome, or Weber syndrome), cerebellar stroke syndrome, pure motor lacunar syndrome, pure sensory lacunar syndrome, or a lacunar syndromes); and a sleep disorder (e.g., insomnia, hyperinsomnia, a disruption in circadian rhythm, sleep apnoea, narcolepsy, or cataplexy).

In one embodiment, the CNS disorder is a paralytic syndrome of the central nervous system. Non-limiting examples of paralytic syndromes that affect the central nervous system include: a cerebral palsy (e.g., spastic quadriplegic cerebral palsy, spastic diplegic cerebral palsy, spastic hemiplegic cerebral palsy, dyskinetic cerebral palsy, or ataxic cerebral palsy); a hemiplegia (e.g., flaccid hemiplegia or spastic hemiplegia); a paraplegia or tetraplegia (e.g., flaccid paraplegia, spastic paraplegia, paralysis of both lower limbs, lower paraplegia, flaccid tetraplegia, spastic tetraplegia, or quadriplegia); diplegia of upper limbs; monoplegia of a lower limb, monoplegia of an upper limb; cauda equina syndrome; and Todd's paralysis (postepileptic).

In one embodiment, the CNS disorder is a nerve, nerve root, or plexus disorder of the central nervous system. Non-limiting examples of nerve, nerve root, or plexus disorders that affect the central nervous system include: a disorder of the trigeminal nerve (V; e.g., trigeminal neuralgia); a facial nerve disorders (VII; e.g., bell's palsy, facial palsy, geniculate ganglionitis, melkersson's syndrome, melkersson-Rosenthal syndrome, a clonic hemifacial spasm, facial myokymia); a disorder of the olfactory nerve (I); a disorder of the glossopharyngeal nerve (IX); a disorder of the vagus nerve (X); a disorder of the hypoglossal nerve (XII); a disorder of multiple cranial nerves; and a nerve root or plexus disorder affecting the CNS (e.g., a brachial plexus disorder—such as thoracic outlet syndrome—a lumbosacral plexus disorder, a cervical root, a thoracic root disorder, a lumbosacral root disorder, a neuralgic amyotrophy—such as Parsonage-Aldren-Turner syndrome—or phantom limb syndrome with or without pain).

In one embodiment, the CNS disorder is an otherwise classified disorder of the central nervous system. Non-limiting examples of these disorders include: hydrocephalus; a toxic encephalopathy, a cerebral cyst; anoxic brain damage; benign intracranial hypertension; postviral fatigue syndrome; an encephalopathy; compression of brain; cerebral oedema; reye's syndrome; postradiation encephalopathy; traumatic brain injury; syringomyelia; syringobulbia; a vascular myelopathy; spinal cord compression; myelopathy; a cerebrospinal fluid leak; a disorder of the meninges (e.g., cerebral or spinal meningeal adhesion); and a post-procedural disorder of nervous system (e.g., cerebrospinal fluid leak from spinal puncture, an adverse reaction to a spinal or lumbar puncture, or intracranial hypotension following ventricular shunting).

In one embodiment, the CNS disorder is an organic mental disorder. Non-limiting examples of organic mental disorders that affect the central nervous system include: dementia (e.g., dementia associated with Alzheimer's disease, Pick's disease, Creutzfeldt-Jakob disease, Huntington's disease, Parkinson's disease, or human immunodeficiency virus (HIV) disease, or vascular dementia—such as multi-infarct dementia); organic amnesic syndrome not induced by alcohol and other psychoactive substances); delirium not induced by alcohol and other psychoactive substances; a mental disorder due to brain damage and dysfunction and to physical disease (e.g., organic hallucinosis, organic catatonic disorder, organic delusional (schizophrenia-like) disorder, organic mood (affective) disorder, organic anxiety disorder, organic dissociative disorder; organic emotionally labile (asthenic) disorder; a mild cognitive disorder, or organic brain syndrome); and a personality and behavioral disorders due to brain disease, damage and dysfunction (e.g., organic personality disorder, postencephalitic syndrome, or postconcussional syndrome).

In one embodiment, the CNS disorder is a mental or behavioral disorder caused by psychoactive substance use. Non-limiting examples of mental or behavioral disorders caused by psychoactive substance use that affect the central nervous system include: acute intoxication (e.g., from alcohol, opioid, cannabis, benzodiazepine, or cocaine use); a dependence syndrome (e.g., from alcohol, opioid, cannabis, benzodiazepine, cocaine, or nicotine addiction); a withdrawal syndrome (e.g., an alcohol or benzodiazepine withdrawal syndrome); delirium tremens; and a psychotic disorder (e.g., alcoholic hallucinosis or stimulant psychosis); an amnesic syndrome (e.g., Korsakoff's syndrome); a residual and late-onset psychotic disorder (e.g., posthallucinogen perception disorder).

In one embodiment, the CNS disorder is an autism spectrum disorder. In certain embodiments, the CNS disorder is autism, Asperger syndrome, pervasive developmental disorder not otherwise specified (PDD-NOS), childhood disintegrative disorder, or Rett syndrome.

In one embodiment, the CNS disorder is a schizophrenia, schizotypal, or delusional disorder. Non-limiting examples of schizophrenia, schizotypal, and delusional disorders that affect the central nervous system include: schizophrenia (e.g., paranoid schizophrenia, hebephrenic schizophrenia (disorganized schizophrenia), catatonic schizophrenia, undifferentiated schizophrenia, post-schizophrenic depression, residual schizophrenia, simple schizophrenia, cenesthopathic schizophrenia, schizophreniform disorder, or schizophreniform psychosis); schizotypal disorder; a persistent delusional disorder (e.g., delusional disorder, delusional dysmorphophobia, involutional paranoid state, or paranoia querulans); an acute or transient psychotic disorder (e.g., acute polymorphic psychotic disorder without symptoms of schizophrenia, acute polymorphic psychotic disorder with symptoms of schizophrenia, or acute schizophrenia-like psychotic disorder); an induced delusional disorder (e.g., folie a deux, induced paranoid disorder, or induced psychotic disorder); a schizoaffective disorder (e.g., manic type, depressive type, or mixed type schizoaffective disorder); and chronic hallucinatory psychosis.

In one embodiment, the CNS disorder is a mood (affective) disorder. Non-limiting examples of mood (affective) disorders that affect the central nervous system include: a manic episode (e.g., hypomania, mania without psychotic symptoms, or mania with psychotic symptoms); a bipolar affective disorder (e.g., bipolar affective disorder—current episode hypomanic, bipolar affective disorder—current episode manic without psychotic symptoms, bipolar affective disorder—current episode manic with psychotic symptoms, bipolar affective disorder—current episode mild or moderate depression, bipolar affective disorder—current episode severe depression without psychotic symptoms, bipolar affective disorder—current episode severe depression with psychotic symptoms, bipolar affective disorder—current episode mixed, bipolar affective disorder—currently in remission, bipolar II disorder, or recurrent manic episodes); a depressive episode (e.g., mild depressive episode, moderate depressive episode, severe depressive episode without psychotic symptoms, severe depressive episode with psychotic symptoms, atypical depression, or single episodes of "masked" depression); a recurrent depressive disorder (e.g., recurrent depressive disorder—current episode mild, recurrent depressive disorder—current episode moderate, recurrent depressive disorder—current episode severe without psychotic symptoms, recurrent depressive disorder—current episode severe with psychotic symptoms, or recurrent depressive disorder—currently in remission); a persistent mood (affective) disorder (e.g., cyclothymia or dysthymia); mixed affective episode; and recurrent brief depressive episodes.

In one embodiment, the CNS disorder is a neurotic, stress-related, or somatoform disorder. Non-limiting examples of neurotic, stress-related, or somatoform disorders that affect the central nervous system include: a phobic anxiety disorder (e.g., agoraphobia, anthropophobia, social neurosis, acrophobia, animal phobias, claustrophobia, or simple phobia); an otherwise categorized anxiety disorder (e.g., panic disorder (episodic paroxysmal anxiety) or generalized anxiety disorder); obsessive-compulsive disorder; an adjustment disorder (e.g., acute stress reaction; posttraumatic stress disorder, or adjustment disorder); a dissociative (conversion) disorder (e.g., dissociative amnesia, dissociative fugue, dissociative stupor; trance disorder, possession disorder, dissociative motor disorder, dissociative convulsions, dissociative anaesthesia and sensory loss, mixed dissociative (conversion) disorder, Ganser's syndrome, or multiple personality disorder); a somatoform disorder (e.g., Briquet's disorder, multiple psychosomatic disorder, a hypochondriacal disorder—such as body dysmorphic disorder, dysmorphophobia (nondelusional), hypochondriacal neurosis, hypochondriasis, and nosophobia—a somatoform autonomic dysfunction—such as cardiac neurosis, Da Costa's syndrome, gastric neurosis, and neurocirculatory asthenia—or psychalgia); neurasthenia; depersonalization-derealization syndrome; Dhat syndrome, occupational neurosis (e.g., writer's cramp); psychasthenia; psychasthenic neurosis; and psychogenic syncope.

In one embodiment, the CNS disorder is a behavioral syndrome associated with physiological disturbances or physical factors. Non-limiting examples of behavioral syndromes associated with physiological disturbances or physical factors that affect the central nervous system include: an eating disorder (e.g., anorexia nervos, atypical anorexia nervosa, bulimia nervosa, atypical bulimia nervosa, overeating associated with other psychological disturbances, vomiting associated with other psychological disturbances, or pica in adults); a nonorganic sleep disorder (e.g., nonorganic insomnia, nonorganic hypersomnia, nonorganic disorder of the sleep-wake schedule, sleepwalking (somnambulism), sleep terrors (night terrors), or nightmares); a sexual dysfunction not caused by organic disorder or disease; a mental or behavioral disorder associated with the puerperium (e.g., postnatal depression, postpartum depression, or puerperal psychosis); and abuse of non-dependence-producing substances.

In one embodiment, the CNS disorder is an adult personality or behavior disorder. Non-limiting examples of adult personality and behavior disorders that affect the central nervous system include: a specific personality disorder (e.g., paranoid personality disorder, schizoid personality disorder, a dissocial personality disorder—such as antisocial personality disorder—an emotionally unstable personality disorder—such as borderline personality disorder—histrionic personality disorder, an anankastic personality disorder—such as obsessive-compulsive personality disorder, anxious (avoidant) personality disorder, dependent personality disorder, eccentric personality disorder, haltlose personality disorder, immature personality disorder, narcissistic personality disorder, passive-aggressive personality disorder, or psychoneurotic personality disorder); mixed personality disorder; a habit or impulse disorder (e.g., pathological gambling, pathological fire-setting (pyromania), pathological stealing (kleptomania), or trichotillomania); and Munchausen syndrome.

In one embodiment, the CNS disorder is a psychological development disorder. Non-limiting examples of psychological development disorders that affect the central nervous system include: a developmental disorder of speech or language (e.g., specific speech articulation disorder, expressive language disorder, receptive language disorder (receptive aphasia), acquired aphasia with epilepsy (Landau-Kleffner disorder), or lisping); a developmental disorder of scholastic skills (e.g., a specific reading disorder—such as developmental dyslexia—specific spelling disorder, a specific disorder of arithmetical skills—such as developmental acalculia and Gerstmann syndrome—or a mixed disorder of scholastic skills); a developmental disorder of motor function (e.g., developmental dyspraxia); a mixed specific developmental disorder; and a pervasive developmental disorder (e.g., childhood autism, atypical autism, Rett's syndrome, overactive disorder associated with mental retardation and stereotyped movements, or Asperger's syndrome).

In one embodiment, the CNS disorder is a behavioral or emotional disorder with onset usually occurring in childhood and adolescence. Non-limiting examples of behavioral or emotional disorders with onset usually occurring in childhood and adolescence that affect the central nervous system include: a hyperkinetic disorder (e.g., a disturbance of activity and attention—such as attention-deficit hyperactivity disorder and attention deficit syndrome with hyperactivity—or hyperkinetic conduct disorder); a conduct disorder (e.g., conduct disorder confined to the family context, unsocialized conduct disorder, socialized conduct disorder, or oppositional defiant disorder); a mixed disorder of conduct or emotions (e.g., depressive conduct disorder); an emotional disorder with onset specific to childhood (e.g., separation anxiety disorder of childhood, phobic anxiety disorder of childhood, social anxiety disorder of childhood, sibling rivalry disorder, identity disorder, or overanxious disorder); a disorder of social functioning with onset specific to childhood and adolescence (e.g., elective mutism, reactive attachment disorder of childhood, or disinhibited attachment disorder of childhood); a tic disorder (e.g., transient tic disorder, chronic motor or vocal tic disorder, or combined vocal and multiple motor tic disorder (de la Tourette); and an otherwise classified behavioral or emotional disorder with onset usually occurring in childhood and adolescence (e.g., nonorganic enuresis, nonorganic encopresis, feeding disorder of infancy and childhood, pica of infancy and childhood, stereotyped movement disorders, stuttering (stammering), cluttering, attention deficit disorder without hyperactivity, Pediatric Autoimmune Neuropsychiatric Disorders Associated with Streptococcal infections (PANDAS), or Pediatric acute-onset neuropyschiatric syndrome (PANS)).

In one embodiment of the method for treating a CNS disorder, the method includes intranasally administering a dry powder composition containing from 0.05 mg/kg to 50 mg/kg pooled human immunoglobulin to a subject in need thereof daily. In other embodiments, the methods provided herein for the treatment of a CNS disorder include intranasally administering a dry powder composition of pooled human IgG in a dosage/frequency combination selected from variations 1 to 816 found in Table 1 and Table 2. In a particular embodiment, the method comprises administering the dry powder composition directly to a nasal epithelium of the subject. In a particular embodiment, the method comprises administering the dry powder composition directly to the olfactory epithelium of the subject.

In one embodiment of the method for treating a CNS disorder, the method includes intranasally administering a liquid (e.g., an aqueous) composition containing from 0.05 mg/kg to 50 mg/kg pooled human immunoglobulin to a subject in need thereof daily. In other embodiments, the methods provided herein for the treatment of a CNS disorder include intranasally administering a liquid (e.g., an aqueous) composition of pooled human IgG in a dosage/frequency combination selected from variations 1 to 816 found in Table 1 and Table 2. In a particular embodiment, the method comprises administering the composition drop-wise directly to a nasal epithelium of the subject. In a particular embodiment, the method comprises administering the composition drop-wise directly to the olfactory epithelium of the subject. In another particular embodiment, the method comprises administering the composition via a spray directly to a nasal epithelium of the subject. In a particular embodiment, the method comprises administering the composition via a spray directly to the olfactory epithelium of the subject.

In one embodiment of the method for treating a CNS disorder, the method includes intranasally administering a gel, cream, or ointment composition containing from 0.05 mg/kg to 50 mg/kg pooled human immunoglobulin to a subject in need thereof daily. In other embodiments, the methods provided herein for the treatment of a CNS disorder include intranasally administering a gel, cream, or ointment composition of pooled human IgG in a dosage/frequency combination selected from variations 1 to 816 found in Table 1 and Table 2. In a particular embodiment, the method comprises administering the gel, cream, or ointment composition directly to a nasal epithelium of the subject. In a particular embodiment, the method comprises administering the gel, cream, or ointment composition directly to the olfactory epithelium of the subject.

Alzheimer's Disease

IVIG has been used in the treatment of Alzheimer's disease. It has been proposed that WIG contains antibodies against β-amyloid. Relkin et al. 2009 (Neurobiol. Aging 30(11): 1728-36). In this study, pooled human IgG was administered intravenously (IVIG therapy) to eight subjects diagnosed with mild Alzheimer's disease (AD). The patients received IVIG therapy for 6 months, discontinued treatment, and then resumed treatment for 9 more months. It was found that β-amyloid antibodies in the serum from AD patients increased in proportion to IVIG dose and plasma levels of β-amyloid increased transiently after each infusion. After 6 months of treatment, mini-mental state tests were performed on the patients. The mini-mental state scores increased an average of 2.5 points after 6 months, returned to baseline during washout and remained stable during subsequent IVIG treatment.

In one aspect, the present invention provides a method for treating Alzheimer's disease in a subject in need thereof by delivering a therapeutically effective amount of a composition comprising pooled human immunoglobulin G (IgG) to the brain of the subject, wherein delivering the composition to the brain comprises intranasally administering the composition directly to an epithelium of the nasal cavity of the subject. In a specific embodiment, the composition is administered directly to the olfactory epithelium of the nasal cavity. In one embodiment, the Alzheimer's disease is early-onset Alzheimer's disease. In another embodiment, the Alzheimer's disease is late-onset Alzheimer's disease.

In one embodiment of the method for treating Alzheimer's disease, the method includes intranasally administering a dry powder composition containing from 0.05 mg/kg to 50 mg/kg pooled human immunoglobulin to a subject in need thereof daily. In other embodiments, the methods provided herein for the treatment of Alzheimer's disease include intranasally administering a dry powder composition of pooled human IgG in a dosage/frequency combination selected from variations 1 to 816 found in Table 1 and Table 2. In a particular embodiment, the method comprises administering the dry powder composition directly to a nasal epithelium of the subject. In a particular embodiment, the method comprises administering the dry powder composition directly to the olfactory epithelium of the subject. In one embodiment, the Alzheimer's disease is early-onset Alzheimer's disease. In another embodiment, the Alzheimer's disease is late-onset Alzheimer's disease.

In one embodiment of the method for treating Alzheimer's disease, the method includes intranasally administering a liquid (e.g., an aqueous) composition containing from 0.05 mg/kg to 50 mg/kg pooled human immunoglobulin to a subject in need thereof daily. In other embodiments, the methods provided herein for the treatment of Alzheimer's disease include intranasally administering a liquid (e.g., an aqueous) composition of pooled human IgG in a dosage/frequency combination selected from variations 1 to 816 found in Table 1 and Table 2. In a particular embodiment, the method comprises administering the composition drop-wise directly to a nasal epithelium of the subject. In a particular embodiment, the method comprises administering the composition drop-wise directly to the olfactory epithelium of the subject. In another particular embodiment, the method comprises administering the composition via a spray directly to a nasal epithelium of the subject. In a particular embodiment, the method comprises administering the composition via a spray directly to the olfactory epithelium of the subject. In one embodiment, the Alzheimer's disease is early-onset Alzheimer's disease. In another embodiment, the Alzheimer's disease is late-onset Alzheimer's disease.

In one embodiment of the method for treating Alzheimer's disease, the method includes intranasally administering a gel, cream, or ointment composition containing from 0.05 mg/kg to 50 mg/kg pooled human immunoglobulin to a subject in need thereof daily. In other embodiments, the methods provided herein for the treatment of Alzheimer's disease include intranasally administering a gel, cream, or ointment composition of pooled human IgG in a dosage/frequency combination selected from variations 1 to 816 found in Table 1 and Table 2. In a particular embodiment, the method comprises administering the gel, cream, or ointment composition directly to a nasal epithelium of the subject. In a particular embodiment, the method comprises administering the gel, cream, or ointment composition directly to the olfactory epithelium of the subject. In one embodiment, the Alzheimer's disease is early-onset Alzheimer's disease. In another embodiment, the Alzheimer's disease is late-onset Alzheimer's disease.

Multiple Sclerosis

Multiple sclerosis (MS) is a chronic neurodegenerative and inflammatory disease of the central nervous system (CNS) that represents one of the most prevalent human autoimmune diseases. Multiple sclerosis (MS) is an autoimmune disease that specifically affects the brain and spinal cord. MS is caused by damage to the myelin sheath, the protective covering that surrounds nerve cells. When the myelin sheath is damaged, nerve signals slow down or stop. Damage to the myelin sheath is caused by inflammation which occurs when the body's own immune cells attack the nervous system. This can occur along any area of the brain, optic nerve, and spinal cord.

MS is classified into four subtypes based on the disease's progression: Relapsing-Remitting MS (RMSS), Secondary Progressive MS (SPMS), Primary-Progressive MS (PPMS), and Progressive-Relapsing MS (PRMS). More than 80 percent of patients who are diagnosed with MS exhibit initial signs of RMSS. RMSS is characterized by relapse (characterized by symptom flare-ups) followed by remission. The relapses can be mild to severe flare-ups and the remissions can last for days to months. RMSS patients often develop SPMS. SPMS is characterized by relapses followed by only partial recoveries. During the partial recovery phase, the symptoms may lessen but do not go into full remission. SPMS is a progressive subtype of MS wherein the symptoms steadily worsen until a chronic disability replaces the cycles of recovery and partial recovery. PPMS accounts for approximately 15 percent of MS occurrences. It is characterized by a slow and steady progression without periods of remission or partial recovery. PRMS is the least common subtype of MS. PRMS is characterized by steadily worsening symptoms and attacks followed by periods of remission.

There are peptide-induced and transgenic mouse model for MS. Experimental autoimmune encephalomyelitis (EAE) is an animal model of brain inflammation. EAE is an inflammatory demyelinating disease of the CNS. Acute and relapsing EAE is characterized by the formation of focal inflammatory demyelinating lesions in the white matter of the brain. This phenotype can be induced in normal SJL mice through the administration of PLP139-151 peptide. Chronic progressive EAE is pathologically associated with a widespread axonal damage in the normal appearing white matter and massive demyelination in the grey matter, particularly in the cortex. This phenotype can be induced in normal C57BL/6 mice through the administration of MOG35-55 peptide.

There is also evidence that tumor necrosis factor (TNF) ligand/receptor superfamily, particularly TNF and Fas/Fas ligand (FasL) are involved in the pathogenesis of MS. Akassoglou et al. 1998 (Am J Pathol. 153(3): 801-813). Accordingly, mouse models deficient in TNF can be used to study the pathologies of MS. The genotype of transgenic TNF knockout mouse models include p55TNFR (p55−/−), p75TNFR (p75−/−), and TNF (TNF−/−).

IVIG has proven useful in the treatment of a number of autoimmune diseases; however its role in the treatment of MS remains uncertain. IVIG trials in different types of MS patients have produced variable results ranging from reports of monthly IVIG being beneficial to IVIG administration not slowing disease progression or reversing disease-induced deficits.

In one aspect, the present invention provides a method for treating multiple sclerosis in a subject in need thereof by delivering a therapeutically effective amount of a composition comprising pooled human immunoglobulin G (IgG) to the brain of the subject, wherein delivering the composition to the brain comprises intranasally administering the composition directly to an epithelium of the nasal cavity of the subject. In a specific embodiment, the composition is administered directly to the olfactory epithelium of the nasal cavity.

In one embodiment of the method for treating multiple sclerosis, the method includes intranasally administering a dry powder composition containing from 0.05 mg/kg to 50 mg/kg pooled human immunoglobulin to a subject in need thereof daily. In other embodiments, the methods provided herein for the treatment of multiple sclerosis include intranasally administering a dry powder composition of pooled human IgG in a dosage/frequency combination selected from variations 1 to 816 found in Table 1 and Table 2. In a particular embodiment, the method comprises administering the dry powder composition directly to a nasal epithelium of the subject. In a particular embodiment, the method comprises administering the dry powder composition directly to the olfactory epithelium of the subject.

In one embodiment of the method for treating multiple sclerosis, the method includes intranasally administering a liquid (e.g., an aqueous) composition containing from 0.05 mg/kg to 50 mg/kg pooled human immunoglobulin to a subject in need thereof daily. In other embodiments, the methods provided herein for the treatment of multiple sclerosis include intranasally administering a liquid (e.g., an aqueous) composition of pooled human IgG in a dosage/frequency combination selected from variations 1 to 816 found in Table 1 and Table 2. In a particular embodiment, the method comprises administering the composition drop-wise directly to a nasal epithelium of the subject. In a particular embodiment, the method comprises administering the composition drop-wise directly to the olfactory epithelium of the subject. In another particular embodiment, the method comprises administering the composition via a spray directly to a nasal epithelium of the subject. In a particular embodiment, the method comprises administering the composition via a spray directly to the olfactory epithelium of the subject.

In one embodiment of the method for treating multiple sclerosis, the method includes intranasally administering a gel, cream, or ointment composition containing from 0.05 mg/kg to 50 mg/kg pooled human immunoglobulin to a subject in need thereof daily. In other embodiments, the methods provided herein for the treatment of multiple sclerosis include intranasally administering a gel, cream, or ointment composition of pooled human IgG in a dosage/frequency combination selected from variations 1 to 816 found in Table 1 and Table 2. In a particular embodiment, the method comprises administering the gel, cream, or ointment composition directly to a nasal epithelium of the subject. In a particular embodiment, the method comprises administering the gel, cream, or ointment composition directly to the olfactory epithelium of the subject.

Parkinson's Disease

Parkinson's disease (PD) is a degenerative disorder of the CNS. PD is notably linked to a decrease in motor control. The loss of motor control caused by PD results from the death of dopamine-generating cells in the substantia nigra, a region of the midbrain. Early in the progression of the disease, the most common symptoms include shaking, rigidity, slowness of movement and difficulty with walking and gait. As the disease progresses, cognitive and behavioral problems arise, with dementia occurring in the advanced stages of the disease. Additional symptoms include sensory, sleep and emotional problems. PD is more common in the elderly, with symptoms most commonly occurring after the age of 50.

There are numerous transgenic mouse models for PD. These models include, for example, Park2 (parkin) transgenic strains, LRRK2 transgenic strains, and synuclein transgenic strains (Jackson Laboratories, Bar Harbor, Me.). In addition to transgenic models, parkinsonian symptoms can also be induced in mice by administering the compounds MPTP, rotenone, paraquat, or maneb.

In one aspect, the present invention provides a method for treating Parkinson's disease in a subject in need thereof by delivering a therapeutically effective amount of a composition comprising pooled human immunoglobulin G (IgG) to the brain of the subject, wherein delivering the composition to the brain comprises intranasally administering the composition directly to an epithelium of the nasal cavity of the subject. In a specific embodiment, the composition is administered directly to the olfactory epithelium of the nasal cavity.

In one embodiment of the method for treating Parkinson's disease, the method includes intranasally administering a dry powder composition containing from 0.05 mg/kg to 50 mg/kg pooled human immunoglobulin to a subject in need thereof daily. In other embodiments, the methods provided herein for the treatment of Parkinson's disease include intranasally administering a dry powder composition of pooled human IgG in a dosage/frequency combination selected from variations 1 to 816 found in Table 1 and Table 2. In a particular embodiment, the method comprises administering the dry powder composition directly to a nasal epithelium of the subject. In a particular embodiment, the method comprises administering the dry powder composition directly to the olfactory epithelium of the subject.

In one embodiment of the method for treating Parkinson's disease, the method includes intranasally administering a liquid (e.g., an aqueous) composition containing from 0.05 mg/kg to 50 mg/kg pooled human immunoglobulin to a subject in need thereof daily. In other embodiments, the methods provided herein for the treatment of Parkinson's disease include intranasally administering a liquid (e.g., an aqueous) composition of pooled human IgG in a dosage/frequency combination selected from variations 1 to 816 found in Table 1 and Table 2. In a particular embodiment, the method comprises administering the composition drop-wise directly to a nasal epithelium of the subject. In a particular embodiment, the method comprises administering the composition drop-wise directly to the olfactory epithelium of the subject. In another particular embodiment, the method comprises administering the composition via a spray directly to a nasal epithelium of the subject. In a particular embodiment, the method comprises administering the composition via a spray directly to the olfactory epithelium of the subject.

In one embodiment of the method for treating Parkinson's disease, the method includes intranasally administering a gel, cream, or ointment composition containing from 0.05 mg/kg to 50 mg/kg pooled human immunoglobulin to a subject in need thereof daily. In other embodiments, the methods provided herein for the treatment of Parkinson's disease include intranasally administering a gel, cream, or ointment composition of pooled human IgG in a dosage/frequency combination selected from variations 1 to 816 found in Table 1 and Table 2. In a particular embodiment, the method comprises administering the gel, cream, or ointment composition directly to a nasal epithelium of the subject. In a particular embodiment, the method comprises administering the gel, cream, or ointment composition directly to the olfactory epithelium of the subject.

Specific Embodiments

In a first aspect, the disclosure provides a method for treating a central nervous system (CNS) disorder in a subject in need thereof, the method comprising: delivering a therapeutically effective amount of a composition comprising pooled human immunoglobulin G (IgG) to the brain of the subject, wherein delivering the composition to the brain comprises intranasally administering the composition directly to a nasal epithelium of the subject.

In one embodiment of the first aspect, at least 40% of the pooled human IgG administered to the subject contacts the nasal epithelium of the subject.

In one embodiment of the first aspect, at least 50% of the pooled human IgG administered to the subject contacts the nasal epithelium of the subject.

In one embodiment of the first aspect, at least 60% of the pooled human IgG administered to the subject contacts the nasal epithelium of the subject.

In one embodiment of the first aspect, the nasal epithelium is the olfactory epithelium of the subject.

In one embodiment of the first aspect, at least 40% of the pooled human IgG administered to the subject contacts the olfactory epithelium of the subject.

In one embodiment of the first aspect, at least 50% of the pooled human IgG administered to the subject contacts the olfactory epithelium of the subject.

In one embodiment of the first aspect, at least 60% of the pooled human IgG administered to the subject contacts the olfactory epithelium of the subject.

In one embodiment of the first aspect, the nasal epithelium is a nasal epithelium of the subject associated with trigeminal nerve endings.

In one embodiment of the first aspect, at least 40% of the pooled human IgG administered to the subject contacts the nasal epithelium of the subject associated with trigeminal nerve endings.

In one embodiment of the first aspect, at least 50% of the pooled human IgG administered to the subject contacts the nasal epithelium of the subject associated with trigeminal nerve endings.

In one embodiment of the first aspect, at least 60% of the pooled human IgG administered to the subject contacts the nasal epithelium of the subject associated with trigeminal nerve endings.

In one embodiment of the first aspect, delivering the composition to the brain comprises intranasally administering the composition to the upper third of the nasal cavity of the subject.

In one embodiment of the first aspect, at least 40% of the pooled human IgG administered to the subject contacts the upper third of the nasal cavity of the subject.

In one embodiment of the first aspect, at least 50% of the pooled human IgG administered to the subject contacts the upper third of the nasal cavity of the subject.

In one embodiment of the first aspect, at least 60% of the pooled human IgG administered to the subject contacts the upper third of the nasal cavity of the subject.

In one embodiment of any of the methods provided above, the CNS disorder is a neurodegenerative disorder of the central nervous system. In a specific embodiment, the neurodegenerative disorder of the central nervous system is Alzheimer's disease. In a specific embodiment, the neurodegenerative disorder of the central nervous system is Parkinson's disease.

In one embodiment of any of the methods provided above, the CNS disorder is a systemic atrophy primarily affecting the central nervous system. In a specific embodiment, the systemic atrophy primarily affecting the central nervous system is amyotrophic lateral sclerosis (ALS). In a specific embodiment, the systemic atrophy primarily affecting the central nervous system is Huntington's disease.

In one embodiment of any of the methods provided above, the CNS disorder is an extrapyramidal and movement disorder.

In one embodiment of any of the methods provided above, the CNS disorder is a demyelinating disorder of the central nervous system. In a specific embodiment, the demyelinating disorder of the central nervous system is multiple sclerosis.

In one embodiment of any of the methods provided above, the CNS disorder is an episodic or paroxysmal disorder of the central nervous system.

In one embodiment of any of the methods provided above, the CNS disorder is a paralytic syndrome of the central nervous system. In a specific embodiment, the CNS disorder is a paralytic syndrome of the central nervous system is cerebral palsy In one embodiment of any of the methods provided above, the CNS disorder is a nerve, nerve root, or plexus disorder of the central nervous system.

In one embodiment of any of the methods provided above, the CNS disorder is an organic mental disorder.

In one embodiment of any of the methods provided above, the CNS disorder is a mental or behavioral disorder caused by psychoactive substance use.

In one embodiment of any of the methods provided above, the CNS disorder is a schizophrenia, schizotypal, or delusional disorder. In a specific embodiment, the schizophrenia, schizotypal, or delusional disorder is schizophrenia.

In one embodiment of any of the methods provided above, the CNS disorder is a mood (affective) disorder. In a specific embodiment, the mood (affective) disorder is bipolar disorder.

In one embodiment of any of the methods provided above, the CNS disorder is a neurotic, stress-related, or somatoform disorder.

In one embodiment of any of the methods provided above, the CNS disorder is a behavioral syndrome.

In one embodiment of any of the methods provided above, the CNS disorder is an adult personality or behavior disorder.

In one embodiment of any of the methods provided above, the CNS disorder is a psychological development disorder.

In one embodiment of any of the methods provided above, the CNS disorder is a child onset behavioral or emotional disorder. In a specific embodiment, the child onset behavioral or emotional disorder is Pediatric acute-onset neuropsychiatric syndrome (PANS). In another specific embodiment, the child onset behavioral or emotional disorder is Pediatric Autoimmune Neuropsychiatric Disorders Associated with Streptococcal infections (PANDAS).

In one embodiment of any of the methods provided above, intranasal administration of the composition comprises the use of a non-invasive intranasal delivery device.

In one embodiment of any of the methods provided above, intranasal administration of the composition comprises administration of a liquid drop of the composition directly onto the nasal epithelium.

In one embodiment of any of the methods provided above, intranasal administration of the composition comprises directed administration of an aerosol of the composition to the nasal epithelium. In a specific embodiment, the aerosol of the composition is a liquid aerosol. In a specific embodiment, the aerosol of the composition is a powder aerosol.

In one embodiment of any of the methods provided above, the composition comprising pooled human IgG does not contain a permeability enhancer.

In one embodiment of any of the methods provided above, the composition comprising pooled human IgG consists essentially of pooled human IgG and an amino acid. In a specific embodiment, the amino acid is glycine. In another specific embodiment, the amino acid is histidine. In another specific embodiment, the amino acid is proline.

In one embodiment of any of the methods provided above, the composition comprising pooled human IgG is an aqueous composition. In one embodiment, the composition comprises: from 10 mg/mL to 250 mg/mL pooled human IgG; and from 50 mM to 500 mM glycine. In a specific embodiment, the pH of the composition is from 4.0 to 7.5. In another specific embodiment, the pH of the composition is from 4.0 to 6.0. In another specific embodiment, the pH of the composition is from 6.0 to 7.5.

In one embodiment of any of the methods provided above, the composition comprising pooled human IgG is a dry powder composition. In one embodiment, the dry powder composition is prepared from an aqueous solution comprising: from 10 mg/mL to 250 mg/mL pooled human IgG; and from 50 mM to 500 mM glycine. In a specific embodiment, the dry powder composition is prepared from an aqueous solution having a pH of from 4.0 to 7.5. In another specific embodiment, the pH of the composition is from 4.0 to 6.0. In another specific embodiment, the pH of the composition is from 6.0 to 7.5.

In one embodiment of any of the methods provided above, the method includes intranasally administering to the subject a dose of from 0.08 mg to 100 mg pooled human IgG per kg body weight of the subject (mg IgG/kg).

In one embodiment of any of the methods provided above, the method includes intranasally administering to the subject a dose of from 0.2 mg to 40 mg pooled human IgG per kg body weight of the subject (mg IgG/kg).

In one embodiment of any of the methods provided above, the method includes intranasally administering to the subject a dose of from 0.5 mg to 20 mg pooled human IgG per kg body weight of the subject (mg IgG/kg).

In one embodiment of any of the methods provided above, the method includes intranasally administering to the subject a dose of from 0.5 mg to 10 mg pooled human IgG per kg body weight of the subject (mg IgG/kg).

In one embodiment of any of the methods provided above, the method includes intranasally administering to the subject a dose of from 1 mg to 5 mg pooled human IgG per kg body weight of the subject (mg IgG/kg).

In one embodiment of any of the methods provided above, the method includes intranasally administering to the subject a fixed dose of from 50 mg to 10 g pooled human IgG.

In one embodiment of any of the methods provided above, the method includes intranasally administering to the subject a fixed dose of from 100 mg to 5 g pooled human IgG.

In one embodiment of any of the methods provided above, the method includes intranasally administering to the subject a fixed dose of from 500 mg to 2.5 g pooled human IgG.

In one embodiment of any of the methods provided above, the method includes intranasally administering to the subject a dose of pooled human IgG at least twice monthly.

In one embodiment of any of the methods provided above, the method includes intranasally administering to the subject a dose of pooled human IgG at least once weekly.

In one embodiment of any of the methods provided above, the method includes intranasally administering to the subject a dose of pooled human IgG at least twice weekly.

In one embodiment of any of the methods provided above, the method includes intranasally administering to the subject a dose of pooled human IgG at least once daily.

In one embodiment of any of the methods provided above, the method includes intranasally administering to the subject a dose of pooled human IgG at least twice daily.

In one embodiment of any of the methods provided above, the composition comprising pooled human IgG comprises at least 0.1% anti-amyloid β IgG.

In one embodiment of any of the methods provided above, the method includes administering a second therapy for the CNS disorder to the subject in need thereof. In one embodiment, the second therapy for the CNS disorder is a cholinesterase inhibitor. In a specific embodiment, the cholinesterase inhibitor is donepezil. In another specific embodiment, the cholinesterase inhibitor is rivastigmine. In another specific embodiment, the cholinesterase inhibitor is galantamine. In another specific embodiment, the cholinesterase inhibitor is tacrine. In another embodiment, the second therapy for the CNS disorder is an inhibitor of NMDA-type glutamate receptor. In a specific embodiment, the inhibitor of NMDA-type glutamate receptor is memantine.

EXAMPLES

Example 1

Tolerability of Intranasal Administration of IgG in Rats

A study was conducted to examine the tolerability of intranasal administration of IgG in rats. The purpose of this study was to determine the tolerability of rats to intranasal IgG administration at various concentrations and preparations.

Experimental Design: IgG was prepared as a liquid protein solution or as a microsphere preparation. The liquid IgG protein solution was prepared in glycine at 200 mg/mL and 100 mg/mL and had a pH of 5.1-5.3. The IgG microsphere preparation was prepared at 200 mg/mL and 150 mg/mL in PEG. The IgG preparations were administered to 8 anesthetized, adult male Sprague Dawley rats.

Prior to anesthesia, each rat was weighed. An anesthesia cocktail was prepared and full, half, and quarter anesthesia doses were calculated according to the animal's weight with a full dose containing 30 mg/kg ketamine, 6 mg/kg xylazine, and 1 mg/kg acepromazine. The anesthesia was administered subcutaneously into the left hind leg, above the thigh. Anesthesia was monitored throughout the procedures by assessing reflexes using pinching of the hind paw or tail. If a reflex was present, a half or quarter dose booster was administered as necessary. During drug administration, animals received a half dose booster roughly 20-25 min after initial dose if needed.

Anesthetized rats were placed on their backs on a heating pad in a metal surgical tray. The heating pad was connected to a thermostat and was automatically regulated to maintain a 37° C. temperature based on continuous measurement from a rectal probe. A 2"×2" gauze pad was rolled tightly into a pillow, taped together, and under the neck to maintain a correct neck position horizontal with the counter.

A 6 µL drop was loaded into a pipette and wiped dry with a tissue. A cotton swab covered in parafilm was used to occlude one naris completely (the flat part of the swab was pushed gently against the naris to prevent airflow), while the 6 µL drop was expelled slowly from the pipette (held at a 45° angle from the rat's midline), forming a drop on the pipette tip. The drop was lowered onto the open naris to be inhaled. The IgG preparations were administered intranasally as described in Table 3.

TABLE 3

Intranasal administration of IgG to 8 rats to test for intranasaltolerability.

| Rat | Weight (g) | Drug/Dose | # Drops delivered | Time to perfusion |
|---|---|---|---|---|
| 1 | 259.87 | Liquid protein solution—200 mg/mL | 10 @ 6 µL/drop (60 µL total) | 23 min |
| 2 | 272.61 | Microsphere—50 mg/mL | 10 @ 6 µL/drop (60 µL total) | 60 min |

TABLE 3-continued

Intranasal administration of IgG to 8 rats to test for intranasaltolerability.

| Rat | Weight (g) | Drug/Dose | # Drops delivered | Time to perfusion |
|---|---|---|---|---|
| 3 | 309.14 | Liquid protein solution—200 mg/mL | 8 @ 6 µL/drop (60 µL total) | 60 min |
| 4 | 309.00 | Liquid protein solution—100 mg/mL | 10 @ 6 µL/drop (60 µL total) | 60 min |
| 5 | 342.62 | Microsphere—200 mg/mL | 10 @ 6 µL/drop (60 µL total) | 60 min |
| 6 | 355.1 | Microsphere—150 mg/mL | 10 @ 6 µL/drop (60 µL total) | 60 min |
| 7 | 364.28 | Microsphere—200 mg/mL | 10 @ 6 µL/drop (60 µL total) | 60 min |
| 8 | 348.93 | Microsphere—150 mg/mL | 28 @ 6 µL/drop (162 µL total) | 60 min |

Results. Three rats received the liquid preparation of intranasal IgG. One rat received 60 µL at 100 mg/ml and it was well tolerated. Two rats received 60 µL at 200 mg/mL. The first rat had some difficulty breathing, most likely due to a problem with light anesthesia. The second rat had some difficulties breathing, but survived. Tracheotomies were not necessary.

Four rats received the microsphere preparation. Two rats received 60 µL at 150 mg/ml. One rat received 60 µL at 200 mg/ml. One rat received 162 µL at 150 mg/ml. These rats tolerated the highest concentration available at 200 mg/ml very well.

The rats tolerated the liquid and microsphere preparations; however, the rats did tolerate the microsphere preparation better than the protein preparation.

Example 2

Comparison of Liquid, Microsphere, and Fragment Biodistribution at 30 and 90 Minutes The purpose of this study was to quantify the amount of intranasally administered IgG that reaches the central nervous system and peripheral tissues in anesthetized rats. Specifically, the biodistribution of different formulations and modes of administration were compared. The different formulations and modes of administration are described in Table 4.

TABLE 4

Formulations and modes of administration used in biodistribution study.

| $^{125}$I radiolabeled IgG Formulation | Mode of Administration |
|---|---|
| Liquid protein formulation | Intranasal (biodistribution measured at 30 min post administration) |
| Liquid protein formulation | Intravenous biodistribution measured at 30 min post administration) |
| Liquid protein formulation | Intranasal (biodistribution measured at 90 min post administration) |
| Microsphere formulation | Intranasal (biodistribution measured at 30 min post administration) |
| Microsphere formulation | Intranasal (biodistribution measured at 90 min post administration) |
| Microsphere formulation (low µCi) | Intranasal (biodistribution measured at 30 min post administration) |
| Antibody fragment (FAb) | Intranasal (biodistribution measured at 30 min post administration) |

Experimental Design: 40 male Sprague-Dawley rats were given one of three preparations of $^{125}$I radiolabeled IgG.

These included liquid IgG protein solution in glycine at pH 5.1-5.3, IgG in a microsphere preparation including PEG, or as Fab antibody fragments in phosphate buffered saline (PBS). Drug administration was either intranasal or intravenous. Rats were sacrificed either 30 or 90 min after the onset of delivery of the IgG preparations for biodistribution studies.

For intranasal delivery, the rats were anesthetized and placed on their backs on a heating pad in a metal surgical tray. The heating pad was connected to a thermostat and was automatically regulated to maintain a 37° C. temperature based on continuous measurement from a rectal probe. A 2"×2" gauze pad was rolled tightly into a pillow, taped together, and under the neck to maintain a correct neck position horizontal with the counter. A lead impregnated shield was placed between the surgical tray and the experimenter for protection against radiation. The dose solution, pipette, pipette tips, and waste receptacle were arranged behind the shield for easy access.

A 6 µL drop was loaded into the pipette behind the shield and wiped dry with a tissue. A cotton swab covered in parafilm was used to occlude one naris completely (the flat part of the swab was pushed gently against the naris to prevent airflow), while the 6 µL drop was expelled slowly from the pipette (held at a 45° angle from the rat's midline), forming a drop on the pipette tip. The drop was lowered onto the open naris to be inhaled. After two minutes, the alternate naris was occluded and a 6 µL drop was administered in the same fashion. A drop was administered as described above every two minutes to alternating nares until a total of 8 drops was delivered (4 to each naris) over 14 min. Delivered time of each drop was noted as well as any details regarding the animal's respiration or success of the delivery. Three 3 µL aliquots of each dosing solution were gamma counted to determine the measured specific activity.

For intravenous IgG delivery, the rats required cannulation of the femoral artery. Anesthetized animals were positioned on their backs in surgical tray on a heating pad maintained at 37° C. Both hind legs were secured by loosely tying a suture around the limbs and weighting them with a hemostat. Small, superficial cuts with blunt scissors were made at the mid inguinal point, making sure not to cut the superficial blood vessels. Gentle, blunt dissection using cotton swabs exposed the femoral vein from the great saphenous vein to the inguinal ligament. Blunt scissors were used to cut away the skin to get a better view the area. Overlying muscle was retracted by threading a 4-0 suture with a curved needle through the muscle, attaching a curved hemostat to the end of the suture and weighting it in place. Connective tissue surrounding the femoral vein and artery was carefully removed with blunt dissection (cotton swabs). Connective tissue between the vein and artery was teased apart using two pairs of forceps carefully using a motion running parallel to the blood vessels and being careful not to rupture the vessels. Saline was applied if the area was dry.

In an area free of branches, the angled forceps was inserted underneath the vein, the tip poked through the connective tissue, and the forceps slowly opened to pull a 12 inch 4-0 suture through very carefully. If the vein collapsed, a cotton swab was used to gently pump the vein full of blood. A second suture was pulled through in a similar manner. The medial and lateral sutures were tied into loose knots. A cotton swab was used to pump the vein full of blood. The lateral suture (closest to the knee) was tied into a tight knot. A hemostat was attached to the suture strings of the medial suture and some tension was added to occlude blood flow.

A 1 mm transverse incision was made in the femoral vein and a blunted 25 G butterfly needle connected to tubing previously filled with 0.9% NaCl and attached to a 3-way stopcock was immediately inserted. The medial suture was tied down around the needle to secure it in place. To confirm placement within the vein, a small amount of blood was withdrawn then saline was pushed. Free suture strings were tied to the butterfly needle securing the cannula in place. Muscles were protracted, sutures securing the limbs removed, and the surgical area was covered with gauze wet with saline.

For the intravenous infusion of $^{125}$I IgG, a syringe pump was placed in the hood behind the lead shield. Parts of the pump were covered with parafilm (or saran wrap) to prevent contamination with radiation. The pump was set for 4.75 mm diameter and rate of 50 µL/min. The dose solution (48 µL) was mixed with 452 µL of saline (0.9% NaCl, total volume 500 mL) in a 1.5 mL microcentrifuge tube. A 1 cc syringe filled with saline was attached to the 3-way stopcock attached to the butterfly needle and placed in the pump. A piece of parafilm was used to secure the saline syringe to the stopcock. With the stopcock closed to the rat, the pump was started to fill the stopcock with saline.

A 1 cc syringe attached to a 27 G or 30 G needle was used to collect the drug from the microcentrifuge tube and then the syringe was connected to the 3-way stopcock. The stopcock was turned so that the flow was open between the dose solution and the rat. The tubing was filled with dose solution making sure that no air bubbles are pushed into the rat and that fluid does not pool near the femoral vein (this would indicate the needle was not in the vein). The stopcock was turned so that flow was open to the saline syringe and the rats.

The time and start volume of the saline syringe was noted and the pump was started. The stop volume of the saline syringe was also noted at the end of the 14 min infusion. At least 700 µL of saline was infused (50 µL/min over 14 min). The volume of saline administered was slightly more than the volume of the tubing which ensured that all of the dose solution was administered.

Two minutes prior to the desired end point time, anesthetized animals were laid flat on their backs in a metal surgical tray. The heating pad, rectal probe, and neck pillow were removed. Tape was used to secure the front limbs to the pan. The back of the pan was elevated slightly to allow blood to run away from the animal. The sternum was exposed by cutting through the skin. The sternum was clamped with a hemostat and the rib cage was cut open laterally, exposing the diaphragm. The diaphragm was cut laterally to expose the pleural cavity.

Surgical scissors were used to cut up the sides of the ribcage toward the armpits of the animal, creating a 'V' shaped incision exposing the heart. The hemostat holding the sternum was taped above the head to hold the cavity open. The heart was stabilized using the blunt forceps while a small cut was made into the left ventricle. A 1 cc-syringe with 18 G, 1" blunt needle was inserted into the left ventricle and approximately 0.1 mL of blood was removed and placed into a pre-weighed tube for gamma counting. A second 18 G blunt needle attached to an extension set filled with 60 cc of saline was inserted through the left ventricle and into the aorta. A large bulldog clamp was placed just above the heart on the aorta, securing the blunt needle in place.

The animal was perfused with 60 mL of saline followed by 360 mL of paraformaldehyde using a syringe pump at a rate of 15 mL/min.

Throughout experimental procedures, strict precautions were followed to prevent radioactive contamination of animal tissues, surgical tools, and equipment. Geiger counters were placed at each work station to continuously screen tools, workspace, and staff. Personal protective equipment including double layered gloves, lab coats, eye protection, masks, and bouffant caps were worn at all times. Lead impregnated shields were used to minimize exposure to radiation. Radioactive monitoring badges were also worn by staff throughout experimental procedures to quantify exposure.

Immediately after collection, each tissue sample was placed into a pre-labeled and pre-weighed gamma tube for later measurement.

For brain dissection, skin and muscle around the neck were cut with a scalpel just above the shoulder blades and a large pair of scissors used to decapitate the animal, cutting dorsal to ventral to avoid contamination from the trachea and esophagus. To expose the brain, a midline incision was made on the dorsal side of the skull, then skin was peeled away, and a straight hemostat was used to break the bone, taking care to leave the dorsal dura attached. Dorsal dura was collected.

To remove the brain from the skull, the head was inverted and a small spatula was used to free it from the cavity. The posterior optic nerve and trigeminal nerves were cut close to the brain. The brain was then placed into a clean Petri dish for dissection.

From the base of the skull, the ventral dura was collected by scraping a forceps on the ventral skull walls. The pituitary, optic chiasm, and trigeminal nerves were collected. The anterior portion of the trigeminal nerve consisted of the portion before the visible branch in the skull, while the remainder containing the trigeminal ganglion was considered as the posterior section. The head was then set aside and covered with a kim-wipe for later dissection.

A microscope was used to help remove vessels from the brain. Using surgical forceps, microscissors, and a 30 G needle, the basilar artery and circle of Willis were removed and placed onto pre-weighed paper (paper was used because of the small weight of this tissue). The needle was used to lift the vessels away from the brain, the forceps to grab hold, and the microscissors to make the cuts. This tissue was weighed immediately upon collection and then the entire paper was crumpled and placed into the bottom of tube).

Prior to placing the brain into the coronal matrix, the olfactory bulbs were cut off at the natural angle using a razor blade. In the coronal brain matrix, a razor blade was inserted at the center of where optic chiasm was before removal to normalize each animal to the same location (bregma). Additional blades were placed every 2 mm from the first blade, resulting in 6×2 mm slices, 3 rostral to the optic chiasm and 3 caudal.

Figure 1G:
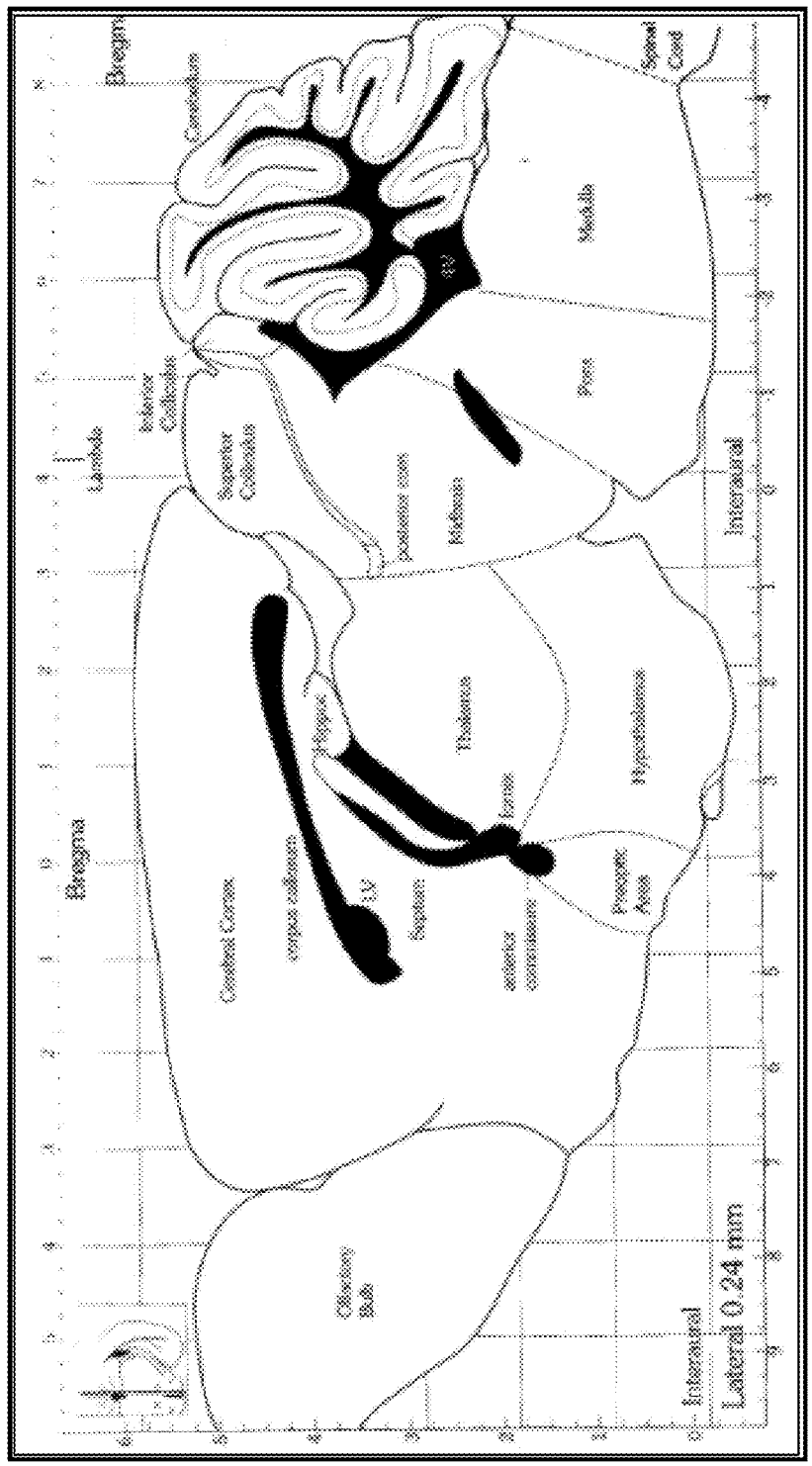
FIG. 1G illustrates a brain bisected along the midline. The bisected brain is further dissected in to midbrain, pons, medulla, and cerebellum for biodistribution analysis.

Blades were removed and tissues were dissected from each slice (FIG. 1A-1F). The remaining section of cortex and hippocampus was dissected from the remaining brain tissue in the matrix and placed in respective tubes. The upper cervical spinal cord was collected. The remaining brain was then bisected along the midline and dissected into midbrain, pons, medulla, and cerebellum according to FIG. 1G.

Returning to the head, the ventral side of the neck was cut anteriorly and skin peeled back exposing lymph nodes, salivary glands, and neck muscles. The superficial nodes, deep cervical nodes, carotid arteries, and thyroid gland were dissected and cleared of connective tissue. A razor blade was used to bisect the skull along the midline. The olfactory epithelium and respiratory epithelium were collected.

For body dissection, bodies were placed on their backs and a longitudinal cut using a scalpel was used to open the peritoneal cavity down to the bladder. 3 mm square samples of liver (superficial right lobe), kidney (left, tip), renal artery, spleen (tip), lung (right, top lobe), and heart were collected. Approximately 0.1-0.2 mL of urine was collected.

Bodies were flipped over onto the stomach and a superficial incision was made down the length of the animal from shoulders to hips, following the spine. The skin was peeled away from the underlying tissue on both sides to expose the shoulder blades. Axillary nodes in the armpits were dissected and cleared of connective tissue. A piece of right deltoid muscle was collected (~3 mm$^2$).

The muscles overlying the spine were scored with a scalpel. To expose the spinal cord, a small hemostat was inserted into the spinal column and used to chip away overlying vertebrae and tissues. A small spatula was used to loosen the cord from the spinal cavity and forceps used to remove it and place into a petri dish. The dura was peeled off of the cord using forceps. The cord was dissected into lower cervical, thoracic, and lumbar portions. The top ~2 mm of lower cervical segment was discarded.

A 2 cm segment of trachea and esophagus was dissected from the body and connective tissues were removed. The top 0.5 cm (closest to the decapitation point) of each was discarded.

Pre-weighed gamma tubes containing samples were reweighed to determine tissue weight. Tissue samples from the rats were counted using a COBRA II Auto-Gamma Counter using a standard $^{125}$I protocol and a 5 min count time. Counters were normalized weekly to ensure a counting efficiency at or above 80%. Background counts were subtracted.

Mean and standard error of the nM concentration of each tissue sample were calculated. Any value outside two standard deviations of the mean for each tissue was considered an outlier and removed from the data set. nM IgG concentrations were calculated for each tissue using the measured specific activity of dosing solutions, the CPM of each tissue, and the volume of each tissue (assuming 1 g=1 mL).

Results, Intranasal IgG Liquid Preparation Distribution at 30 min End Point. Eight rats received IN IgG liquid preparation at an average dose of 6.0 mg in 47.4 µL containing 69.6 µCi with a 30 min end point. Animals tolerated the IN administration well and all survived until the 30 min desired end point.

At the site of IN drug administration, the average IgG concentrations in the respiratory and olfactory epithelia were 136,213 nM and 442 nM respectively. A rostral to caudal gradient of 13.1 nM to 6.0 nM IgG was observed in the trigeminal nerve. A similar gradient from the olfactory bulb to the anterior olfactory nucleus of 4.1 nM to 1.5 nM IgG was observed. The average cortex concentration of IgG after IN administration was 1.3 nM. Concentrations of IgG in other brain regions ranged from a low of 0.7 nM in the striatum to a high of 1.7 nM in the hypothalamus. The hippocampus was found to contain 0.6 nM IgG. A rostral to caudal concentration gradient (1.6 nM to 0.7 nM) was observed within the extra brain material sampled. Similarly, a rostral to caudal concentration gradient (1.2 nM to 0.3 nM) was observed in the spinal cord. The average concentration of IgG in the dura of the brain was 15.2 nM compared to a spinal cord dura concentration of 2.8 nM. The dura likely also contains some or most of the arachnoid membrane and together comprise two of the three components of the meninges. Other tissues sampled from the cavity of the ventral skull (pituitary and optic chiasm) contained 8.2 nM and 7.4 nM IgG respectively.

The blood concentration of IgG at the 30 min end point was 13.9 nM. Concentrations of IgG in peripheral organs ranged from a low of 1.3 nM in the heart to a high of 6.1 nM in the spleen and kidney, with urine containing 8.1 nM. Concentrations of IgG in the basilar and carotid arteries were considerably higher than the renal artery (11.7 and 14.1 nM versus 4.4 nM). Average concentration of IgG in the sampled lymph nodes was 4.7 nM. Levels of IgG in tissues measured to assess variability of IN administration and breathing difficulty (lung, esophagus, and trachea) were consistent across animals.

Results, Intranasal IgG Microsphere Preparation (low μCi) Distribution at 30 min End Point. Four rats received IN IgG microsphere preparation (low μCi) at an average dose of 7.2 mg in 48.0 μA containing 24.7 μCi with a 30 min end point. The raw data from the four rats is provided in Table 5. The measured specific activity from this dosing solution was much lower than expected based upon the provided specific activity. Animals tolerated the IN administration well and all survived until the 30 min desired end point. Zero statistically significant outliers and fourteen non-statistically significant outliers were identified out of a total of 211 concentration values.

TABLE 5

Biodistribution (nM concentrations) of intranasally administered IgG microsphere preparations (with low uCi) at the 30 min end point with outliers included.

| | BAX-17 | BAX-18 | BAX-19 | BAX-20 | Avg | SE |
|---|---|---|---|---|---|---|
| Volume Delivered (μL) | 48.0 | 48.0 | 48.0 | 48.0 | 48.0 | ±0.00 |
| uCi Delivered | 20.9 | 20.9 | 28.6 | 28.6 | 24.7 | ±2.2 |
| mg Delivered | 7.2 | 7.2 | 7.2 | 7.2 | 7.2 | ±0.00 |
| Olfactory Epithelium | 6,806.0 | 3,931.1 | 15,573.6 | 203.9 | 6,628.6 | ±3,273.6 |
| Respiratory Epithelium | 559,241.5 | 268,256.5 | 219,595.4 | 25,412.0 | 268,126.3 | ±110,307.7 |
| Anterior Trigeminal Nerve | 9.7 | 28.6 | 11.4 | 4.6 | 13.6 | ±5.2 |
| Posterior Trigeminal Nerve | 5.4 | 14.5 | 6.3 | 4.1 | 7.6 | ±2.4 |
| Olfactory Bulbs | 5.9 | 3.4 | 3.7 | 4.1 | 4.3 | ±0.6 |
| Anterior Olfactory Nucleus | 1.9 | 2.4 | 2.1 | 1.4 | 1.9 | ±0.2 |
| Frontal Cortex | 1.2 | 1.6 | 2.0 | 1.4 | 1.6 | ±0.2 |
| Parietal Cortex | 0.8 | 1.2 | 1.1 | 0.5 | 0.9 | ±0.2 |
| Temporal Cortex | 0.9 | * | 1.2 | 0.6 | 0.9 | ±0.2 |
| Occipital Cortex | 0.0 | 1.3 | 0.4 | 1.6 | 0.8 | ±0.4 |
| Extra Cortex | 1.6 | 1.4 | 1.1 | 0.9 | 1.3 | ±0.2 |
| Amygdala | 1.6 | 5.1 | 1.9 | 0.7 | 2.3 | ±0.9 |
| Striatum | 0.8 | 16.5 | 0.6 | 0.6 | 4.6 | ±4.0 |
| Septal Nucleus | 1.8 | 4.2 | 0.6 | 0.3 | 1.7 | ±0.9 |
| Hypothalamus | 1.8 | 3.9 | 2.5 | 1.1 | 2.3 | ±0.6 |
| Thalamus | 0.3 | 0.9 | 0.6 | 0.4 | 0.5 | ±0.1 |
| Midbrain | 0.8 | 1.6 | 0.7 | 0.6 | 0.9 | ±0.2 |
| Hippocampus | 0.6 | 1.3 | 0.7 | 0.4 | 0.7 | ±0.2 |
| Pons | 0.6 | 1.9 | 1.2 | 0.8 | 1.1 | ±0.3 |
| Medulla | 0.7 | 1.2 | 1.1 | 0.8 | 1.0 | ±0.1 |
| Cerebellum | 0.6 | 1.2 | 0.8 | 0.6 | 0.8 | ±0.2 |
| Extra Slice #1 | 1.3 | 2.6 | 2.4 | 1.5 | 2.0 | ±0.3 |
| Extra Slice #2 | 1.0 | 1.1 | 1.2 | 1.1 | 1.1 | ±0.05 |
| Extra Slice #3 | 0.7 | 1.1 | 1.0 | 0.7 | 0.9 | ±0.1 |
| Extra Slice #4 | 0.7 | 1.2 | 0.8 | 0.6 | 0.8 | ±0.1 |
| Extra Slice #5 | 0.6 | 1.0 | 0.8 | 0.5 | 0.7 | ±0.1 |
| Extra Slice #6 | 0.7 | 1.3 | 1.0 | 0.6 | 0.9 | ±0.2 |
| Pituitary | 7.0 | 18.1 | 6.2 | 3.6 | 8.7 | ±3.2 |
| Optic Chiasm | 14.9 | 19.0 | 8.2 | 8.1 | 12.5 | ±2.7 |
| Dorsal Dura | 12.0 | 20.7 | 15.1 | 20.6 | 17.1 | ±2.1 |
| Ventral Dura | 18.5 | 56.5 | 16.2 | 15.2 | 26.6 | ±10.0 |
| Spinal Dura | 2.9 | 1.0 | 1.7 | 3.6 | 2.3 | ±0.6 |
| Upper Cervical Spinal Cord | 1.0 | 1.2 | 1.0 | 1.5 | 1.2 | ±0.1 |
| Lower Cervical Spinal Cord | 0.4 | 0.3 | 0.4 | 0.9 | 0.5 | ±0.1 |
| Thoracic Spinal Cord | 0.5 | 0.4 | 0.6 | 0.7 | 0.5 | ±0.1 |
| Lumbar Spinal Cord | 0.2 | 0.2 | 0.2 | 0.3 | 0.2 | ±0.03 |
| Circle of Willis & Basilar Artery | 24.9 | 29.7 | 17.7 | 9.3 | 20.4 | ±4.4 |
| Carotid Artery | 207.3 | 17.9 | 14.1 | 13.1 | 63.1 | ±48.1 |
| Renal artery (L) | 6.1 | 2.4 | 4.5 | 2.4 | 3.8 | ±0.9 |
| Superficial Nodes (2) | 30.8 | 17.1 | 6.9 | 0.8 | 13.9 | ±6.6 |
| Cervical Nodes (2) | 7.7 | 3.4 | 9.2 | 62.7 | 20.8 | ±14.0 |
| Axillary Nodes (2) | 4.2 | 2.1 | 2.2 | 2.8 | 2.8 | ±0.5 |
| Blood Sample | 2,889.3 | 8.0 | 1,730.1 | 7.1 | 1,158.6 | ±705.4 |
| Muscle (R, deltoid) | 3.7 | 2.1 | 1.2 | 1.4 | 2.1 | ±0.6 |
| Liver (R, superficial lobe) | 1.2 | 1.0 | 0.9 | 0.9 | 1.0 | ±0.1 |
| Kidney (L, tip) | 13.1 | 2.5 | 6.9 | 3.0 | 6.4 | ±2.5 |
| Urine | 5.4 | 4.0 | 9.3 | 3.0 | 5.4 | ±1.4 |
| Spleen (tip) | 3.1 | 1.2 | 3.0 | 1.8 | 2.3 | ±0.5 |

TABLE 5-continued

Biodistribution (nM concentrations) of intranasally administered IgG microsphere preparations (with low uCi) at the 30 min end point with outliers included.

|  | BAX-17 | BAX-18 | BAX-19 | BAX-20 | Avg | SE |
|---|---|---|---|---|---|---|
| Heart | 4.4 | 2.9 | 0.4 | 0.7 | 2.1 | ±0.9 |
| Lung (R, top lobe) | 3.4 | 5.2 | 2.3 | 2.6 | 3.4 | ±0.6 |
| Thyroid | 28,623.9 | 102.6 | 30,320.6 | 15.7 | 14,765.7 | ±8,497.9 |
| Esophagus | 3.7 | 2.5 | 2.7 | 4.7 | 3.4 | ±0.5 |
| Trachea | 2.7 | 1.5 | 2.0 | 4.9 | 2.8 | ±0.8 |
| Drug Standard CPM | 2,316,335 | 2,316,335 | 3,256,120 | 3,256,120 | 2,786,228 | ±271,292.6 |
| Drug Standard CPM | 2,380,434 | 2,380,434 | 3,216,298 | 3,216,298 | 2,798,366 | ±241,293.2 |
| Drug Standard CPM | 2,259,775 | 2,259,775 | 3,051,466 | 3,051,466 | 2,655,621 | ±228,541.5 |

* = negative tube weight, so nM could not be calculated

Results, Intranasal IgG Microsphere Preparation Distribution at 30 min End Point. Eight rats received IN IgG microsphere preparation at an average dose of 7.2 mg in 48.0 µL containing 60.0 µCi with a 30 min end point. The raw data from the eight rats is provided in Table 6. Animals tolerated the IN administration well and all survived until the 30 min desired end point.

TABLE 6

Biodistribution (nM concentrations) of intranasally administered IgG microsphere preparations at the 30 min end point with outliers excluded.

|  | BAX-21 | BAX-22 | BAX-23 | BAX-25 | BAX-26 | BAX-28 | Avg | SE |
|---|---|---|---|---|---|---|---|---|
| Volume Delivered (µL) | 48.0 | 48.0 | 48.0 | 48.0 | 48.0 | 48.0 | 48.0 | ±0.00 |
| uCi Delivered | 59.9 | 56.3 | 73.4 | 60.8 | 53.1 | 56.5 | 60.0 | ±2.9 |
| mg Delivered | 7.2 | 7.2 | 7.2 | 7.2 | 7.2 | 7.2 | 7.2 | ±0.00 |
| Olfactory Epithelium | X | 377.5 | 629.1 | X | 97.9 | 201.0 | 326.4 | ±116.3 |
| Respiratory Epithelium | 23,108.2 | 20,219.7 | 33,657.6 | 87,547.5 | 183,182.6 | 101,353.0 | 74,844.8 | +25,792.8 |
| Anterior Trigeminal Nerve | 2.0 | 1.7 | 2.1 | 1.3 | 0.8 | 1.2 | 1.5 | ±0.2 |
| Posterior Trigeminal Nerve | 2.0 | 1.2 | 1.3 | 0.8 | 0.7 | 0.9 | 1.1 | ±0.2 |
| Olfactory Bulbs | 2.7 | 1.0 | 1.1 | 0.6 | 1.0 | 0.7 | 1.2 | ±0.3 |
| Anterior Olfactory Nucleus | 0.7 | 1.2 | 0.4 | 0.4 | 0.3 | 0.3 | 0.6 | ±0.1 |
| Frontal Cortex | 0.8 | 0.3 | 0.8 | 0.4 | 0.4 | 0.4 | 0.5 | ±0.1 |
| Parietal Cortex | 0.3 | 0.6 | 0.6 | 0.2 | 0.4 | 0.4 | 0.4 | ±0.1 |
| Temporal Cortex | 0.2 | 0.4 | 0.2 | 1.3 | 0.2 | 0.3 | 0.5 | ±0.2 |
| Occipital Cortex | 0.3 | 0.1 | 0.4 | 0.4 | 2.3 | 0.6 | 0.7 | ±0.3 |
| Extra Cortex | 0.3 | 0.3 | 0.9 | 0.3 | 0.2 | 0.3 | 0.4 | ±0.1 |
| Amygdala | 0.2 | X | 0.2 | 0.4 | 0.3 | 0.3 | 0.3 | ±0.04 |
| Striatum | 0.6 | 1.5 | 0.3 | 1.1 | X | 2.1 | 1.1 | ±0.3 |
| Septal Nucleus | 0.4 | 0.7 | 0.1 | 1.1 | 0.6 | 0.6 | 0.6 | ±0.1 |
| Hypothalamus | 0.7 | 0.5 | 0.3 | 0.4 | 0.3 | 0.6 | 0.5 | ±0.1 |
| Thalamus | 0.1 | 0.1 | 0.2 | 0.1 | 0.1 | 0.1 | 0.1 | ±0.01 |
| Midbrain | 0.2 | 0.2 | 0.5 | 0.2 | 0.2 | 0.2 | 0.3 | ±0.05 |
| Hippocampus | 0.2 | 0.3 | 0.2 | 0.2 | 0.1 | 0.1 | 0.2 | ±0.03 |
| Pons | 0.4 | 0.3 | 0.5 | 0.3 | 0.5 | 0.3 | 0.4 | ±0.04 |
| Medulla | 0.3 | 0.2 | 0.4 | 0.3 | 0.2 | 0.2 | 0.3 | ±0.04 |
| Cerebellum | 0.3 | 1.1 | X | 1.7 | 0.2 | 0.2 | 0.7 | ±0.3 |
| Extra Slice #1 | 1.1 | 0.3 | 0.4 | 0.4 | 0.3 | 0.4 | 0.5 | ±0.1 |
| Extra Slice #2 | 0.6 | 0.2 | 0.2 | 0.2 | 0.2 | 2.4 | 0.6 | ±0.4 |
| Extra Slice #3 | 0.4 | 0.3 | 0.3 | 0.2 | 0.2 | 0.5 | 0.3 | ±0.04 |
| Extra Slice #4 | 0.3 | 0.2 | 0.2 | 0.2 | 0.1 | 2.8 | 0.6 | ±0.4 |
| Extra Slice #5 | 0.2 | 0.2 | 0.3 | 0.2 | 0.2 | 0.2 | 0.2 | ±0.02 |
| Extra Slice #6 | 0.2 | 0.2 | 0.2 | 0.2 | 0.2 | 0.2 | 0.2 | ±0.01 |
| Pituitary | 1.8 | 1.3 | 3.2 | 2.9 | 1.7 | 2.6 | 2.2 | ±0.3 |
| Optic Chiasm | 2.2 | 1.4 | 2.5 | 2.1 | 1.4 | 0.7 | 1.7 | ±0.3 |
| Dorsal Dura | 5.4 | 7.8 | 5.0 | 2.4 | 5.1 | 1.6 | 4.6 | ±0.9 |
| Ventral Dura | 9.4 | 3.1 | 2.9 | 3.7 | 3.1 | 1.7 | 4.0 | ±1.1 |
| Spinal Dura | 0.6 | 0.4 | 0.8 | 0.2 | X | 0.6 | 0.5 | ±0.1 |
| Upper Cervical Spinal Cord | 0.50 | 0.36 | 0.52 | 0.28 | 0.34 | 0.53 | 0.42 | ±0.04 |
| Lower Cervical Spinal Cord | 0.06 | 0.14 | 0.13 | 0.10 | 0.12 | 0.12 | 0.11 | ±0.01 |
| Thoracic Spinal Cord | 0.06 | 0.03 | 0.08 | 0.09 | X | 0.04 | 0.06 | ±0.0 |
| Lumbar Spinal Cord | 0.08 | 0.07 | 0.10 | 0.05 | 0.07 | 0.03 | 0.06 | ±0.01 |
| Circle of Willis & Basilar Artery | 11.5 | X | 15.7 | 12.4 | 2.0 | 5.2 | 9.3 | ±2.5 |

TABLE 6-continued

Biodistribution (nM concentrations) of intranasally administered IgG microsphere preparations at the 30 min end point with outliers excluded.

| | BAX-21 | BAX-22 | BAX-23 | BAX-25 | BAX-26 | BAX-28 | Avg | SE |
|---|---|---|---|---|---|---|---|---|
| Carotid Artery | 4.6 | 5.4 | 1.6 | 1.9 | X | 1.9 | 3.1 | ±0.8 |
| Renal artery (L) | 0.9 | 0.4 | 0.5 | 0.7 | 0.6 | 0.5 | 0.6 | ±0.1 |
| Superficial Nodes (2) | 0.8 | 0.7 | 0.9 | X | 4.3 | 0.8 | 1.5 | ±0.7 |
| Cervical Nodes (2) | 1.2 | 1.9 | 1.1 | 0.8 | X | 0.5 | 1.1 | ±0.2 |
| Axillary Nodes (2) | 0.4 | X | 0.3 | 0.5 | 1.0 | 0.5 | 0.5 | ±0.1 |
| Blood Sample | 156.7 | 261.5 | 1.1 | 1.9 | 362.3 | 268.7 | 175.4 | ±61.1 |
| Muscle (R, deltoid) | 0.1 | 0.9 | 0.3 | 0.3 | 0.7 | 0.2 | 0.4 | ±0.1 |
| Liver (R, superficial lobe) | 0.0 | X | 0.1 | 0.2 | 0.3 | 0.3 | 0.2 | ±0.05 |
| Kidney (L, tip) | 0.6 | 0.3 | 0.4 | 1.0 | 1.0 | 1.2 | 0.8 | ±0.1 |
| Urine | 0.6 | 1.1 | 0.9 | 0.9 | 3.5 | 2.7 | 1.6 | ±0.5 |
| Spleen (tip) | 0.3 | 0.4 | 0.6 | 0.6 | 0.4 | 0.9 | 0.5 | ±0.1 |
| Heart | 0.3 | 0.4 | 0.3 | 0.1 | 0.1 | 0.3 | 0.3 | ±0.04 |
| Lung (R, top lobe) | 0.5 | 0.4 | 0.3 | 2.2 | 0.2 | 1.3 | 0.8 | ±0.3 |
| Thyroid | 1,697.8 | 3,275.2 | 16.1 | 36.2 | X | 35.6 | 1012.2 | ±651.5 |
| Esophagus | 0.6 | 0.4 | 0.1 | 0.7 | 1.3 | 0.4 | 0.6 | ±0.2 |
| Trachea | 0.5 | 1.0 | 0.3 | 0.6 | 0.8 | 0.6 | 0.6 | ±0.1 |
| Drug Standard CPM | 6,936,801 | 6,170,223 | 8,071,624 | 7,024,714 | 6,006,357 | 6,587,524 | 6,799,540.2 | ±303,198.0 |
| Drug Standard CPM | 6,854,563 | 6,687,656 | 8,239,126 | 6,958,531 | 6,134,932 | 6,360,075 | 6,872,480.3 | ±300,895.5 |
| Drug Standard CPM | 6,894,326 | 6,596,846 | 9,035,030 | 7,046,819 | 6,205,338 | 6,576,363 | 7,059,120.2 | ±412,602.5 |

X = outlier removed from analysis

At the site of IN drug administration, the average IgG concentrations in the respiratory and olfactory epithelia were 74,844.8 nM and 326 nM respectively. A rostral to caudal gradient of 1.5 nM to 1.1 nM IgG was observed in the trigeminal nerve. A similar gradient from the olfactory bulb to the anterior olfactory nucleus of 1.2 nM to 0.6 nM IgG was observed. The average cortex concentration of IgG after IN administration was 0.5 nM. Concentrations of IgG in other brain regions ranged from a low of 0.1 nM in the thalamus to a high of 1.1 nM in the striatum. The hippocampus was found to contain 0.2 nM IgG. The average concentration of IgG in the extra brain material sampled was 0.4 nM, similar to the average cortex concentration, and a concentration gradient was not observed. A rostral to caudal concentration gradient (0.42 nM to 0.06 nM) was observed in the spinal cord. The average concentration of IgG in the dura of the brain was 4.3 nM compared to a spinal cord dura concentration of 0.6 nM. Other tissues sampled from the ventral skull, the pituitary and optic chiasm, contained 2.2 nM and 1.7 nM IgG respectively.

The blood concentration of IgG at the 30 min end point was 175 nM. Concentrations of IgG in peripheral organs ranged from a low of 0.2 nM in the liver to a high of 0.8 nM in the kidney, with urine containing 1.6 nM. Concentrations of IgG in the basilar and carotid arteries were considerable greater than the concentration in the renal artery (9.3 and 3.1 nM versus 0.6 nM). Average concentration of IgG in the sampled lymph nodes was 1.0 nM. Levels of IgG in tissues measured to assess variability of IN administration and breathing difficulty (lung, esophagus, and trachea) were consistent across animals. IgG levels in the thyroid varied greatly ranging from 16.1 nM to 3,275 nM, even after the removal of outliers.

Results, Intranasal IgG Fragment Preparation Distribution at 30 min End Point. Four rats received an IN IgG Fab antibody fragment preparation at an average dose of approximately 3.3 mg in 48.2 µL containing 76.4 µCi. The raw data from the four rats is provided in Table 7. All four experiments were completed with an end point of 30 min, and as expected the animals tolerated the IN administration well and all survived until the desired end point.

TABLE 7

Biodistribution (nM concentrations) of intranasally administered IgG Fab preparations at the 30 min end point with outliers excluded.

| | BAX-41 | BAX-42 | BAX-43 | BAX-44 | Avg | SE |
|---|---|---|---|---|---|---|
| Volume Delivered (µL) | 48.1 | 48.1 | 48.2 | 48.2 | 48.2 | ±0.0 |
| uCi Delivered | 76.7 | 76.7 | 76.0 | 76.0 | 76.4 | ±0.2 |
| mg Delivered | 3.3 | 3.3 | 3.3 | 3.3 | 3.3 | ±0.0 |
| Olfactory Epithelium | 232.4 | 435.2 | 271.2 | X | 312.9 | ±62.1 |
| Respiratory Epithelium | 93,166.9 | 138,501.7 | 59,830.3 | 140,806.9 | 108076.4 | ±19,465.7 |
| Anterior Trigeminal Nerve | 72.8 | 101.4 | 141.5 | 73.3 | 97.2 | ±16.2 |
| Posterior Trigeminal Nerve | 32.4 | 34.2 | 33.9 | 19.8 | 30.1 | ±3.4 |
| Olfactory Bulbs | 54.0 | 26.3 | 45.2 | 23.7 | 37.3 | ±7.3 |
| Anterior Olfactory Nucleus | 20.4 | 14.1 | 25.0 | 15.9 | 18.8 | ±2.4 |
| Frontal Cortex | 20.0 | 11.9 | 21.5 | X | 17.8 | ±3.0 |

TABLE 7-continued

Biodistribution (nM concentrations) of intranasally administered IgG
Fab preparations at the 30 min end point with outliers excluded.

|  | BAX-41 | BAX-42 | BAX-43 | BAX-44 | Avg | SE |
|---|---|---|---|---|---|---|
| Parietal Cortex | 7.0 | 5.8 | 11.6 | 6.7 | 7.8 | ±1.3 |
| Temporal Cortex | 5.6 | 4.3 | 9.5 | 4.3 | 5.9 | ±1.2 |
| Occipital Cortex | 9.3 | 5.6 | 7.1 | 10.0 | 8.0 | ±1.0 |
| Extra Cortex | 8.9 | 7.0 | 8.5 | 4.2 | 7.2 | ±1.1 |
| Amygdala | 10.3 | 14.3 | 15.2 | 6.9 | 11.7 | ±1.9 |
| Striatum | 5.0 | 5.0 | 8.6 | 3.8 | 5.6 | ±1.0 |
| Septal Nucleus | 8.4 | 6.8 | 10.8 | 5.1 | 7.8 | ±1.2 |
| Hypothalamus | 18.0 | 18.1 | 22.7 | 6.3 | 16.3 | ±3.5 |
| Thalamus | 5.1 | 8.2 | 9.8 | 2.9 | 6.5 | ±1.5 |
| Midbrain | 8.9 | 10.3 | 11.0 | 4.0 | 8.6 | ±1.6 |
| Hippocampus | 6.1 | 7.4 | 7.2 | 2.6 | 5.8 | ±1.1 |
| Pons | 11.0 | 12.4 | 12.4 | 4.9 | 10.2 | ±1.8 |
| Medulla | 11.0 | 10.5 | 11.3 | 5.0 | 9.4 | ±1.5 |
| Cerebellum | 9.2 | 5.5 | 6.1 | 8.3 | 7.3 | ±0.9 |
| Extra Slice #1 | 27.6 | 16.8 | 31.2 | 32.5 | 27.0 | ±3.6 |
| Extra Slice #2 | 12.5 | 9.8 | 16.0 | X | 12.8 | ±1.8 |
| Extra Slice #3 | 8.5 | 8.1 | 11.5 | 13.9 | 10.5 | ±1.4 |
| Extra Slice #4 | 7.4 | 6.5 | 9.2 | 6.2 | 7.3 | ±0.7 |
| Extra Slice #5 | 6.8 | X | 8.1 | 14.3 | 9.7 | ±2.3 |
| Extra Slice #6 | 6.0 | 5.5 | 7.4 | 4.1 | 5.7 | ±0.7 |
| Pituitary | 41.6 | 44.2 | 50.6 | 34.0 | 42.6 | ±3.4 |
| Optic Chiasm | 31.8 | 21.8 | 36.4 | 12.4 | 25.6 | ±5.4 |
| Dorsal Dura | 138.2 | 115.3 | 129.9 | 101.5 | 121.2 | ±8.1 |
| Ventral Dura | 123.1 | 109.7 | 106.0 | 81.1 | 105.0 | ±8.8 |
| Spinal Dura | 3.4 | 8.1 | 2.7 | 4.5 | 4.7 | ±1.2 |
| Upper Cervical Spinal Cord | 20.5 | 13.7 | 16.7 | 7.9 | 14.7 | ±2.7 |
| Lower Cervical Spinal Cord | 1.0 | 0.7 | 0.9 | 1.3 | 1.0 | ±0.1 |
| Thoracic Spinal Cord | 0.9 | 0.7 | 0.8 | 1.3 | 0.9 | ±0.1 |
| Lumbar Spinal Cord | 0.7 | 0.6 | 0.6 | 0.8 | 0.7 | ±0.1 |
| Circle of Willis & Basilar Artery | 64.0 | 84.6 | 69.8 | 44.4 | 65.7 | ±8.3 |
| Carotid Artery | X | 36.0 | 35.5 | 42.9 | 38.1 | ±2.4 |
| Renal artery (L) | 9.9 | 14.8 | 4.0 | 5.9 | 8.6 | ±2.4 |
| Superficial Nodes (2) | 9.0 | 9.4 | 5.5 | 6.7 | 7.6 | ±0.9 |
| Cervical Nodes (2) | 19.5 | X | 23.8 | 32.0 | 25.1 | ±3.7 |
| Axillary Nodes (2) | 3.2 | 6.2 | 3.6 | 4.1 | 4.3 | ±0.7 |
| Blood Sample | 31.2 | 38.4 | 28.9 | 33.2 | 32.9 | ±2.0 |
| Muscle (R, deltoid) | 2.87 | 5.05 | 2.26 | 2.18 | 3.1 | ±0.7 |
| Liver (R, superficial lobe) | 3.8 | 3.3 | 4.0 | 2.4 | 3.4 | ±0.3 |
| Kidney (L, tip) | 11.1 | 21.5 | 4.0 | 13.1 | 12.4 | ±3.6 |
| Urine | 10.6 | 10.3 | 19.9 | 9.0 | 12.4 | ±2.5 |
| Spleen (tip) | 9.7 | 12.9 | 3.4 | 9.0 | 8.7 | ±2.0 |
| Heart | 0.8 | 3.0 | 4.5 | 1.5 | 2.5 | ±0.8 |
| Lung (R, top lobe) | 3.5 | 9.1 | 6.7 | 4.4 | 5.9 | ±1.2 |
| Thyroid | 228.2 | 411.7 | 230.1 | 273.2 | 285.8 | ±43.2 |
| Esophagus | 4.1 | 6.4 | X | 5.8 | 5.4 | ±0.7 |
| Trachea | 5.6 | 8.7 | 11.3 | 4.8 | 7.6 | ±1.5 |
| Drug Standard CPM | 7,158,905 | 7,158,905 | 6,994,454 | 6,994,454 | 7076679.3 | ±47,472.8 |
| Drug Standard CPM | 6,974,631 | 6,974,631 | 7,215,418 | 7,215,418 | 7095024.0 | ±69,509.2 |
| Drug Standard CPM | 7,280,104 | 7,280,104 | 7,020,805 | 7,020,805 | 7150454.3 | ±74,853.3 |

X = outlier removed from analysis

At the site of IN drug administration, the average IgG Fab concentrations in the respiratory and olfactory epithelia were 108,076 nM and 313 nM respectively. A rostral to caudal gradient of 97.2 nM to 30.1 nM IgG Fab was observed in the trigeminal nerve. A similar gradient from the olfactory bulb to the anterior olfactory nucleus of 37.3 nM to 18.8 nM IgG Fab was observed. The average cortex concentration of IgG Fab after IN administration was 9.3 nM. Concentrations of IgG in other brain regions ranged from a low of 5.6 nM in the striatum to a high of 16.3 nM in the hypothalamus. The hippocampus was found to contain 5.8 nM IgG Fab. A rostral to caudal concentration gradient (27.0 nM to 5.7 nM) was observed within the extra brain material sampled. Similarly, a rostral to caudal concentration gradient (14.7 nM to 0.7 nM) was observed in the spinal cord. The average concentration of IgG Fab in the dura of the brain was 113.1 nM compared to a spinal cord dura concentration of 4.7 nM. Other tissues sampled from the cavity of the ventral skull (pituitary and optic chiasm) contained 42.6 nM and 25.6 nM IgG Fab respectively.

The blood concentration of IgG Fab at the 30 min end point was 32.9 nM. Concentrations of IgG Fab in peripheral organs ranged from a low of 2.5 nM in the heart to a high of 12.4 nM in the kidney and urine, with the spleen containing 8.7 nM. Concentrations of IgG Fab in the basilar and carotid arteries were considerably higher than the renal artery (65.7 and 38.1 nM versus 8.6 nM).

Results, Comparison of 30 min and 90 min end points. Concentrations of IgG in brain tissues were generally similar or slightly higher with the extended 90 min end point as compared to the 30 min end point for the IgG liquid preparation. There was more variability in the IgG microsphere preparation, with some tissues containing much more (thalamus, midbrain) and some tissues containing much less (striatum, occipital cortex) at the 90 min vs. the 30 min end points. Summaries of the IgG concentrations in tissues are provided in Table 8 and Table 9.

TABLE 8

Summary of tissue concentrations (nM ± SE) of IN, IV, and Fab IgG at 30 min and 90 min endpoints with outliers removed.

| | Treatment | | | | | |
|---|---|---|---|---|---|---|
| | IgG Protein (mean nM ± SE) | | | IgG Microspheres (mean nM ± SE) | | IgG FAB (mean nM ± SE) |
| Route | Intravenous | Intranasal | | Intranasal | | Intranasal |
| Time Point | 30 min | | 90 min | 30 min | 90 min | 30 min |
| Sample Size | n = 7 | n = 8 | n = 6 | n = 6 | n = 5 | n = 4 |
| Volume Delivered (μL) | 47.7 ± 0.2 | 47.4 ± 0.2 | 47.6 ± 0.1 | 48.0 ± 0.00 | 48.0 ± 0.00 | 48.2 ± 0.0 |
| uCi Delivered | 69.5 ± 0.3 | 69.6 ± 0.3 | 70.0 ± 0.1 | 60.0 ± 2.9 | 59.7 ± 2.0 | 76.4 ± 0.2 |
| mg Delivered | 6.0 ± 0.03 | 6.0 ± 0.02 | 7.4 ± 0.00 | 7.2 ± 0.00 | 7.2 ± 0.00 | 3.3 ± 0.0 |
| Olfactory Epithelium | 43.0 ± 3.7 | 441 ± 185 | 355 ± 71 | 326 ± 116 | 3,192 ± 1,625 | 312.9 ± 62.1 |
| Respiratory Epithelium | 41.1 ± 4.3 | 136,213 ± 27,325 | 163,627 ± 16,376 | 74,845 ± 25,793 | 124,509 ± 20,723 | 108076.4 ± 19,465.7 |
| Anterior Trigeminal Nerve | 10.5 ± 1.0 | 13.1 ± 2.6 | 19.3 ± 2.8 | 1.5 ± 0.2 | 8.0 ± 1.3 | 97.2 ± 16.2 |
| Posterior Trigeminal Nerve | 6.3 ± 1.0 | 6.0 ± 1.1 | 8.4 ± 1.7 | 1.1 ± 0.2 | 3.1 ± 0.2 | 30.1 ± 3.4 |
| Olfactory Bulbs | 3.4 ± 0.5 | 4.1 ± 0.9 | 9.9 ± 1.6 | 1.2 ± 0.3 | 1.5 ± 0.2 | 37.3 ± 7.3 |
| Anterior Olfactory Nucleus | 1.9 ± 0.3 | 1.5 ± 0.2 | 2.5 ± 0.3 | 0.6 ± 0.1 | 0.6 ± 0.1 | 18.8 ± 2.4 |
| Frontal Cortex | 2.9 ± 0.5 | 1.4 ± 0.1 | 3.8 ± 0.6 | 0.5 ± 0.1 | 0.7 ± 0.1 | 17.8 ± 3.0 |
| Parietal Cortex | 3.3 ± 0.7 | 0.9 ± 0.1 | 1.5 ± 0.1 | 0.4 ± 0.1 | 0.3 ± 0.1 | 7.8 ± 1.3 |
| Temporal Cortex | 2.9 ± 0.7 | 1.1 ± 0.1 | 1.4 ± 0.2 | 0.5 ± 0.2 | 0.5 ± 0.1 | 5.9 ± 1.2 |
| Occipital Cortex | 2.3 ± 0.2 | 1.8 ± 0.3 | 2.5 ± 0.2 | 0.7 ± 0.3 | 0.3 ± 0.1 | 8.0 ± 1.0 |
| Extra Cortex | 1.8 ± 0.3 | 1.0 ± 0.1 | 1.9 ± 0.2 | 0.4 ± 0.1 | 0.5 ± 0.1 | 7.2 ± 1.1 |
| Amygdala | 1.9 ± 0.1 | 1.4 ± 0.2 | 1.6 ± 0.2 | 0.3 ± 0.04 | 0.4 ± 0.1 | 11.7 ± 1.9 |
| Striatum | 1.8 ± 0.2 | 0.7 ± 0.1 | 0.9 ± 0.1 | 1.1 ± 0.3 | 0.6 ± 0.2 | 5.6 ± 1.0 |
| Septal Nucleus | 1.8 ± 0.1 | 0.9 ± 0.1 | 1.1 ± 0.1 | 0.6 ± 0.1 | 0.6 ± 0.4 | 7.8 ± 1.2 |
| Hypothalamus | 2.0 ± 0.2 | 1.7 ± 0.3 | 1.9 ± 0.2 | 0.5 ± 0.1 | 0.6 ± 0.1 | 16.3 ± 3.5 |
| Thalamus | 1.7 ± 0.3 | 0.4 ± 0.03 | 0.6 ± 0.04 | 0.1 ± 0.01 | 0.3 ± 0.1 | 6.5 ± 1.5 |
| Midbrain | 1.8 ± 0.3 | 0.7 ± 0.1 | 1.3 ± 0.1 | 0.3 ± 0.05 | 0.5 ± 0.1 | 8.6 ± 1.6 |
| Hippocampus | 1.1 ± 0.1 | 0.6 ± 0.1 | 1.0 ± 0.1 | 0.2 ± 0.03 | 0.5 ± 0.1 | 5.8 ± 1.1 |
| Pons | 1.7 ± 0.2 | 0.9 ± 0.1 | 1.6 ± 0.2 | 0.4 ± 0.04 | 0.5 ± 0.1 | 10.2 ± 1.8 |
| Medulla | 1.8 ± 0.3 | 0.9 ± 0.1 | 1.6 ± 0.2 | 0.3 ± 0.04 | 0.4 ± 0.04 | 9.4 ± 1.5 |
| Cerebellum | 1.9 ± 0.3 | 0.8 ± 0.1 | 1.7 ± 0.2 | 0.7 ± 0.3 | 0.5 ± 0.1 | 7.3 ± 0.9 |
| Extra Slice #1 | 2.0 ± 0.2 | 1.6 ± 0.3 | 3.3 ± 0.4 | 0.5 ± 0.1 | 0.8 ± 0.1 | 27.0 ± 3.6 |
| Extra Slice #2 | 2.1 ± 0.3 | 1.0 ± 0.1 | 1.9 ± 0.2 | 0.6 ± 0.4 | 0.5 ± 0.1 | 12.8 ± 1.8 |
| Extra Slice #3 | 2.2 ± 0.3 | 0.8 ± 0.1 | 1.6 ± 0.2 | 0.3 ± 0.04 | 0.4 ± 0.04 | 10.5 ± 1.4 |
| Extra Slice #4 | 2.4 ± 0.4 | 0.7 ± 0.1 | 1.2 ± 0.1 | 0.6 ± 0.4 | 0.3 ± 0.03 | 7.3 ± 0.7 |
| Extra Slice #5 | 2.6 ± 0.6 | 0.7 ± 0.1 | 1.2 ± 0.1 | 0.2 ± 0.02 | 0.3 ± 0.04 | 9.7 ± 2.3 |
| Extra Slice #6 | 2.6 ± 0.5 | 0.9 ± 0.1 | 1.3 ± 0.1 | 0.2 ± 0.01 | 0.3 ± 0.05 | 5.7 ± 0.7 |
| Pituitary | 10.1 ± 0.8 | 8.2 ± 1.8 | 8.4 ± 1.1 | 2.2 ± 0.3 | 2.8 ± 0.5 | 42.6 ± 3.4 |
| Optic Chiasm | 5.1 ± 0.7 | 7.4 ± 1.7 | 8.0 ± 0.7 | 1.7 ± 0.3 | 1.9 ± 0.9 | 25.6 ± 5.4 |
| Dorsal Dura | 27.6 ± 3.0 | 15.3 ± 2.6 | 31.1 ± 4.0 | 4.6 ± 0.9 | 5.8 ± 1.8 | 121.2 ± 8.1 |
| Ventral Dura | 23.5 ± 3.1 | 15.0 ± 2.5 | 32.3 ± 4.4 | 4.0 ± 1.1 | 11.4 ± 3.8 | 105.0 ± 8.8 |
| Spinal Dura | 47.2 ± 3.0 | 2.8 ± 0.3 | 3.3 ± 0.7 | 0.5 ± 0.1 | 0.7 ± 0.1 | 4.7 ± 1.2 |
| Upper Cervical Spinal Cord | 2.0 ± 0.2 | 1.2 ± 0.1 | 2.0 ± 0.3 | 0.4 ± 0.04 | 0.6 ± 0.2 | 14.7 ± 2.7 |
| Lower Cervical Spinal Cord | 2.6 ± 0.3 | 0.6 ± 0.1 | 0.6 ± 0.1 | 0.1 ± 0.01 | 0.3 ± 0.1 | 1.0 ± 0.1 |
| Thoracic Spinal Cord | 1.6 ± 0.2 | 0.4 ± 0.1 | 0.5 ± 0.1 | 0.1 ± 0.01 | 0.2 ± 0.05 | 0.9 ± 0.1 |
| Lumbar Spinal Cord | 2.1 ± 0.3 | 0.3 ± 0.04 | 0.4 ± 0.1 | 0.1 ± 0.01 | 0.2 ± 0.02 | 0.7 ± 0.1 |
| Circle of Willis & Basilar Artery | 18.1 ± 2.8 | 11.7 ± 2.5 | 14.8 ± 1.1 | 9.3 ± 2.5 | 5.8 ± 1.1 | 65.7 ± 8.3 |
| Carotid Artery | 33.2 ± 3.3 | 14.1 ± 2.0 | 16.1 ± 2.3 | 3.1 ± 0.8 | 6.3 ± 0.4 | 38.1 ± 2.4 |
| Renal artery (L) | 111.2 ± 10.1 | 4.4 ± 1.0 | 11.4 ± 3.3 | 0.6 ± 0.1 | 3.7 ± 1.5 | 8.6 ± 2.4 |
| Superficial Nodes (2) | 25.3 ± 2.9 | 4.8 ± 0.4 | 10.4 ± 2.2 | 1.5 ± 0.7 | 2.4 ± 0.1 | 7.6 ± 0.9 |
| Cervical Nodes (2) | 62.6 ± 9.2 | 5.6 ± 0.7 | 6.9 ± 0.8 | 1.1 ± 0.2 | 2.6 ± 0.03 | 25.1 ± 3.7 |
| Axillary Nodes (2) | 42.8 ± 12.8 | 3.7 ± 0.5 | 6.0 ± 0.6 | 0.5 ± 0.1 | 2.6 ± 0.6 | 4.3 ± 0.7 |
| Blood Sample | 1,361 ± 42.5 | 13.9 ± 0.9 | 19.7 ± 1.4 | 175 ± 61 | 223 ± 84.2 | 32.9 ± 2.0 |
| Muscle (R, deltoid) | 19.1 ± 3.8 | 2.7 ± 0.5 | 2.9 ± 0.7 | 0.4 ± 0.1 | 0.9 ± 0.3 | 3.1 ± 0.7 |
| Liver (R, superficial lobe) | 135 ± 23.7 | 1.7 ± 0.2 | 2.6 ± 0.4 | 0.2 ± 0.05 | 0.8 ± 0.2 | 3.4 ± 0.3 |
| Kidney (L, tip) | 355 ± 30.8 | 6.1 ± 0.8 | 8.5 ± 1.6 | 0.8 ± 0.1 | 2.6 ± 0.6 | 12.4 ± 3.6 |
| Urine | 92.6 ± 26.0 | 8.1 ± 1.4 | 17.5 ± 2.2 | 1.6 ± 0.5 | 6.3 ± 1.7 | 12.4 ± 2.5 |
| Spleen (tip) | 228 ± 17.5 | 6.1 ± 1.0 | 6.8 ± 0.4 | 0.5 ± 0.1 | 2.0 ± 0.5 | 8.7 ± 2.0 |
| Heart | 63.2 ± 11.7 | 1.3 ± 0.2 | 2.7 ± 0.6 | 0.3 ± 0.04 | 0.6 ± 0.1 | 2.5 ± 0.8 |
| Lung (R, top lobe) | 261 ± 51.3 | 2.9 ± 0.4 | 4.5 ± 0.7 | 0.8 ± 0.3 | 1.2 ± 0.4 | 5.9 ± 1.2 |
| Thyroid | 534 ± 65.0 | 148 ± 12.8 | 620 ± 30.8 | 1,012 ± 652 | 216 ± 50 | 285.8 ± 43.2 |

TABLE 8-continued

Summary of tissue concentrations (nM ± SE) of IN, IV, and Fab IgG at 30 min and 90 min endpoints with outliers removed.

| | Treatment | | | | | |
|---|---|---|---|---|---|---|
| | IgG Protein (mean nM ± SE) | | | IgG Microspheres (mean nM ± SE) | | IgG FAB (mean nM ± SE) |
| Route | Intravenous | Intranasal | | Intranasal | | Intranasal |
| Time Point | 30 min | | 90 min | 30 min | 90 min | 30 min |
| Sample Size | n = 7 | n = 8 | n = 6 | n = 6 | n = 5 | n = 4 |
| Esophagus | 28.1 ± 3.9 | 4.3 ± 0.6 | 7.7 ± 1.3 | 0.6 ± 0.2 | 4.7 ± 1.3 | 5.4 ± 0.7 |
| Trachea | 28.2 ± 6.2 | 3.9 ± 0.6 | 6.6 ± 1.4 | 0.6 ± 0.1 | 2.0 ± 0.6 | 7.6 ± 1.5 |
| Drug Standard CPM | 7,448,243 ± 128,562 | 7,630,853 ± 169,309 | 7,166,204 ± 76,377 | 6,799,540 ± 303,198 | 6,861,351 ± 210,321 | 7076679.3 ± 47,472.8 |
| Drug Standard CPM | 7,089,796 ± 272,234 | 7,470,182 ± 171,868 | 7,200,437 ± 154,753 | 6,872,480 ± 300,896 | 6,758,588 ± 176,717 | 7095024.0 ± 69,509.2 |
| Drug Standard CPM | 7,390,784 ± 351,624 | 7,689,073 ± 214,590 | 7,022,761 ± 10,481 | 7,059,120 ± 412,602 | 7,027,097 ± 316,344 | 7150454.3 ± 74,853.3 |

TABLE 9

Summary of tissue concentrations of IgG normalized to a 6 mg dose.

| | Treatment | | | | | |
|---|---|---|---|---|---|---|
| | IgG Protein (mean nM) | | | IgG Microspheres (mean nM) | | IgG FAB (mean nM) |
| Route | Intravenous | Intranasal | | Intranasal | | Intranasal |
| Time Point | 30 min | | 90 min | 30 min | 90 min | 30 min |
| Sample Size | n = 7 | n = 8 | n = 6 | n = 6 | n = 5 | n = 4 |
| Volume Delivered (μL) | 47.7 | 47.4 | 47.6 | 48.0 | 48.0 | 48.2 |
| uCi Delivered | 69.5 | 69.6 | 70.0 | 60.0 | 59.7 | 76.4 |
| mg Delivered | 6.0 | 6.0 | 7.4 | 7.2 | 7.2 | 3.3 |
| Olfactory Epithelium | 43.0 | 441 | 288 | 272 | 2,660 | 569.0 |
| Respiratory Epithelium | 41.1 | 136,213 | 132,671 | 62,371 | 103,758 | 196502.6 |
| Anterior Trigeminal Nerve | 10.5 | 13.1 | 15.6 | 1.3 | 6.7 | 176.8 |
| Posterior Trigeminal Nerve | 6.3 | 6.0 | 6.8 | 0.9 | 2.6 | 54.7 |
| Olfactory Bulbs | 3.4 | 4.1 | 8.0 | 1.0 | 1.2 | 67.8 |
| Anterior Olfactory Nucleus | 1.9 | 1.5 | 2.1 | 0.5 | 0.5 | 34.3 |
| Frontal Cortex | 2.9 | 1.4 | 3.1 | 0.4 | 0.5 | 32.3 |
| Parietal Cortex | 3.3 | 0.9 | 1.3 | 0.3 | 0.3 | 14.1 |
| Temporal Cortex | 2.9 | 1.1 | 1.1 | 0.4 | 0.4 | 10.8 |
| Occipital Cortex | 2.3 | 1.8 | 2.0 | 0.6 | 0.3 | 14.5 |
| Extra Cortex | 1.8 | 1.0 | 1.6 | 0.3 | 0.4 | 13.0 |
| Amygdala | 1.9 | 1.4 | 1.3 | 0.2 | 0.3 | 21.2 |
| Striatum | 1.8 | 0.7 | 0.7 | 0.9 | 0.5 | 10.2 |
| Septal Nucleus | 1.8 | 0.9 | 0.9 | 0.5 | 0.5 | 14.2 |
| Hypothalamus | 2.0 | 1.7 | 1.6 | 0.4 | 0.5 | 29.6 |
| Thalamus | 1.7 | 0.4 | 0.5 | 0.1 | 0.3 | 11.8 |
| Midbrain | 1.8 | 0.7 | 1.1 | 0.2 | 0.4 | 15.6 |
| Hippocampus | 1.1 | 0.6 | 0.8 | 0.2 | 0.4 | 10.6 |
| Rons | 1.7 | 0.9 | 1.3 | 0.3 | 0.4 | 18.5 |
| Medulla | 1.8 | 0.9 | 1.3 | 0.2 | 0.3 | 17.1 |
| Cerebellum | 1.9 | 0.8 | 1.3 | 0.6 | 0.4 | 13.2 |
| Extra Slice #1 | 2.0 | 1.6 | 2.7 | 0.4 | 0.6 | 49.1 |
| Extra Slice #2 | 2.1 | 1.0 | 1.6 | 0.5 | 0.4 | 23.2 |
| Extra Slice #3 | 2.2 | 0.8 | 1.3 | 0.2 | 0.3 | 19.1 |
| Extra Slice #4 | 2.4 | 0.7 | 0.9 | 0.5 | 0.2 | 13.3 |
| Extra Slice #5 | 2.6 | 0.7 | 1.0 | 0.2 | 0.3 | 17.7 |
| Extra Slice #6 | 2.6 | 0.9 | 1.0 | 0.2 | 0.3 | 10.4 |
| Pituitary | 10.1 | 8.2 | 6.8 | 1.9 | 2.3 | 77.5 |
| Optic Chiasm | 5.1 | 7.4 | 6.5 | 1.4 | 1.6 | 46.5 |
| Dorsal Dura | 27.6 | 15.3 | 25.2 | 3.8 | 4.9 | 220.4 |
| Ventral Dura | 23.5 | 15.0 | 26.2 | 3.3 | 9.5 | 190.8 |
| Spinal Dura | 47.2 | 2.8 | 2.7 | 0.4 | 0.6 | 8.5 |
| Upper Cervical Spinal Cord | 2.0 | 1.2 | 1.6 | 0.4 | 0.5 | 26.7 |
| Lower Cervical Spinal Cord | 2.6 | 0.6 | 0.5 | 0.1 | 0.3 | 1.8 |
| Thoracic Spinal Cord | 1.6 | 0.4 | 0.4 | 0.1 | 0.2 | 1.7 |
| Lumbar Spinal Cord | 2.1 | 0.3 | 0.4 | 0.1 | 0.1 | 1.2 |
| Circle of Willis & Basilar Artery | 18.1 | 11.7 | 12.0 | 7.8 | 4.8 | 119.4 |
| Carotid Artery | 33.2 | 14.1 | 13.1 | 2.6 | 5.3 | 69.3 |

TABLE 9-continued

Summary of tissue concentrations of IgG normalized to a 6 mg dose.

| | Treatment | | | | |
|---|---|---|---|---|---|
| | IgG Protein (mean nM) | | IgG Microspheres (mean nM) | | IgG FAB (mean nM) |
| Route | Intravenous | Intranasal | Intranasal | | Intranasal |
| Time Point | 30 min | 90 min | 30 min | 90 min | 30 min |
| Sample Size | n = 7 | n = 8 | n = 6 | n = 6 | n = 5 | n = 4 |
| Renal artery (L) | 111.2 | 4.4 | 9.2 | 0.5 | 3.1 | 15.7 |
| Superficial Nodes (2) | 25.3 | 4.8 | 8.5 | 1.2 | 2.0 | 13.9 |
| Cervical Nodes (2) | 62.6 | 5.6 | 5.6 | 0.9 | 2.2 | 45.6 |
| Axillary Nodes (2) | 42.8 | 3.7 | 4.9 | 0.4 | 2.2 | 7.8 |
| Blood Sample | 1,361 | 13.9 | 16.0 | 146 | 186 | 59.8 |
| Muscle (R, deltoid) | 19.1 | 2.7 | 2.3 | 0.4 | 0.8 | 5.6 |
| Liver (R, superficial lobe) | 135 | 1.7 | 2.1 | 0.2 | 0.7 | 6.1 |
| Kidney (L, tip) | 355 | 6.1 | 6.9 | 0.6 | 2.1 | 22.6 |
| Urine | 92.6 | 8.1 | 14.2 | 1.3 | 5.2 | 22.6 |
| Spleen (tip) | 228 | 6.1 | 5.5 | 0.4 | 1.7 | 15.9 |
| Heart | 63.2 | 1.3 | 2.2 | 0.2 | 0.5 | 4.5 |
| Lung (R, top lobe) | 261 | 2.9 | 3.6 | 0.7 | 1.0 | 10.8 |
| Thyroid | 534 | 148 | 502 | 843 | 180 | 519.6 |
| Esophagus | 28.1 | 4.3 | 6.2 | 0.5 | 3.9 | 9.9 |
| Trachea | 28.2 | 3.9 | 5.4 | 0.5 | 1.6 | 13.8 |

Results, Intranasal IgG Liquid Preparation Distribution at 90 min End Point. Six rats received IN IgG liquid preparation at an average dose of 7.4 mg in 47.6 µL containing 70.0 µCi with a 90 min end point. Animals tolerated the IN administration well and all survived until the 90 min desired end point. The nanomolar IgG concentrations in tissues for IN IgG liquid preparation administrations taken at the 90 min end point are presented in Table 10.

TABLE 10

Tissue concentrations (nM) of IgG after intranasal IgG liquid preparation administration at the 90 min end point with outliers excluded.

| | BAX-24 | BAX-33 | BAX-34 | BAX-35 | BAX-36 | BAX-40 | Avg | SE |
|---|---|---|---|---|---|---|---|---|
| Volume Delivered (µL) | 47.8 | 47.4 | 47.4 | 47.5 | 47.5 | 47.8 | 47.6 | ±0.1 |
| uCi Delivered | 70.0 | 70.0 | 70.0 | 70.0 | 70.0 | 70.0 | 70.0 | ±0.01 |
| mg Delivered | 7.4 | 7.4 | 7.4 | 7.4 | 7.4 | 7.4 | 7.4 | ±0.00 |
| Olfactory Epithelium | 669.3 | 389.3 | 196.5 | 203.8 | 307.7 | 365.8 | 355.4 | ±70.8 |
| Respiratory Epithelium | 205,721.0 | 194,945.7 | 189,621.1 | 139,524.3 | 150,482.2 | 101,469.9 | 163,627.4 | ±16,376.5 |
| Anterior Trigeminal Nerve | 16.8 | 30.0 | 15.0 | 10.6 | 20.1 | 23.1 | 19.3 | ±2.8 |
| Posterior Trigeminal Nerve | X | 13.4 | 5.2 | 6.7 | 5.6 | 11.3 | 8.4 | ±1.7 |
| Olfactory Bulbs | 15.5 | 9.1 | 10.1 | 10.5 | 3.6 | 10.8 | 9.9 | ±1.6 |
| Anterior Olfactory Nucleus | 3.0 | 3.4 | 2.3 | 2.7 | 1.5 | 2.4 | 2.5 | ±0.3 |
| Frontal Cortex | 3.3 | 5.9 | 2.4 | 5.0 | 2.7 | 3.3 | 3.8 | ±0.6 |
| Parietal Cortex | 1.4 | 1.6 | 1.3 | 2.1 | 1.4 | X | 1.5 | ±0.1 |
| Temporal Cortex | 1.1 | 0.9 | 1.7 | 1.4 | 1.2 | 2.0 | 1.4 | ±0.2 |
| Occipital Cortex | 2.1 | 3.43 | 1.8 | 2.6 | 2.4 | 2.8 | 2.5 | ±0.2 |
| Extra Cortex | 1.6 | 1.6 | 1.6 | 2.6 | 1.9 | 2.5 | 1.9 | ±0.2 |
| Amygdala | 1.7 | 1.6 | 1.3 | 1.2 | 1.1 | 2.6 | 1.6 | ±0.2 |
| Striatum | 0.9 | 0.4 | 0.6 | 1.0 | 1.2 | 1.0 | 0.9 | ±0.1 |
| Septal Nucleus | 1.4 | 1.1 | 1.1 | 0.9 | 1.4 | 0.9 | 1.1 | ±0.1 |
| Hypothalamus | 2.5 | 1.8 | 1.6 | 2.3 | 1.3 | 2.2 | 1.9 | ±0.2 |
| Thalamus | 0.6 | 0.6 | 0.6 | 0.5 | 0.6 | 0.78 | 0.6 | ±0.04 |
| Midbrain | 1.4 | 1.1 | 1.4 | 1.0 | 1.2 | 1.8 | 1.3 | ±0.1 |
| Hippocampus | 1.0 | 0.9 | 1.1 | 0.7 | 0.8 | 1.2 | 1.0 | ±0.1 |

TABLE 10-continued

Tissue concentrations (nM) of IgG after intranasal IgG liquid preparation administration at the 90 min end point with outliers excluded.

| | BAX-24 | BAX-33 | BAX-34 | BAX-35 | BAX-36 | BAX-40 | Avg | SE |
|---|---|---|---|---|---|---|---|---|
| Pons | 1.9 | 1.2 | 1.1 | 1.9 | 1.2 | 2.2 | 1.6 | ±0.2 |
| Medulla | 1.7 | 1.0 | 1.1 | 1.9 | 1.5 | 2.4 | 1.6 | ±0.2 |
| Cerebellum | 1.4 | 1.0 | 1.6 | 2.1 | 1.4 | 2.5 | 1.7 | ±0.2 |
| Extra Slice #1 | 3.6 | 4.2 | 2.5 | 4.1 | 1.6 | 3.7 | 3.3 | ±0.4 |
| Extra Slice #2 | X | 2.4 | 1.4 | 2.1 | 1.4 | 2.3 | 1.9 | ±0.2 |
| Extra Slice #3 | 1.4 | 1.9 | 1.1 | 1.6 | 1.1 | 2.3 | 1.6 | ±0.2 |
| Extra Slice #4 | 1.2 | 1.56 | 0.8 | 1.2 | 1.1 | 1.2 | 1.2 | ±0.1 |
| Extra Slice #5 | 1.2 | 1.3 | 0.9 | 1.1 | 1.1 | 1.43 | 1.2 | ±0.1 |
| Extra Slice #6 | 1.5 | 1.2 | 1.0 | 1.1 | 1.0 | 1.9 | 1.3 | ±0.1 |
| Pituitary | 12.7 | 5.5 | 5.6 | 8.1 | 8.4 | 10.4 | 8.4 | ±1.1 |
| Optic Chiasm | 7.2 | 8.4 | 7.1 | 9.9 | 5.7 | 9.6 | 8.0 | ±0.7 |
| Dorsal Dura | 12.3 | 33.0 | 37.7 | 37.7 | 29.6 | 36.5 | 31.1 | ±4.0 |
| Ventral Dura | 21.6 | 47.6 | 41.2 | 26.5 | 21.4 | 35.4 | 32.3 | ±4.4 |
| Spinal Dura | 2.0 | 3.2 | 1.4 | 2.6 | 4.3 | 6.4 | 3.3 | ±0.7 |
| Upper Cervical Spinal Cord | 2.8 | 1.2 | 1.9 | 1.8 | 1.5 | 2.8 | 2.0 | ±0.3 |
| Lower Cervical Spinal Cord | 0.7 | 0.6 | 0.4 | 0.7 | 0.7 | X | 0.6 | ±0.1 |
| Thoracic Spinal Cord | 0.5 | 0.4 | 0.4 | 0.3 | 0.5 | 0.9 | 0.5 | ±0.08 |
| Lumbar Spinal Cord | 0.4 | 0.3 | 0.2 | 0.4 | 0.5 | 0.8 | 0.4 | ±0.08 |
| Circle of Willis & Basilar Artery | 16.8 | 11.7 | 15.1 | X | 17.7 | 12.9 | 14.8 | ±1.1 |
| Carotid Artery | 17.4 | 13.5 | 12.6 | 13.0 | 13.5 | 26.9 | 16.1 | ±2.3 |
| Renal artery (L) | 22.4 | 8.4 | 7.7 | 14.6 | 3.7 | X | 11.4 | ±3.3 |
| Superficial Nodes (2) | 7.4 | 20.5 | 5.0 | 8.7 | 9.6 | 11.5 | 10.4 | ±2.2 |
| Cervical Nodes (2) | 6.7 | 8.9 | 4.4 | 5.2 | 6.9 | 9.1 | 6.9 | ±0.8 |
| Axillary Nodes (2) | 7.2 | 5.8 | 4.3 | 4.5 | 7.9 | 6.3 | 6.0 | ±0.6 |
| Blood Sample | 17.7 | 23.3 | 16.1 | X | 22.5 | 19.0 | 19.7 | ±1.4 |
| Muscle (R, deltoid) | 2.6 | 3.2 | 1.0 | 1.3 | 5.4 | 3.6 | 2.9 | ±0.7 |
| Liver (R, superficial lobe) | 2.8 | 1.4 | 3.9 | 1.1 | 2.7 | 3.4 | 2.6 | ±0.4 |
| Kidney (L, tip) | 16.0 | 7.6 | 8.8 | 4.7 | 6.6 | 7.3 | 8.5 | ±1.6 |
| Urine | 25.9 | 10.8 | 18.7 | 12.3 | 18.0 | 19.3 | 17.5 | ±2.2 |
| Spleen (tip) | 5.8 | 7.8 | 6.8 | 7.1 | 5.3 | 7.7 | 6.8 | ±0.4 |
| Heart | 2.1 | 4.8 | 1.5 | X | 1.8 | 3.4 | 2.7 | ±0.6 |
| Lung (R, top lobe) | 5.4 | 2.0 | 4.6 | 7.3 | 4.5 | 3.1 | 4.5 | ±0.7 |
| Thyroid | 543.6 | 566.7 | 700.5 | X | 680.7 | 606.1 | 619.5 | ±30.8 |
| Esophagus | 13.5 | 8.7 | 6.3 | 7.4 | 5.5 | 4.8 | 7.7 | ±1.3 |
| Trachea | 13.5 | 6.6 | 5.6 | 3.4 | 5.6 | 5.0 | 6.6 | ±1.4 |
| Drug Standard CPM | 7,390,846 | 7,130,719 | 7,130,719 | 6,977,049 | 6,977,049 | 7,390,846 | 7166204.3 | ±76,377.4 |
| Drug Standard CPM | 7,285,169 | 7,575,479 | 7,575,479 | 6,740,664 | 6,740,664 | 7,285,169 | 7200437.0 | ±154,753.0 |
| Drug Standard CPM | 6,990,473 | 7,032,426 | 7,032,426 | 7,045,383 | 7,045,383 | 6,990,473 | 7022760.5 | ±10,480.7 |

X = outlier removed from analysis

At the site of IN drug administration, the average IgG concentrations in the respiratory and olfactory epithelia were 163,627 nM and 355 nM respectively. A rostral to caudal gradient of 19.3 nM to 8.4 nM IgG was observed in the trigeminal nerve. A similar gradient from the olfactory bulb to the anterior olfactory nucleus of 9.9 nM to 2.5 nM IgG was observed. The average cortex concentration of IgG after IN administration was 2.2 nM. Concentrations of IgG in other brain regions ranged from a low of 0.6 nM in the thalamus to a high of 1.9 nM in the hypothalamus. The hippocampus was found to contain 1.0 nM IgG. A rostral to caudal concentration gradient (3.3 nM to 1.2 nM) was observed within the extra brain material sampled. Similarly, a rostral to caudal concentration gradient (2.0 nM to 0.4 nM) was observed in the spinal cord. The average concentration of IgG in the dura of the brain was 31.7 nM compared to a spinal cord dura concentration of 3.3 nM. Other tissues sampled from the ventral skull, the pituitary and optic chiasm, contained 8.4 nM and 8.0 nM IgG respectively.

The blood concentration of IgG at the 30 min end point was 19.7 nM. Concentrations of IgG in peripheral organs ranged from a low of 2.6 nM in the liver to a high of 7.7 nM in the spleen, with urine containing 17.5 nM. Concentrations of IgG in the basilar and carotid arteries were similar to the concentration in the renal artery (14.8 and 16.1 nM versus 11.4 nM). Average concentration of IgG in the sampled lymph nodes was 7.8 nM. Levels of IgG in tissues measured to assess variability of IN administration and breathing difficulty (lung, esophagus, and trachea) were consistent across animals.

Results, Intranasal IgG Microsphere Preparation Distribution at 90 min End Point. Six rats received IN IgG microsphere preparation at an average dose of 7.2 mg in 48.0 μA containing 59.7 μCi with a 90 min end point. Animals tolerated the IN administration well and all survived until the 90 min desired end point. The nanomolar IgG concentrations in tissues for IN IgG microsphere preparation administrations taken at the 90 min end point in five of the six rats are presented in Table 11.

TABLE 11

Tissue concentrations (nM) of IgG after intranasal IgG microsphere preparation administration at the 90 min end point with outliers excluded.

|  | BAX-31 | BAX-32 | BAX-37 | BAX-38 | BAX-39 | Avg | SE |
|---|---|---|---|---|---|---|---|
| Volume Delivered (μL) | 48.0 | 48.0 | 48.0 | 48.0 | 48.0 | 48.0 | ±0.00 |
| uCi Delivered | 57.5 | 52.7 | 62.8 | 62.8 | 62.8 | 59.7 | ±2.0 |
| mg Delivered | 7.2 | 7.2 | 7.2 | 7.2 | 7.2 | 7.2 | ±0.00 |
| Olfactory Epithelium | 293.5 | 3,632.7 | 853.2 | 1,898.5 | 9,281.1 | 3,191.8 | ±1,625 |
| Respiratory Epithelium | 169,083.6 | 169,807.3 | 128,471.3 | 69,460.0 | 85,723.8 | 124,509.2 | ±20,723 |
| Anterior Trigeminal Nerve | 11.1 | 5.9 | 10.7 | 7.6 | 4.5 | 8.0 | ±1.3 |
| Posterior Trigeminal Nerve | 2.6 | 3.3 | 3.6 | X | 3.1 | 3.1 | ±0.2 |
| Olfactory Bulbs | 2.0 | 1.9 | 1.2 | 1.2 | 1.2 | 1.5 | ±0.2 |
| Anterior Olfactory Nucleus | 0.7 | 0.5 | 0.5 | 0.4 | 0.8 | 0.6 | ±0.1 |
| Frontal Cortex | 0.7 | 0.8 | 0.4 | 0.8 | 0.6 | 0.7 | ±0.1 |
| Parietal Cortex | 0.3 | X | 0.1 | 0.4 | 0.5 | 0.3 | ±0.1 |
| Temporal Cortex | 0.7 | 0.7 | 0.3 | 0.5 | 0.5 | 0.5 | ±0.1 |
| Occipital Cortex | 0.6 | 0.4 | 0.1 | 0.4 | 0.2 | 0.3 | ±0.1 |
| Extra Cortex | 0.6 | 0.81 | 0.4 | 0.4 | X | 0.5 | ±0.1 |
| Amygdala | 0.2 | X | 0.3 | 0.49 | 0.53 | 0.4 | ±0.1 |
| Striatum | 0.2 | 1.3 | 0.2 | 0.4 | 0.9 | 0.6 | ±0.2 |
| Septal Nucleus | 0.4 | 1.9 | 0.1 | 0.2 | X | 0.6 | ±0.4 |
| Hypothalamus | 0.6 | 0.8 | 0.4 | 0.4 | 0.9 | 0.6 | ±0.1 |
| Thalamus | 0.2 | 0.6 | 0.1 | 0.2 | 0.4 | 0.3 | ±0.1 |
| Midbrain | 0.3 | 0.5 | 0.2 | X | 0.8 | 0.5 | ±0.1 |
| Hippocampus | 0.3 | 0.5 | 0.2 | 0.2 | 1.0 | 0.5 | ±0.1 |
| Pons | 0.5 | 0.7 | 0.4 | 0.5 | 0.5 | 0.5 | ±0.1 |
| Medulla | 0.5 | 0.4 | 0.3 | 0.4 | 0.5 | 0.4 | ±0.04 |
| Cerebellum | 0.5 | 0.8 | 0.2 | 0.4 | 0.7 | 0.5 | ±0.1 |
| Extra Slice #1 | 1.0 | 1.0 | 0.4 | 0.8 | 0.7 | 0.8 | ±0.1 |
| Extra Slice #2 | 0.4 | 0.50 | 0.2 | 0.4 | 0.96 | 0.5 | ±0.1 |
| Extra Slice #3 | 0.3 | 0.4 | 0.2 | 0.4 | 0.5 | 0.4 | ±0.04 |
| Extra Slice #4 | 0.3 | X | 0.2 | 0.3 | 0.3 | 0.3 | ±0.03 |
| Extra Slice #5 | 0.3 | 0.4 | X | 0.5 | 0.3 | 0.3 | ±0.04 |
| Extra Slice #6 | 0.4 | X | 0.2 | 0.4 | 0.4 | 0.3 | ±0.05 |
| Pituitary | 4.4 | 2.1 | 2.9 | 2.7 | 1.6 | 2.8 | ±0.5 |
| Optic Chiasm | X | 3.4 | X | 1.9 | 0.4 | 1.9 | ±0.9 |
| Dorsal Dura | X | 11.3 | 3.8 | 3.7 | 4.5 | 5.8 | ±1.8 |
| Ventral Dura | 11.8 | 26.0 | 7.4 | 3.9 | 8.1 | 11.4 | ±3.8 |
| Spinal Dura | 0.6 | 0.8 | 0.7 | X | X | 0.7 | ±0.1 |
| Upper Cervical Spinal Cord | 0.5 | 0.3 | 1.1 | 0.9 | 0.3 | 0.6 | ±0.2 |
| Lower Cervical Spinal Cord | 0.2 | 0.2 | 0.1 | 0.4 | 0.6 | 0.3 | ±0.1 |
| Thoracic Spinal Cord | 0.1 | 0.1 | 0.1 | 0.3 | 0.3 | 0.2 | ±0.05 |
| Lumbar Spinal Cord | X | 0.1 | 0.1 | 0.2 | 0.2 | 0.2 | ±0.02 |
| Circle of Willis & Basilar Artery | 8.9 | 5.0 | 3.4 | X | 5.9 | 5.8 | ±1.1 |
| Carotid Artery | 5.3 | 7.1 | 5.9 | 7.5 | 5.9 | 6.3 | ±0.4 |
| Renal artery (L) | 1.8 | 3.3 | 1.9 | 9.6 | 1.8 | 3.7 | ±1.5 |
| Superficial Nodes (2) | 2.3 | 2.1 | 2.7 | 2.6 | 2.3 | 2.4 | ±0.1 |
| Cervical Nodes (2) | 2.5 | 2.6 | 2.7 | 2.5 | 2.7 | 2.6 | ±0.0 |
| Axillary Nodes (2) | 2.2 | 1.4 | 1.9 | 4.6 | 3.1 | 2.6 | ±0.6 |
| Blood Sample | 249.6 | 388.4 | 53.0 | 6.6 | 417.6 | 223.0 | ±84.2 |
| Muscle (R, deltoid) | 0.0 | 0.9 | 1.2 | X | 1.5 | 0.9 | ±0.3 |
| Liver (R, superficial lobe) | 1.1 | 0.5 | 0.6 | 0.5 | 1.5 | 0.8 | ±0.2 |
| Kidney (L, tip) | 1.6 | 1.9 | 1.3 | 3.7 | 4.3 | 2.6 | ±0.6 |
| Urine | 4.7 | 4.6 | 6.7 | 2.7 | 12.8 | 6.3 | ±1.7 |
| Spleen (tip) | 1.4 | 1.5 | 0.8 | 2.9 | 3.4 | 2.0 | ±0.5 |
| Heart | 0.5 | 0.7 | 0.2 | 0.5 | 0.9 | 0.6 | ±0.1 |
| Lung (R, top lobe) | 0.9 | 2.3 | 0.8 | 0.9 | X | 1.2 | ±0.4 |

TABLE 11-continued

Tissue concentrations (nM) of IgG after intranasal IgG microsphere preparation administration at the 90 min end point with outliers excluded.

|  | BAX-31 | BAX-32 | BAX-37 | BAX-38 | BAX-39 | Avg | SE |
|---|---|---|---|---|---|---|---|
| Thyroid | 181.3 | 153.4 | X | 314.3 | X | 216.4 | ±49.6 |
| Esophagus | 2.4 | 5.6 | 1.2 | 5.3 | 8.8 | 4.7 | ±1.3 |
| Trachea | 1.7 | 1.6 | 0.9 | 3.7 | X | 2.0 | ±0.6 |
| Drug Standard CPM | 6,696,942 | 6,103,589 | 7,168,742 | 7,168,742 | 7,168,742 | 6,861,351 | ±210,321 |
| Drug Standard CPM | 6,548,447 | 6,157,644 | 7,028,950 | 7,028,950 | 7,028,950 | 6,758,588 | ±176,717 |
| Drug Standard CPM | 6,631,733 | 5,962,084 | 7,513,889 | 7,513,889 | 7,513,889 | 7,027,097 | ±316,344 |

X = outlier removed from analysis at the site of IN drug administration, the average IgG concentrations in the respiratory and olfactory epithelia were 124,509 nM and 3,191 nM respectively. A rostral to caudal gradient of 8.0 nM to 3.1 nM IgG was observed in the trigeminal nerve. A similar gradient from the olfactory bulb to the anterior olfactory nucleus of 1.5 nM to 0.6 nM IgG was observed. The average cortex concentration of IgG after IN administration was 0.5 nM. Concentrations of IgG in other brain regions ranged from a low of 0.3 nM in the thalamus to a high of 0.65 nM in the septal nucleus. The hippocampus was found to contain 0.5 nM IgG. The average concentration of IgG in the extra brain material sampled was 0.4 nM, similar to the average cortex concentration, and a rostral to caudal concentration gradient was observed. Similarly, a rostral to caudal concentration gradient (0.6 nM to 0.2 nM) was observed in the spinal cord. The average concentration of IgG in the dura of the brain was 8.6 nM compared to a spinal cord dura concentration of 0.7 nM. Other tissues sampled from the ventral skull, the pituitary and optic chiasm, contained 2.8 nM and 1.9 nM IgG respectively.

The blood concentration of IgG at the 30 min end point was 223.0 nM. Concentrations of IgG in peripheral organs ranged from a low of 0.6 nM in the heart to a high of 2.6 nM in the kidney, with urine containing 6.3 nM. Concentrations of IgG in the basilar and carotid arteries were similar to the concentration in the renal artery (5.8 and 6.3 nM versus 3.7 nM). Average concentration of IgG in the sampled lymph nodes was 2.5 nM. Levels of IgG in tissues measured to assess variability of IN administration and breathing difficulty (lung, esophagus, and trachea) were fairly consistent across animals. IgG levels in the thyroid varied greatly prior to the removal of outliers.

Overall, IN administration of the IgG liquid preparation resulted in higher brain concentrations than the microsphere preparation when normalizing to a 6.0 mg dose with brain concentrations ranging from 0.4 to 1.7 nM. A summary of the IN, IV and Fab data is presented in Table 8. This could be explained by lower concentrations of the microsphere IgG reaching the olfactory and respiratory epithelium. Intranasal microsphere preparation also resulted in about ten times higher concentrations of IgG in the blood than the liquid preparation.

Normalized to a 6 mg IN dose, Fab tissue concentrations were on average 19-fold higher in the brain than the liquid IgG preparations. A summary of the tissue concentrations of IgG normalized to a 6 mg dose is presented in Table 9. The three times smaller molecular weight of Fab versus intact IgG is likely responsible for the increased efficiency of direct delivery from the nasal cavity to the CNS. If the Fab has similar biological effects as IgG for the treatment of Alzheimer's disease, it would be a promising candidate for IN delivery.

Figure 2A:
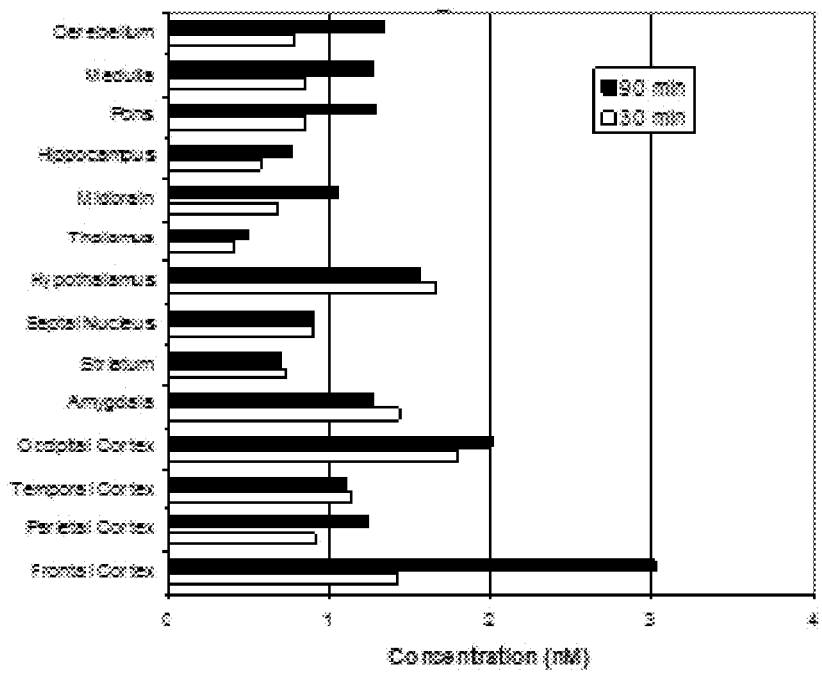
FIGS. 2A-2B illustrate results of average brain tissue $^{125}$I IgG concentrations (nM) 30 and 90 minutes after intranasal administration of IgG.
Figure 2B:
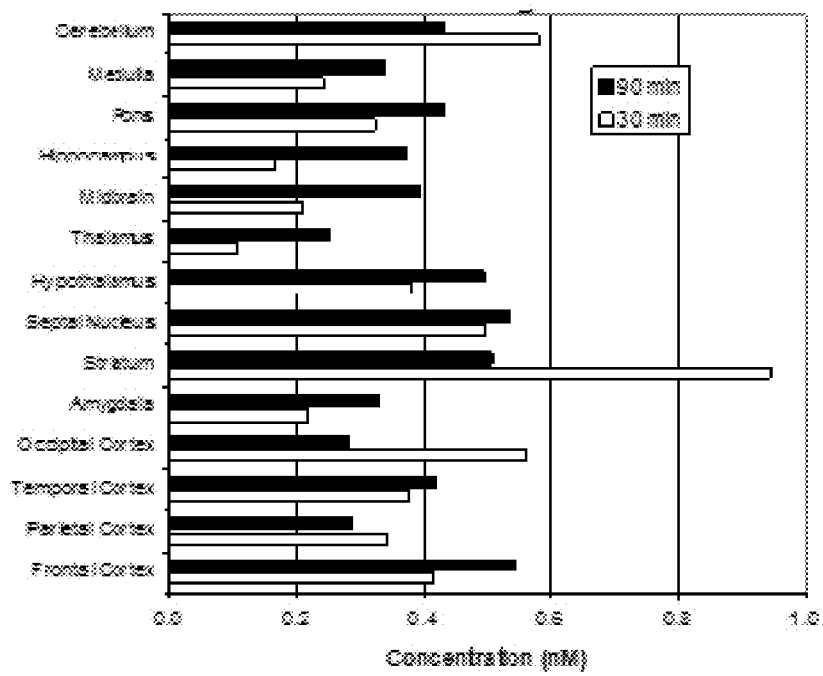

Comparisons of brain tissue concentrations (nM) after intranasal IgG liquid and microsphere preparations at 30 and 90 min end points are depicted in FIG. 2A and FIG. 2B.

Results of IN and IV delivery of the liquid protein preparation after 30 min. On average, IN administration of the IgG liquid preparation resulted in lower brain concentrations than an equivalent IV dose administered at the 30 min end point (for example the average cortex concentration of 1.3 nM vs. 2.6 nM). However, to achieve these brain concentrations of IgG, IV administration resulted in blood concentrations that were a hundred times higher than IN administration (1,361 nM vs. 13.9 nM). Higher IgG concentrations in peripheral organs and systems were also observed with IV vs. IN administration. For example, IgG concentrations in the lymphatic system were ten times greater with IV vs. IN administration (43.6 nM vs. 4.7 nM).

When normalizing tissue concentrations to blood, liver, or lymphatic concentrations, it was apparent that IN administration targets the central nervous system. The ratio of tissue concentrations to blood concentrations of intranasal and intravenous IgG is presented in Table 12. For example for frontal cortex, IN administration results in a 48 fold higher concentration than IV when normalizing for blood concentration, 40 fold higher when normalizing to liver concentration, and 5 fold higher when normalizing to average lymph concentration. Intranasal administration increased IgG targeting about 50-fold more than IV administration (relative to the blood) to areas of the brain known to accumulate β-amyloid and heme (both known to bind IgG) including the frontal cortex, hippocampus, and the blood vessel walls of the cerebrovasculature. Importantly, β-amyloid tightly binds heme and heme is both a strong pro-oxidant and pro-inflammatory agent known to inactivate brain receptors involved in memory.

TABLE 12

Comparison of intranasal and intravenous targeting of IgG.

| | Tissue to Blood Ratios | | | Tissue to Liver Ratios | | | Tissue to Avg Lymph Ratios | | |
|---|---|---|---|---|---|---|---|---|---|
| | IV | IN | IN/IV | IV | IN | IN/IV | IV | IN | IN/IV |
| Olfactory Epithelium | 0.032 | 31.649 | 1002.1 | 0.319 | 266.650 | 836.2 | 0.986 | 94.481 | 95.8 |

TABLE 12-continued

Comparison of intranasal and intravenous targeting of IgG.

| | Tissue to Blood Ratios | | | Tissue to Liver Ratios | | | Tissue to Avg Lymph Ratios | | |
|---|---|---|---|---|---|---|---|---|---|
| | IV | IN | IN/IV | IV | IN | IN/IV | IV | IN | IN/IV |
| Respiratory Epithelium | 0.030 | 9764.511 | 323269.6 | 0.305 | 82267.965 | 269754.1 | 0.943 | 29149.726 | 30898.8 |
| Anterior Trigeminal Nerve | 0.008 | 0.937 | 122.0 | 0.078 | 7.896 | 101.8 | 0.240 | 2.798 | 11.7 |
| Posterior Trigeminal Nerve | 0.005 | 0.427 | 92.8 | 0.046 | 3.600 | 77.5 | 0.144 | 1.276 | 8.9 |
| Olfactory Bulbs | 0.002 | 0.294 | 119.4 | 0.025 | 2.478 | 99.6 | 0.077 | 0.878 | 11.4 |
| Anterior Olfactory Nucleus | 0.001 | 0.105 | 73.3 | 0.014 | 0.883 | 61.2 | 0.045 | 0.313 | 7.0 |
| Frontal Cortex | 0.002 | 0.102 | 48.1 | 0.022 | 0.863 | 40.1 | 0.067 | 0.306 | 4.6 |
| Parietal Cortex | 0.002 | 0.066 | 26.9 | 0.025 | 0.556 | 22.5 | 0.077 | 0.197 | 2.6 |
| Temporal Cortex | 0.002 | 0.081 | 38.2 | 0.022 | 0.686 | 31.9 | 0.067 | 0.243 | 3.7 |
| Occipital Cortex | 0.002 | 0.130 | 78.1 | 0.017 | 1.093 | 65.2 | 0.052 | 0.387 | 7.5 |
| Extra Cortex | 0.001 | 0.073 | 54.9 | 0.013 | 0.611 | 45.8 | 0.041 | 0.217 | 5.3 |
| Amygdala | 0.001 | 0.103 | 73.5 | 0.014 | 0.867 | 61.3 | 0.044 | 0.307 | 7.0 |
| Striatum | 0.001 | 0.052 | 39.2 | 0.014 | 0.442 | 32.7 | 0.042 | 0.156 | 3.7 |
| Septal Nucleus | 0.001 | 0.065 | 48.9 | 0.013 | 0.549 | 40.8 | 0.042 | 0.194 | 4.7 |
| Hypothalamus | 0.001 | 0.120 | 80.8 | 0.015 | 1.008 | 67.4 | 0.046 | 0.357 | 7.7 |
| Thalamus | 0.001 | 0.030 | 24.7 | 0.012 | 0.254 | 20.6 | 0.038 | 0.090 | 2.4 |
| Midbrain | 0.001 | 0.049 | 37.7 | 0.013 | 0.411 | 31.4 | 0.040 | 0.146 | 3.6 |
| Hippocampus | 0.001 | 0.041 | 51.8 | 0.008 | 0.346 | 43.2 | 0.025 | 0.123 | 5.0 |
| Pons | 0.001 | 0.062 | 48.3 | 0.013 | 0.522 | 40.3 | 0.040 | 0.185 | 4.6 |
| Medulla | 0.001 | 0.062 | 47.4 | 0.013 | 0.526 | 39.5 | 0.041 | 0.186 | 4.5 |
| Cerebellum | 0.001 | 0.056 | 40.0 | 0.014 | 0.470 | 33.4 | 0.044 | 0.166 | 3.8 |
| Extra Slice #1 | 0.001 | 0.116 | 77.8 | 0.015 | 0.978 | 64.9 | 0.047 | 0.346 | 7.4 |
| Extra Slice #2 | 0.002 | 0.071 | 47.2 | 0.015 | 0.602 | 39.4 | 0.047 | 0.213 | 4.5 |
| Extra Slice #3 | 0.002 | 0.059 | 36.5 | 0.016 | 0.497 | 30.5 | 0.050 | 0.176 | 3.5 |
| Extra Slice #4 | 0.002 | 0.050 | 28.2 | 0.018 | 0.422 | 23.5 | 0.056 | 0.149 | 2.7 |
| Extra Slice #5 | 0.002 | 0.053 | 28.1 | 0.019 | 0.451 | 23.5 | 0.059 | 0.160 | 2.7 |
| Extra Slice #6 | 0.002 | 0.066 | 33.9 | 0.020 | 0.553 | 28.3 | 0.060 | 0.196 | 3.2 |
| Pituitary | 0.007 | 0.585 | 79.0 | 0.075 | 4.928 | 65.9 | 0.231 | 1.746 | 7.5 |
| Optic Chiasm | 0.004 | 0.528 | 141.8 | 0.038 | 4.450 | 118.3 | 0.116 | 1.577 | 13.6 |
| Dorsal Dura | 0.020 | 1.100 | 54.2 | 0.205 | 9.268 | 45.2 | 0.634 | 3.284 | 5.2 |
| Ventral Dura | 0.017 | 1.075 | 62.2 | 0.174 | 9.053 | 51.9 | 0.539 | 3.208 | 5.9 |
| Spinal Dura | 0.035 | 0.200 | 5.8 | 0.351 | 1.688 | 4.8 | 1.084 | 0.598 | 0.6 |
| Upper Cervical Spinal Cord | 0.001 | 0.089 | 60.3 | 0.015 | 0.749 | 50.3 | 0.046 | 0.265 | 5.8 |
| Lower Cervical Spinal Cord | 0.002 | 0.044 | 23.2 | 0.019 | 0.372 | 19.4 | 0.059 | 0.132 | 2.2 |
| Thoracic Spinal Cord | 0.001 | 0.032 | 27.7 | 0.012 | 0.269 | 23.1 | 0.036 | 0.095 | 2.6 |
| Lumbar Spinal Cord | 0.002 | 0.022 | 14.4 | 0.016 | 0.188 | 12.0 | 0.049 | 0.067 | 1.4 |
| Circle of Willis & Basilar Artery | 0.013 | 0.837 | 62.8 | 0.135 | 7.048 | 52.4 | 0.416 | 2.497 | 6.0 |
| Carotid Artery | 0.024 | 1.013 | 41.6 | 0.246 | 8.537 | 34.7 | 0.761 | 3.025 | 4.0 |
| Renal artery (L) | 0.082 | 0.315 | 3.9 | 0.825 | 2.651 | 3.2 | 2.552 | 0.939 | 0.4 |
| Superficial Nodes (2) | 0.019 | 0.341 | 18.4 | 0.187 | 2.876 | 15.3 | 0.580 | 1.019 | 1.8 |
| Cervical Nodes (2) | 0.046 | 0.398 | 8.7 | 0.465 | 3.356 | 7.2 | 1.438 | 1.189 | 0.8 |
| Axillary Nodes (2) | 0.031 | 0.265 | 8.4 | 0.318 | 2.235 | 7.0 | 0.983 | 0.792 | 0.8 |
| Blood Sample | 1.000 | 1.000 | 1.0 | 10.097 | 8.425 | 0.8 | 31.233 | 2.985 | 0.1 |
| Muscle (R, deltoid) | 0.014 | 0.190 | 13.6 | 0.142 | 1.603 | 11.3 | 0.438 | 0.568 | 1.3 |
| Liver (R, superficial lobe) | 0.099 | 0.119 | 1.2 | 1.000 | 1.000 | 1.0 | 3.093 | 0.354 | 0.1 |
| Kidney (L, tip) | 0.261 | 0.440 | 1.7 | 2.635 | 3.711 | 1.4 | 8.150 | 1.315 | 0.2 |
| Urine | 0.068 | 0.584 | 8.6 | 0.687 | 4.917 | 7.2 | 2.124 | 1.742 | 0.8 |
| Spleen (tip) | 0.168 | 0.434 | 2.6 | 1.693 | 3.658 | 2.2 | 5.236 | 1.296 | 0.2 |
| Heart | 0.046 | 0.095 | 2.0 | 0.469 | 0.803 | 1.7 | 1.452 | 0.284 | 0.2 |
| Lung (R, top lobe) | 0.192 | 0.210 | 1.1 | 1.936 | 1.769 | 0.9 | 5.990 | 0.627 | 0.1 |
| Thyroid | 0.393 | 10.607 | 27.0 | 3.963 | 89.366 | 22.5 | 12.259 | 31.665 | 2.6 |
| Esophagus | 0.021 | 0.312 | 15.1 | 0.209 | 2.627 | 12.6 | 0.645 | 0.931 | 1.4 |
| Trachea | 0.021 | 0.281 | 13.5 | 0.209 | 2.365 | 11.3 | 0.647 | 0.838 | 1.3 |

Eight rats received IV IgG liquid preparation at an average dose of 6.0 mg in 47.4 μL containing 69.5 μCi (diluted in saline to a total volume of 500 μL for injection) with a 30 min end point. Animals tolerated the IV administration well and all survived until the 30 min desired end point. One animal (BAX-3) was removed from analysis of mean, standard error, and outliers because the blood concentration was less than 20% of the value observed in all other animals, suggesting the IV infusion was not successful. Nanomolar concentrations of intravenously administered IgG liquid preparation were measured in seven rats at the 30 min end point and presented in Table 13.

TABLE 13

Tissue concentrations of intravenously administered IgG liquid preparation was measured in rats at the 30 min end point and outliers were removed.

| | BAX-5 | BAX-7 | BAX-9 | BAX-10 | BAX-11 | BAX-13 | BAX-15 | Avg | SE |
|---|---|---|---|---|---|---|---|---|---|
| Volume Delivered (μL) | 47.0 | 47.0 | 48.0 | 48.0 | 48.0 | 48.0 | 48.0 | 47.7 | ±0.2 |
| uCi Delivered | 69.7 | 69.5 | 70.5 | 70.3 | 70.1 | 68.3 | 68.3 | 69.5 | ±0.3 |
| mg Delivered | 6.0 | 6.0 | 6.0 | 6.0 | 6.0 | 5.9 | 5.9 | 6.0 | ±0.03 |
| Olfactory Epithelium | 33.0 | 40.5 | 40.4 | 43.0 | 56.5 | 32.0 | 55.5 | 43.0 | ±3.7 |
| Respiratory Epithelium | 30.4 | 33.5 | 46.7 | 39.1 | 59.5 | 29.0 | 49.4 | 41.1 | ±4.3 |
| Anterior Trigeminal Nerve | 7.4 | 14.8 | 13.5 | 10.3 | 10.1 | 7.9 | 9.2 | 10.5 | ±1.0 |
| Posterior Trigeminal Nerve | 4.2 | 11.0 | 8.3 | 6.7 | 5.4 | 3.5 | 4.8 | 6.3 | ±1.0 |
| Olfactory Bulbs | 2.2 | 2.8 | 5.5 | 3.7 | 3.2 | 1.9 | 4.2 | 3.4 | ±0.5 |
| Anterior Olfactory Nucleus | 1.1 | 2.1 | 3.3 | 1.8 | 1.9 | 1.2 | 2.2 | 1.9 | ±0.3 |
| Frontal Cortex | 2.5 | 4.0 | 3.2 | 1.8 | 2.7 | 1.2 | 4.9 | 2.9 | ±0.5 |
| Parietal Cortex | 3.3 | 5.2 | 3.0 | 1.6 | 2.6 | 1.3 | 6.4 | 3.3 | ±0.7 |
| Temporal Cortex | 1.7 | 3.7 | 2.5 | 2.2 | 5.8 | 1.5 | X | 2.9 | ±0.7 |
| Occipital Cortex | 1.9 | 2.8 | 2.5 | 2.3 | X | 1.8 | X | 2.3 | ±0.2 |
| Extra Cortex | 1.4 | 2.1 | 2.6 | 1.8 | X | 1.1 | X | 1.8 | ±0.3 |
| Amygdala | 1.5 | 1.9 | X | 2.1 | 2.0 | 1.8 | 2.2 | 1.9 | ±0.1 |
| Striatum | 2.4 | 1.6 | 1.6 | 1.3 | 1.5 | 1.8 | 2.6 | 1.8 | ±0.2 |
| Septal Nucleus | 1.6 | 1.4 | 2.0 | 1.6 | X | 2.0 | 2.2 | 1.8 | ±0.1 |
| Hypothalamus | 1.2 | 2.4 | 2.7 | 1.7 | 1.9 | 1.5 | 2.7 | 2.0 | ±0.2 |
| Thalamus | 1.2 | 1.3 | 1.8 | 1.3 | 2.1 | 0.9 | 3.1 | 1.7 | ±0.3 |
| Midbrain | 1.1 | 1.4 | 2.3 | 1.3 | 2.2 | 1.1 | 2.9 | 1.8 | ±0.3 |
| Hippocampus | 1.1 | 1.3 | 0.6 | 1.3 | X | 1.1 | X | 1.1 | ±0.1 |
| Pons | 1.1 | 1.6 | 2.4 | 1.4 | 1.6 | 1.3 | 2.8 | 1.7 | ±0.2 |
| Medulla | 1.2 | 1.4 | 2.7 | 1.5 | X | 1.2 | 2.7 | 1.8 | ±0.3 |
| Cerebellum | 1.3 | 1.7 | 2.5 | 1.8 | 2.9 | 1.2 | X | 1.9 | ±0.3 |
| Extra Slice #1 | 1.5 | 2.8 | 2.7 | 1.7 | 2.2 | 1.3 | 2.1 | 2.0 | ±0.2 |
| Extra Slice #2 | 1.6 | 3.6 | 2.2 | 1.4 | 1.8 | 1.2 | 2.7 | 2.1 | ±0.3 |
| Extra Slice #3 | 1.9 | 3.3 | 2.1 | 1.4 | 2.0 | 1.1 | 3.6 | 2.2 | ±0.3 |
| Extra Slice #4 | 1.9 | 3.1 | 2.5 | 1.4 | 2.6 | 1.1 | 4.3 | 2.4 | ±0.4 |
| Extra Slice #5 | 1.7 | 3.0 | 2.1 | 1.5 | 3.4 | 1.1 | 5.3 | 2.6 | ±0.6 |
| Extra Slice #6 | 1.9 | 2.4 | 2.2 | 1.6 | 3.9 | 1.3 | 5.3 | 2.6 | ±0.5 |
| Pituitary | 10.9 | X | 12.7 | 9.4 | 8.7 | 7.1 | 11.8 | 10.1 | ±0.8 |
| Optic Chiasm | 5.9 | 5.2 | 8.4 | 3.9 | 4.7 | 2.9 | 4.6 | 5.1 | ±0.7 |
| Dorsal Dura | 14.8 | 31.7 | 30.7 | 31.0 | 29.5 | 18.2 | 37.4 | 27.6 | ±3.0 |
| Ventral Dura | 16.4 | 31.0 | 34.4 | 19.6 | 18.9 | 13.8 | 30.4 | 23.5 | ±3.1 |
| Spinal Dura | 52.3 | 45.9 | 54.8 | 37.6 | X | 53.4 | 39.5 | 47.2 | ±3.0 |
| Upper Cervical Spinal Cord | 1.4 | 2.3 | 2.7 | 1.8 | 2.1 | 1.7 | 2.0 | 2.0 | ±0.2 |
| Lower Cervical Spinal Cord | 2.5 | 2.5 | 3.7 | 3.4 | 1.4 | 2.4 | 2.2 | 2.6 | ±0.3 |
| Thoracic Spinal Cord | 1.6 | 1.9 | 2.8 | 1.1 | 1.0 | 1.2 | 1.3 | 1.6 | ±0.2 |
| Lumbar Spinal Cord | 2.8 | 1.8 | 2.5 | 2.0 | 1.3 | 1.3 | 3.1 | 2.1 | ±0.3 |
| Circle of Willis & Basilar Artery | 16.8 | 23.8 | X | 14.2 | 15.7 | 9.9 | 28.4 | 18.1 | ±2.8 |
| Carotid Artery | 21.7 | 33.8 | 37.2 | 37.5 | 37.4 | 43.9 | 20.6 | 33.2 | ±3.3 |
| Renal artery (L) | 98.8 | 129.2 | 76.5 | 94.4 | 129.3 | 139.0 | X | 111.2 | ±10.1 |
| Superficial Nodes (2) | 20.3 | 29.6 | 22.9 | 31.9 | 35.3 | 12.6 | 24.1 | 25.3 | ±2.9 |
| Cervical Nodes (2) | 32.5 | 39.6 | 78.7 | 43.4 | 83.9 | 65.5 | 94.9 | 62.6 | ±9.2 |
| Axillary Nodes (2) | 103.2 | 31.9 | 75.4 | 18.6 | 37.9 | 14.1 | 18.6 | 42.8 | ±12.8 |
| Blood Sample | 1,224.9 | 1,234.2 | 1,543.3 | 1,322.6 | 1,364.7 | 1,413.4 | 1,422.9 | 1,360.9 | ±42.5 |
| Muscle (R, deltoid) | 39.06 | 19.5 | 24.6 | 13.3 | 13.0 | 10.7 | 13.4 | 19.1 | ±3.8 |
| Liver (R, superficial lobe) | 74.2 | 72.2 | 115.0 | 126.1 | 122.2 | 186.3 | 247.5 | 134.8 | ±23.7 |
| Kidney (L, tip) | 347.7 | 313.9 | 287.3 | 459.1 | 397.7 | 441.0 | 238.9 | 355.1 | ±30.8 |
| Urine | 32.9 | 174.5 | 187.3 | 41.1 | 68.3 | 122.8 | 21.1 | 92.6 | ±26.0 |
| Spleen (tip) | 234.3 | 241.9 | 196.8 | 317.5 | 232.6 | 175.8 | 198.1 | 228.1 | ±17.5 |
| Heart | 57.7 | 42.1 | 87.5 | 53.5 | 44.2 | 35.6 | 122.1 | 63.2 | ±11.7 |
| Lung (R, top lobe) | 392.8 | 289.6 | 219.1 | 104.5 | 482.5 | 177.0 | 161.4 | 261.0 | ±51.3 |
| Thyroid | 317.8 | 651.8 | 832.2 | 522.9 | 545.5 | 372.0 | 496.9 | 534.2 | ±65.0 |

TABLE 13-continued

Tissue concentrations of intravenously administered IgG liquid preparation
was measured in rats at the 30 min end point and outliers were removed.

|  | BAX-5 | BAX-7 | BAX-9 | BAX-10 | BAX-11 | BAX-13 | BAX-15 | Avg | SE |
|---|---|---|---|---|---|---|---|---|---|
| Esophagus | 24.8 | 41.3 | 28.0 | 42.8 | 24.4 | 20.5 | 15.1 | 28.1 | ±3.9 |
| Trachea | 14.6 | 29.2 | 17.9 | 39.2 | 13.4 | 59.0 | 24.2 | 28.2 | ±6.2 |
| Drug Standard CPM | 7,378,277 | 7,493,218 | 7,635,815 | 7,367,611 | 7,809,027 | 6,770,035 | 7,683,717 | 7,448,243 | ±128,561.8 |
| Drug Standard CPM | 7,962,330 | 7,709,707 | 6,369,627 | — | 6,846,596 | 6,401,005 | 7,249,509 | 7,089,796 | ±272,233.7 |
| Drug Standard CPM | 7,947,735 | 8,077,594 | — | — | 6,447,049 | 6,626,261 | 7,855,283 | 7,390,784 | ±351,624.3 |

X = outlier removed from analysis

The blood concentration of IgG at the 30 min end point was 1,361 nM. Concentrations of IgG in the respiratory and olfactory epithelia were low as expected (43 nM and 41 nM respectively). A rostral to caudal gradient of 10.5 nM to 6.3 nM IgG was observed in the trigeminal nerve. A similar gradient from the olfactory bulb to the anterior olfactory nucleus of 3.4 nM to 1.9 nM IgG was observed. The average cortex concentration of IgG after IV administration was 2.6 nM. Concentrations of IgG in other brain regions ranged from a low of 1.1 nM in the hippocampus to a high of 2.0 nM in the hypothalamus. The average concentration of IgG in the extra brain material sampled was 2.3 nM, similar to the average cortex concentration, and a concentration gradient was not observed. Similarly, a concentration gradient was not observed in the spinal cord and the average IgG concentration was 2.1 nM. The average concentration of IgG in the dura of the brain was 25.6 nM compared to a spinal cord dura concentration of 47.2 nM. Other tissues sampled from the ventral skull, the pituitary and optic chiasm, contained 10.1 nM and 5.1 nM IgG respectively.

Concentrations of IgG in peripheral organs ranged from a low of 19.1 nM in the muscle to a high of 355.1 in the kidney, with urine containing 92.6 nM. IgG concentrations in basilar and carotid arteries were considerably lower than the renal artery (18.1 and 33.2 nM versus 111.2 nM). Average concentration of IgG in the sampled lymph nodes was 43.6 nM.

Example 3

The Effect of IN and IV Delivery on the Intactness of IgG

A study was conducted to examine whether IgG remains intact after IN and IV administration. Specifically, rats were administered $^{125}$I radiolabeled IgG either intranasally or intravenously and the total intact and degraded IgG was determined 30 min after administration.

Experimental Design: The rats were anesthetized and IgG was administered as described above in Example 2. Blood and brain was sampled and intact IgG was detected.

Blood was sampled approximately 30 minutes after intranasal administration prior to perfusing with at least 100 mL of saline containing protease inhibitors and serum was processed.

Each blood sample (1.0 mL) was added to glass/tissue homogenizer containing 2.0 mL of homogenization buffer (H.B., 10 mM tris buffer, pH 8.0 containing protease inhibitors) and aprotinin (100 μL per mL blood). The sample was manually homogenized (30 passes) and then transferred into a pre-weighed conical tube (15 mL) and stored on ice. Triplicate 25 μL samples were removed for gamma counting.

The sample was centrifuged at 1,000×g (3,160 rpm) for 10 minutes at 4° C. Blood supernatant was removed into a pre-weighed ultracentrifuge tube and stored on ice. The extraction procedure was repeated on the blood pellet a second time (i.e. same volume of homogenization buffer added to conical test tube containing pellet, inverted several times to dislodge the pellet, transferred into glass homogenizer, homogenized with 15 passes, transferred to same pre-weighed conical test tube, centrifuged, and blood supernatant removed). All blood supernatant was pooled and stored in the same pre-weighed conical tube. The extraction procedure was repeated on the blood pellet a third time. Triplicate 25 μL samples from pooled blood supernatant were remove for gamma counting.

2 mL of the pooled blood supernatant was ultracentrifuged at 5,000×g (7,071 rpm) for 90 minutes at 4° C. to in a 100 kDa filter tube. After the first two rats, it was found that 2 mL took a lot of time to filter so for and animals that followed, we centrifuged only 1 mL of the pooled blood supernatant. At the same time, 2 mL of the pooled blood supernatant in the ultracentrifuged at 5,000×g (7,071 rpm) for 90 minutes at 4° C. to in a 30 kDa filter tube. After the first two rats, it was found that 2 mL took a lot of time to filter so for and animals that followed, only 1 mL of the pooled blood supernatant was centrifuged.

And 2 mL of the pooled blood supernatant was ultracentrifuged at 5,000×g (7,071 rpm) for 90 minutes at 4° C. to in a 10 kDa filter tube. After the first two rats, it was found that 2 mL took a lot of time to filter, for subsequent animals only 1 mL of the pooled blood supernatant was centrifuged. Triplicate 25 μL samples were removed for gamma counting from the filtrate (100 kDa filter tube), the retentate (100 kDa filter tube), the filtrate (30 kDa filter tube), the retentate (30 kDa filter tube), the filtrate (10 kDa filter tube) for gamma counting, the retentate (10 kDa filter tube) for gamma counting.

Each brain was removed (on ice), weighed, and placed into a glass tissue homogenizer. the brain was manually homogenized (40-50 passes) with homogenization buffer at a 1:3 dilution (i.e., 2 mL buffer per g wet brain) and the homogenate was transferred into a pre-weighed conical tube (15 mL) and stored on ice. Triplicate 25 μL samples from brain homogenate were removed for gamma counting. The sample was centrifuged at 1,000×g (3,160 rpm) for 10 minutes at 4° C. Brain supernatant was removed into pre-weighed ultracentrifuge tube and stored on ice.

The extraction procedure was repeated a second time on the pellet (i.e., added same volume of homogenization buffer to conical test tube containing pellet, inverted several times to dislodge the pellet, transferred into glass homogenizer, homogenized with 20-30 passes, transferred to same pre-weighed conical test tube, centrifuged, and removed supernatant). All brain supernatant was pooled and stored in the same pre-weighed conical tube. The extraction procedure was repeated a third time on the pellets. Triplicate 25 μL samples from pooled brain supernatant were removed for gamma counting.

2 mL of the pooled brain supernatant was ultracentrifuged at 5,000×g (7,071 rpm) for 90 minutes at 4° C. to in a 100 kDa filter tube. After the first two rats, it was found that 2 mL took a lot of time to filter, for subsequent animals only 1 mL of the pooled blood supernatant was centrifuged. At the same time, 2 mL of the pooled brain supernatant in the ultracentrifuged at 5,000×g (7,071 rpm) for 90 minutes at 4° C. to in a 30 kDa filter tube. After the first two rats, it was found that 2 mL took a lot of time to filter, for subsequent animals only 1 mL of the pooled blood supernatant was centrifuged. And 2 mL of the pooled brain supernatant was ultracentrifuged at 5,000×g (7,071 rpm) for 90 minutes at 4° C. to in a 10 kDa filter tube. After the first two rats, it was found that 2 mL took a lot of time to filter, for subsequent animals only 1 mL of the pooled blood supernatant was centrifuged.

Triplicate 25 μL samples were removed for gamma counting from the filtrate (100 kDa filter tube), the retentate (100 kDa filter tube), the filtrate (30 kDa filter tube), the retentate (30 kDa filter tube), the filtrate (10 kDa filter tube) for gamma counting, the retentate (10 kDa filter tube) for gamma counting.

Results: Two rats received IV IgG liquid preparation and two rats received IN IgG liquid preparation at an average dose of 52 μL containing 56 μCi (diluted in saline to a total volume of 500 μL for IV injection) with a 30 min end point. Animals tolerated the administration well and all survived until the 30 min desired end point.

In the brain, approximately 80% of gamma counts from $^{125}$I-labeled IgG after both IN and IV delivery were greater than 100 kD, suggesting intact protein. In the blood, 100% gamma counts from $^{125}$I-labeled IgG after IV delivery were greater than 100 kD, suggesting all was intact. With IN delivery, only 33% of gamma counts from $^{125}$I-labeled IgG found in blood was greater than 100 kD, suggesting that $^{125}$I-labeled IgG may be broken down and enter the blood as part of the clearance process from the nasal cavity, the brain or both. This also provides additional evidence that IgG entering the CNS after IN administration does not travel from the nasal cavity to the blood to the brain, but rather along direct pathways involving the olfactory and trigeminal nerves. A summary of the intactness of IgG in the brain and blood after intranasal or intravenous administration is presented in Table 14.

TABLE 14

Summary of Intactness of IgG in the Brain and Blood.

| | IN | | | IV | | |
|---|---|---|---|---|---|---|
| | R1 | R3 | Avg | R2 | R4 | Avg |
| BLOOD | | | | | | |
| % greater than 100 kD | 30 | 36 | 33 | 123 | 113 | 118 |
| % greater than 30 kD | 34 | 34 | 34 | 123 | 110 | 116 |
| % greater than 10 kD | 67 | 57 | 62 | 99 | 108 | 104 |
| BRAIN | | | | | | |
| % greater than 100 kD | 93 | 70 | 81 | 78 | 77 | 77 |
| % greater than 30 kD | 87 | 78 | 82 | 83 | 84 | 83 |
| % greater than 10 kD | 88 | 78 | 83 | 88 | 93 | 91 |

Example 4

Effect of Intranasal Administration of IgG on Amyloid Plaque Loads

A study was conducted to examine whether intranasal administration of IgG decreases amyloid plaque loads in the brain in vivo. The purpose of the study was to determine whether chronic treatment with intranasally delivered IgG at two doses (0.4 g/kg/2 wk and 0.8 g/kg/2 wk) would have any effect on the amyloid plaque load in a transgenic amyloid mouse model of Alzheimer's disease.

Experimental Design: The TG2576 ("TG") amyloid mouse model was used in this study as a mouse model for Alzheimer's disease and C57 mice were used as controls. TG2576 mice (cat. #1349-RD1-M) were acquired from Taconic, Inc. in two batches of 50 spaced one month apart (Batch 1 and Batch 2). Animals were individually housed with free access to food and water, and were kept on a 12 hour light cycle. For dosing with drug in a mg/kg dosing scheme, mice were divided into three size classes within each treatment group, small, medium, and large. Size groups were made to include ⅓ of animals in each size group. Mice were re-evaluated to make new size groups every two weeks. The mice were divided into five treatment groups of 20 mice as described in Table 15.

TABLE 15

Treatment groups assigned for intranasal administration of IgG.

| Mouse Strain | Drug Administration | Description |
|---|---|---|
| Tg2576 | IN IgG 0.4 g/kg/2 wk | "TG-High" |
| Tg2576 | IN IgG 0.8 g/kg/2 wk | "TG-Low" |
| Tg2576 | IN Saline (control) | "TG-Saline" |
| C57 | IN IgG 0.8 g/kg/2 wk | "WT-High" |
| C57 | IN Saline (control) | "WT-Saline" |

The mice were ordered and received in the animal facility at 2 months of age and were singly housed and aged for 6 months. At 8 months of age, the mice were acclimated to handling for awake intranasal delivery over the course of 1 month. Mice were then intranasally treated with IgG or saline three times/week for 7 months. At 16 months of age, behavioral testing occurred for 5 weeks while intranasal treatment continued. At ~17 months of age, 12 mice/group were euthanized and brain tissue was collected for analysis.

IgG and saline for IN delivery was prepared Friday afternoons from stocks sent by Baxter, and stored at ~4° C. for use the following week. Solutions were made to deliver a dose of either 0.4 mg/kg/2 wk IgG or 0.8 mg/kg/2 wk IgG, and were made to deliver a total of 24 μL. Drug was also made to cater to each of the three size classes within a treatment group.

Mice were acclimated to handling for a period of two-four weeks before the onset of intranasal dosing. Acclimation to handling was important, as it helped ensure a correct body position for maximum effectiveness of awake intranasal drug delivery. In addition, mice that have not been properly accustomed to this process can have a severe anxiety reaction after dosing. Mice spent about 1-3 days on each of nine steps before progressing to the next step, depending upon the animal's comfort to handling. The mouse's stress level was used as a measure of progress. This means monitoring the mouse's movements, the amount/frequency of urination, defecation, trembling, and biting. If a mouse had a high stress response, it remained on that step before progressing to the next until the response is reduced. A sample acclimation schedule can be seen in Table 16. Acclimation of the mice progressed through the following once-a-day steps. The steps were not performed more than once per day in order to minimize the anxiety in the mice.

First, the mouse was placed in the palm of the hand for a period of two to three minutes, no more than one foot above the cage top, as animals frequently jumped during this introductory step. If the mouse attempted to crawl out of the hand and up one's arm, the mouse was lifted by the base of the tail and placed back in one's hand. Second, the mouse was placed in the palm of the hand for three minutes and petted gently. The mouse was petted directionally from head to tail, while allowing the animal to move about freely. Third, the mouse was placed in the palm of the hand for three minutes while massaging behind the ears (lightly pinching together the skin on the back of the neck using the thumb and pointer finger). Fourth, the mouse was held/lifted by the scruff of its neck for 30 seconds, letting the mouse rest on the cage top for 30 seconds before repeating the hold again. Fifth, the mouse was held using the intranasal grip, without inverting the animal, for a period of 30 seconds and then released back to the cage top. This was repeated a second time after a one-minute rest period. Sixth, the mouse was held with the intranasal grip while inverting the animal so its ventral side was facing up towards the ceiling with the animal's neck is parallel to the floor. This position was held for 30 seconds and was then repeated a second time after a one-minute rest period. If the mouse freed itself from the grip, the mouse was put back on the cage top and re-gripped. If the mouse's stress level increased too much, the mouse was returned it to the cage. Seventh, the mouse was held with the intranasal grip, inverted and a pipettor with an empty tip was briefly placed over each nostril for 30 seconds. This step was repeated after a one-minute rest period. Eighth, the mouse was held with the intranasal grip, inverted, and intranasally administered 6 μl of saline into the left and right nare. Ninth, the mouse was held with the intranasal grip, inverted, and intranasally administered 6 μl of saline into the left and right nare twice placing the animal back on the cage top in between.

TABLE 16

Sample schedule for acclimation to awake IN drug delivery.

| Day # | Day | Action |
| --- | --- | --- |
| 1 | M | Hold for ~2-3 min |
| 2 | Tu | Hold for ~2-3 min |

TABLE 16-continued

Sample schedule for acclimation to awake IN drug delivery.

| Day # | Day | Action |
| --- | --- | --- |
| 3 | W | Hold and pet ~2-3 min |
| 4 | Th | Hold and pet ~2-3 min |
| 5 | F | Lightly pinch/scruff |
| 6 | M | Lightly pinch/scruff |
| 7 | Tu | Scruff and lift |
| 8 | W | Scruff and lift |
| 9 | Th | Intranasal Grip |
| 10 | F | Intranasal Grip |
| 11 | M | Intranasal (IN) Grip and Invert |
| 12 | Tu | Intranasal (IN) Grip and Invert |
| 13 | W | IN Grip, Invert, empty pipette tip |
| 14 | Th | IN Grip, Invert, empty pipette tip |
| 15 | F | IN Grip, Invert, deliver 1 round saline to each nare |
| 16 | M | IN Grip, Invert, deliver 1 round saline to each nare |
| 17 | Tu | IN Grip, Invert, deliver 2 rounds saline to each nare |
| 18 | W | IN Grip, Invert, deliver 2 rounds saline to each nare |

For awake intranasal delivery of drug, the intranasal grip, each mouse was restrained twice and held with their necks parallel to the floor while a volume of 24 μl of liquid was administered. Specifically, un-anesthetized mice were grabbed by the scruff of their necks and held gently, but firmly, in an inverted position so that the mouse cannot move around. Each mouse was given four 6 μl nose drops (alternating nares) using a 20-μl pipettor. Intranasal drug delivery began when mice were 9 months of age.

At 16 months of age, mice were subjected to a five week battery of behavioral tests to assess for memory, sensorimotor, and anxiolytic changes. These included Morris water maze hidden and visual platform tests (reference memory, visual ability), radial arm water maze (working memory), passive avoidance task (memory), Barnes maze (memory), open field test (exploratory behavior), elevated plus maze (anxiety), and rotarod (motor skills).

After behavior, 12 mice from each treatment group were euthanized and their brains collected for biochemical analyses. These analyses include immunohistochemistry (IHC) for amyloid plaques, inflammatory markers, and soluble and insoluble amyloid.

Prior to euthanasia via transcardial perfusion, mice were anesthetized with sodium pentobarbital (60 mg/kg diluted 1:4 with sterile saline). A first booster of half the full dose was given followed by additional quarter-dose boosters, if necessary. The level of anesthesia and sensitivity to pain was monitored every five minutes throughout the procedure by testing reflexes including pinching the hind paw and tail. Mice were then euthanized with transcardial perfusion with 15 ml ice cold saline (no protease inhibitor needed) and blood was collected from the heart. Briefly, the arms of the mouse were taped down. The skin was cut to expose the sternum. A hemostat was used to hold the sternum while blunt dissection scissors were used to cut vertically on both sides of the sternum making an incision with a V-shape to expose the heart. Blood was collected from the heart prior to perfusion and processed into serum. A small hole in the left ventricle was made using a 24-gauge cannula. The cannula was inserted into the aorta and held in place. Extension tubing (filled with 5 mL of 0.9% NaCl) was attached to the cannula and the animal was manually perfused with 15 ml saline.

Blood was spun down and serum divided into two aliquots. One aliquot was 50 μL and will be eventually pooled and sent for analyses of overall health of the treatment group. The remaining serum was placed into its own tube and snap frozen for other analyses.

The brain was collected and hemisected sagitally in a mouse brain matrix. The left half of the brain was dissected into olfactory bulbs, cortex/hippocampus mix, septum, midbrain/diencephalon, brainstem (down to the V of the upper cervical spinal cord), and cerebellum. These tissues were placed into microcentrifuge tube and snap frozen in liquid nitrogen. The right half was left in the matrix and sliced 3 mm from the centerline. The inner portion towards the center of the brain was post-fixed in formalin (in a 15 ml conical tube filled with 10 ml formalin) and sliced for IHC analyses. The outer portion was snap frozen in liquid nitrogen for eventual analysis for inflammation.

The medial 3 mm sagittal section of the right half of the mouse brain was fixed by placing them each into 20 mL of 10% formalin. These samples were fixed for several hours at room temperature and then overnight at 4° C. on slow moving rocker. The fixed sagittal brain sections were placed medial side down into labeled pathology cassettes. The pathology department at Region's Hospital conducted the paraffin processing and embedding (dehydrate, infiltrate with paraffin, mount into paraffin blocks). The paraffin blocks were blinded by coding/relabeling.

The paraffin blocks were sectioned at a thickness of 5 µm using the Leica RM2235 microtome and collected on Superfrost Plus microscope slides (Cardinal Health, cat# M6146-PLUS). Seven sections were collected per mouse, with at least/approximately 100 µm of tissue removed between tissue section collections (labeled 1-6 from, medial to lateral). To increase the quality of the sections to be stained, a dissection microscope was used to identify and remove one of the seven sections.

Slides were deparaffinized and hydrated. Specifically, the slides were placed in a glass staining jar rack for easy transfer between staining dishes. The paraffin wax was removed with xylene washes (clearing) and then hydrated with ethanol/water. Specifically, the slides were washed in xylene three times for five minute intervals, washed in 100% ethanol two times for five minute intervals, washed in 95% ethanol one time for five minutes, rinsed in running water for five minutes, and rinsed in PBS for five minutes.

Heat induced epitope retrieval (HIER) was used to pretreat the slides prior to antibody staining A Tris/EDTA Buffer (pH 9) was used. The slides were immersed in a steamer proof dish containing the Target Retrieval Solution (Tris/EDTA pH 9) pre-warmed to 70° C. The dish with slides was then placed in the steamer and incubate for 30 minutes at 97° C. The steamer was turned off and allowed to cool to at least 65° C. The container of slides was removed from the steamer and allowed to cool for another 10-15 minutes. The slides were then removed from the container and rinsed in PBS for 10 min in a coplan jar.

Non-specific binding sites were then blocked with normal serum blocking solution (300 µL/slide) for 1 hour in a humidity chamber. Sections were incubated in a humid box with primary antibody against amyloid (purified Anti-Beta-Amyloid, 17-24 (4G8) Monoclonal Antibody, from Covance (SIG-39220)) at a 1:200 dilution in primary antibody dilution buffer (0.01 M PBS pH 7.2) for 1 hour at room temperature. Sections were incubated in secondary antibody (Goat anti-mouse IgG, Alexa Fluor 647 (2 mg/ml) from Invitrogen (A21235)) dilution buffer (0.01 M PBS, pH 7.2) with a 1:200 secondary concentration for 1 hr at room temperature.

Slides were then counterstained with DAPI. Diluted 300 nM DAPI in PBS was used. 1 µl of 14.3 mM DAPI stock was diluted into 48 ml PBS, vortexed, and mix thoroughly. The DAPI solution was poured into coplan jar containing the slides. The slides were incubate for 20 min at RT. The slides were rinsed quickly in PBS, then 2×10 min in washing buffer, followed by a 10 min incubation in PBS.

Immediately after staining, the slides were then dehydrated, cleared, and mounted. Specifically, the slides were incubated in 95% ethanol for 5 minutes, 100% ethanol for two five minute increments, xylene for three five minute increments, and mounted with a coverslip in DPX without letting the specimen dry. The mounted slides were stored at room temperature.

Images of the fluorescently stained plaques were captured with the AZ100 Multizoom Macroscope with the C1si Spectral Confocal attachment and an AZ Plan Apo 4× objective. Initial localization and focusing of the hippocampus and cortex was conducted through epifluorescence imaging using filters for the DAPI stain. The scope was then switched to confocal imaging using the 637 nm laser for acquisition of the IHF-labeled amyloid. Fine tuning within the z-axis for optimal signal detection was confirmed with a 512×512 pixel resolution. Images were then captured at 1024×1024 with the Nikon EZ-C1 software and the raw image files were saved in Nikon's ".ids" file format. Corresponding tiff files of the 637 nm channel were generated using Fiji (ImageJ). The tiff files were then converted to 8-bit images (from 16-bit) and the contrast was enhanced by 0.5% through batch processing (Macro programming) in Fiji (ImageJ).

Plaques were quantitated in selected regions of interest in the hippocampus and cortex by determining the average number of plaques detected in each region and by determining the percent area covered by plaques within each region. Image processing and analysis was conducted in Fiji. Plaques were defined within Fiji by using the particle analysis and the threshold function to select a minimum pixel value that defined each identified particle as qualifying as a plaque. These values were determined by analyzing multiple positive and negative controls and verifying which values correctly identified the plaques in these control slides. The region of interest within each image was chosen by a blinded researcher who was instructed to place the region of interest in the position that would maximize the inclusion of plaques. The size (pixels) and number of plaques identified were copied into excel for data analysis. The plaques were then characterized by their relative size. The plaque sizes reported in this study refer to the calculated radius of a plaque assuming the particle conformed to the shape of a perfect circle. The number of plaques and percent area covered by plaques calculated from each region of interest was used as a single data point in comparing the treatment groups. Two tailed t-tests were used to assess the significance between groups.

Prior to staining the complete set of collected tissue sections, an initial verification of the staining and microscopy analysis was conducted with relevant staining controls. These controls included, a positive control using sections from one of the transgenic mice receiving saline, negative controls in which either the primary or secondary antibody incubation was omitted from the staining procedure and a negative control using sections from one of the wild-type mice receiving saline. Additional controls, including the titration of primary and secondary antibodies and the comparison of different epitope retrieval methods have been conducted previously in our lab using these antibodies and the same experimental procedure.

Tissue supernatants were analyzed using kits from Life Technologies (formerly Invitrogen; Carlsbad, Calif.; part #s KHB3482 (Aβ40) and KHB3442 (Aβ42)). Generally, the proper dilutions were first determined with three samples from either TG or WT mice, and then all samples were run at that dilution. Samples were quantified using a polynomial equation fit to a standard curve. Quantities of AB measured in the wells were then corrected for dilutions and total protein (as determined by a BCA assay).

Results: Immunohistochemical measurement of amyloid plaques in brain tissue slices demonstrated that there was a significant drug effect. Both groups of TG mice administered IgG intranasally had significantly decreased plaque loads in the cortex (FIGS. 3A, 3B, and 3E).

Figure 3A:
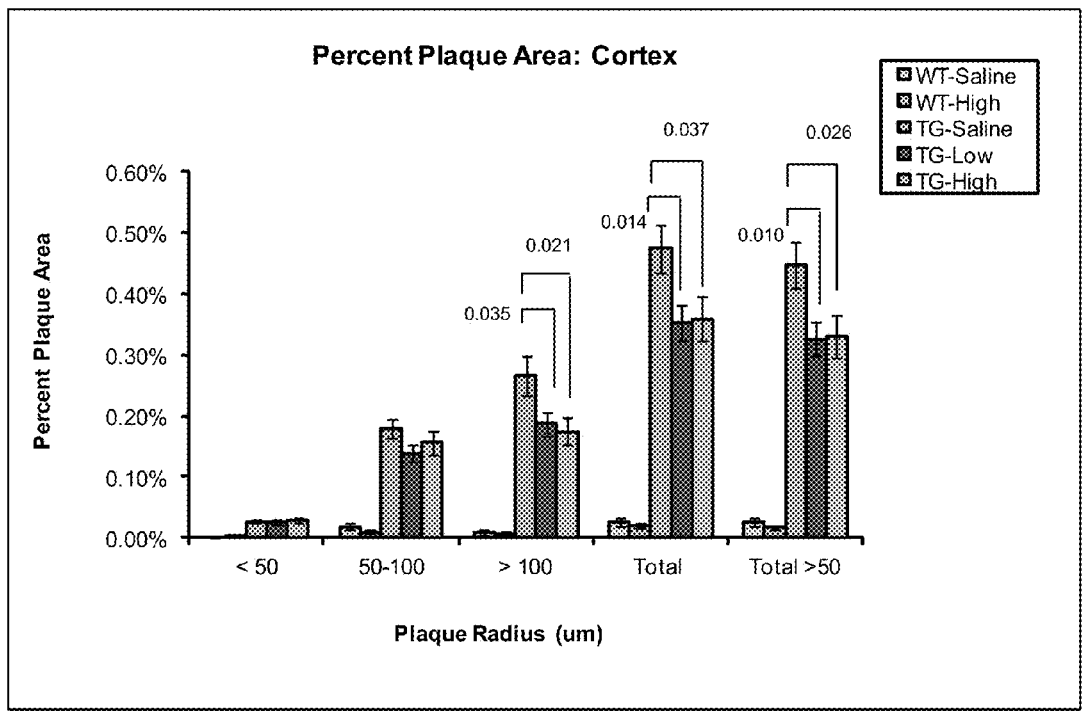
FIGS. 3A-3E illustrate IHC data on cortical and hippocampal brain slices. Plaque content was determined for 12 mice from each cohort (WT-Saline, WT-High, TG-Saline, TG-Low, and TG-High; shown left to right in the charts, respectively).

Nasal administration of both the low dose and high dose of IgG significantly reduced the total percent area covered by plaques in the cortex of TG2576 mice (FIG. 3A). The percent area covered by plaques decreased by 25.7% (low dose; p=0.014) and 24.3%, (high dose; p=0.037), respectively. The change in the percent area covered by plaques was slightly more pronounced at 27.1% for the low dose and 26.0% for the high dose when the minimum threshold for defining a plaque was increased from a radius of 25 μm to 50 μm (p values of 0.01 and 0.026, respectively). The decrease in plaque load was also found to be significant when the minimum threshold was set at 100 μm (p values of 0.035 and 0.021, respectively). A change in the percent area covered by plaques was not apparent when the smaller plaques (less than 50 μm radius) were used exclusively in the analysis. Thus, plaque reduction in the cortex appears to be more pronounced plaques larger than 50 μm.

Figure 3B:
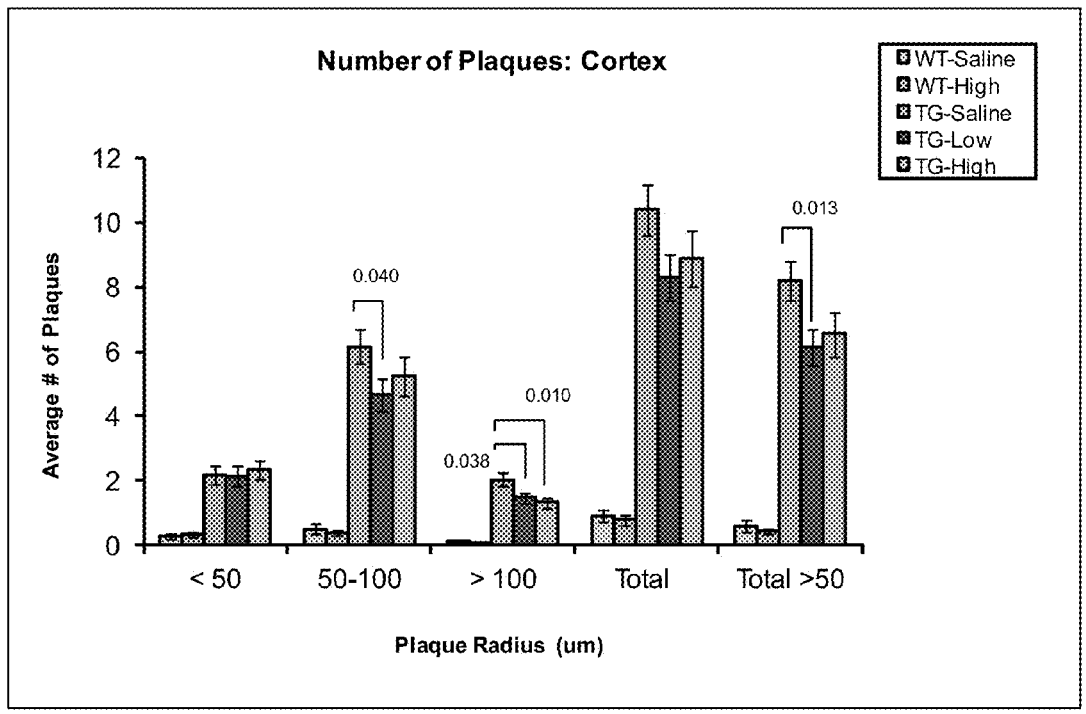

The number of plaques in the cortex of both low dose and high dose IgG treatment groups showed a trend toward a decrease in the numbers of plaques detected (FIG. 3B). This decrease reached significance in the low dose IgG treatment group when small plaques (less than 50 μm radius) were not included in the analysis. Specifically, treatment with intranasally administered IgG provided a significant reduction in plaque load when the data were analyzed by inclusion of plaques having a radius of from 50 μm to 100 μm, greater than 100 μm, and greater than 50 μm. The decrease in plaque load reached significance for the high dose IgG treatment group when the radius of analyzed plaques was set at greater than 100 μm.

Figure 3C:
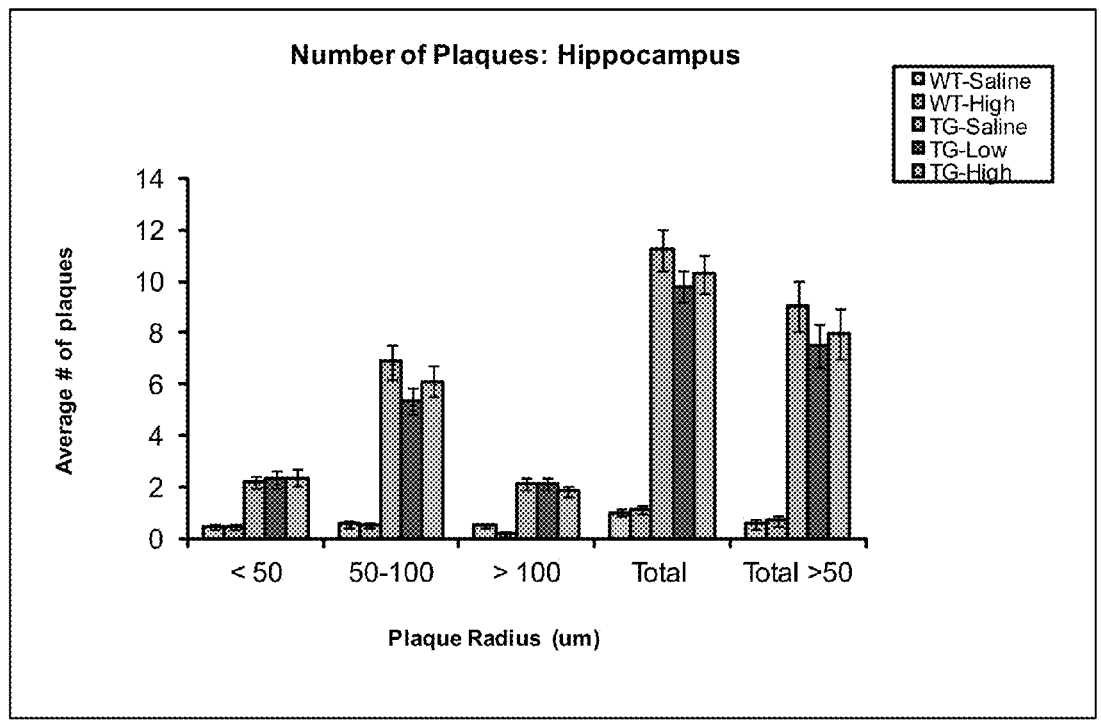
Figure 3D:
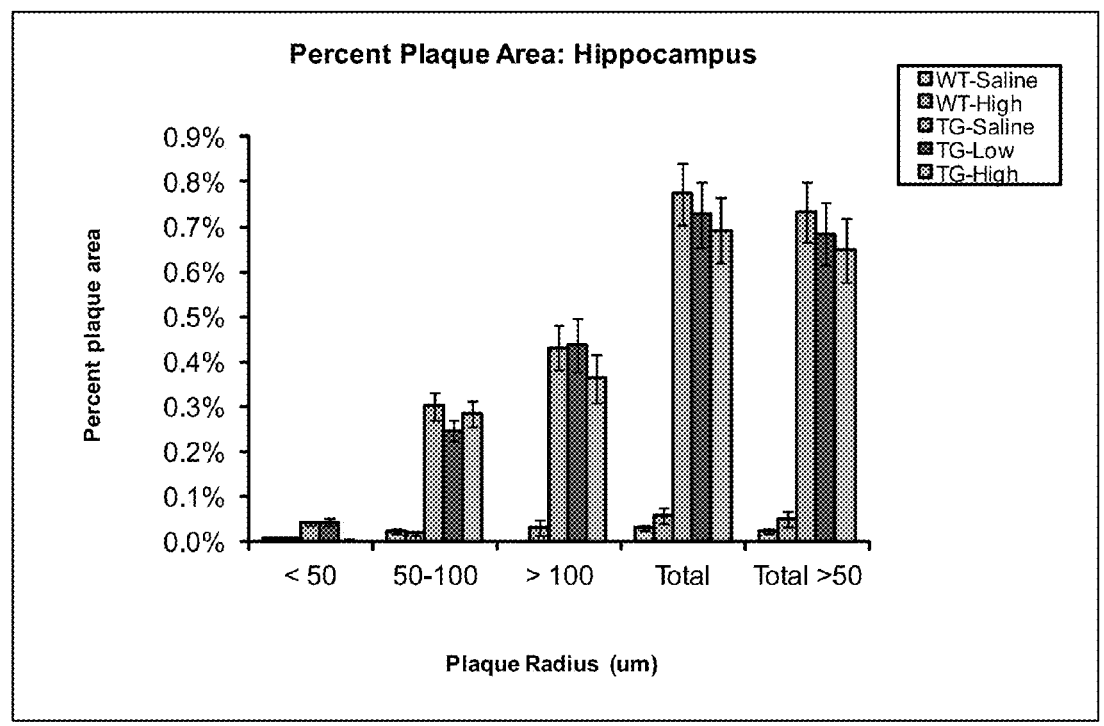
Figure 3E:
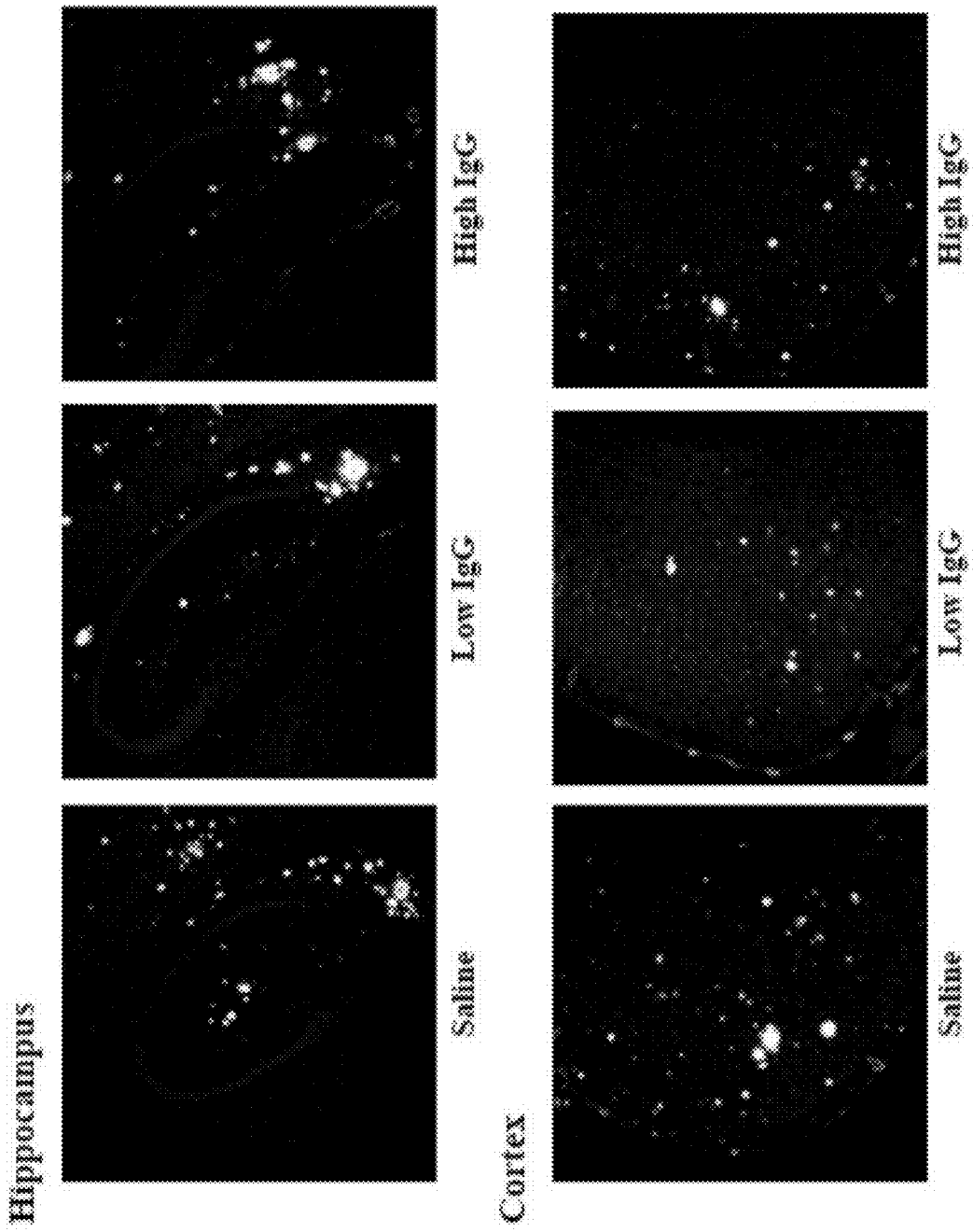

In contrast to the results seen in the brain cortex, IgG treatments did not result in a significant change in either the percent area covered by plaques or the numbers of plaques detected in the hippocampus (FIGS. 3C and 3D). Although intranasal administration of both low and high dose IgG appeared to result in a slightly reduced plaque load in the hippocampus, the reduction was minimal and did not reach significance in this region of the brain.

Immunofluorescent staining of amyloid plaques in the hippocampus and cortex of aged TG mice is depicted in FIG. 3E. As show, there is a decrease staining for amyloid plaques in the hippocampus and cortex in mice that were treated with low and high IgG doses compared to TG mice treated with saline.

Example 5

Effect of Intranasally Administered IgG on Soluble and Insoluble AB40 and AB42

A study was conducted to assess the efficacy of chronic intranasal (IN) administration of IgG at two doses in a transgenic amyloid mouse model. Specifically, measurements of the soluble and insoluble amyloid beta peptides Aβ40 and Aβ42 were taken in wild type and Tg2576 (amyloid mouse model) pre- and post-intranasal IgG administration. The purpose of the study was to determine whether chronic treatment with intranasally delivered IgG at two doses (0.4 g/kg/2 wk and 0.8 g/kg/2 wk) would have any effect on the amyloid plaque load in a transgenic amyloid mouse model of Alzheimer's disease.

Experimental Design: As described in Example 4, the TG2576 ("TG") amyloid mouse model was used in this study as a mouse model for Alzheimer's disease and C57 mice were used as controls. The handling of the mice, preparation of drug, and administration of drug was conducted as described above in Example 4.

The mice were divided into five treatment groups of 20 mice as described in Table 15. At approximately 17 months of age and 12 months of treatment, 12 mice from each treatment group were euthanized and the concentration of the Aβ40 and Aβ42 amyloid peptides in the brains of the TG and control mice were measured by ELISA to determine whether amyloid plaque concentrations changes could be detected.

Aβ40 and Aβ42 were measured by ELISA using Invitrogen ELISA kits. The ELISA kits were stored in refrigerator until they were ready to use. The kits were removed from refrigerator and allowed to warm to room temperature before use.

Standards and samples were run in duplicate. The samples and standards were run in a protease inhibitor cocktail with 1 mM AEBSF (a serine protease inhibitor). AEBSF was important because serine proteases can rapidly degrade Aβ peptides. The samples were kept on ice until they were ready to be applied to the ELISA Plate.

Sample matrix has a dramatic impact on Aβ recovery. To ensure accurate quantitation, the standard curves were generated in the same diluent as the samples. A standard reconstitution buffer was prepared by dissolving 2.31 grams of sodium bicarbonate in 500 mL of deionized water and the pH was adjusted using 2 N sodium hydroxide until the pH was 9.0.

The standards for a quantitative standard curve were prepared. The Hu Aβ42 Standard was used. The Hu Aβ42 Standard was allowed to equilibrate to room temperature (RT) and then reconstituted to 100 ng/mL with Standard Reconstitution Buffer (55 mM sodium bicarbonate, pH 9.0). The standard mixture was swirled and mixed gently and allowed to sit for 10 minutes to ensure complete reconstitution. The standard was then briefly vortexed prior to preparing standard curve. Generation of the standard curve using the Aβ peptide standard was performed using the same composition of buffers used for the diluted experimental samples. 0.1 mL of the reconstituted standard was added to a tube containing 0.9 mL of the Standard Diluent Buffer and labeled as 10,000 pg/mL Hu Aβ40. The standard was mixed and then 0.1 mL of the 10,000 pg/mL standard was added to a tube containing 1.9 mL Standard Diluent Buffer and labeled as 500 pg/mL Hu Aβ40. Mix. The standard was mixed and then 0.15 mL of Standard Diluent Buffer was added to each of 6 tubes labeled 250, 125, 62.5, 31.25, 15.63, 7.81, and 0 pg/mL Hu Aβ40 to make serial dilutions of the standard.

The samples were then prepared for the plate. Specifically, the samples were remove from the freezer, allowed to thaw, and diluted to the desired dilution using dilution buffer provided with the kit mixed with a protease inhibitor tablet. The samples were kept on ice until loaded into the wells on the plate.

The plates were labeled as being either AB40 or AB42 with a sharpie. 50 ul of standards and sample were added to the pre-labeled wells. 50 μL of Hu Aβ40 or Aβ42 Detection Antibody solution provided with the kit was added to each well. The plate was covered and incubated for 3 hours at room temperature with shaking Shortly before the 3 hours expired, the Anti-Rabbit IgG HRP Working Solution was prepared. To make this, 10 μL of Anti-Rabbit IgG HRP (100×) concentrated solution was diluted in 1 mL of HRP Diluent for each 8-well strip used in the assay and labeled as Anti-Rabbit IgG HRP Working Solution.

The solution was thoroughly decanted from wells and the wells were washed 5 times with 300 μL of wash solution. The plates were banged hard on lab bench to be sure it was dry. 100 μL of the Anti-Rabbit IgG HRP working solution was added to each well. The plate was covered and allowed to sit at room temp for 30 min. The solution was thoroughly decanted from wells and the wells were washed 5 times with 300 μL of wash solution. The plates were banged hard on lab bench to be sure it was dry. 100 μL of Stabilized Chromogen was added to each well and the plate was immediately placed in the dark and allowed to sit for 20 min. 100 μL of Stop Solution was added to each well and the sides of the plate were gently tapped to mix.

The absorbance of each well was read at 450 nm having blanked the plate reader within 30 minutes after adding the Stop Solution. The concentrations were determined using the standard curve.

Results: The ELISA plates for both Aβ40 and Aβ42 purchased from Invitrogen yielded consistent standard curves. The best dilutions of brain supernatant for samples for soluble Aβ40 and Aβ42, and insoluble Aβ40 and Aβ42 were 10×, undiluted, 10000×, and 2500×, respectively. Brain concentrations of each protein were analyzed by first determining the concentration of the sample in the well in the ELISA plate based on the standard curve. These values were then corrected for dilution of supernatant, dilution from the extraction process, and then given a correction factor from a BCA analysis of total protein extracted. For each protein, between 1 and 4 samples were excluded for either being statistical outliers or being too high/low to fit within the standard curve. A summary of the soluble and insoluble Aβ40 concentrations are presented in Table 17 and Table 18. A summary of the soluble and insoluble Aβ42 concentrations are presented in Table 19 and Table 20. The ratios of soluble Aβ40/Aβ42 are provided in Table 21 and the ratios of insoluble Aβ40/Aβ42 are provided in Table 22.

TABLE 17

Soluble Aβ40 detected in brain.

| Mouse sac order # | Group | Date measured | Concentration (pg/ml) | Mouse sac order # | Group | Date measured | Concentration (pg/ml) |
|---|---|---|---|---|---|---|---|
| 1 | TG-Low | 1-Oct | 9078 | 33 | TG-Saline | 1-Oct | 3940 |
| 6 | TG-Low | 1-Oct | 3964 | 38 | TG-Saline | 1-Oct | 1328 |
| 11 | TG-Low | 1-Oct | 3110 | 43 | TG-Saline | 1-Oct | 1983 |
| 16 | TG-Low | 1-Oct | 2788 | 48 | TG-Saline | 1-Oct | 3656 |
| 21 | TG-Low | 1-Oct | 3934 | 53 | TG-Saline | 1-Oct | 6650 |
| 26 | TG-Low | 1-Oct | 3747 | 58 | TG-Saline | 1-Oct | 6159 |
| 31 | TG-Low | 1-Oct | 3796 | 4 | WT-High | 9-Oct | 0 |
| 36 | TG-Low | 1-Oct | 5450 | 9 | WT-High | 9-Oct | 0 |
| 41 | TG-Low | 27-Sep | 5261 | 14 | WT-High | 9-Oct | 0 |
| 46 | TG-Low | 1-Oct | 2082 | 19 | WT-High | 9-Oct | 0 |
| 51 | TG-Low | 1-Oct | 2520 | 24 | WT-High | 9-Oct | 0 |
| 56 | TG-Low | 1-Oct | 9448 | 29 | WT-High | 9-Oct | 0 |
| 2 | TG-High | 1-Oct | 3061 | 34 | WT-High | 9-Oct | 0 |
| 7 | TG-High | 1-Oct | 1814 | 39 | WT-High | 9-Oct | 0 |
| 12 | TG-High | 1-Oct | 4681 | 44 | WT-High | 9-Oct | 0 |
| 17 | TG-High | 1-Oct | 2509 | 49 | WT-High | 9-Oct | 0 |
| 22 | TG-High | 1-Oct | 7869 | 54 | WT-High | 9-Oct | 0 |
| 27 | TG-High | 1-Oct | 6363 | 59 | WT-High | 9-Oct | 0 |
| 32 | TG-High | 1-Oct | 5541 | 5 | WT-Saline | 9-Oct | 0 |
| 37 | TG-High | 27-Sep | 5190 | 10 | WT-Saline | 9-Oct | 0 |
| 42 | TG-High | 1-Oct | 3609 | 15 | WT-Saline | 9-Oct | 0 |
| 47 | TG-High | 1-Oct | 1122 | 20 | WT-Saline | 9-Oct | 0 |
| 52 | TG-High | 1-Oct | 12163 | 25 | WT-Saline | 9-Oct | 0 |
| 57 | TG-High | 1-Oct | 1502 | 30 | WT-Saline | 9-Oct | 0 |
| 3 | TG-Saline | 27-Sep | 3708 | 35 | WT-Saline | 9-Oct | 0 |
| 8 | TG-Saline | 1-Oct | 4833 | 40 | WT-Saline | 9-Oct | 0 |
| 13 | TG-Saline | 1-Oct | 1673 | 45 | WT-Saline | 9-Oct | 0 |
| 18 | TG-Saline | 1-Oct | 4039 | 50 | WT-Saline | 9-Oct | 0 |
| 23 | TG-Saline | 1-Oct | 2373 | 55 | WT-Saline | 9-Oct | 0 |
| 28 | TG-Saline | 1-Oct | 4133 | 60 | WT-Saline | 9-Oct | 0 |

| | Average | Std deviation | Std error |
|---|---|---|---|
| TG-Low | 4598.418 | 2395.218 | 691.4399 |
| TG-High | 3932.644 | 1782.644 | 630.2598 |
| TG-Saline | 3706.334 | 1570.737 | 473.595 |
| WT-High | 0 | 0 | 0 |
| WT-Saline | 0 | 0 | 0 |

TABLE 18

Insoluble Aβ40 detected in brain.

| Mouse sac order # | Group | Date measured | Concentration (pg/ml) | Concentration (ug/ml) | Mouse sac order # | Group | Date measured | Concentration (pg/ml) | Concentration (ug/ml) |
|---|---|---|---|---|---|---|---|---|---|
| 1 | TG-Low | 8-Oct | 10257199 | 10.26 | 33 | TG-Saline | 8-Oct | 25512730 | 25.51 |
| 6 | TG-Low | 8-Oct | 11697779 | 11.70 | 38 | TG-Saline | 8-Oct | 19414980 | 19.41 |
| 11 | TG-Low | 8-Oct | 7575663 | 7.58 | 43 | TG-Saline | 8-Oct | 26032547 | 26.03 |
| 16 | TG-Low | 8-Oct | 8322854 | 8.32 | 48 | TG-Saline | 8-Oct | 39277004 | 39.28 |
| 21 | TG-Low | 8-Oct | 28084221 | 28.08 | 53 | TG-Saline | 8-Oct | 19280789 | 19.28 |
| 26 | TG-Low | 8-Oct | 22248049 | 22.25 | 58 | TG-Saline | 8-Oct | 39064072 | 39.06 |
| 31 | TG-Low | 8-Oct | 14817934 | 14.82 | 4 | WT-High | 18-Oct | 79052 | 0.07905 |
| 36 | TG-Low | 8-Oct | 25661660 | 25.66 | 9 | WT-High | 18-Oct | 48296 | 0.04830 |
| 41 | TG-Low | 3-Oct | 25537069 | 25.54 | 14 | WT-High | 18-Oct | 48256 | 0.04826 |
| 46 | TG-Low | 8-Oct | 9547715 | 9.55 | 19 | WT-High | 18-Oct | 9511 | 0.00951 |
| 51 | TG-Low | 8-Oct | 5688511 | 5.69 | 24 | WT-High | 18-Oct | 249003 | 0.24900 |
| 56 | TG-Low | 8-Oct | 9606698 | 9.61 | 29 | WT-High | 18-Oct | 31520 | 0.03152 |
| 2 | TG-High | 8-Oct | 4410637 | 4.41 | 34 | WT-High | 18-Oct | 39666 | 0.03967 |
| 7 | TG-High | 8-Oct | 15713013 | 15.71 | 39 | WT-High | 18-Oct | 25225 | 0.02522 |
| 12 | TG-High | 8-Oct | 18125865 | 18.13 | 44 | WT-High | 18-Oct | 134629 | 0.13463 |
| 17 | TG-High | 8-Oct | 4945207 | 4.95 | 54 | WT-High | 18-Oct | 15163 | 0.01516 |
| 22 | TG-High | 8-Oct | 33296598 | 33.30 | 59 | WT-High | 18-Oct | 23228 | 0.02323 |
| 27 | TG-High | 8-Oct | 68491264 | 68.49 | 5 | WT-Saline | 18-Oct | 3764 | 0.00376 |
| 32 | TG-High | 8-Oct | 50062749 | 50.06 | 10 | WT-Saline | 18-Oct | | |
| 37 | TG-High | 3-Oct | 36070736 | 36.07 | 15 | WT-Saline | 18-Oct | 10815 | 0.01081 |
| 42 | TG-High | 8-Oct | 26864520 | 26.86 | 20 | WT-Saline | 18-Oct | 38643 | 0.03864 |
| 47 | TG-High | 8-Oct | 3774286 | 3.77 | 25 | WT-Saline | 18-Oct | | |
| 52 | TG-High | 8-Oct | 42493407 | 42.49 | 30 | WT-Saline | 18-Oct | 4356 | 0.00436 |
| 57 | TG-High | 8-Oct | 8907543 | 8.91 | 35 | WT-Saline | 18-Oct | | |
| 3 | TG-Saline | 3-Oct | 13934212 | 13.93 | 40 | WT-Saline | 18-Oct | 5701 | 0.00570 |
| 8 | TG-Saline | 8-Oct | 28128069 | 28.13 | 45 | WT-Saline | 18-Oct | 14256 | 0.01426 |
| 13 | TG-Saline | 8-Oct | 18908021 | 18.91 | 50 | WT-Saline | 18-Oct | 2986 | 0.00299 |
| 18 | TG-Saline | 8-Oct | 18777770 | 18.78 | 55 | WT-Saline | 18-Oct | 3072 | 0.00307 |
| 28 | TG-Saline | 8-Oct | 20470065 | 20.47 | 60 | WT-Saline | 18-Oct | 3008 | 0.00301 |

| | Average | Std deviation | Std error |
|---|---|---|---|
| TG-Low | 14.92045 | 8.129698 | 2.346842 |
| TG-High | 24.60567 | 20.93301 | 6.31154 |
| TG-Saline | 24.43837 | 8.31824 | 2.401306 |
| WT-High | 0.063959 | 0.070783 | 0.021342 |
| WT-Saline | 0.009622 | 0.011582 | 0.003861 |

TABLE 19

Soluble Aβ42 detected in brain.

| Mouse sac order # | Group | Date measured | Concentration (pg/ml) | Mouse sac order # | Group | Date measured | Concentration (pg/ml) |
|---|---|---|---|---|---|---|---|
| 1 | TG-Low | 1-Oct | 1455 | 33 | TG-Saline | 2-Oct | 626 |
| 6 | TG-Low | 2-Oct | 551 | 38 | TG-Saline | 2-Oct | 393 |
| 11 | TG-Low | 2-Oct | 511 | 43 | TG-Saline | 2-Oct | 562 |
| 16 | TG-Low | 2-Oct | 744 | 48 | TG-Saline | 2-Oct | 432 |
| 21 | TG-Low | 2-Oct | 705 | 53 | TG-Saline | 1-Oct | 1295 |
| 26 | TG-Low | 2-Oct | 623 | 58 | TG-Saline | 1-Oct | 1361 |
| 31 | TG-Low | 2-Oct | 463 | 4 | WT-High | 9-Oct | 0 |
| 36 | TG-Low | 2-Oct | 609 | 9 | WT-High | 9-Oct | 0 |
| 41 | TG-Low | 27-Sep | 1564 | 14 | WT-High | 9-Oct | 0 |
| 46 | TG-Low | 2-Oct | 606 | 19 | WT-High | 9-Oct | 0 |
| 51 | TG-Low | 1-Oct | 825 | 24 | WT-High | 9-Oct | 0 |
| 56 | TG-Low | 1-Oct | 1526 | 29 | WT-High | 9-Oct | 0 |
| 2 | TG-High | 2-Oct | 579 | 34 | WT-High | 9-Oct | 0 |
| 7 | TG-High | 2-Oct | 446 | 39 | WT-High | 9-Oct | 0 |
| 12 | TG-High | 2-Oct | 880 | 44 | WT-High | 9-Oct | 0 |
| 17 | TG-High | 2-Oct | 410 | 49 | WT-High | 9-Oct | 0 |
| 22 | TG-High | 1-Oct | 1198 | 54 | WT-High | 9-Oct | 0 |
| 27 | TG-High | 2-Oct | 851 | 59 | WT-High | 9-Oct | 0 |
| 32 | TG-High | 2-Oct | 877 | 5 | WT-Saline | 9-Oct | 0 |
| 37 | TG-High | 27-Sep | 1470 | 10 | WT-Saline | 9-Oct | 0 |
| 42 | TG-High | 2-Oct | 880 | 15 | WT-Saline | 9-Oct | 0 |
| 47 | TG-High | 2-Oct | 290 | 20 | WT-Saline | 9-Oct | 0 |
| 52 | TG-High | 1-Oct | 3050 | 25 | WT-Saline | 9-Oct | 0 |
| 57 | TG-High | 2-Oct | 385 | 30 | WT-Saline | 9-Oct | 0 |
| 3 | TG-Saline | 27-Sep | 791 | 35 | WT-Saline | 9-Oct | 0 |
| 8 | TG-Saline | 2-Oct | 990 | 40 | WT-Saline | 9-Oct | 0 |
| 13 | TG-Saline | 2-Oct | 562 | 45 | WT-Saline | 9-Oct | 0 |

TABLE 19-continued

Soluble Aβ42 detected in brain.

| | | | | | | | |
|---|---|---|---|---|---|---|---|
| 18 | TG-Saline | 2-Oct | 733 | 50 | WT-Saline | 9-Oct | 0 |
| 23 | TG-Saline | 2-Oct | 521 | 55 | WT-Saline | 9-Oct | 0 |
| 28 | TG-Saline | 2-Oct | 737 | 60 | WT-Saline | 9-Oct | 0 |

| | Average | Std deviation | Std error |
|---|---|---|---|
| TG-Low | 848.4637 | 414.464 | 119.6455 |
| TG-High | 751.4925 | 368.8014 | 111.1978 |
| TG-Saline | 750.1043 | 315.7884 | 91.16026 |
| WT-High | 0 | 0 | 0 |
| WT-Saline | 0 | 0 | 0 |

TABLE 20

Insoluble Aβ42 detected in brain.

| Mouse sac order # | Group | Date measured | Concentration (pg/ml) | Concentration (ug/ml) | Mouse sac order # | Group | Date measured | Concentration (pg/ml) | Concentration (ug/ml) |
|---|---|---|---|---|---|---|---|---|---|
| 1 | TG-Low | 3-Oct | 4493237 | 4.49 | 33 | TG-Saline | 3-Oct | 3705386 | 3.71 |
| 6 | TG-Low | 3-Oct | 7320913 | 7.32 | 38 | TG-Saline | 3-Oct | 6032562 | 6.03 |
| 11 | TG-Low | 3-Oct | 2641985 | 2.64 | 43 | TG-Saline | 3-Oct | 6871640 | 6.87 |
| 16 | TG-Low | 3-Oct | 1644845 | 1.64 | 48 | TG-Saline | 3-Oct | 12292890 | 12.29 |
| 21 | TG-Low | 3-Oct | 10670528 | 10.67 | 53 | TG-Saline | 3-Oct | 6847851 | 6.85 |
| 26 | TG-Low | 3-Oct | 2902253 | 2.90 | 58 | TG-Saline | 3-Oct | 11978111 | 11.98 |
| 31 | TG-Low | 3-Oct | 5435473 | 5.44 | 4 | WT-High | 18-Oct | 32757 | 0.0328 |
| 36 | TG-Low | 3-Oct | 5458033 | 5.46 | 9 | WT-High | 18-Oct | 53457 | 0.0535 |
| 41 | TG-Low | 2-Oct | 5807761 | 5.81 | 14 | WT-High | 18-Oct | 38889 | 0.0389 |
| 46 | TG-Low | 3-Oct | 2751646 | 2.75 | 19 | WT-High | 18-Oct | 5910 | 0.0059 |
| 51 | TG-Low | 3-Oct | 1474153 | 1.47 | 24 | WT-High | 18-Oct | 76083 | 0.0761 |
| 56 | TG-Low | 3-Oct | 6022267 | 6.02 | 29 | WT-High | 18-Oct | 19765 | 0.0198 |
| 2 | TG-High | 3-Oct | 1984182 | 1.98 | 34 | WT-High | 18-Oct | 26479 | 0.0265 |
| 7 | TG-High | 3-Oct | 2733892 | 2.73 | 39 | WT-High | 18-Oct | 20134 | 0.0201 |
| 12 | TG-High | 3-Oct | 10072470 | 10.07 | 44 | WT-High | 18-Oct | 79499 | 0.0795 |
| 17 | TG-High | 3-Oct | 1786008 | 1.79 | 54 | WT-High | 18-Oct | 19179 | 0.0192 |
| 22 | TG-High | 3-Oct | 7201686 | 7.20 | 59 | WT-High | 18-Oct | 23360 | 0.0234 |
| 27 | TG-High | 3-Oct | 11756896 | 11.76 | 5 | WT-Saline | 18-Oct | 3891 | 0.0039 |
| 32 | TG-High | 3-Oct | 7338861 | 7.34 | 10 | WT-Saline | 18-Oct | 3916 | 0.0039 |
| 37 | TG-High | 2-Oct | 10547976 | 10.55 | 15 | WT-Saline | 18-Oct | 9542 | 0.0095 |
| 42 | TG-High | 3-Oct | 6116270 | 6.12 | 20 | WT-Saline | 18-Oct | 13878 | 0.0139 |
| 47 | TG-High | 3-Oct | 954559 | 0.95 | 25 | WT-Saline | 18-Oct | | |
| 52 | TG-High | 3-Oct | 14015195 | 14.02 | 30 | WT-Saline | 18-Oct | 4040 | 0.0040 |
| 57 | TG-High | 3-Oct | 1353498 | 1.35 | 35 | WT-Saline | 18-Oct | | |
| 3 | TG-Saline | 2-Oct | 3362018 | 3.36 | 40 | WT-Saline | 18-Oct | 4698 | 0.0047 |
| 8 | TG-Saline | 3-Oct | 6261392 | 6.26 | 45 | WT-Saline | 18-Oct | 15173 | 0.0152 |
| 13 | TG-Saline | 3-Oct | 6056766 | 6.06 | 50 | WT-Saline | 18-Oct | 2862 | 0.0029 |
| 18 | TG-Saline | 3-Oct | 5685368 | 5.69 | 55 | WT-Saline | 18-Oct | 3151 | 0.0032 |
| 28 | TG-Saline | 3-Oct | 3122150 | 3.12 | 60 | WT-Saline | 18-Oct | 3320 | 0.0033 |

| | Average | Std deviation | Std error |
|---|---|---|---|
| TG-Low | 4.718591 | 2.656887 | 0.766977 |
| TG-High | 5.622391 | 4.045875 | 1.219877 |
| TG-Saline | 6.565103 | 3.065648 | 0.884976 |
| WT-High | 0.035956 | 0.024034 | 0.007247 |
| WT-Saline | 0.006447 | 0.004669 | 0.001477 |

TABLE 21

Ratios of soluble Aβ40/Aβ42.

| Mouse sac order # | Group | Ratio of AB42/AB40 | Mouse sac order # | Group | Ratio of AB42/AB40 |
|---|---|---|---|---|---|
| 1 | TG-Low | 0.160295 | 33 | TG-Saline | 0.1588125 |
| 6 | TG-Low | 0.13894 | 38 | TG-Saline | 0.2960768 |
| 11 | TG-Low | 0.164329 | 43 | TG-Saline | 0.2834986 |
| 16 | TG-Low | 0.266987 | 48 | TG-Saline | 0.1180902 |
| 21 | TG-Low | 0.179196 | 53 | TG-Saline | 0.19472 |
| 26 | TG-Low | 0.16629 | 58 | TG-Saline | 0.2209363 |
| 31 | TG-Low | 0.1219 | 4 | WT-High | 0 |
| 36 | TG-Low | 0.111683 | 9 | WT-High | 0 |
| 41 | TG-Low | 0.297232 | 14 | WT-High | 0 |
| 46 | TG-Low | 0.290904 | 19 | WT-High | 0 |
| 51 | TG-Low | 0.327174 | 24 | WT-High | 0 |
| 56 | TG-Low | 0.161546 | 29 | WT-High | 0 |
| 2 | TG-High | 0.189314 | 34 | WT-High | 0 |
| 7 | TG-High | 0.245964 | 39 | WT-High | 0 |
| 12 | TG-High | 0.188097 | 44 | WT-High | 0 |
| 17 | TG-High | 0.163459 | 49 | WT-High | 0 |
| 22 | TG-High | 0.152272 | 54 | WT-High | 0 |
| 27 | TG-High | 0.13377 | 59 | WT-High | 0 |
| 32 | TG-High | 0.158201 | 5 | WT-Saline | 0 |
| 37 | TG-High | 0.283163 | 10 | WT-Saline | 0 |

TABLE 21-continued

Ratios of soluble Aβ40/Aβ42.

| | | | | | |
|---|---|---|---|---|---|
| 42 | TG-High | 0.243714 | 15 | WT-Saline | 0 |
| 47 | TG-High | 0.258574 | 20 | WT-Saline | 0 |
| 52 | TG-High | 0.250769 | 25 | WT-Saline | 0 |
| 57 | TG-High | 0.25651 | 30 | WT-Saline | 0 |
| 3 | TG-Saline | 0.2132 | 35 | WT-Saline | 0 |
| 8 | TG-Saline | 0.204815 | 40 | WT-Saline | 0 |
| 13 | TG-Saline | 0.335658 | 45 | WT-Saline | 0 |
| 18 | TG-Saline | 0.181432 | 50 | WT-Saline | 0 |
| 23 | TG-Saline | 0.219518 | 55 | WT-Saline | 0 |
| 28 | TG-Saline | 0.1783 | 60 | WT-Saline | 0 |

| | Average | Std deviation | Std error |
|---|---|---|---|
| TG-Low | 0.198873 | 0.075008 | 0.0217 |
| TG-High | 0.20664 | 0.05204 | 0.0157 |
| TG-Saline | 0.217088 | 0.061325 | 0.0177 |
| WT-High | 0 | 0 | 0 |
| WT-Saline | 0 | 0 | 0 |

TABLE 22

Ratios of insoluble Aβ40/Aβ42.

| Mouse sac order # | Group | Ratio of AB42/AB40 | Mouse sac order # | Group | Ratio of AB42/AB40 |
|---|---|---|---|---|---|
| 1 | TG-Low | 0.43806 | 33 | TG-Saline | 0.14524 |
| 6 | TG-Low | 0.62584 | 38 | TG-Saline | 0.31072 |
| 11 | TG-Low | 0.34875 | 43 | TG-Saline | 0.26396 |
| 16 | TG-Low | 0.19763 | 48 | TG-Saline | 0.31298 |
| 21 | TG-Low | 0.37995 | 53 | TG-Saline | 0.35516 |
| 26 | TG-Low | 0.13045 | 58 | TG-Saline | 0.30663 |
| 31 | TG-Low | 0.36682 | 4 | WT-High | 0.41437 |
| 36 | TG-Low | 0.21269 | 9 | WT-High | 1.10685 |
| 41 | TG-Low | 0.22742 | 14 | WT-High | 0.80589 |
| 46 | TG-Low | 0.2882 | 19 | WT-High | 0.62142 |
| 51 | TG-Low | 0.25915 | 24 | WT-High | 0.30555 |
| 56 | TG-Low | 0.62688 | 29 | WT-High | 0.62708 |
| 2 | TG-High | 0.44986 | 34 | WT-High | 0.66754 |
| 7 | TG-High | 0.17399 | 39 | WT-High | 0.79817 |
| 12 | TG-High | 0.5557 | 44 | WT-High | 0.5905 |
| 17 | TG-High | 0.36116 | 54 | WT-High | 1.26484 |
| 22 | TG-High | 0.21629 | 59 | WT-High | 1.00566 |
| 27 | TG-High | 0.17166 | 5 | WT-Saline | 1.0335 |
| 32 | TG-High | 0.14659 | 10 | WT-Saline | |
| 37 | TG-High | 0.29242 | 15 | WT-Saline | 0.88232 |
| 42 | TG-High | 0.22767 | 20 | WT-Saline | 0.35914 |
| 47 | TG-High | 0.25291 | 25 | WT-Saline | |
| 52 | TG-High | 0.32982 | 30 | WT-Saline | 0.92744 |
| 57 | TG-High | 0.15195 | 35 | WT-Saline | |
| 3 | TG-Saline | 0.24128 | 40 | WT-Saline | 0.82407 |
| 8 | TG-Saline | 0.2226 | 45 | WT-Saline | 1.06434 |
| 13 | TG-Saline | 0.32033 | 50 | WT-Saline | 0.95864 |
| 18 | TG-Saline | 0.30277 | 55 | WT-Saline | 1.02571 |
| 28 | TG-Saline | 0.15252 | 60 | WT-Saline | 1.10371 |

| | Average | Std deviation | Std error |
|---|---|---|---|
| TG-Low | 0.3418191 | 0.15905 | 0.04591 |
| TG-High | 0.2727456 | 0.13256 | 0.04192 |
| TG-Saline | 0.2667446 | 0.06933 | 0.02001 |
| WT-High | 0.7461702 | 0.28933 | 0.08724 |
| WT-Saline | 0.9087633 | 0.22479 | 0.07493 |

The most obvious and expected result was that both soluble and insoluble Aβ40 and Aβ42 were drastically higher in all TG mice than WT mice. Soluble Aβ40 and Aβ42 were not detectable in WT mice, while insoluble Aβ40 and Aβ42 were present, though at about 1000 times lower than in TG mice. The next most obvious result was that in all TG mice, the concentration of insoluble Aβ40 and Aβ42 was much higher than soluble Aβ40 and Aβ42, roughly about 5000 and 7500 times higher, respectively.

Regarding group comparisons among the three TG groups, there were no significant differences among any of the groups for either soluble or insoluble Aβ40 or Aβ42 using an ANOVA. This was somewhat surprising for insoluble amyloid as there were clear differences in plaques in the cortex between drug-treated and saline-treated TG mice. The most likely explanation is that the ELISA was not as sensitive to these differences as the IHC slides of plaques.

Example 6

Effect of Intranasal Administration of IgG on Weight and Survival

A study was conducted to assess the efficacy of chronic intranasal (IN) administration of IgG at two doses in a transgenic amyloid mouse model. The purpose of the study was to determine whether chronic treatment with intranasally delivered IgG at two doses (0.4 g/kg/2 wk and 0.8 g/kg/2 wk) would have any effect on the mouse weight and survival.

Experimental Design: As described in Example 4, the TG2576 ("TG") amyloid mouse model was used in this study as a mouse model for Alzheimer's disease and C57 mice were used as controls. The handling of the mice, preparation of drug, and administration of drug was conducted as described above in Example 4.

The mice were divided into five treatment groups of 20 mice as described in Table 15. The weight and survival of the mice were monitored for 103 weeks. The weight of each mouse was recorded weekly (data not shown).

Figure 4:
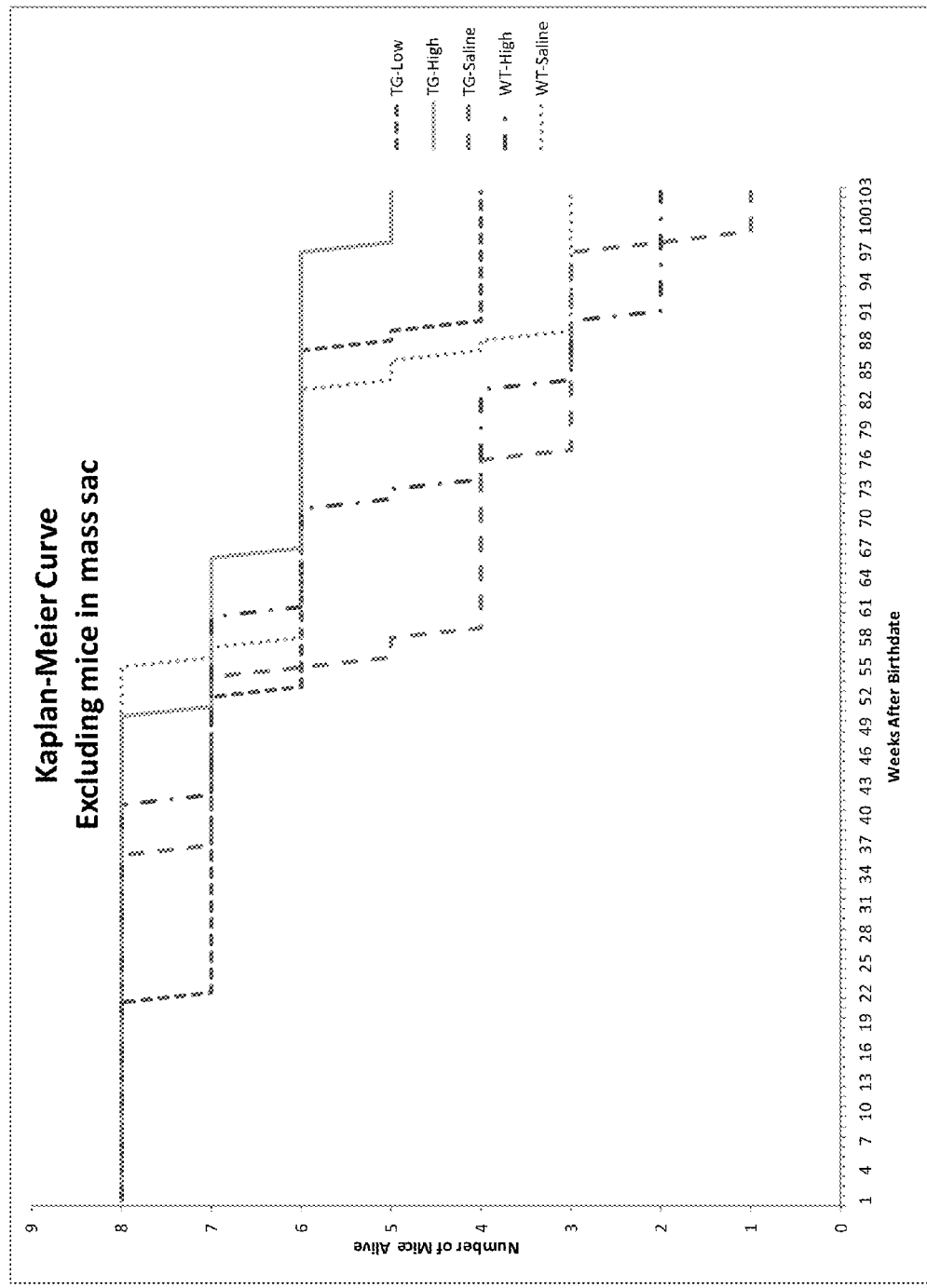
FIG. 4 illustrates a Kaplan-Meier curve for survival rates of transgenic and wild-type mice administered IgG intranasally. These mice belong to a different cohort than the mice used for plaque analysis in FIG. 3.

Results: These experiments showed that intranasal IgG increases the lifespan of TG mice. FIG. 4A shows that TG mice have an increased lifespan when they are administered a high (0.8 g/kg/2 wk) or a low (0.4 g/kg/2 wk) dose of intranasal IgG compared to TG mice administered saline intranasally (control). FIG. 4B shows that TG mice administered intranasal IgG had longer lifespans than WT mice. Although this study begun with 20 mice in each cohort, due to the mass euthanasia performed to evaluate amyloid plaque content (as described in Example 5), Kaplan-Meier survival analysis was performed using the sub-group of 8 mice in each cohort that were not euthanized. Dosing to the mice in the sub-groups was continued as described above through the entirety of the experiment.

Example 7

Effect of Intranasal Administration of IgG on Memory

A study was conducted to examine whether intranasal administration of IgG affects the memory in the brain in vivo. The purpose of this study was to examine whether chronic treatment with intranasally delivered IgG at two doses (0.4 g/kg/2 wk and 0.8 g/kg/2 wk) would have any effect on memory in a transgenic amyloid mouse model of Alzheimer's disease.

Experimental Design: At 15 months of age, the mice described in Example 4 were subjected to a six week battery of behavioral tests to assess for memory, sensorimotor, and anxiolytic changes. These included Morris water maze hidden and visual platform tests (reference memory, visual ability), radial arm water maze (working memory), passive avoidance task (memory), Barnes maze (memory), open field test (exploratory behavior), elevated plus maze (anxiety), and rotarod (motor skills).

Results: For each behavioral test, comparison data was analyzed using T-tests as described above in Table 23. Statistical tests were performed on data after removal of both statistical outliers and non-compliant mice, which were specified for each behavioral test. Data was first analyzed by comparing WT-saline (WT-Sal) mice to TG-saline (TG-Sal) mice to determine whether there is a transgenic (model) effect for that test. Comparisons between all TG and all WT mice were also performed. Although the latter analysis is confounded by drug treatment, it gains power by increasing sample size and serves to give an overall picture of a potential transgenic (model) effect. Comparisons were made among individual drug treatment groups. Specifically, the drug treated TG groups were compared directly to the TG-saline group to determine whether the drug had any effect.

4 trials/day). Before trials began, the mice were acclimated to swimming in the water. For each of these blocks of trials, mice were randomly dropped into four quadrants within the MWM (round tub with water) and allowed to swim for 60 seconds or until they reached the platform. The mouse's ability to reach the platform depended on his ability to remember visual cues from previous trials and their location in relation to the platform. Mice that did not reach the platform after 60 seconds were placed on the platform. Mice were allowed to remain/rest on the platform for 20 seconds between trials. All data was recorded using MouseApp software, which records escape latency.

The Morris Water Maze Visual Platform is designed to assess visual ability. It was run just like the MWM hidden platform, except the platform was raised just above the surface of the water, has a flag on top to identify it, and stripes along the side to make it more visual. It was only run for one day. Analysis was performed the same as with the MWM hidden platform tests.

Overall, the Morris Water Maze Hidden Platform tests showed that there was a clear trend of learning both throughout the week and during individual days, demonstrating that the test was effective for measuring memory. Escape laten-

TABLE 23

T-tests used to evaluate results of behavioral studies in wild type and Alzheimer's disease mouse models administered IgG intranasally.

| Comparison | Reason for Comparison |
| --- | --- |
| WT-saline vs. TG-saline | To determine whether there is a transgenic effect of the model. |
| WT-all vs. TG-all (all = saline and IN IgG) | To provide a larger scale view of the transgenic effect of the model. |
| TG-saline vs TG-low dose IN IgG | To determine whether TG mice treated with the low dose of performed differently than TG mice treated with saline. |
| TG-saline vs TG-high dose IN IgG | To determine whether TG mice treated with the high dose of IgG performed differently than TG mice treated with saline. |

Overall, in the three visio-spatial memory tests, mice learned over time, and there was generally improved performance in the WT mice as compared to the TG mice, which was expected. There was also a difference between WT and TG mice in the Elevated Plus Maze. There were minimal observed differences in the Rotarod and Open Field Tests, but differences were not expected. Compliance was only a problem in the Barnes Maze, however, when non-compliant mice were removed the learning trends were present, and the model effect mirrored those seen in the MWM and RAWM.

The Morris Water Maze (MWM) Hidden Platform. MWM is a standard test of spatial memory. MWM performance was assessed using hidden-platform testing (4 days, cies were lowest during days 3 and 4, and were especially lowest during trials 3 and 4 on these days.

There was evidence of a transgenic model effect. Table 25 and Table 26 show that both WT groups had lower escape latencies than all three TG groups on days 3 and 4. WT-Sal mice had lower escape latencies than TG-Sal mice (Table 24, Table 25, Table 26, Table 27, and Table 28). However, when the WT and TG groups were put together, there were several significant differences, including B1-T2, B3-T4, B4-T1, B4-T3, and B4-T4 ($p<0.05$ or $0.01$; Table 24, Table 27, and Table 28). Much of the power for this difference came from the TG-high mice, which performed particularly well in this task.

TABLE 24

Summary of T-tests for specific comparisons in behavior tests. Tests are 2-sided and unpaired.
Reported numbers are p-values. Gray cells p < 0.05; Boxed cells p < 0.1.

| Test | Measure | Block | Trial | WT-Sal vsTG-Sal | WT-All vs TG-All | TG-Sal vsTG-Low | TG-Sal vsTG-High |
|---|---|---|---|---|---|---|---|
| RAWM | Escape | 1 | 1 | 0.023 | 0 | 0.883 | 0.539 |
| RAWM | Escape | 1 | 2 | 0.689 | 0.558 | 0.141 | 0.298 |
| RAWM | Escape | 1 | 3 | 0.088 | 0.215 | 0.592 | 0.15 |
| RAWM | Escape | 1 | 4 | 0.615 | 0.358 | 0.803 | 0.335 |
| RAWM | Escape | 2 | 1 | 0.159 | 0.215 | 0.653 | 0.607 |
| RAWM | Escape | 2 | 2 | 0.194 | 0.926 | 0.675 | 0.13 |
| RAWM | Escape | 2 | 3 | 0.161 | 0.497 | 0.06 | 0.046 |
| RAWM | Escape | 2 | 4 | 0.446 | 0.219 | 0.271 | 0.918 |
| RAWM | Escape | 3 | 1 | 0.959 | 0.767 | 0.619 | 0.65 |
| RAWM | Escape | 3 | 2 | 0.069 | 0.001 | 0.5 | 0.202 |
| RAWM | Escape | 3 | 3 | 0.995 | 0.806 | 0.185 | 0.597 |
| RAWM | Escape | 3 | 4 | 0.281 | 0.002 | 0.198 | 0.257 |
| RAWM | Escape | 4 | 1 | 0.785 | 0.487 | 0.217 | 0.701 |
| RAWM | Escape | 4 | 2 | 0.35 | 0.274 | 0.433 | 0.627 |
| RAWM | Escape | 4 | 3 | 0.357 | 0.149 | 0.348 | 0.292 |
| RAWM | Escape | 4 | 4 | 0.232 | 0.008 | 0.583 | 0.513 |
| RAWM | Errors | 1 | 1 | 0.538 | 0.001 | 0.154 | 0.881 |
| RAWM | Errors | 1 | 2 | 0.284 | 0.105 | 0.06 | 0.233 |
| RAWM | Errors | 1 | 3 | 0.062 | 0.196 | 0.236 | 0.089 |
| RAWM | Errors | 1 | 4 | 0.443 | 0.255 | 0.577 | 0.293 |
| RAWM | Errors | 2 | 1 | 0.656 | 0.753 | 0.223 | 0.136 |
| RAWM | Errors | 2 | 2 | 0.227 | 0.642 | 0.606 | 0.022 |
| RAWM | Errors | 2 | 3 | 0.17 | 0.706 | 0.247 | 0.139 |
| RAWM | Errors | 2 | 4 | 0.719 | 0.385 | 0.601 | 0.954 |
| RAWM | Errors | 3 | 1 | 0.86 | 0.678 | 0.783 | 0.551 |
| RAWM | Errors | 3 | 2 | 0.043 | 0.002 | 0.207 | 0.336 |
| RAWM | Errors | 3 | 3 | 0.946 | 0.75 | 0.55 | 0.526 |
| RAWM | Errors | 3 | 4 | 0.393 | 0.02 | 0.998 | 0.391 |
| RAWM | Errors | 4 | 1 | 0.437 | 0.229 | 0.397 | 0.814 |
| RAWM | Errors | 4 | 2 | 0.064 | 0.048 | 0.154 | 0.263 |
| RAWM | Errors | 4 | 3 | 0.357 | 0.214 | 0.296 | 0.432 |
| RAWM | Errors | 4 | 4 | 0.135 | 0.007 | 0.935 | 0.566 |
| MWM hid | Escape | 1 | 1 | 0.262 | 0.186 | 0.007 | 0.095 |

TABLE 24-continued

Summary of T-tests for specific comparisons in behavior tests. Tests are 2-sided and unpaired.
Reported numbers are p-values. Gray cells p < 0.05; Boxed cells p < 0.1.

| | | | | | | | |
|---|---|---|---|---|---|---|---|
| MWM hid | Escape | 1 | 2 | 0.069 | 0.086 | 0.663 | 0.532 |
| MWM hid | Escape | 1 | 3 | 0.62 | 0.26 | 0.5 | 0.419 |
| MWM hid | Escape | 1 | 4 | 0.663 | 0.171 | 0.111 | 0.189 |
| MWM hid | Escape | 2 | 1 | 0.882 | 0.555 | 0.357 | 0.702 |
| MWM hid | Escape | 2 | 2 | 0.24 | 0.568 | 0.091 | 0.963 |
| MWM hid | Escape | 2 | 3 | 0.393 | 0.71 | 0.802 | 0.276 |
| MWM hid | Escape | 2 | 4 | 0.986 | 0.256 | 0.638 | 0.963 |
| MWM hid | Escape | 3 | 1 | 0.475 | 0.419 | 0.906 | 0.163 |
| MWM hid | Escape | 3 | 2 | 0.681 | 0.173 | 0.109 | 0.549 |
| MWM hid | Escape | 3 | 3 | 0.905 | 0.106 | 0.908 | 0.864 |
| MWM hid | Escape | 3 | 4 | 0.355 | 0.072 | 0.874 | 0.6 |
| MWM hid | Escape | 4 | 1 | 0.672 | 0.045 | 0.044 | 0.102 |
| MWM hid | Escape | 4 | 2 | 0.147 | 0.127 | 0.264 | 0.991 |
| MWM hid | Escape | 4 | 3 | 0.592 | 0.03 | 0.585 | 0.802 |
| MWM hid | Escape | 4 | 4 | 0.507 | 0.02 | 0.436 | 0.192 |
| Barnes | Escape | 1 | 1 | 0.681 | 0.35 | 0.946 | 0.696 |
| Barnes | Escape | 1 | 2 | 0.925 | 0.643 | 0.587 | 0.337 |
| Barnes | Escape | 1 | 3 | 0.098 | 0.277 | 0.876 | 0.408 |
| Barnes | Escape | 2 | 1 | 0.478 | 0.576 | 0.542 | 0.63 |
| Barnes | Escape | 2 | 2 | 0.673 | 0.64 | 0.132 | 0.534 |
| Barnes | Escape | 2 | 3 | 0.501 | 0.529 | 0.284 | 0.496 |
| Barnes | Escape | 3 | 1 | 0.943 | 0.313 | 0.189 | 0.764 |
| Barnes | Escape | 3 | 2 | 0.764 | 0.88 | 0.678 | 0.626 |
| Barnes | Escape | 3 | 3 | 0.581 | 0.274 | 0.826 | 0.657 |
| Barnes | Escape | 4 | 1 | 0.623 | 0.052 | 0.072 | 0.606 |
| Barnes | Escape | 4 | 2 | 0.138 | 0.21 | 0.29 | 0.482 |
| Barnes | Escape | 4 | 3 | 0.916 | 0.986 | 0.925 | 0.845 |
| Barnes | Errors | 1 | 1 | 0.485 | 0.851 | 0.807 | 0.75 |
| Barnes | Errors | 1 | 2 | 0.057 | 0.033 | 0.436 | 0.416 |
| Barnes | Errors | 1 | 3 | 0.231 | 0.414 | 0.541 | 0.603 |
| Barnes | Errors | 2 | 1 | 0.48 | 0.519 | 0.731 | 0.434 |
| Barnes | Errors | 2 | 2 | 0.085 | 0.15 | 0.41 | 0.383 |
| Barnes | Errors | 2 | 3 | 0.423 | 0.079 | 0.17 | 0.341 |

TABLE 24-continued

Summary of T-tests for specific comparisons in behavior tests. Tests are 2-sided and unpaired.
Reported numbers are p-values. Gray cells p < 0.05; Boxed cells p < 0.1.

| | | | | | | | |
|---|---|---|---|---|---|---|---|
| Barnes | Errors | 3 | 1 | 0.979 | 0.894 | 0.875 | 0.759 |
| Barnes | Errors | 3 | 2 | 0.54 | 0.741 | 0.802 | 0.535 |
| Barnes | Errors | 3 | 3 | 0.864 | 0.952 | 0.806 | 0.764 |
| Barnes | Errors | 4 | 1 | 0.928 | 0.245 | 0.185 | 0.355 |
| Barnes | Errors | 4 | 2 | 0.885 | 0.965 | 0.736 | 0.758 |
| Barnes | Errors | 4 | 3 | 0.013 | 0.116 | 0.19 | 0.707 |
| MWM vis | Escape | 1 | 1 | 0.074 | 0.282 | 0.134 | 0.589 |
| MWM vis | Escape | 1 | 2 | 0.507 | 0.222 | 0.665 | 0.597 |
| MWM vis | Escape | 1 | 3 | 0.863 | 0.237 | 0.516 | 0.959 |
| MWM vis | Escape | 1 | 4 | 0.898 | 0.448 | 0.46 | 0.593 |
| Open field | Line Crossings | n/a | n/a | 0.534 | 0.138 | 0.112 | 0.688 |
| Open field | Velocity | n/a | n/a | 0.38 | 0.057 | 0.25 | 0.618 |
| Elev. plus | Time in open arms | n/a | n/a | 0.036 | 0.001 | 0.726 | 0.225 |
| Elev. plus | Frequency in open arms | n/a | n/a | 0.034 | 0 | 0.372 | 0.13 |
| Rotarod | Best run | n/a | n/a | 0.98 | 0.153 | 0.64 | 0.875 |
| Rotarod | Average run | n/a | n/a | 0.856 | 0.131 | 0.557 | 0.973 |
| Pass Avoid | Escape | Learn | n/a | 0.032 | 0.001 | 0.952 | 0.825 |
| Pass Avoid | Escape | Test | n/a | 0.072 | 0 | 0.34 | 0.207 |

TABLE 25

Average escape latencies (sec) from the Morris Water Maze tests.

| Group | Day 1 | Day 2 | Day 3 | Day 4 |
|---|---|---|---|---|
| TG-Low (N = 18) | 34.54 | 30.47 | 25.03 | 24.68 |
| TG-High (N = 18) | 33.38 | 27.06 | 24.50 | 30.51 |
| TG-Saline (N = 16) | 24.80 | 22.20 | 24.25 | 24.02 |
| WT-High (N = 16) | 23.38 | 23.58 | 17.73 | 16.11 |
| WT-Saline (N = 18) | 27.26 | 26.82 | 24.85 | 26.82 |

TABLE 26

Average escape latencies (sec) from the Morris Water Maze tests with non-compliance removed.

| Group | Day 1 | Day 2 | Day 3 | Day 4 |
|---|---|---|---|---|
| TG-Low (N = 15-18) | 31.36 | 25.53 | 25.03 | 23.46 |
| TG-High (N = 15-16) | 28.73 | 20.55 | 20.06 | 25.57 |
| TG-Saline (N = 14-15) | 23.25 | 19.68 | 21.87 | 19.68 |
| WT-High (N = 14-15) | 20.93 | 19.30 | 14.92 | 13.18 |
| WT-Saline (N = 13-16) | 21.65 | 22.67 | 18.07 | 15.87 |

TABLE 27

Averagedaily escape latencies (sec) from the Morris Water Maze tests.

| Group | Day 1 | Day 2 | Day 3 | Day 4 |
|---|---|---|---|---|
| TG ALL (N = 52) | 31.14 | 26.75 | 24.61 | 26.50 |
| WT ALL (N = 34) | 25.43 | 25.29 | 21.50 | 21.78 |

TABLE 28

Average daily escape latencies (sec) from the Morris Water Maze tests with noncompliance removed.

| Group | Day 1 | Day 2 | Day 3 | Day 4 |
|---|---|---|---|---|
| TG ALL (N = 45-49) | 27.86 | 21.92 | 22.44 | 22.99 |
| WT ALL (N = 28-30) | 21.29 | 21.10 | 16.49 | 14.43 |

Like with RAWM, the three transgenic groups are grouped closely in Table 25 and Table 26. The only significant differences between TG-Sal and TG-low came on B1-T1, B2-T2, and B4-T1 (Table 24), and in each case, TG-Sal mice had shorter escape latencies than TG-low mice, who performed particularly poor in this task. There was only one example in which there was a statistical difference between TG-high and TG-Sal (B1-T1). In this instance, TG-Sal did very well and outperformed the TG-high mice. However, it should be noted that the WT-high mice consistently outperformed all other groups in this task. Although T-tests performed at each trial showed no statistical differences between WT-high and WT-Saline, repeated measures ANOVA would demonstrate a difference between these two groups.

For the MWM hidden platform test, the escape latency (time to find the platform) was collected. T-tests were conducted for each day of each trial (1-4). Data was analyzed with non-compliant mice removed in order to more accurately represent memory. Non-compliant mice were defined as any mice that had escape latencies of 60 seconds (the full time allotted) for trials 3 and 4, when they should have been learning to some extent. The percent of non-compliant mice for each group was recorded. For hidden platform tests non-compliance was as follows: TG-low=8.3%; TG-high=15.3%; TG-saline=7.8%; WT-high=7.8%; and WT-saline=18.1%.

The Radial Arm Water Maze (RAWM). RAWM is used to evaluate short-term, working memory. Similar to a MWM, this test has a round tub with water, visual cues throughout the room and a hidden platform. It is unique in that inserts are placed into the tank to create six radially distributed arms of equal size that emanate from the center. Before trials began, the mice were acclimated to swimming in the water. Mice were dropped into 4 radial arms, in an order selected randomly for each trial, and given 1 minute to find the platform, with 20 seconds of rest between each trial. Trials occurred daily for twelve days and each day the platform was moved to a new location. Halfway through the testing, an extra intra-maze visual cue was added to the tank in an effort to make the test a little easier. The visual cue was a large 'X' made of tape and placed on the inner wall of the maze above the arm with the escape platform. Both errors and escape latency were recorded.

TABLE 29

RAWM escape latency (seconds) of mice grouped in blocks 1-4.

| | Block 1 | | | | Block 2 | | | | Block 3 | | | | Block 4 | | | |
|---|---|---|---|---|---|---|---|---|---|---|---|---|---|---|---|---|
| | T1(1) | T2(1) | T3(1) | T4(1) | T1(2) | T2(2) | T3(2) | T4(2) | T1(3) | T2(3) | T3(3) | T4(3) | T1(4) | T2(4) | T3(4) | T4(4) |
| TG-Low (N = 18) | 49.20 | 50.48 | 49.44 | 45.02 | 48.06 | 42.98 | 40.42 | 46.66 | 44.17 | 35.45 | 36.25 | 40.67 | 37.46 | 26.44 | 22.72 | 29.89 |
| TG-High (N = 18) | 49.72 | 47.13 | 44.94 | 47.33 | 47.78 | 34.09 | 42.11 | 42.96 | 40.00 | 45.02 | 35.56 | 41.59 | 32.70 | 27.20 | 29.76 | 29.57 |
| TG-Saline (N = 16) | 50.58 | 44.13 | 48.96 | 42.94 | 49.92 | 41.58 | 34.98 | 43.50 | 39.94 | 36.21 | 28.45 | 32.98 | 32.75 | 29.06 | 28.04 | 29.42 |
| WT-High (N = 18) | 39.96 | 47.11 | 43.04 | 42.02 | 44.81 | 41.61 | 34.72 | 41.70 | 41.91 | 33.52 | 39.54 | 34.93 | 40.15 | 28.28 | 24.78 | 24.43 |
| WT-Saline (N = 18) | 40.62 | 38.50 | 41.76 | 40.26 | 43.28 | 35.98 | 40.15 | 40.81 | 42.41 | 31.70 | 33.83 | 33.70 | 33.09 | 27.87 | 24.96 | 25.20 |

Overall, RAWM was too difficult for mice in blocks 1 and 2, as evidenced by a general trend for the escape latency not to go below about 35 seconds (Table 30). After the addition of the extra visual cue in blocks 3 and 4, a clear trend of decreased time to find the platform and errors became apparent in all treatment groups from trial 1 to trial 4 (Table 30, Table 31, and Table 32). This demonstrated that the test was effective for measuring memory.

TABLE 30

RAWM escape latency (seconds) of blocks 1 and 2.
ESCAPE LATENCY (BLOCK)

| | T1(1) | T2(1) | T1(2) | T2(2) | T1(3) | T2(3) | T1(4) | T2(4) |
|---|---|---|---|---|---|---|---|---|
| TG-Low (N = 18) | 49.20 | 50.48 | 48.06 | 42.98 | 44.17 | 35.45 | 37.46 | 26.44 |
| TG-High (N = 18) | 49.72 | 47.13 | 47.78 | 34.09 | 40.00 | 45.02 | 32.70 | 27.20 |
| TG-Saline (N = 16) | 50.58 | 44.13 | 49.92 | 41.58 | 39.94 | 36.21 | 32.75 | 29.06 |
| WT-High (N = 18) | 39.96 | 47.11 | 44.81 | 41.61 | 41.91 | 33.52 | 40.15 | 28.28 |
| WT-Saline (N = 18) | 40.62 | 38.50 | 43.28 | 35.98 | 42.41 | 31.70 | 33.09 | 27.87 |

TABLE 31

RAWM escape latency (seconds) of blocks 1 and 3.
ESCAPE LATENCY (BLOCK)

| | T1(1) | T3(1) | T1(2) | T3(2) | T1(3) | T3(3) | T1(4) | T3(4) |
|---|---|---|---|---|---|---|---|---|
| TG-Low (N = 18) | 49.20 | 49.44 | 48.06 | 40.42 | 44.17 | 36.25 | 37.46 | 22.72 |
| TG-High (N = 18) | 49.72 | 44.94 | 47.78 | 42.11 | 40.00 | 35.56 | 32.70 | 29.76 |
| TG-Saline (N = 16) | 50.58 | 48.96 | 49.92 | 34.98 | 39.94 | 28.45 | 32.75 | 28.04 |
| WT-High (N = 18) | 39.96 | 43.04 | 44.81 | 34.72 | 41.91 | 39.54 | 40.15 | 24.78 |
| WT-Saline (N = 18) | 40.62 | 41.76 | 43.28 | 40.15 | 42.41 | 33.83 | 33.09 | 24.96 |

TABLE 32

RAWM escape latency (seconds) of blocks 1 and 4.
ESCAPE LATENCY (BLOCK)

| | T1(1) | T4(1) | T1(2) | T4(2) | T1(3) | T4(3) | T1(4) | T4(4) |
|---|---|---|---|---|---|---|---|---|
| TG-Low (N = 18) | 49.20 | 45.02 | 48.06 | 46.66 | 44.17 | 40.67 | 37.46 | 29.89 |
| TG-High (N = 18) | 49.72 | 47.33 | 47.78 | 42.96 | 40.00 | 41.59 | 32.70 | 29.57 |
| TG-Saline (N = 16) | 50.58 | 42.94 | 49.92 | 43.50 | 39.94 | 32.98 | 32.75 | 29.42 |
| WT-High (N = 18) | 39.96 | 42.02 | 44.81 | 41.70 | 41.91 | 34.93 | 40.15 | 24.43 |
| WT-Saline (N = 18) | 40.62 | 40.26 | 43.28 | 40.81 | 42.41 | 33.70 | 33.09 | 25.20 |

There was clear evidence of a transgenic model effect in RAWM (Table 33 and Table 34). In Table 35 an overall summary of all groups averaged out over all days shows that in all four trials, both WT groups had lower times to find the platform than all three TG groups. This was also true of errors for trials 2-4 (Table 36). In Table 33, Table 34, Table 35, and Table 36, individual blocks and trials can be seen. For escape latency, WT-Sal mice had significantly shorter escape latencies than TG-Sal mice in B1-T1 (Batch 1-Trial 1), B1-T3, and B3-T2 (p<0.05 or 0.1) (Table 24). For errors (Table 36), WT-Sal mice had significantly fewer errors than TG-Sal mice in B1-T3, B3-T2, and B4-T2 (p<0.05 or 0.1) (Table 24). When all WT mice were combined and compared to all TG mice (irrespective of treatment), it was clear that WT mice outperformed TG mice. When all days were combined, WT mice had shorter escape latency and fewer errors than TG mice in all trials (Table 35 and Table 36).

Similarly, in individual blocks and trials, all WT mice had shorter escape latency and fewer errors in all trials in blocks 2-4 (Table 35 and Table 36). Statistically, WT mice had shorter escape latencies than TG mice in B1-T1, B3-T2, B3-T4, and B4-T4 ($p<0.05$) (Table 24). Statistically, WT mice had fewer errors than TG mice in B1-T1, B3-T2, B3-T4, B4-T2, and B4-T4 ($p<0.05$) (Table 24).

TABLE 33

RAWM escape latencies (seconds) recorded for 12 days of RAWM testing.

| | TG ALL (N = 52) | | | | WT ALL (N = 36) | | | |
|---|---|---|---|---|---|---|---|---|
| | Arm 1 | Arm 2 | Arm 3 | Arm 4 | Arm 1 | Arm 2 | Arm 3 | Arm 4 |
| Day 1 | 51.67 | 53.33 | 49.08 | 45.24 | 45.94 | 45.56 | 46.81 | 45.22 |
| Day 2 | 51.15 | 45.58 | 48.54 | 46.87 | 36.11 | 40.22 | 40.06 | 37.47 |
| Day 3 | 46.60 | 43.19 | 45.60 | 43.41 | 38.86 | 42.64 | 40.33 | 40.72 |
| Day 4 | 50.29 | 37.31 | 39.87 | 43.27 | 43.17 | 37.67 | 37.03 | 34.83 |
| Day 5 | 49.85 | 40.62 | 38.27 | 44.76 | 41.94 | 38.14 | 36.61 | 44.08 |
| Day 6 | 45.41 | 40.45 | 39.84 | 45.20 | 47.00 | 40.58 | 38.67 | 44.86 |
| Day 7 | 45.76 | 38.76 | 37.14 | 42.38 | 41.53 | 32.08 | 34.53 | 40.67 |
| Day 8 | 38.79 | 41.61 | 39.20 | 38.92 | 43.36 | 28.36 | 38.36 | 28.97 |
| Day 9 | 39.75 | 36.79 | 24.71 | 34.63 | 41.57 | 37.39 | 37.17 | 33.31 |
| Day 10 | 34.42 | 29.90 | 29.69 | 29.94 | 39.81 | 27.19 | 27.50 | 25.47 |
| Day 11 | 34.13 | 23.69 | 24.10 | 31.15 | 35.50 | 27.50 | 26.08 | 28.94 |
| Day 12 | 34.54 | 28.94 | 26.60 | 27.81 | 34.56 | 29.53 | 21.03 | 20.03 |

TABLE 34

RAWM escape latencies (seconds) of blocks 1-4.

| | Block 1 | | | | Block 2 | | | | Block 3 | | | | Block 4 | | | |
|---|---|---|---|---|---|---|---|---|---|---|---|---|---|---|---|---|
| | T1(1) | T2(1) | T3(1) | T4(1) | T1(2) | T2(2) | T3(2) | T4(2) | T1(3) | T2(3) | T3(3) | T4(3) | T1(4) | T2(4) | T3(4) | T4(4) |
| TG ALL (N = 52) | 49.81 | 47.37 | 47.73 | 45.18 | 48.54 | 39.45 | 39.32 | 44.40 | 41.42 | 39.04 | 33.62 | 38.62 | 34.37 | 27.51 | 26.79 | 29.63 |
| WT ALL (N = 36) | 40.29 | 42.81 | 42.40 | 41.14 | 44.06 | 38.80 | 37.44 | 41.26 | 42.16 | 32.61 | 36.69 | 34.31 | 36.62 | 28.07 | 24.87 | 24.81 |

TABLE 35

12 day average of RAWM escape latencies (seconds).

| | Trial 1 | Trial 2 | Trial 3 | Trial 4 |
|---|---|---|---|---|
| TG ALL (N = 52) | 43.53 | 38.35 | 36.89 | 39.46 |
| WT ALL (N = 36) | 40.78 | 35.57 | 35.35 | 35.38 |

TABLE 36

12 day average of RAWM errors (trial averages).

| | Trial 1 | Trial 2 | Trial 3 | Trial 4 |
|---|---|---|---|---|
| TG ALL (N = 52) | 4.77 | 4.64 | 4.28 | 4.42 |
| WT ALL (N = 36) | 4.52 | 3.84 | 3.71 | 3.72 |

There was evidence of a TG model effect in RAWM. A summary of all groups averaged out over all days (Table 35) shows that in all four trials, both WT groups had lower times to find the platform than all three TG groups. This was also true of errors for trials 2-4 (Table 35 and Table 36). In Table 35 and Table 36, individual blocks and trials can be seen. For escape latency, WT-Sal mice had significantly shorter escape latencies than TG-Sal mice in B1-T1 (Batch 1-Trial 1), B1-T3, and B3-T2 ($p<0.05$ or 0.1) (Table 24). As shown in Table 36, WT-Sal mice had significantly fewer errors than TG-Sal mice in B1-T3, B3-T2, and B4-T2 ($p<0.05$ or 0.1) (Table 24). When all WT mice were combined and compared to all TG mice (irrespective of treatment), it was clear that WT mice outperformed TG mice. When all days were combined, WT mice had shorter escape latency and fewer errors than TG mice in all trials (Table 35). Similarly, in individual blocks and trials, all WT mice had shorter escape latency and fewer errors in all trials in blocks 2-4 (Table 35 and Table 36). Statistically, WT mice had shorter escape latencies than TG mice in B1-T1, B3-T2, B3-T4, and B4-T4 ($p<0.05$) (Table 24). Statistically, WT mice had fewer errors than TG mice in B1-T1, B3-T2, B3-T4, B4-T2, and B4-T4 ($p<0.05$) (Table 24).

The Barnes Maze. The Barnes maze is a visual memory task based on finding an escape hole on a table, aided by visual cues throughout the room. The table was round, elevated 1 m from the floor, and had 40 escape holes spaced equally around the periphery of the table. One of these holes had an escape box directly underneath, while the others were open. The motivation to find the escape box was aversive stimuli in the form of bright lights and fans blowing above the surface of the table. The escape box was located in one location for the duration of the study. The mouse was given 4 days, with 3 trials/day to learn the location of the escape box. Mice were given up to two minutes on the table to find the escape hole. If after 2 minutes they did not find the escape box, they were placed into the box. Both escape latency to find the hole and errors were recorded and analyzed. Errors were defined as head-pokes through holes that do not have the escape box.

Overall, the Barnes maze test did not work well for the mice in this study. This was the only behavior test in which non-compliance was an issue (roughly 50% of all mice did not perform the task). While running the tests, the mice were generally not scared of the aversive stimuli. However, among the mice that were compliant and included in the analyses, there was a learning trend across the days and trials, which can be seen in the escape latencies.

There was evidence of a model effect with this test. Table 37 and Table 38 shows that both WT groups have lower escape latencies on days 3 and 4 than all three TG groups. This mirrors data collected with the RAWM and MWM tests, the other two long-term memory tasks. This difference is also seen when all WT mice and TG mice are combined as in Table 39 and Table 40.

TABLE 37

Average escape latencies (sec) from the Barnes Water Maze by treatment.

| Time (s) | Day 1 | Day 2 | Day 3 | Day 4 |
|---|---|---|---|---|
| TG-Low (N = 18) | 105.15 | 99.76 | 95.44 | 85.67 |
| TG-High (N = 18) | 107.74 | 94.57 | 100.30 | 97.33 |
| TG-Saline (N = 16) | 95.48 | 89.10 | 90.10 | 82.31 |

TABLE 37-continued

Average escape latencies (sec) from the Barnes Water Maze by treatment.

| Time (s) | Day 1 | Day 2 | Day 3 | Day 4 |
|---|---|---|---|---|
| WT-High (N = 17) | 99.06 | 95.98 | 93.65 | 82.04 |
| WT-Saline (N = 18) | 94.15 | 97.41 | 93.43 | 87.63 |

TABLE 38

Average escape latencies (sec) from the Barnes Water Maze by treatment with noncompliance removed.

| Time (s) | Day 1 | Day 2 | Day 3 | Day 4 |
|---|---|---|---|---|
| TG-Low (N = 7-12) | 82.81 | 78.25 | 83.60 | 72.75 |
| TG-High (N = 6-8) | 84.28 | 72.14 | 75.71 | 68.86 |
| TG-Saline (N = 7-9) | 79.71 | 65.38 | 74.30 | 71.48 |
| WT-High (N = 8-10) | 83.74 | 79.17 | 66.29 | 60.13 |
| WT-Saline (N = 7-10) | 69.17 | 68.43 | 73.00 | 60.74 |

TABLE 39

Average escape latencies (sec) from the Barnes Water Maze by genotype.

| Time (s) | Day 1 | Day 2 | Day 3 | Day 4 |
|---|---|---|---|---|
| TG ALL (N = 52) | 103.07 | 94.69 | 95.48 | 88.67 |
| WT ALL (N = 35) | 96.53 | 96.71 | 93.53 | 84.91 |

TABLE 40

Average escape latencies (sec) from the Barnes Water Maze by genotype with noncompliance removed.

| Time (s) | Day 1 | Day 2 | Day 3 | Day 4 |
|---|---|---|---|---|
| TG All (N = 21-28) | 82.05 | 72.21 | 78.16 | 71.37 |
| WT All (N = 17-19) | 76.88 | 74.75 | 70.02 | 60.42 |

There was no evidence of a drug effect in the Barnes Maze tests (Table 37, Table 38, Table 39, Table 40, Table 41, Table 42). The only statistical significance was in B4-T1, in which TG-low mice performed very poorly and had longer escape latency than TG-Sal mice ($p<0.1$; Table 24).

TABLE 41

Average number of errors from the Barnes Water Maze by treatment.

| | Day 1 | Day 2 | Day 3 | Day 4 |
|---|---|---|---|---|
| TG-Low (N = 18) | 8.48 | 5.57 | 6.24 | 5.39 |
| TG-High (N = 18) | 6.85 | 5.54 | 4.15 | 4.04 |

TABLE 41-continued

Average number of errors from the Barnes Water Maze by treatment.

| | Day 1 | Day 2 | Day 3 | Day 4 |
|---|---|---|---|---|
| TG-Saline (N = 16) | 11.90 | 8.02 | 6.29 | 5.69 |
| WT-High (N = 17) | 6.96 | 6.45 | 4.69 | 4.00 |
| WT-Saline (N = 18) | 9.46 | 8.44 | 5.35 | 4.89 |

TABLE 42

Average errors from the Barnes Water Maze by genotype.

| | Day 1 | Day 2 | Day 3 | Day 4 |
|---|---|---|---|---|
| TG ALL (N = 52) | 8.97 | 6.31 | 5.53 | 5.01 |
| WT ALL (N = 35) | 8.25 | 7.48 | 5.03 | 4.46 |

For Barnes Maze, both the escape latency (time to find the escape hole) and errors (number of times a mouse pokes his head into a hole that does not have the escape box) were collected. T-tests were conducted for each day of each trial (1-3). Data was analyzed with non-compliant mice removed in order to more accurately represent memory. Non-compliant mice were defined as any mice that had escape latencies of 120 seconds (the full time allotted) for trials 3, when they should have been learning to some extent. The percent of non-compliant mice for each group was recorded and was as follows: TG-low=48.6%; TG-high=61.1%; TG-saline=48.4%; WT-high=45.6%; and WT-saline=52.8%.

Elevated Plus Maze. The Elevated Plus Maze is a standard test of baseline anxiety in which the animal is placed in the center of an elevated 4-arm maze that consists of two arms that are open and two arms that are enclosed. The number of times the animal entered each of the arms and the time spent in each arm over 4 minutes was recorded. The test was used to determine the unconditioned response to a potentially dangerous environment (the open, unprotected arms) and anxiety-related behavior was measured by the degree to which the rodent avoids the open arms of the maze.

There was a transgenic effect in the Elevated Plus Maze. In this model, all TG mice spent more time and made more frequent arm entries into the open arms of the maze than all WT mice, demonstrating inhibition of exploratory behavior and anxiety that WT mice have regarding open spaces. When WT-Sal mice were compared to TG-Sal mice, TG mice spent significantly more time and have significantly more arm entries into the open arms (Table 24, Table 43, and Table 44). When all WT-mice and all TG-mice were combined, the same results were seen (Table 44 and Table 45), $p<0.05$; Table 24).

TABLE 43

Average time spent in open arms during the Elevated Plus Maze.

| | TIME (SEC) | | | | | | | |
|---|---|---|---|---|---|---|---|---|
| | SUM | | | | PERCENTAGE | | | |
| | Avg. Time Enclosed | Avg Time Open | Std Error Enclosed | Std Error Open | Avg. Time Enclosed | Avg Time Open | Std Error Enclosed | Std Error Open |
| TG-Low (N = 18) | 115.2 | 31.4 | 10.8 | 5.3 | 48.0 | 13.1 | 4.5 | 2.2 |
| TG-High (N = 16) | 128.7 | 48.9 | 11.2 | 8.7 | 53.7 | 20.4 | 4.7 | 3.6 |
| TG-Saline (N = 15) | 117.5 | 34.6 | 11.6 | 7.4 | 49.0 | 14.4 | 4.9 | 3.1 |
| WT-High (N = 16) | 151.9 | 20.6 | 8.6 | 3.7 | 63.4 | 8.6 | 3.6 | 1.6 |

TABLE 43-continued

Average time spent in open arms during the Elevated Plus Maze.

| | TIME (SEC) | | | | | | | |
|---|---|---|---|---|---|---|---|---|
| | SUM | | | | PERCENTAGE | | | |
| | Avg. Time Enclosed | Avg Time Open | Std Error Enclosed | Std Error Open | Avg. Time Enclosed | Avg Time Open | Std Error Enclosed | Std Error Open |
| WT-Saline (N = 16) | 169.8 | 15.9 | 11.6 | 4.4 | 70.8 | 6.6 | 4.8 | 1.8 |
| TG ALL (N = 49) | 120.3 | 38.1 | 6.4 | 4.2 | 50.2 | 15.9 | 2.7 | 1.8 |
| WT ALL (N = 32) | 160.8 | 18.3 | 7.3 | 2.9 | 67.1 | 7.6 | 3.0 | 1.2 |

TABLE 44

Average frequency of entries into open arms during the Elevated Plus Maze.

| | FREQUENCY | | | | | | | |
|---|---|---|---|---|---|---|---|---|
| | SUM | | | | PERCENTAGE | | | |
| | Avg. Freq Enclosed | Avg. Freq Open | Std Error Enclosed | Std Error Open | Avg. Freq Enclosed | Avg. Freq Open | Std Error Enclosed | Std Error Open |
| TG-Low (N = 18) | 16.6 | 10.8 | 2.0 | 2.0 | 60.9 | 39.1 | 5.1 | 5.1 |
| TG-High (N = 16) | 16.0 | 14.8 | 2.2 | 3.6 | 57.8 | 42.2 | 5.2 | 5.2 |
| TG-Saline (N = 15) | 15.9 | 8.1 | 2.4 | 2.2 | 69.6 | 30.4 | 5.8 | 5.8 |
| WT-High (N = 16) | 13.8 | 3.4 | 1.5 | 0.5 | 82.1 | 17.9 | 2.4 | 2.4 |
| WT-Saline (N = 16) | 9.8 | 3.0 | 1.1 | 0.8 | 81.9 | 18.1 | 3.8 | 3.8 |
| TG ALL (N = 49) | 16.2 | 11.3 | 1.2 | 1.6 | 62.5 | 37.5 | 3.1 | 3.1 |
| WT ALL (N = 32) | 11.8 | 3.2 | 1.0 | 0.5 | 82.0 | 18.0 | 2.2 | 2.2 |

There was no evidence of a drug effect in the Elevated Plus Maze tests. Although the TG-high group had the most arm-entries and spent the most time in the open arms, it was not significantly different from any other groups (Table 24, Table 43, and Table 44).

For the Elevated Plus Maze, both the time spent in open and enclosed arms and the number of arm entries (also called frequency of arm entries) were recorded. Mice were not included in the analyses if they fell off the maze in less than 120 seconds. There were 3 mice that fell off, all from different groups. For outliers, mice were removed if both their time spent in open arms and frequency of entries into open arms were more than two standard deviations from the mean of their treatment group. Outliers included 3 mice, all from different groups.

The Open Field Maze Test. The Open Field Maze Test is used to detect any change in spontaneous locomotor activity due to drug treatment or anxiety. Each mouse was given 4 minutes to individually explore a rectangular box, while being tracked by the EthoVision video tracking system. For analysis, the box was subdivided into 16 equally sized squares that are separated by manually drawn lines using the "line draw" feature in EthoVision. The number of line crossings and patterns of exploration were measured.

There was no evidence of a transgenic or drug effect in the Open Field Maze tests. All groups of mice had very similar line crossings and velocity (Table 24, Table 45, Table 46, Table 47, and Table 48).

TABLE 45

Average velocity of mice.

| | Avg Velocity | Std Dev | Std Error |
|---|---|---|---|
| TG Low (N = 18) | 7.66 | 2.48 | 0.58 |
| TG High (N = 18) | 9.32 | 3.73 | 0.88 |

TABLE 45-continued

Average velocity of mice.

| | Avg Velocity | Std Dev | Std Error |
|---|---|---|---|
| TG Saline (N = 15) | 8.73 | 2.78 | 0.72 |
| WT High (N = 16) | 10.03 | 2.50 | 0.63 |
| WT Saline (N = 17) | 9.71 | 3.38 | 0.82 |

TABLE 46

Average velocity of mice, averaged by genotype.

| | Avg Velocity | Std Error |
|---|---|---|
| TG ALL (N = 51) | 8.66 | 0.44 |
| WT ALL (N = 33) | 9.46 | 0.56 |

TABLE 47

Average number of line crossings by mice.

| | Avg Line Crossings | Std Dev | Std Error |
|---|---|---|---|
| TG Low (N = 18) | 87.56 | 32.93 | 7.76 |
| TG High (N = 18) | 110.94 | 44.01 | 10.37 |
| TG Saline (N = 15) | 105.53 | 29.47 | 7.61 |
| WT High (N = 16) | 113.06 | 30.10 | 7.53 |
| WT Saline (N = 17) | 112.59 | 33.44 | 8.11 |

TABLE 48

Average number of line crossings by mice, averaged by genotype.

|  | Avg Line Crossings | Std Error |
|---|---|---|
| TG ALL (N = 51) | 102.65 | 5.33 |
| WT ALL (N = 33) | 107.83 | 6.21 |

For the Open Field Maze, both the number of line crossings and the overall velocity were measured. Outliers were removed if an individual mouse's line crossings were more than 2 standard deviations from the mean of the treatment group. This included 3 mice, each from different treatment groups. Analysis was performed for both line crossings and velocity.

The Rotarod Performance Test. The Rotarod Performance Testis used to detect any changes in endurance, balance, and coordination. Mice were placed on an automated rotating bar and allowed to walk on the bar for up to 60 seconds. The speed of rotation was gradually increased and the rodent's ability to remain on the rotating bar was recorded as the total time spent on the bar. Mice were given three trials, and the best time is used for analysis.

There was no transgenic model effect on the Rotarod tests. All groups performed essentially the same and there were no statistical differences among groups (Table 24 and Table 49, Table 50, and Table 51). There was a non-significant trend for all WT mice to outperform all TG mice (Table 49, Table 50, and Table 51).

TABLE 49

Longest average runs on the rotarod by treatment group.

|  | Best Trial (Average) (sec) |
|---|---|
| TG-Low (N = 18) | 30.59 |
| TG-High (N = 18) | 37.33 |
| TG-Saline (N = 16) | 35.38 |
| WT-High (N = 16) | 54.13 |
| WT-Saline (N = 18) | 35.67 |
| TG ALL (N = 52) | 37.33 |
| WT ALL (N = 34) | 35.38 |

TABLE 50

Average run time on the rotarod by treatment group.

|  | Avg. Time (sec) |
|---|---|
| TG-Low (N = 18) | 19.43 |
| TG-High (N = 18) | 23.30 |
| TG-Saline (N = 16) | 22.35 |
| WT-High (N = 16) | 35.24 |
| WT-Saline (N = 18) | 22.25 |
| TG ALL (N = 52) | 23.30 |
| WT ALL (N = 34) | 22.35 |

TABLE 51

Trial averages of run time (sec) on the rotarod by treatment group.

|  | Trial 1 | Trial 2 | Trial 3 |
|---|---|---|---|
| TG-Low (N = 18) | 10.53 | 21.25 | 27.06 |
| TG-High (N = 18) | 15.72 | 20.44 | 33.72 |
| TG-Saline (N = 16) | 16.60 | 25.63 | 24.60 |
| WT-High (N = 16) | 19.56 | 43.00 | 44.20 |
| WT-Saline (N = 18) | 17.00 | 17.06 | 32.39 |
| TG ALL (N = 52) | 15.72 | 20.44 | 33.72 |
| WT ALL (N = 34) | 16.60 | 25.63 | 24.60 |

There was no evidence of a drug effect among transgenic groups (Table 49, Table 50, and Table 51). However, it was observed that the WT-high mice had longer times on the rotarod than the WT-Sal mice. A t-test between WT-Sal and WT-high yielded a p-value of 0.089 for the longest run, and a p-value of 0.041 for the average run (T-tests not shown, Table 49, Table 50, and Table 51).

For the Rotarod test, the time on the rotating bar before the mouse fell off was recorded. Three trials were conducted. If a mouse reached 120 seconds (the maximum time) before trial 3, subsequent runs were not conducted. For each treatment group, both the average time on the bar and the maximum time on the bar for each mouse were analyzed. Data could not be recorded if the mouse did not stay on the rod long enough before starting (~3 seconds), and there was only 1 mouse that did not stay on long enough to start for all three trials.

The Passive Avoidance Task. The Passive Avoidance Task is a classical conditioning test used to assess short-term or long-term memory for mice and rats. The passive avoidance apparatus consists of equal-sized light and dark compartments with a light bulb fixed in the center of the roof of the light compartment. The floor consists of a metal grid connected to a shocker. The two compartments are separated by a trap door. On the learning day (day 1), a mouse was placed in the light compartment and the time taken to enter the dark compartment was recorded and termed as initial latency. Immediately after the mouse entered the dark chamber a door was automatically closed and an electric footshock (0.7 mA) was delivered for 3 seconds. Twenty-four hours after the acquisition trial, a second retention trial was conducted and the time the mouse takes to enter the dark compartment as designated retention latency (RL; recorded to a maximum of 500 seconds, no shock is administered during this entry). T-tests were performed to compare the effects of IN IgG WT vs. TG.

Whereas RAWM, MWM hidden platform, and Barnes maze tests all showed evidence of learning and improved learning in WT mice over TG mice, this test consistently showed the opposite effect, regardless of drug treatment. There was no evidence of a drug effect among transgenic groups (Table 24, Table 52, Table 53, and Table 54).

TABLE 52

Passive avoidance learn day escape latency (sec).

|  | Learn Esc. | St. Err |
|---|---|---|
| TG-Low (N = 17) | 44.5 | 9.4 |
| TG-High (N = 19) | 46.3 | 7.6 |
| TG-Saline (N = 15) | 43.7 | 9.2 |
| WT-High (N = 17) | 21.6 | 6.4 |
| WT-Saline (N = 18) | 22.4 | 3.9 |
| TG ALL (N = 51) | 44.9 | 4.9 |
| WT ALL (N = 35) | 22 | 3.6 |

TABLE 53

Passive avoidance test day escape latency (sec).

|  | Learn Esc. | St. Err |
|---|---|---|
| TG-Low (N = 15) | 224.6 | 8.5 |
| TG-High (N = 17) | 229.5 | 8.3 |
| TG-Saline (N = 13) | 207.0 | 16.8 |
| WT-High (N = 16) | 114.3 | 22.0 |
| WT-Saline (N = 18) | 153.8 | 20.9 |
| TG ALL (N = 45) | 221.4 | 4.9 |
| WT ALL (N = 34) | 135.2 | 3.6 |

TABLE 54

Passive avoidance average of escape latency differences (sec).

|  | Average of Differences | St. Err |
|---|---|---|
| TG-Low (N = 15) | 190.2 | 8.5 |
| TG-High (N = 17) | 191.9 | 8.2 |
| TG-Saline (N = 13) | 175.1 | 16.8 |
| WT-High (N = 16) | 98.8 | 22.4 |
| WT-Saline (N = 18) | 131.4 | 21.4 |
| TG ALL (N = 45) | 186.5 | 6.3 |
| WT ALL (N = 34) | 116.1 | 15.5 |

This test demonstrated an unexpected TG effect. Whereas TG mice with impaired memory should normally have trouble remembering not to enter the dark chamber and receive a shock after training, this was not the case. TG mice generally did not enter the chamber on the test day, whereas WT mice seemed not to care whether they received a shock on the test day. These results can be seen in Table 52, Table 53, and Table 54. The poor performance of the WT mice compared to the TG mice is statistically significant (p<0.05; Table 24). The same willingness for WT mice to enter the dark chamber can be seen in the learning phase and may play a role in the willingness of normal, WT mice to go receive a painful shock.

For the Passive Avoidance Task, the escape latency on both the learning day (day 1) and the test day (day 2) were recorded and the difference between the escape latency between the test and learn day were calculated. Mice were not run on the test day (day 2) if they did not receive a shock on day 1, which included 7 mice spread across 4 groups. Mice did not receive a shock simply because they did not enter the dark chamber. There were no outliers calculated. Analyses were performed for the learn trial and the test trial.

Morris Water Maze—Visual Platform. Differences in performance in this test were not expected as all mice were genetically tested for the RD 1 gene and the mice did not have problems with vision. There was no transgenic model effect. All groups performed essentially the same and there were no statistical differences among groups (Table 24). The one statistical difference came in trial 1, due to a strong performance by WT-Sal that did not carry over into subsequent trials. There was also no evidence of a drug effect among transgenic groups (Table 24, Table 55, Table 56, Table 57, and Table 58). However, much like with the MWM hidden platform tests, there was a trend for WT-high mice to outperform all other groups (Table 55, Table 56, Table 57, and Table 58). T-test comparisons between WT-Sal and WT-high for each individual trial were not significant, but a T-test for all trials between these two groups had a p-value of 0.06.

TABLE 55

Visual escape (sec) by treatment group.

| Group | Trial 1 | Trial 2 | Trial 3 | Trial 4 | Average |
|---|---|---|---|---|---|
| TG-Low (N = 18) | 34.83 | 33.44 | 39.17 | 30.22 | 33.44 |
| TG-High (N = 18) | 31.44 | 33.67 | 35.33 | 37.89 | 33.67 |
| TG-Saline (N = 16) | 23.19 | 36.56 | 29.75 | 28.94 | 36.56 |
| WT-High (N = 16) | 28.25 | 23.44 | 23.13 | 22.00 | 23.44 |
| WT-Saline (N = 18) | 29.78 | 29.06 | 26.11 | 25.50 | 29.06 |

TABLE 56

Visual escape (sec) by treatment group, with non-compliance removed.

| Group | Trial 1 | Trial 2 | Trial 3 | Trial 4 | Average |
|---|---|---|---|---|---|
| TG-Low (N = 13) | 30.46 | 29.15 | 31.15 | 18.77 | 29.15 |
| TG-High (N = 13) | 21.69 | 27.92 | 25.85 | 29.38 | 27.92 |
| TG-Saline (N = 14) | 17.93 | 33.21 | 25.43 | 24.50 | 33.21 |
| WT-High (N = 14) | 25.07 | 18.57 | 17.86 | 16.57 | 18.57 |
| WT-Saline (N = 17) | 31.41 | 27.24 | 24.12 | 23.47 | 27.24 |

TABLE 57

Visual escape (sec) by genotype group.

| Group | Trial 1 | Trial 2 | Trial 3 | Trial 4 | Average |
|---|---|---|---|---|---|
| TG ALL (N = 52) | 30.08 | 34.48 | 34.94 | 32.48 | 34.48 |
| WT ALL (N = 34) | 29.06 | 26.41 | 24.71 | 23.85 | 26.41 |

TABLE 58

Visual escape (sec) by genotype, with non-compliance removed.

| Group | Trial 1 | Trial 2 | Trial 3 | Trial 4 | Average |
|---|---|---|---|---|---|
| TG ALL (N = 40) | 23.23 | 30.18 | 27.43 | 24.23 | 30.18 |
| WT ALL (N = 31) | 28.55 | 23.32 | 21.29 | 20.35 | 23.32 |

For the visual platform MWM, the escape latency (time to find the platform) was collected. T-tests were conducted for each day of each trial (1-4). Data was analyzed with non-compliant mice removed in order to more accurately represent memory. Non-compliant mice were defined as any mice that had escape latencies of 60 seconds (the full time allotted) for trials 3 and 4, when they should have been learning to some extent. The percent of non-compliant mice for each group was recorded. For visual platform tests non-compliance was as follows: TG-low=6.9%; TG-high=6.9%; TG-saline=3.1%; WT-high=3.1%; and WT-saline=1.4%.

Example 8

Radiolabeled $^{125}$I IgG Reaches the CNS with Intranasal Delivery

A study was conducted to determine the feasibility and to optimize the methods used to determine the amount of intravenously and intranasally delivered radiolabed $^{125}$I IgG reaching the CNS in rats and mice at a two hour time point.

Experimental Design: There were two phases of this experiment. In phase 1, six mice and rats were used to test a variety of different methods including anesthesia with 2 hour survival, drug administration methods (intravenous infusion through cannulations of the jugular vein in rats and mice, intranasal tube method in rats), transcardial perfusion (with and without a non-ionic detergent), and tissue processing for capillary depletion and gamma counting. Animals and the methods tested with each are shown in Table 51.

TABLE 59

Experimental design of phase 1 of Example 8. R = rat and M = mouse.

| Animal | Surgery | IV delivery | IN delivery | Perfusion | Brain Dissection |
|---|---|---|---|---|---|
| 1a-R-1 | Jugular Vein Cannulation | No infusion | IN tube method | Saline | Whole Brain removal |
| 1a-R-2 | Jugular Vein Cannulation | 2 mg/mL BSA until death | IN tube method | 0.05% Triton X | Whole Brain removal |
| 1a-R-3 | Jugular Vein Cannulation | 2 mg/mL BSA over 1 hour | IN tube method | Saline | Capillary Depletion |
| 1a-R-4 | Jugular Vein Cannulation | No infusion | No IN delivery | 0.1% Triton X | Whole Brain removal |
| 1a-R-5 | Jugular Vein Cannulation | No infusion | IN tube method | 0.1% Triton X | Whole Brain removal |
| 1a-R-6 | Jugular Vein Cannulation | No infusion | No IN delivery | Saline | Capillary Depletion |
| 1a-M-1 | Jugular Vein Cannulation | No infusion | No IN delivery | Saline | Capillary Depletion |
| 1a-M-2 | Jugular Vein Cannulation | 2 mg/mL BSA over 1 hour | No IN delivery | 0.05% Triton X | Whole Brain removal |
| 1a-M-3 | Jugular Vein Cannulation | 2 mg/mL BSA over 1 hour | No IN delivery | 0.1% Triton X | Whole Brain removal |
| 1a-M-4 | Jugular Vein Cannulation | 2 mg/mL BSA over 1 hour | No IN delivery | Saline | Whole Brain removal |
| 1a-M-5 | Jugular Vein Cannulation | 8 g/kg IgG over 1 hour | No IN delivery | 0.05% Triton X | Whole Brain removal |
| 1a-M-6 | Jugular Vein Cannulation | 8 g/kg IgG over 1 hour | No IN delivery | 0.05% Triton X | Whole Brain removal |

In Phase 2, three tissue processing techniques after administration of high IVIG does in 18 rats were tested in order to determine the optimal technique of subsequent Phase 1 experiments. The 18 rats were divided into 3 experimental groups (Table 60).

TABLE 60

Experimental groups for Phase 2.

| | Group 1 | Group 2 | Group 3 |
|---|---|---|---|
| $^{125}$I-IVIG dose | 200 mg | 200 mg | 200 mg |
| Perfusion | 140 mL saline | 140 mL saline with capillary depletion | 90 mL saline, 25 mL 0.025% Triton X-100, 25 mL saline |
| n = | 6 rats | 6 rats | 6 rats |

Adult male Sprague Dawley rats (N=6, average weight 250 g) and adult male C57blk mice (n=6, 7-8 weeks) were used for Phase 1. Adult male Sprague Dawley rats (N=18, average weight 264 g) were used for Phase 2. The animals were housed in pairs with free access to food and water and were kept on a 12 h light cycle.

Prior to commencing the Phase 1 and 2 experiments, the animals were allowed to normalize in the facility for a period of three days before handling occurred. Animals were slowly acclimated to human handling over a period of about two weeks. Enrichment food treats are given after handling to encourage a human-animal bond while the acclimation process proceeds. Restraint techniques were kept brief and facilitated by using a towel, restraint device, or scruffing, when working with mice.

An anesthesia cocktail containing Ketamine HCl (30 mg/kg), Xylazine HCl (6 mg/kg), and Acepromazine (1 mg/kg) was used. All anesthesia was administered as subcutaneous injections. Boosters alternated between the Cocktail above and 50 mg/kg Ketamine. Reflexes were tested to assess level of anesthesia every 10-15 minutes throughout the study.

Intranasal deliver in rats was performed using a specialized pipette tip. The specialized pipette tip was inserted into the rat naris. The pipette tip was created by cutting 23 mm off the end of a gel loading pipette tip and attaching a 16 mm length of tubing (ID=0.04 mm, OD=0.07 mm). The tubing was placed over the wide end of the pipette tip with an overlap of 5.5 mm, and a black mark with a sharpie was made at 14.5 mm from the narrowest end of the pipette tip. The narrow end was ultimately inserted into the rat's nose up to the black mark.

For intranasal delivery, the fully anesthetized rat was placed on its back on a heating pad in a metal surgical tray. The heating pad and rectal probe was used to maintain the rat's core temperature at 37° C. A 2"×2" gauze pad was rolled into a pillow and was securely taped. The pillow was then placed under the rat's neck to ensure that the underside from nostril to torso was planar and horizontal.

A lead impregnated shield was placed between the surgical tray and the experimenter for protection against radiation. The dose solution, pipette, pipette tips, and waste receptacle were arranged behind the shield for easy access. The modified pipette tip was inserted into the rat naris up to the black mark. The sample to be delivered (40-50 µl) was drawn into a pipettor, the tip of the pipettor placed into the open tube at the end of the modified pipette tip (while carefully holding the modified pipette tip in place in the rat's nose), and then the entire dose was slowly expelled into the rat's nostril.

After the animals were euthanized, their brains were removed for analysis. With a large surgical scissors, the head of the animal was removed by cutting dorsal to ventral to avoid contamination. Using a scalpel, the fur and skin on the top of the skull was cut from nose to point of decapitation.

The skin was folded back and held with a small gauze pad to expose the top of the skull. Using a small hemostat, the remainder of the spinal column was chipped away exposing the upper cervical spinal cord and posterior brain (cerebellum). Next, the top of the skull was removed to the olfactory bulbs exposing the entire dorsal side of the brain. The hemostat was inserted with one blade scraping the ventral surface of the skull. This ensured the integrity of the dorsal surface of the brain was maintained. A small spatula was used to loosen the lateral surfaces of the brain from the skull and dura. The brain was inverted over a clean Petri dish. The optic nerve was severed, which released the brain from the skull. The brain was assessed for quality of perfusion.

Figure 5:
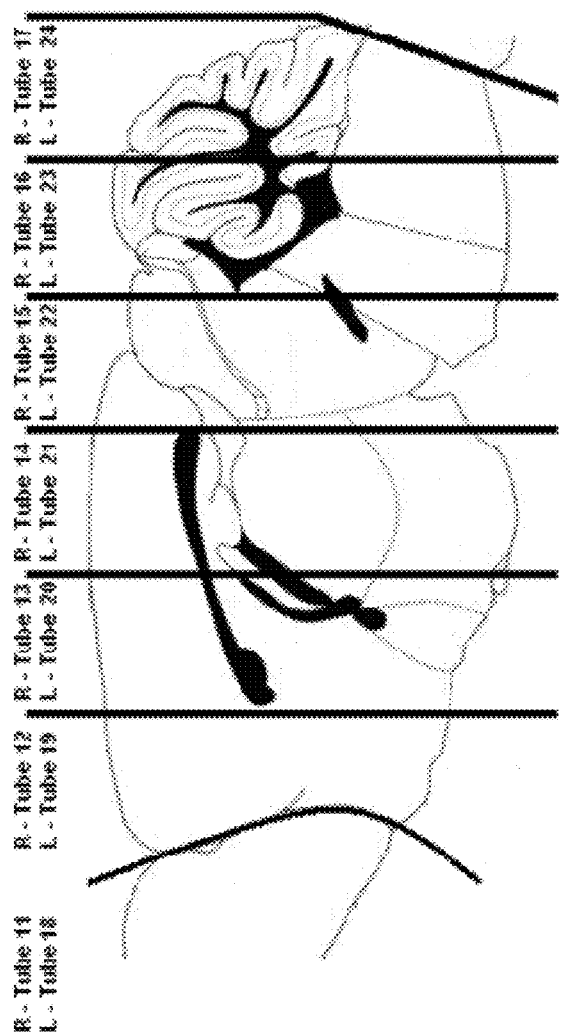
FIG. 5 Illustrates the seven coronal brain slices which were hemisected from intranasal $^{125}$I IgG treated rats used to assess CNS delivery in Example 8.
Figure 6A:
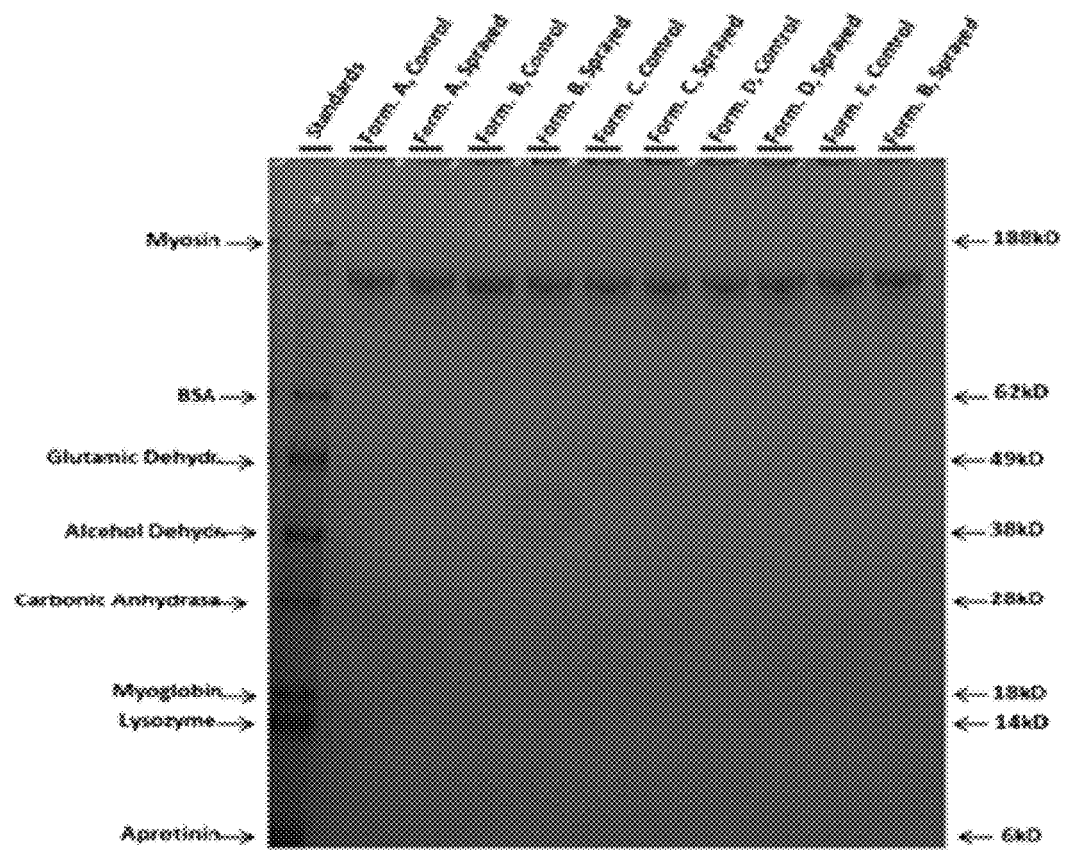
FIGS. 6A-6B show comparative results of the intactness of IgG sprayed through a device designed for intranasal delivery with that of non-sprayed control.
Figure 6B:
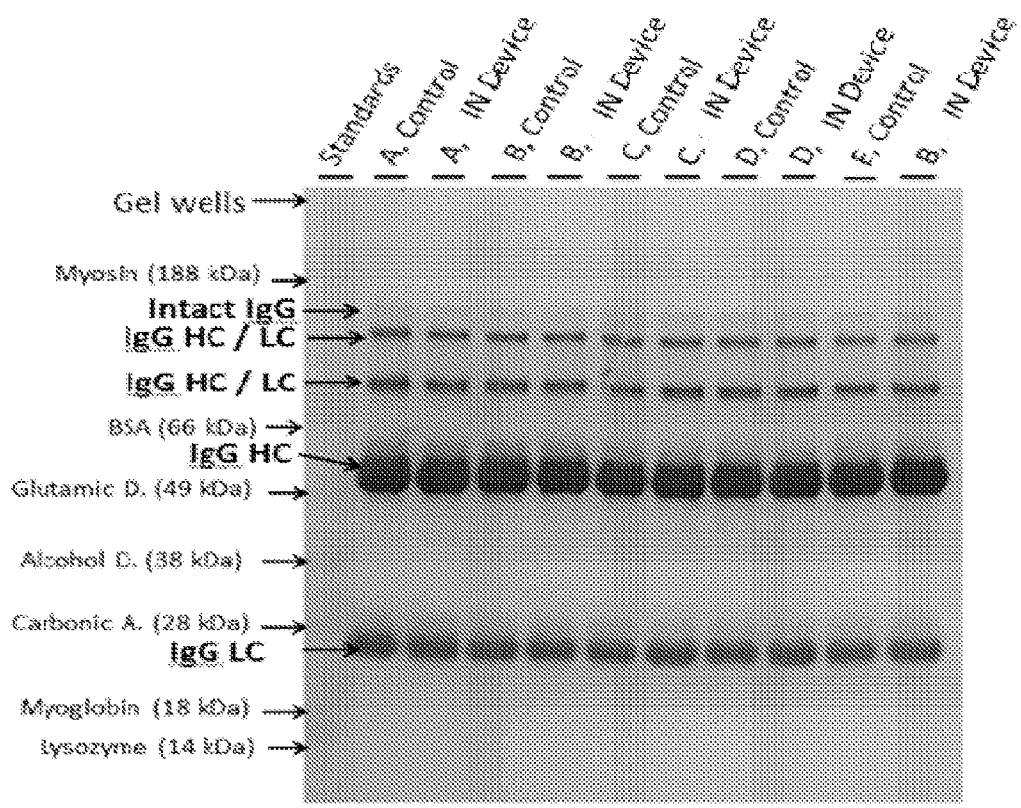
Figure 7:
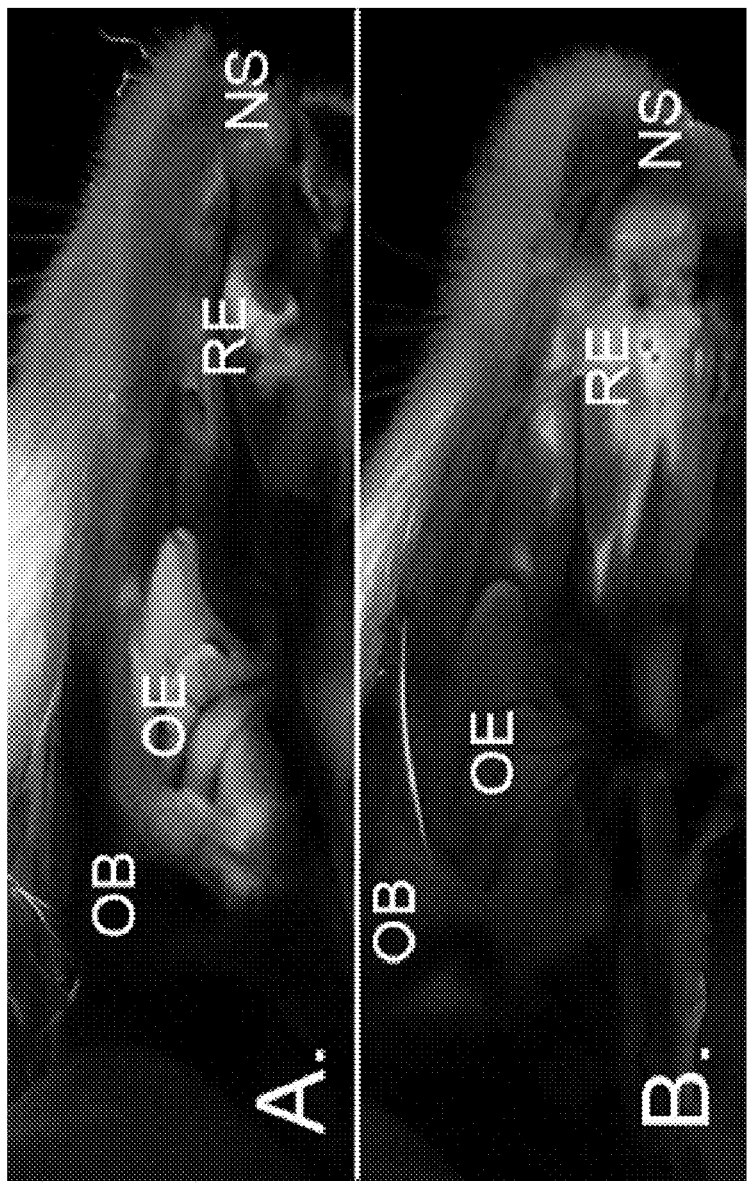
FIG. 7 shows results demonstrating the highly efficient olfactory epithelium targeting of IN device administration in rats. The upper panel shows the deposition of IN IgG after device administration of 15 µL of 25% IVIG solution spiked with 0.01% fluorescein tracer in a rat. The lower panel shows the deposition pattern after deposition of 15 µL of 25% IVIG solution spiked with 0.01% fluorescein tracer administered via nose drops. OB=olfactory bulb, OE=olfactory epithelium, RE=respiratory epithelium, NS=naris.

The brain was placed dorsal side up. A single edged razor blade was used to sever the olfactory bulbs from the brain at the natural angle. Olfactory bulbs were collected. Razor blades were used to cut the brain into seven coronal sections (see FIG. 5). Each section was hemisected and placed into tubes for counting.

For capillary deletion, each brain section was weighed and transferred to an ice cold ground glass homogonizer. A volume of 2.857 times the tissue sample weight of buffer, pH 7.4 (10 mM HEPES, 141 mM NaCl, 4 mM KCl, 2.8 mM $CaCl_2$, 1 mM $MgSO_4$—$H_2O$, 1 mM $NaH_2PO_4$, and 10 mM D-Glucose), was added to the homogonizer. The brain sample was homogenized using vertical strokes. A small volume of 26% dextran solution was added to the homogenized brain sample in order to provide a final concentration of 15.5% Dextran in the homogenate. The homogenate was then vortexted, homogenized for a second time with vertical strokes, and then decanted into a small glass centrifuge tube. The homogenate was then centrifuged in a swinging bucket rotor for 15 minutes at 4° C. at a speed of 5400×g. The homogenate was separated into the following layers: a bottom pellet containing the capillary segments, a clear liquid layer, and a top "cream" layer containing the nervous tissue. Using a transfer pipette, the cream and clear liquid layers were transferred into new tubes. The radioactivity of the supernatant and the pellet was determined using a gamma counter.

Results: The data from Phase 2 shows that intravenous $^{125}$I-IVIG reached the central nervous system. The animals with capillary depletion tissue processing had the most WIG in the brain tissue (49,791 ng). The animals perfused with 0.025% Triton X as a second perfusate had the least IVIG in the brain tissue (33,855 ng) (Table 61 and Table 62). The capillary depletion pellet which should hold all of the IVIG stuck to the capillary walls only accounted for ~3% of the whole brain IVIG in those animals (Table 63). The low amount of IVIG in the capillary pellet could be a result of homogenization friction during processing, releasing the IVIG stuck to the capillary walls and allowing it to be mixed in with the supernatant instead of staying with the capillaries in the pellet.

TABLE 61

$^{125}$I-IVIG present in the central nervous system measured in CPM.

| Rat | Method | Total CPM Whole Brain | Total CPM Liquid | Total CPM Pellet | Total CPM R. Hemisphere | Total CPM L. Hemisphere | Perfusate(CPM/ul) (2nd) | (3rd) |
|---|---|---|---|---|---|---|---|---|
| 1b-1 | Cap Dep | 68,554 | 65,326 | 3,228 | 30,687 | 37,867 | | |
| 1b-4 | Cap Dep | 40,791 | 39,372 | 1,419 | 28,352 | 12,439 | | |
| 1b-7 | Cap Dep | 29,048 | 28,229 | 819 | 13,374 | 15,674 | | |
| 1b-10 | Cap Dep | 15,498 | 14,851 | 647 | 8,104 | 7,393 | | |
| 1b-13 | Cap Dep | 47,908 | 46,533 | 1,376 | 28,757 | 19,151 | | |
| 1b-16 | Cap Dep | 69,964 | 68,128 | 1,836 | 29,458 | 40,505 | | |
| 1b-3 | Control | 98,341 | | | 52,972 | 45,368 | 278 | 356 |
| 1b-6 | Control | 21,141 | | | 10,557 | 10,584 | 112 | 144 |
| 1b-11 | Control | 36,457 | | | 19,077 | 17,380 | 141 | 121 |
| 1b-15 | Control | 28,303 | | | 14,228 | 14,075 | 126 | 66 |
| 1b-17 | Control | 20,524 | | | 9,508 | 11,016 | 231 | 127 |
| 1b-18 | Control | 38,683 | | | 19,350 | 19,333 | 125 | 73 |
| 1b-2 | Triton X | 36,984 | | | 16,622 | 20,362 | 540 | 216 |
| 1b-5 | Triton X | 49,882 | | | 25,617 | 24,264 | 98 | 219 |
| 1b-8 | Triton X | 19,194 | | | 11,031 | 8,163 | 243 | no sample |
| 1b-9 | Triton X | 33,716 | | | 15,026 | 18,690 | 422 | 82 |
| 1b-12 | Triton X | 21,255 | | | 7,639 | 13,616 | 527 | 151 |
| 1b-14 | Triton X | 14,013 | | | 6,712 | 7,301 | 441 | 117 |
| Average Cap Dep | | 45,294 | 43,740 | 1,554 | 23,122 | 22,172 | | |
| Average Control | | 40,575 | | | 20,949 | 19,626 | 169 | 148 |
| Average Triton X | | 29,174 | | | 13,775 | 15,399 | 379 | 157 |

TABLE 62 ng by Group

| Rat | Method | Total ng Whole Brain | Total ng Liquid | Total ng Pellet | Total ng R. Hemisphere | Total ng L. Hemisphere | Perfusate(ng/ul) (2nd) | (3rd) |
|---|---|---|---|---|---|---|---|---|
| 1b-1 | Cap Dep | 68,537 | 65,310 | 3,227 | 30,679 | 37,858 | | |
| 1b-4 | Cap Dep | 45,383 | 43,804 | 1,579 | 31,544 | 13,840 | | |
| 1b-7 | Cap Dep | 32,060 | 31,156 | 904 | 14,761 | 17,300 | | |
| 1b-10 | Cap Dep | 18,231 | 17,470 | 761 | 9,534 | 8,697 | | |
| 1b-13 | Cap Dep | 57,258 | 55,614 | 1,644 | 34,369 | 22,889 | | |
| 1b-16 | Cap Dep | 77,276 | 75,248 | 2,028 | 32,537 | 44,739 | | |
| 1b-3 | Control | 108,404 | | | 58,393 | 50,011 | 306 | 392 |

TABLE 62-continued

| | | | | | ng by Group | | | |
| | | Total ng | Total ng | Total ng | Total ng | Total ng | Perfusate(ng/ul) | |
| Rat | Method | Whole Brain | Liquid | Pellet | R. Hemisphere | L. Hemisphere | (2nd) | (3rd) |
| --- | --- | --- | --- | --- | --- | --- | --- | --- |
| 1b-6 | Control | 24,824 | | | 12,397 | 12,428 | 132 | 169 |
| 1b-11 | Control | 35,411 | | | 18,530 | 16,881 | 137 | 118 |
| 1b-15 | Control | 36,686 | | | 18,442 | 18,244 | 163 | 86 |
| 1b-17 | Control | 25,940 | | | 12,017 | 13,923 | 292 | 160 |
| 1b-18 | Control | 50,757 | | | 25,390 | 25,367 | 165 | 95 |
| 1b-2 | Triton X | 46,547 | | | 20,921 | 25,626 | 680 | 272 |
| 1b-5 | Triton X | 56,294 | | | 28,910 | 27,383 | 111 | 247 |
| 1b-8 | Triton X | 22,577 | | | 12,975 | 9,601 | 285 | no sample |
| 1b-9 | Triton X | 39,032 | | | 17,396 | 21,637 | 488 | 95 |
| 1b-12 | Triton X | 22,099 | | | 7,943 | 14,157 | 548 | 157 |
| 1b-14 | Triton X | 16,581 | | | 7,942 | 8,639 | 522 | 138 |
| Average Cap Dep | | 49,791 | 48,101 | 1,690 | 25,571 | 24,220 | | |
| Average Control | | 47,004 | | | 24,195 | 22,809 | 199 | 170 |
| Average Triton X | | 33,855 | | | 16,014 | 17,841 | 439 | 182 |

TABLE 63

| | | | | ng by Group | | | | |
| | est. ng in blood | est. ng in 2nd perfusate | est. ng in 3rd perfusate | est. Percent ng in blood | Percent of ng delivered (Whole Brain) | Percent of whole brain (Liquid) | Percent of whole brain (Pellet) | Percent of ng delivered (2nd perfusate) | Percent of ng delivered (3rd perfusate) |
| --- | --- | --- | --- | --- | --- | --- | --- | --- | --- |
| Average Cap Dep | 124,564,379 | | | 62% | 0.02% | 97% | 3% | | |
| Average Control | 151,853,766 | 4,978,470 | 4,249,634 | 76% | 0.02% | | | 2.5% | 2.1% |
| Average Triton X | 134,662,521 | 10,980,039 | 4,543,372 | 67% | 0.02% | | | 5.5% | 2.3% |

*The total estimated blood volume was determined as the body weight times 0.06 plus 0.77 (Lee and Blaufox, 1985).

The Triton X perfusion methods resulted in a 28% reduction of IVIG whole brain concentration versus the saline perfusion control. The perfusate should show the amount of IVIG cleared from the blood vessels over the course of the 25 ml (perfused at a rate of 15 ml/min). Three 250 µA samples of each perfusate were counted in the gamma counter. Averages of the three were than calculated. To determine the total amount of IVIG in each perfusate, the ng/µl IVIG concentration was determined and multiplied by 25000 (the 25 ml of perfusate used). The first perfusates (~90 ml at 15 ml/min) were not collected since this step was the same in all of the animals in the study. In the group perfused with 0.025% Triton X, more $^{125}$I-IVIG was removed (439 ng/µl) than the groups perfused with saline (199 ng/µl). This difference was not seen in the 3$^{rd}$ perfusate, meant to clear any remaining Triton X from the blood vessels, (170 ng/µl and 182 ng/µl, respectively) (Tables 1 and 2) suggesting that the maximum clearance of IVIG from the vessels at this concentration of Triton X was achieved. A higher Triton X concentration in the perfusate may yield a further reduction.

In these results, approximately 0.02% of the total delivered IVIG that was infused reached the brain (Table 55) in all methods. During the Phase 2 experiments it was noted that the brain tissues were slightly pinkish, suggesting the total volume perfused was not adequate to completely remove blood from the brain. This slight coloration appeared consistent throughout all animals in each experimental group. An increase in the total volume of perfusate in the next Phase should solve this issue.

Example 9

Biodistribution of IgG administered Intranasally and Intravenously in Mice

A study was conducted to compare the biodistribution of pooled human immunoglobulin G (IgG) administered to mice intranasally and intravenously. Delivery of IgG to the brain and residual IgG in the bloodstream were determined.

Experimental Design: IgG radiolabeled with iodine-125 ($^{125}$I-IgG) was either infused into the left femoral vein (intravenous administration; IV) or intranasally administered (IN) as drops to anesthetized rats over 14 minutes. Animals were sacrificed and concentrations of $^{125}$I-IgG were determined in the brain, blood, and body of the mice at nine different time points (15 min, 30 min, 1 h, 2 h, 4 h, 8 h, 12 h, 24 h, and 72 h post-IgG administration). Blood samples were taken from the heart, animals were perfused, and brains removed. Radiolabeled IgG was detected with a gamma counter for quantitative analysis. Half of each brain was processed into supernatant and run through a size exclusion column to explore intactness of the $^{125}$I-label. The three experimental cohorts were administered IgG as described in Table 64.

TABLE 64

Treatment groups assigned for intranasal administration of IgG.

| Cohort | IgG Dosage | Administration |
| --- | --- | --- |
| Intranasal Drops - High Dose (IN Drop - high) | 0.02 g/kg | one drop every 2 minutes to alternating naris; infusion of saline |
| Intranasal Drops - Low Dose (IN Drop - low) | 0.002 g/kg | one drop every 2 minutes to alternating naris; infusion of saline |
| Intranasal Device - (IN Device) | 0.02 g/kg | two puffs to alternating naris at 0 and 10 minutes, with accompanying control intravenous infusion of saline |
| Intravenous (IV) | 0.02 g/kg | infusion to left femoral vein over fourteen minutes |

*3 rats/time point for a total of 27 rats per experimental group

On the day of delivery, each $^{125}$I-IgG aliquot was removed from the freezer and allowed to come to room temperature (about 20 minutes). The aliquots were then gently vortexed. A sample of 1 μl was placed into 999 μl of water and vortexed (1:1,000 dilution). Three 20 μl samples were removed from the dilution and placed into labeled gamma tubes. An additional 10 μl was placed into 90 μl of water and vortexed (1:10,000 dilution). Three 20 μl samples were removed from the 1:10,000 dilution and placed into labeled gamma tubes. Standards were later quantified through gamma counting. All doses within groups were equalized for volume, weight (mg), and radioactivity (μCi) by varying the dilution with saline to account for the decay of $^{125}$I.

Adult male Sprague-Dawley rats (Animal Care Facility at Regions Hospital from Harlan) with the left femoral vein canulated were used in this experiment. All rats weighed approximately 250 g to ensure accurate dosing. The animals were housed individually with free access to food and water. Animals were kept on a 12-hour light cycle.

For the IN Drop, IN Device, and IV administrations, an anesthesia cocktail containing ketamine HCl (30 mg/kg), xylazine HCl (6 mg/kg), and acepromazine (1 mg/kg) was used. All anesthesia was administered as subcutaneous injections. Boosters alternated between the cocktail described above and 50 mg/kg ketamine. Reflexes were tested to assess level of anesthesia every 10-15 minutes throughout the study. Animals in groups sacrificed at 4 hr and beyond were allowed to recover from anesthesia and were re-anesthetized prior to euthanasia.

For IN Drop delivery, anesthetized rats were placed on their backs on a heating pad. $^{125}$I-IgG was administered intranasally as 8×6 μL nose drops with an Eppendorf pipettor to alternating nares every 2 minutes for a total volume of 48 μL. Animals were then monitored for adverse effects and anesthesia levels until the euthanasia time point was reached. During intranasal delivery, a 500 μL sample of saline was infused over 14 minutes through the left femoral vein. All animals were rolled off of their backs at 15 minutes after the completion of delivery.

For IN Device delivery, anesthetized animals were placed on their backs and a tube was inserted about 14 mm deep into the nostril. The tube was connected to an actuator that delivered 15 μL of dosing solution toward the olfactory epithelium. One bolus was sprayed at the start of delivery, one was sprayed at 10 minutes after the onset of delivery. Animals were then monitored for adverse effects and anesthesia levels until the euthanasia time point was reached. During intranasal delivery, a 500 μl sample of saline was infused over 14 minutes through the left femoral vein. All animals were rolled off of their backs at 15 min after the completion of delivery.

For IV delivery, anesthetized animals were placed on their backs. A blunt 22 gauge needle attached to a 1 cc syringe was inserted into the femoral vein canula. $^{125}$I-IgG was prepared in 500 μl aliquots and infused over 14 minutes. Animals were then monitored for adverse effects and anesthesia levels until the euthanasia time point was reached.

At the experimental end time, blood was drawn directly from the heart and animals were perfused with 120 ml ice cold saline directly through the heart. One small drop of blood was placed into a pre-weighed, labeled gamma tube and approximately 0.6 mL was placed into a labeled serum separator tube. The serum separator tube was spun and serum was collected. The serum was diluted in homogenization buffer. The diluted serum was further spun down in a 100 kDa size exclusion filtration device. Samples were collected from both the top of the filter and the bottom and placed into labeled gamma tubes. The filter was also collected and placed into a labeled gamma tube.

The brain was extracted from the skull and hemisected. The left hemisphere was further processed as described below. The right hemisphere was weighed, cut into 7 pieces and placed into labeled gamma tubes.

Additionally, the olfactory and respiratory epithelia were collected separately. The epithelia were expected to contain higher amounts of $^{125}$I than the quantitation limit of the gamma counter, so both were split into multiple pieces. Each piece of epithelia was placed into a pre-weighed, labeled gamma tube.

The left hemisphere was weighed after removal from the skull. It was homogenized and spun down to retrieve supernatant. The supernatant was further spun down in a 100 kDa size exclusion filtration device. Samples were collected from both the top of the filter and the bottom and placed into labeled gamma tubes. The pellet was collected and placed into a pre-weighed labeled gamma tube. The filter was also collected and placed into a labeled gamma tube.

3-5 mm samples of body tissues were collected and placed into pre-weighed, labeled gamma tubes. Body tissues include: liver, spleen, kidney, small intestine, lung, esophagus, trachea, and blood (drawn directly from the heart as described above). The gamma tubes containing samples were counted using a COBRA II Auto-Gamma Counter.

Results: Intactness of IgG in the brain was slightly less with intranasal administrations (example: IN high—49%, IN low—49%, IN device—40% at 15 minutes) as compared to intravenous administration (69% at 15 minutes) in the earlier time points (Table 65, Table 66, Table 67, and Table 68). However, because of the non-validated method of calculating the intactness and the limitations of the gamma counting machine, non-intact or "free" $^{125}$I may be magnified. The CPM counts from gamma tubes for aliquots representing the "bottom" of the filtration device tubes (where the non-intact IgG would be expected) were rather low in many of IN treated animals. It is usually desired that the counts reach at least two times background (in this study would be ~50 CPM).

TABLE 65

Biodistribution and intactness of IgG administered to rats via high dose nasal drops (0.02 g IgG/kg).

| | ug/g IN-Drops High | | | | | | | | |
|---|---|---|---|---|---|---|---|---|---|
| | IN High | IN High | IN High | IN High | IN High | IN High | IN High | IN High | IN High |
| | | | | | Time | | | | |
| | 15 min | 30 min | 1 hr | 2 hr | 4 hr | 8 hr | 12 hr | 24 hr | 72 hr |
| | Raw ug/g Dosed ug/g 60 uCi) | | | | | | | | |
| | 92,625,403 | 99,889,203 | 97,886,218 | 111,043,619 | 101,049,672 | 99,398,932 | 78,063,258 | 108,114,877 | 76,689,700 |
| Total ug/g | | | | | | | | | |
| Olfactory Epithelium | 585 | 127 | 120 | 938 | 167 | 118 | 20 | 10 | 0.56 |
| Respiratory Epithelium | 8,614 | 11,790 | 13,222 | 16,686 | 5,189 | 1,312 | 41 | 10 | 2.4 |
| R. Hemisphere | 0.24 | 0.22 | 0.18 | 0.10 | 0.11 | 0.15 | 0.22 | 0.16 | 0.039 |
| L. Hemisphere (total recovered) | 0.11 | 0.272 | 0.200 | 0.126 | 0.095 | 0.128 | 0.231 | 0.145 | 0.029 |
| Dosing Solution (1:1,000) | 38,594 | 41,621 | 40,786 | 46,268 | 42,104 | 41,416 | 32,526 | 45,048 | 31,954 |
| ug/g | | | | | | | | | |
| Blood | 3.1 | 3.3 | 4.4 | 4.0 | 3.7 | 5.3 | 7.3 | 5.4 | 0.8 |
| Liver | 0.23 | 0.46 | 0.51 | 0.43 | 0.44 | 1.0 | 0.9 | 1.1 | 0.24 |
| Spleen | 0.55 | 1.1 | 1.4 | 1.2 | 1.4 | 1.2 | 2.4 | 1.5 | 0.16 |
| Kidney | 0.9 | 1.9 | 2.7 | 1.5 | 1.6 | 2.8 | 3.8 | 2.2 | 0.39 |
| Small Intestines | 0.32 | 0.4 | 0.91 | 0.75 | 2.2 | 2.5 | 6.3 | 1.3 | 0.09 |
| Lung | 0.9 | 1.8 | 1.5 | 1.0 | 1.3 | 2.1 | 2.4 | 1.7 | 0.26 |
| Esophagus | 0.51 | 0.61 | 1.1 | 0.9 | 33 | 126 | 4.9 | 6 | 0.22 |
| Trachea | 0.75 | 0.77 | 4.0 | 1.7 | 3.0 | 2.4 | 17 | 5 | 0.25 |
| Intactness | | | | | | | | | |
| IN1 Brain | 49% | 46% | 40% | 48% | 51% | 53% | 49% | 49% | 66% |
| IN1 Blood | 39% | 32% | 35% | 33% | 16% | 27% | 30% | 27% | 54% |

TABLE 66

Biodistribution and intactness of IgG administered to rats via low dose nasal drops (0.002 g IgG/kg).

| | ug/g IN Drops-Low | | | | | | | | |
|---|---|---|---|---|---|---|---|---|---|
| | IN Low | IN Low | IN Low | IN Low | IN Low | IN Low | IN Low | IN Low | IN Low |
| | | | | | Time | | | | |
| | 15 min | 30 min | 1 hr | 2 hr | 4 hr | 8 hr | 12 hr | 24 hr | 72 hr |
| | Dosed ug/g (60 uCi) | | | | | | | | |
| | 91,152,030 | 71,046,179 | 83,024,122 | 109,042,942 | 102,934,060 | 64,471,560 | 78,549,717 | 72,139,899 | 64,456,268 |
| Total ug/g | | | | | | | | | |
| Olfactory Epithelium | 118 | 57.6 | 58.7 | 58.0 | 56 | 1.9 | 25.9 | 6.69 | 0.571 |
| Respiratory Epithelium | 9,930 | 12,284 | 10,402 | 6,716 | 3,055 | 101 | 111 | 7.8 | 1.20 |
| R. Hemisphere | 0.060 | 0.048 | 0.031 | 0.020 | 0.015 | 0.026 | 0.032 | 0.015 | 0.0044 |
| L. Hemisphere (total recovered) | 0.057 | 0.042 | 0.023 | 0.018 | 0.016 | 0.027 | 0.030 | 0.014 | 0.0040 |
| Dosing Solution (1:1,000) | 37,980 | 29,602 | 34,593 | 45,435 | 42,889 | 26,863 | 32,729 | 30,058 | 26,856 |
| ug/g | | | | | | | | | |
| Blood | 0.41 | 0.56 | 0.51 | 0.44 | 0.37 | 0.78 | 0.99 | 0.57 | 0.067 |
| Liver | 0.091 | 0.09 | 0.06 | 0.086 | 0.061 | 0.15 | 0.19 | 0.12 | 0.036 |
| Spleen | 0.15 | 0.21 | 0.31 | 0.19 | 0.12 | 0.38 | 0.30 | 0.20 | 0.023 |
| Kidney | 0.22 | 0.26 | 0.27 | 0.1 | 0.20 | 0.53 | 0.63 | 0.28 | 0.042 |
| Small Intestines | 0.075 | 0.16 | 0.10 | 0.13 | 0.18 | 0.33 | 0.29 | 0.058 | 0.012 |
| Lung | 0.14 | 0.25 | 0.09 | 0.15 | 0.17 | 0.26 | 0.43 | 0.29 | 0.032 |

TABLE 66-continued

Biodistribution and intactness of IgG administered to rats via low dose nasal drops (0.002 g IgG/kg).

| | ug/g IN Drops-Low | | | | | | | | |
|---|---|---|---|---|---|---|---|---|---|
| | IN Low | IN Low | IN Low | IN Low | IN Low Time | IN Low | IN Low | IN Low | IN Low |
| | 15 min | 30 min | 1 hr | 2 hr | 4 hr | 8 hr | 12 hr | 24 hr | 72 hr |
| | | | | | Dosed ug/g (60 uCi) | | | | |
| | 91,152,030 | 71,046,179 | 83,024,122 | 109,042,942 | 102,934,060 | 64,471,560 | 78,549,717 | 72,139,899 | 64,456,268 |
| Esophagus | 0.076 | 0.13 | 0.13 | 0.17 | 14 | 3.4 | 0.69 | 0.47 | 0.028 |
| Trachea | 0.14 | 0.36 | 0.26 | 0.19 | 0.58 | 4 | 0.50 | 0.30 | 0.034 |
| | | | | | Intactness | | | | |
| IN2 Brain | 49% | 46% | 45% | 48% | 50% | 65% | 48% | 49% | 72% |
| IN2 Blood | 28% | 22% | 29% | 19% | 26% | 37% | 25% | 31% | 52% |

TABLE 67

Biodistribution and intactness of IgG administered to rats via high dose intranasal device (0.02 g IgG/kg).

| | ug/g IN Device | | | | | | | | |
|---|---|---|---|---|---|---|---|---|---|
| | IN Device | IN Device | IN Device | IN Device | IN Device Time | IN Device | IN Device | IN Device | IN Device |
| | 15 min | 30 min | 1 hr | 2 hr | 4 hr | 8 hr | 12 hr | 24 hr | 72 hr |
| | | | | | Dosed ug/g (60 uCi) | | | | |
| | 99,099,000 | 125,565,000 | 60,108,000 | 77,362,000 | 73,446,000 | 67,726,000 | 87,418,000 | 83,486,000 | 74,898,000 |
| | | | | | Total ug/g | | | | |
| Olfactory Epithelium | 5,076 | 5,276 | 2,016 | 3,917 | 2,134 | 381 | 103 | 14 | 1.7 |
| Respiratory Epithelium | 5,658 | 5,970 | 3,285 | 6,850 | 3,099 | 262 | 46 | 10 | 1.4 |
| R. Hemisphere | 0.6 | 1.07 | 1.5 | 0.22 | 0.2 | 0.36 | 0.23 | 0.14 | 0.042 |
| L. Hemisphere (total recovered) | 0.831 | 1.32 | 0.365 | 0.229 | 0.139 | 0.15 | 0.202 | 0.122 | 0.0527 |
| Dosing Solution (1:1,000) | 66,067 | 83,710 | 40,072 | 51,575 | 48,964 | 45,151 | 58,279 | 55,657 | 49,932 |
| | | | | | ug/g | | | | |
| Blood | 11 | 18 | 11 | 8.3 | 4.7 | 6.7 | 5.9 | 4.7 | 0.61 |
| Liver | 0.45 | 4.3 | 1.6 | 0.57 | 0.4 | 0.8 | 1.1 | 0.76 | 0.23 |
| Spleen | 1.4 | 3.2 | 4.8 | 1.7 | 1.3 | 2.1 | 2.3 | 1.2 | 0.13 |
| Kidney | 1.5 | 4.9 | 5.6 | 2.3 | 1.3 | 3.3 | 3.2 | 1.0 | 0.26 |
| Small Intestines | 0.52 | 1.2 | 3.2 | 1.3 | 1.2 | 6.6 | 2.5 | 0.61 | 0.079 |
| Lung | 1.4 | 4.5 | 5.9 | 2.0 | 1.8 | 3.1 | 5.1 | 3.2 | 0.17 |
| Esophagus | 1.5 | 3.1 | 4.9 | 3.4 | 488 | 19 | 2.5 | 1.3 | 0.12 |
| Trachea | 1.8 | 2.5 | 4.2 | 22 | 5.2 | 3.6 | 3.3 | 1.7 | 0.22 |
| | | | | | Intactness | | | | |
| IN3 Brain | 40% | 44% | 46% | 43% | 45% | 46% | 51% | 47% | 66% |
| IN3 Blood | 34% | 29% | 34% | 30% | 26% | 32% | 25% | 30% | 67% |

TABLE 68

Biodistribution and intactness of IgG administered to rats via high dose intravenous infusion (0.02 g IgG/kg).

| | ug/g IV High | | | | | | | | |
|---|---|---|---|---|---|---|---|---|---|
| | IV | IV | IV | IV | IV Time | IV | IV | IV | IV |
| | 15 min | 30 min | 1 hr | 2 hr | 4 hr | 8 hr | 12 hr | 24 hr | 72 hr |
| | | | | | Dosed ug/g (60 uCi) | | | | |
| | 125,946,138 | 76,865,000 | 88,715,556 | 150,181,389 | 86,270,833 | 105,588,889 | 81,584,098 | 74,669,134 | 64,916,672 |
| | | | | | Total ug/g | | | | |
| Olfactory Epithelium | 14.4 | 19 | 21 | 24 | 7 | 18 | 18 | 12 | 0.41 |
| Respiratory Epithelium | 9.8 | 14 | 17 | 13.1 | 5.3 | 20 | 10 | 7 | 0.7 |
| R. Hemisphere | 0.425 | 0.5 | 0.6 | 0.63 | 0.36 | 0.34 | 0.39 | 0.14 | 0.038 |
| L. Hemisphere (total recovered) | 0.533 | 0.52 | 0.56 | 0.548 | 0.411 | 0.306 | 0.315 | 0.134 | 0.036 |
| Dosing Solution (1:1,000) | 5,038 | 3,075 | 3,549 | 6,007 | 3,451 | 4,224 | 3,263 | 2,987 | 2,597 |
| | | | | | ug/g | | | | |
| Blood | 141 | 96 | 79 | 59 | 35 | 26 | 13 | 8 | 0.8 |
| Liver | 80 | 34 | 28 | 34 | 25 | 15 | 15 | 10 | 3.6 |
| Spleen | 57 | 30 | 28 | 32 | 20 | 14 | 14 | 10 | 2.6 |
| Kidney | 112 | 100 | 77 | 59 | 38 | 29 | 29 | 19 | 10 |
| Small Intestines | 13.4 | 8 | 9 | 9.2 | 7.1 | 5.2 | 3.1 | 2.4 | 0.29 |
| Lung | 24 | 89 | 21 | 33 | 13.1 | 7.2 | 6.8 | 4.2 | 0.7 |
| Esophagus | 7.0 | 4 | 4 | 5.0 | 5.7 | 5.5 | 2.8 | 4.3 | 0.28 |
| Trachea | 9.7 | 9 | 11 | 9.4 | 8.8 | 6.3 | 2.1 | 5.4 | 0.34 |
| | | | | | Intactness | | | | |
| IV Brain | 69% | 68% | 63% | 59% | 56% | 56% | 48% | 51% | 68% |
| IV Blood | 94% | 92% | 94% | 90% | 83% | 74% | 57% | 53% | 79% |

TABLE 69

Biodistribution and intactness of IgG administered to rats via high dose nasal drops (0.02 g IgG/kg), as corrected for intactness of immunoglobulin G.

| | ug/g IN Drops High - corrected for intactness | | | | | | | | |
|---|---|---|---|---|---|---|---|---|---|
| | IN Drops High | IN Drops High | IN Drops High | IN Drops High | IN Drops High | IN Drops High | IN Drops High | IN Drops High | IN Drops High |
| | | | | | Minutes | | | | |
| | 15 | 30 | 60 | 120 | 240 | 480 | 720 | 1,440 | 4,320 |
| | | | | | Corrected | | | | |
| R. Hemisphere | 0.12 | 0.10 | 0.07 | 0.05 | 0.05 | 0.08 | 0.11 | 0.08 | 0.03 |
| L. Hemisphere (total recovered) | 0.05 | 0.12 | 0.08 | 0.06 | 0.05 | 0.07 | 0.11 | 0.07 | 0.02 |
| Blood | 1.20 | 1.07 | 1.53 | 1.331 | 0.604 | 1.427 | 2.20 | 1.47 | 0.454 |
| | | | | | Uncorrected | | | | |
| R. Hemisphere | 0.24 | 0.22 | 0.18 | 0.10 | 0.11 | 0.15 | 0.22 | 0.16 | 0.04 |
| L. Hemisphere (total recovered) | 0.11 | 0.27 | 0.20 | 0.13 | 0.10 | 0.13 | 0.23 | 0.15 | 0.03 |
| Blood | 3.05 | 3.32 | 4.38 | 4.01 | 3.73 | 5.27 | 7.31 | 5.44 | 0.84 |
| Trap. Calcs | | | | | | | | | AUC |
| R. Hemisphere | 1.6 | 2.6 | 3.5 | 6.0 | 16.0 | 22.2 | 66.6 | 151.9 | 270.4 |
| L. Hemisphere (total recovered) | 1.3 | 3.1 | 4.2 | 6.5 | 13.9 | 21.6 | 65.7 | 129.0 | 245.4 |
| Blood | 17.0 | 39.0 | 86.0 | 116.1 | 243.7 | 435.3 | 1,323.3 | 2,777.1 | 5,038 |
| | | | | | Uncorrected Trap. Calcs | | | | |
| R. Hemisphere | 3.4 | 5.9 | 8.2 | 12.1 | 30.7 | 44.0 | 137.1 | 293.1 | 534.5 |
| L. Hemisphere (total recovered) | 2.9 | 7.1 | 9.8 | 13.3 | 26.8 | 43.0 | 135.2 | 250.8 | 488.8 |

TABLE 69-continued

Biodistribution and intactness of IgG administered to rats via high dose nasal drops (0.02 g IgG/kg), as corrected for intactness of immunoglobulin G.

| | ug/g IN Drops High - corrected for intactness | | | | | | | | |
|---|---|---|---|---|---|---|---|---|---|
| | IN Drops High | IN Drops High | IN Drops High | IN Drops High | IN Drops High | IN Drops High | IN Drops High | IN Drops High | IN Drops High |
| | Minutes | | | | | | | | |
| | 15 | 30 | 60 | 120 | 240 | 480 | 720 | 1,440 | 4,320 |
| Blood | 47.8 | 115.5 | 251.6 | 464.2 | 1,079.2 | 1,508.9 | 4,587.5 | 9,041.8 | 17,096 |
| | Intactness | | | | | | | | |
| IN1 Brain | 49% | 46% | 40% | 48% | 51% | 53% | 49% | 49% | 66% |
| IN1 Blood | 39% | 32% | 35% | 33% | 16% | 27% | 30% | 27% | 54% |

TABLE 70

Biodistribution and intactness of IgG administered to rats via low dose nasal drops (0.002 g IgG/kg), as corrected for intactness of immunoglobulin G.

| | ug/g IN Drops Low - corrected for intactness | | | | | | | | |
|---|---|---|---|---|---|---|---|---|---|
| | IN Low | IN Low | IN Low | IN Low | IN Low | IN Low | IN Low | IN Low | IN Low |
| | Minutes | | | | | | | | |
| | 15 | 30 | 60 | 120 | 240 | 480 | 720 | 1,440 | 4,320 |
| | Corrected | | | | | | | | |
| R. Hemisphere | 0.029 | 0.022 | 0.014 | 0.0096 | 0.0073 | 0.017 | 0.016 | 0.0072 | 0.0032 |
| L. Hemisphere (total recovered) | 0.028 | 0.019 | 0.010 | 0.009 | 0.0078 | 0.0175 | 0.014 | 0.0068 | 0.0029 |
| Blood | 0.12 | 0.12 | 0.14 | 0.08 | 0.10 | 0.28 | 0.25 | 0.17 | 0.035 |
| | Uncorrected | | | | | | | | |
| R. Hemisphere | 0.060 | 0.048 | 0.031 | 0.020 | 0.015 | 0.026 | 0.032 | 0.015 | 0.004 |
| L. Hemisphere (total recovered) | 0.057 | 0.042 | 0.023 | 0.018 | 0.016 | 0.027 | 0.030 | 0.014 | 0.004 |
| Blood | 0.41 | 0.56 | 0.51 | 0.44 | 0.37 | 0.78 | 1.0 | 0.57 | 0.067 |
| Corrected Trap. Calcs | | | | | | | | | AUC |
| R. Hemisphere | 0.4 | 0.5 | 0.7 | 1.0 | 2.9 | 3.9 | 8.2 | 15.0 | 33 |
| L. Hemisphere (total recovered) | 0.4 | 0.4 | 0.6 | 1.0 | 3.0 | 3.8 | 7.7 | 14.0 | 31 |
| Blood | 1.8 | 4.0 | 6.9 | 10.8 | 45.7 | 63.7 | 151.3 | 302.0 | 586 |
| | Uncorrected Trap. Calcs | | | | | | | | |
| R. Hemisphere | 0.8 | 1.2 | 1.5 | 2.1 | 4.9 | 7.1 | 17.0 | 27.6 | 62 |
| L. Hemisphere (total recovered) | 0.7 | 1.0 | 1.2 | 2.0 | 5.1 | 6.9 | 15.9 | 25.9 | 59 |
| Blood | 7.3 | 15.9 | 28.4 | 48.8 | 137.7 | 212.1 | 562.4 | 919.3 | 1,932 |
| | Intactness | | | | | | | | |
| IN2 Brain | 49% | 46% | 45% | 48% | 50% | 65% | 48% | 49% | 72% |
| IN2 Blood | 28% | 22% | 29% | 19% | 26% | 37% | 25% | 31% | 52% |

TABLE 71

Biodistribution and intactness of IgG administered to rats via high dose intranasal device (0.02 g IgG/kg), as corrected for intactness of immunoglobulin G.

| | ug/g IN Device - corrected for intactness | | | | | | | | |
|---|---|---|---|---|---|---|---|---|---|
| | IN3 | IN3 | IN3 | IN3 | IN3 | IN3 | IN3 | IN3 | IN3 |
| | | | | | Minutes | | | | |
| | 15 | 30 | 60 | 120 | 240 | 480 | 720 | 1,440 | 4,320 |
| | Corrected | | | | | | | | |
| R. Hemisphere | 0.23 | 0.47 | 0.71 | 0.09 | 0.08 | 0.16 | 0.12 | 0.07 | 0.03 |
| L. Hemisphere (total recovered) | 0.33 | 0.58 | 0.17 | 0.10 | 0.06 | 0.07 | 0.10 | 0.06 | 0.03 |
| Blood | 3.9 | 5.3 | 3.9 | 2.5 | 1.2 | 2.2 | 1.5 | 1.4 | 0.41 |
| | Uncorrected | | | | | | | | |
| R. Hemisphere | 0.6 | 1.1 | 1.5 | 0.2 | 0.2 | 0.4 | 0.2 | 0.1 | 0.0 |
| L. Hemisphere (total recovered) | 0.8 | 1.3 | 0.4 | 0.2 | 0.1 | 0.2 | 0.2 | 0.1 | 0.1 |
| Blood | 11.5 | 18.2 | 11.4 | 8.3 | 4.7 | 6.7 | 5.9 | 4.7 | 0.6 |
| Trap. Calcs | | | | | | | | | AUC |
| R. Hemisphere | 5.3 | 17.7 | 24.0 | 10.2 | 28.9 | 33.6 | 65.4 | 133.2 | 318 |
| L. Hemisphere (total recovered) | 6.9 | 11.2 | 8.0 | 9.7 | 15.8 | 20.5 | 57.4 | 132.1 | 262 |
| Blood | 68.8 | 137.6 | 189.9 | 221.6 | 409.6 | 436.8 | 1,047.2 | 2,669.4 | 5,181 |
| | Uncorrected Trap. Calcs | | | | | | | | |
| R. Hemisphere | 12.3 | 39.3 | 52.8 | 23.1 | 63.3 | 70.5 | 132.6 | 259.6 | 654 |
| L. Hemisphere (total recovered) | 16.2 | 25.3 | 17.8 | 22.0 | 34.6 | 42.2 | 116.4 | 250.8 | 525 |
| Blood | 222.4 | 444.2 | 591.4 | 778.3 | 1,369.6 | 1,516.1 | 3,826.3 | 7,703.8 | 16,452 |
| | Intactness | | | | | | | | |
| IN3 Brain | 40% | 44% | 46% | 43% | 45% | 46% | 51% | 47% | 66% |
| IN3 Blood | 34% | 29% | 34% | 30% | 26% | 32% | 25% | 30% | 67% |

TABLE 72

Biodistribution and intactness of IgG administered to rats via high dose intravenous infusion (0.02 g IgG/kg), as corrected for intactness of immunoglobulin G.

| | ug/g IV High - corrected for intactness | | | | | | | | |
|---|---|---|---|---|---|---|---|---|---|
| | IV | IV | IV | IV | IV | IV | IV | IV | IV |
| | | | | | Minutes | | | | |
| | 15 | 30 | 60 | 120 | 240 | 480 | 720 | 1,440 | 4,320 |
| | Corrected | | | | | | | | |
| R. Hemisphere | 0.29 | 0.35 | 0.40 | 0.37 | 0.20 | 0.19 | 0.19 | 0.07 | 0.03 |
| L. Hemisphere (total recovered) | 0.37 | 0.36 | 0.35 | 0.32 | 0.23 | 0.17 | 0.15 | 0.07 | 0.02 |
| Blood | 132.3 | 88.4 | 74.0 | 53.2 | 28.6 | 19.2 | 7.2 | 4.2 | 0.6 |
| | Uncorrected | | | | | | | | |
| R. Hemisphere | 0.43 | 0.52 | 0.628 | 0.632 | 0.36 | 0.34 | 0.39 | 0.14 | 0.038 |
| L. Hemisphere (total recovered) | 0.53 | 0.52 | 0.56 | 0.55 | 0.41 | 0.31 | 0.32 | 0.13 | 0.036 |
| Blood | 141.1 | 96.2 | 79.1 | 58.8 | 34.6 | 26.1 | 12.7 | 7.8 | 0.80 |
| Trap. Calcs | | | | | | | | | AUC |

TABLE 72-continued

Biodistribution and intactness of IgG administered to rats via high dose intravenous infusion (0.02 g IgG/kg), as corrected for intactness of immunoglobulin G.

| | ug/g IV High - corrected for intactness | | | | | | | | |
|---|---|---|---|---|---|---|---|---|---|
| | IV | IV | IV | IV | IV | IV | IV | IV | IV |
| | | | | | Minutes | | | | |
| | 15 | 30 | 60 | 120 | 240 | 480 | 720 | 1,440 | 4,320 |
| R. Hemisphere | 4.8 | 11.2 | 23.1 | 34.6 | 47.4 | 45.5 | 92.7 | 139.0 | 398 |
| L. Hemisphere (total recovered) | 5.4 | 10.6 | 20.3 | 33.3 | 48.1 | 38.6 | 78.6 | 133.5 | 369 |
| Blood | 1,655.5 | 2,437.1 | 3,817.6 | 4,908.0 | 5,738.1 | 3,165.3 | 4,074.7 | 6,898.1 | 32,694 |
| | | | | Uncorrected Trap. Calcs | | | | | |
| R. Hemisphere | 7.1 | 17.2 | 37.8 | 59.6 | 84.8 | 88.3 | 191.1 | 254.9 | 741 |
| L. Hemisphere (total recovered) | 7.69 | 16.56 | 34.25 | 67.06 | 93.15 | 76.73 | 230.14 | 360.25 | 886 |
| Blood | 1,779.9 | 2,630.8 | 4,138.5 | 5,602.1 | 7,279.5 | 4,651.1 | 7,366.9 | 12,398.1 | 45,847 |
| | | | | Intactness | | | | | |
| IV Brain | 69% | 68% | 63% | 59% | 56% | 56% | 48% | 51% | 68% |
| IV Blood | 94% | 92% | 94% | 90% | 83% | 74% | 57% | 53% | 79% |

The maximum brain delivery of intact IgG achieved with the intranasal IN Device (0.71 μg IgG/g tissue) was almost twice the maximum brain delivery achieved with intravenous (IV) administration (0.40 μg IgG/g tissue) of the same dose (0.02 g/kg), while resulting in a maximum blood concentration of 25 times less (IN Device—5.3 μg IgG/g, IV—132 μg IgG/g) (Table 71 and Table 72).

The AUC of brain exposure over 72 hr was fairly equivalent with the IN Device versus intravenous administration (318/262 IN Device vs 398/369 IV in right/left hemisphere as corrected for intactness) while the AUC of blood exposure was almost six times greater with intravenous (5,181 Device vs. 32,694 as corrected for intactness; Table 73).

TABLE 73

Area under the curve and maximum concentrations of IN and IV $^{125}$I-IgG over time in rats administered pooled human IgG via IN1, IN2, or IV.

| AUC - Corrected | IN1 | IN2 | IN3 | IV |
|---|---|---|---|---|
| R. Hemisphere | 270 | 33 | 318 | 398 |
| L. Hemisphere (total recovered) | 245 | 31 | 262 | 369 |
| Blood | 5,038 | 586, | 5,181 | 32,694 |

| Max Concentrations - Corrected | ug/g | time (min) | ug/g | time | ug/g | time | ug/g | time |
|---|---|---|---|---|---|---|---|---|
| R. Hemisphere | 0.12 | 15 | 0.029 | 15 | 0.71 | 60 | 0.40 | 60 |
| L. Hemisphere (total recovered) | 0.12 | 30 | 0.028 | 15 | 0.58 | 30 | 0.37 | 15 |
| Blood | 2.2 | 720 | 0.28 | 480 | 5.3 | 30 | 132 | 15 |

| AUC - Uncorrected | IN1 | IN2 | IN3 | IV |
|---|---|---|---|---|
| R. Hemisphere | 534 | 62 | 654 | 741 |
| L. Hemisphere (total recovered) | 489 | 59 | 525 | 682 |
| Blood | 17,096 | 1,932 | 16,452 | 45,847 |

| Max Concentrations - Uncorrected | ug/g | time (min) | ug/g | time | ug/g | time | ug/g | time |
|---|---|---|---|---|---|---|---|---|
| R. Hemisphere | 0.24 | 15 | 0.060 | 15 | 1.54 | 60 | 0.63 | 120 |
| L. Hemisphere (total recovered) | 0.27 | 30 | 0.057 | 15 | 1.32 | 30 | 0.56 | 60 |
| Blood | 7.3 | 720 | 0.99 | 720 | 18.2 | 30 | 141 | 15 |

All four delivery methods showed decreasing concentrations of IgG in the brain over time (Table 65, Table 66, Table 67, Table 68, Table 69, Table 70, Table 71, and Table 72). Intranasal drop delivery to the brain was dose dependent (Table 65, Table 66, Table 69, and Table 70). Animals treated with the high dose of IgG had a maximum brain concentration when corrected for intactness (0.12 µg IgG/g) that was approximately four times higher than the brain concentration (0.029 µg IgG/g) of animals treated with the lower dose of IgG (Table 69, Table 70, and Table 73).

A second $^{125}$I-IgG peak was observed most of the tissues in the IN administration groups (Table 65, Table 66, and Table 67). This second peak may be due to an artifact of the animal model. The animals began waking up from anesthesia around 2 hours and were able to eat, drink, and groom normally. As a result, they may have ingested some of the residue IgG that was on their noses and passed through the nasopharynx into the mouth and esophagus once they were upright. Therefore this second peak that occurred after 4 hours is likely a result of blood-to-brain delivery of degraded IgG instead of direct nose to brain delivery of intact IgG.

A small group of three rats was also treated intranasally with a non-enhancer based dosing solution (Table 74). This group had only one time point (30 minutes) and was dosed with the same concentration and method as the IN high group described in Example 9 and Table 65. At the 30 minute time point, the concentration was much lower in both the respiratory (2,097 µg IgG/g) and olfactory (37 µg IgG/g) compared to the IN high group at 15 minutes (8,614 µg IgG/g and 585 µg IgG/g) and 30 minutes (11,790 µg IgG/g and 127 µg IgG/g) respectively. The right hemisphere is equal (0.22 µg IgG/g for both the non-enhancer and IN high groups), however the left hemisphere is much lower (0.04 µg IgG/g) compared to the IN high group

TABLE 74

Biodistribution and intactness of IgG administered to rats via high dose nasal drops (0.02 g IgG/kg) (IN High) compared to IgG administered with a non-enhancer based dosing solution (IN4).

| | ug/g IN High | | |
|---|---|---|---|
| | IN High | IN High Raw ug/g | IN4 |
| | 15 min | 30 min | 30 min |
| | Dosed ug/g (60 uCi) | | |
| | 92,625,403 | 99,889,203 | 685,291,111 |
| | Total ug/g | | |
| Olfactory Epithelium | 585 | 127 | 37 |
| Respiratory Epithelium | 8,614 | 11,790 | 2,097 |
| R. Hemisphere | 0.24 | 0.22 | 0.22 |
| L. Hemisphere | 0.11 | 0.27 | 0.04 |
| (total recovered) | | | |
| Dosing Solution (1:1,000) | 38,594 | 41,621 | 27,412 |
| | ug/g | | |
| Blood | 3.1 | 3.3 | 6.9 |
| Liver | 0.23 | 0.46 | 0.3 |
| Spleen | 0.55 | 1.1 | 0.8 |
| Kidney | 0.9 | 1.9 | 2.6 |
| Small Intestines | 0.32 | 0.4 | 0.6 |
| Lung | 0.9 | 1.8 | 1.1 |

TABLE 74-continued

Biodistribution and intactness of IgG administered to rats via high dose nasal drops (0.02 g IgG/kg) (IN High) compared to IgG administered with a non-enhancer based dosing solution (IN4).

| | ug/g IN High | | |
|---|---|---|---|
| | IN High | IN High Raw ug/g | IN4 |
| | 15 min | 30 min | 30 min |
| | Dosed ug/g (60 uCi) | | |
| | 92,625,403 | 99,889,203 | 685,291,111 |
| Esophagus | 0.51 | 0.61 | 1.1 |
| Trachea | 0.75 | 0.77 | 1.3 |
| | Intactness | | |
| IN1 Brain | 49% | 46% | 39% |
| IN1 Blood | 39% | 32% | 37% |

The bioavailability was calculated as the percent of CPMs measured in the brain (or estimated blood volume) of the total amount of CPMs delivered. Delivery via the intranasal device resulted in the highest bioavailability of all methods (0.037% at 30 min) and was twice as high as the maximum bioavailability with intravenous delivery (0.018% at 2 hr) (Table 75 and Table 76).

TABLE 75

Bioavailability - Brain (% of CPMs delivered that reached the brain - not corrected for intactness).

| Time | IN high | IN low | IN device | IV |
|---|---|---|---|---|
| 15 min | 0.0037% | 0.016% | 0.020% | 0.015% |
| 30 min | 0.0072% | 0.014% | 0.037% | 0.016% |
| 1 h | 0.0056% | 0.008% | 0.030% | 0.018% |
| 2 h | 0.0034% | 0.0053% | 0.007% | 0.0180% |
| 4 h | 0.0030% | 0.0047% | 0.004% | 0.012% |
| 8 h | 0.0041% | 0.008% | 0.006% | 0.010% |
| 12 h | 0.0068% | 0.010% | 0.006% | 0.011% |
| 24 h | 0.0047% | 0.0045% | 0.0039% | 0.0041% |
| 72 h | 0.0010% | 0.0012% | 0.0014% | 0.0011% |

TABLE 76

Bioavailability - Blood (% of CPMs delivered that reached the brain - not corrected for intactness).

| Time | IN high | IN low | IN device | IV |
|---|---|---|---|---|
| 15 min | 1.09% | 1.47% | 4% | 50.3% |
| 30 min | 1.18% | 2.0% | 6% | 34.3% |
| 1 h | 1.56% | 1.8% | 4% | 28.2% |
| 2 h | 1.43% | 1.58% | 3% | 21.0% |
| 4 h | 1.33% | 1.32% | 1.7% | 12.3% |
| 8 h | 1.9% | 2.8% | 2.4% | 9.3% |
| 12 h | 2.6% | 3.5% | 2.1% | 4.5% |
| 24 h | 1.9% | 2.0% | 1.7% | 2.79% |
| 72 h | 0.30% | 0.24% | 0.22% | 0.29% |

As well as being a less invasive option than intravenous infusion, the increased targeting to the brain (i.e. less blood and systemic exposure) achieved using IN Drops or an IN Device would be expected to reduce the risk of systemic side effects of IgG therapy.

Example 10

Stability of IgG administered by IN Drops and IN Device & Olfactory Epithelium Targeting The stability of IgG administered by IN Drops or IV and IN Device was compared to determine optimal modes of administration. Degradation and aggregation of the IgG administered via the IN Device was measured and olfactory targeting was assessed.

Stability of IgG: Samples of sprayed IgG from the IN Device were compared to unsprayed IgG solution (representative of IVIG and IN Drops). Five IgG formulations were prepared and divided into spray and solution trial groups (A=25% pooled IgG, B=5% pooled IgG, C=10% pooled IgG, D=20% pooled IgG, E=25% pooled IgG). The sprayed and solution IgG samples were run on non-reducing and reducing gels. The gels were either stained or blotted as follows: 1) a Coomassie stained, non-reduced gel, and 2) a reducing SDS-Page gel which was Western blotted and Coomassie stained.

In the non-reduced gel (FIG. 6A), there were no apparent higher order aggregates or IgG degradation forms for both the solution and sprayed IgG. In the reduced Western blot (FIG. 6B), intact IgG was seen as well as the heavy chain (HC) and light chain (LC) fragments of the IgG. Combinations of heavy chain and light chain (HC/LC) were also seen on the reducing gel. Based on these results, spraying the IgG through an IN Device does not increase IgG degradation or increase IgG aggregation.

Olfactory Epithelium Targeting: IgG was administered to rats with the intranasal Device and with intranasal drops. A 25% solution of IgG formulated in histidine buffer was spiked with 0.01% fluorescein tracer. It was then intranasally delivered to a rat using an intranasal Device or drops and the brain of the rat was imaged to detect neural IgG-fluorescein deposition.

Representative images of the deposition pattern of intranasal IgG (less than 2 minutes after drug administration) are depicted in FIGS. 7A and 7B. FIG. 7A shows the deposition after Device administration of 15 μL of 25% IgG solution spiked with 0.01% fluorescein tracer in a rat. FIG. 7B shows the deposition patter after deposition of the same compound that was administered with nose drops. As can be seen by FIG. 7, there is greater olfactory epithelium (OE) staining from Device administration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 11

Intranasal IgG Administration Decreases the Area of the Brain Covered by Plaques An experiment was designed to assess the effect of intranasal IgG on brain plaques and vascular amyloid. Congo Red staining of Tg2576 mouse brains revealed a decrease in the area covered by plaques, the number of plaques and the total intensity of the plaques in both the low-dose and high-dose IgG intranasal treatment groups. The decrease approximates the reduction of β-amyloid identified with immuno-staining in the cortex. For example, in the low dose group amyloid decreased by 25.7% when assessed with IHC and 22% when analyzed with Congo Red. However, unlike the immuno-staining, the reduction in Congo Red plaque staining did not reach a level of statistical significance.

Plaque amyloid reduction was not observed with the vascular amyloid in either the low or high dose IgG groups. Although not statistically significant, a slight increase in vascular amyloid was observed with the high-dose IgG group.

Experimental Design: The aim of this study was to determine if intranasal IgG treatment alters plaque and/or vascular amyloid in the brains of Tg2576 mice. At 9 months of age, the mice were intranasally treated with IgG or saline three times per week for 7 months (a description of the experimental groups is provided in Table 15). At 16 months of age, behavioral testing occurred and at ~17 months of age, 12 mice per group were euthanized (transcardial perfusion with saline) and brain tissue was collected for analysis. The brain was sagittally hemisected, the right half was fixed in formalin, embedded in paraffin and sectioned at 5 μm. Sections approximately 2.5 mm from sagittal midline were used for Congo Red staining.

Quantification of both the plaque and vascular amyloid in the brains of the control groups, WT-PBS and WT-High Dose, and the experimental Tg2576 groups, Tg-PBS, Tg-Low Dose (400 μg/kg/2 wk) and Tg-High Does (800 μg/kg/2 wk) were analyzed using Congo Red staining and fluorescent microscopy. In this procedure sagittal sections were stained with a standard Congo Red procedure and imaged fluorescently using a Nikon A1 Spectral Confocal Microscope. Specifically, NIS Elements imaging software was used to control acquisition and analysis. An objective with 10× magnification was used for capturing images. With this magnification the smaller blood vessels could be easily distinguish from plaques. At this magnification a 6×5 tiling of 30 images (5% overlap) was needed to capture the whole brain section. Each of these 30 images was created from a max intensity projection of a z-stack of 5 individual images. This corrected any change in the captured focal plane across the whole tissue section. Laser excitation at 561 nm (voltage at 10%) was used to excite the Congo Red and the spectrum between 570-620 nm was captured for quantifying the fluorescence.

A single image of the complete sagittal section was obtained by stitching together 150 individual images (thirty in the x-y plane and five in z dimension). Representative examples of these images are included in FIG. 12. The plaque and vasculature amyloid deposits were distinguished manually by a blinded researcher through the de-selection of the vascular components from the total amyloid using Nikon's Elements AR software. The area covered by the amyloid (Area), the number of individual amyloid deposits (#) and the sum of the intensities of these objects (Sum Intensity) were determined for the total of the amyloid deposits (both plaque and vascular), and for the plaque and vascular deposits individually.

Specifically, image analysis and quantification consisted of first adjusting look-up tables (LUTs) for optimal and consistent viewing to distinguish vascular and plaque amyloid. Second, the whole brain area of the brain section was quantified to determine the fraction of total brain covered by amyloid wherein the threshold was set so all tissue was highlighted and the cerebellum was deselected. Third, the total amyloid occupied areas were quantified by setting the threshold to accurately select the amyloid stained objects, deselect any staining due to background or tissue/staining artifacts prior to quantification, and deselect object in the cerebellum. Fourth, the vasculature amyloid was deselected by manually zooming into the image to a 1:1 resolution and individually deselecting the highlighted selections that were associated with blood vessels. Fifth, the plaque amyloid occupied areas were quantified.

For each sagittal section, the total amyloid stained objects (Total), the amyloid stained plaques (Plaques), and the amyloid stained vascular deposits (Vasculature) were measured and data collected. Separate measurements were directly captured for Total and Plaques. Values for Vascular were obtained by subtracting Plaques from Total. For each of the data sets, parapeters were determined, including 1) number of objects, 2) area (% area occupied by the collection of objects), and 3) SumIntensity (equals the sum of [Mean Intensity*Area] for each individual object). Two separate values were calculated for the area parameter: 1) AreaImg (areas summed from image divided by total area of Image*100), and 2) AreaTis (Areas summed from image divided by the area occupied by brain tissue*100).

Average values, standard deviations, and standard errors were calculated for each of the three parameters for each of the five experimental groups described in Table 15. The five experimental groups were analyzed for significance using a two-tailed t-test and the following comparisons were performed: WT-Saline vs. Tg-Saline, Tg-Saline vs. Tg-Low, Tg-Saline vs. Tg-High, and Tg-Low vs. Tg-High.

Results: Changes in the accumulation of total, plaque or vascular amyloid did not reach significance with t-tests in the comparison of the Tg-PBS group to either the Tg-low or Tg-high group (Table 77). However, for each of the three parameters assessed, area covered by the amyloid (FIG. 8A and FIG. 8B), the number of individual amyloid deposits (FIG. 8B and FIG. 9B) and the sum of the intensities of these objects (Sum Intensity, which represents the total quantity of amyloid, FIG. 8C and FIG. 9C), for both total amyloid and plaque amyloid were found to decrease with both the low and high IgG intranasal treatments. The area covered by plaques was reduced by 22% for the low dose and 20% for the high dose. The number of plaques was reduced by 17% for low dose and 19% for the high dose. The sum intensity of these plaques decreased 16% in the low dose group and 24% in the high dose group.

TABLE 77

Percent change between groups and associated t-test p-values.

| | % change | T-test (p =) | | % change | T-test (p =) | | % change | T-test (p =) |
|---|---|---|---|---|---|---|---|---|
| Total Amyloid Area (Plaque and Vascular) | | | # Amyloid Deposits (Plaque and Vascular) | | | Total Intestity All Amyloid Deposits (Sum Intensity) | | |
| WT-saline vs TG-saline | 2517% | 0.000109 | WT-saline vs TG-saline | 1633% | 0.000010 | WT-saline vs TG-saline | 3854% | 0.000132 |
| TG-saline vs TG-low | −14% | 0.520 | TG-saline vs TG-low | −8% | 0.381 | TG-saline vs TG-low | −9% | 0.713 |
| TG-saline vs TG-high | −7% | 0.809 | TG-saline vs TG-high | −1% | 0.667 | TG-saline vs TG-high | −11% | 0.715 |
| TG-low vs TG-high | −7% | 0.824 | TG-low vs TG-high | −1% | 0.745 | TG-low vs TG-high | −11% | 0.958 |
| Plaque Amyloid Area | | | # Amyloid Plaques | | | Total Intestity Amyloid Plaques (Sum Intensity) | | |
| WT-saline vs TG-saline | 3919% | 0.000220 | WT-saline vs TG-saline | 6355% | 0.000109 | WT-saline vs TG-saline | 4520% | 0.000171 |
| TG-saline vs TG-low | −22% | 0.345 | TG-saline vs TG-low | −20% | 0.381 | TG-saline vs TG-low | −16% | 0.531 |
| TG-saline vs TG-high | −20% | 0.478 | TG-saline vs TG-high | −11% | 0.667 | TG-saline vs TG-high | −24% | 0.391 |
| TG-low vs TG-high | −20% | 0.931 | TG-low vs TG-high | −11% | 0.745 | TG-low vs TG-high | −24% | 0.801 |
| Vascular Amyloid Area | | | # Vascular Deposits | | | Total Intestity Vascular Deposits (Sum Intensity) | | |
| WT-saline vs TG-saline | 1708% | 0.000357 | WT-saline vs TG-saline | 787% | 0.000001 | WT-saline vs TG-saline | 3037% | 0.000648 |
| TG-saline vs TG-low | −1% | 0.887 | TG-saline vs TG-low | 6% | 0.710 | TG-saline vs TG-low | 3% | 0.927 |
| TG-saline vs TG-high | 9% | 0.882 | TG-saline vs TG-high | 12% | 0.598 | TG-saline vs TG-high | 11% | 0.796 |
| TG-low vs TG-high | 9% | 0.750 | TG-low vs TG-high | 12% | 0.828 | TG-low vs TG-high | 11% | 0.855 |

Figure 10A:
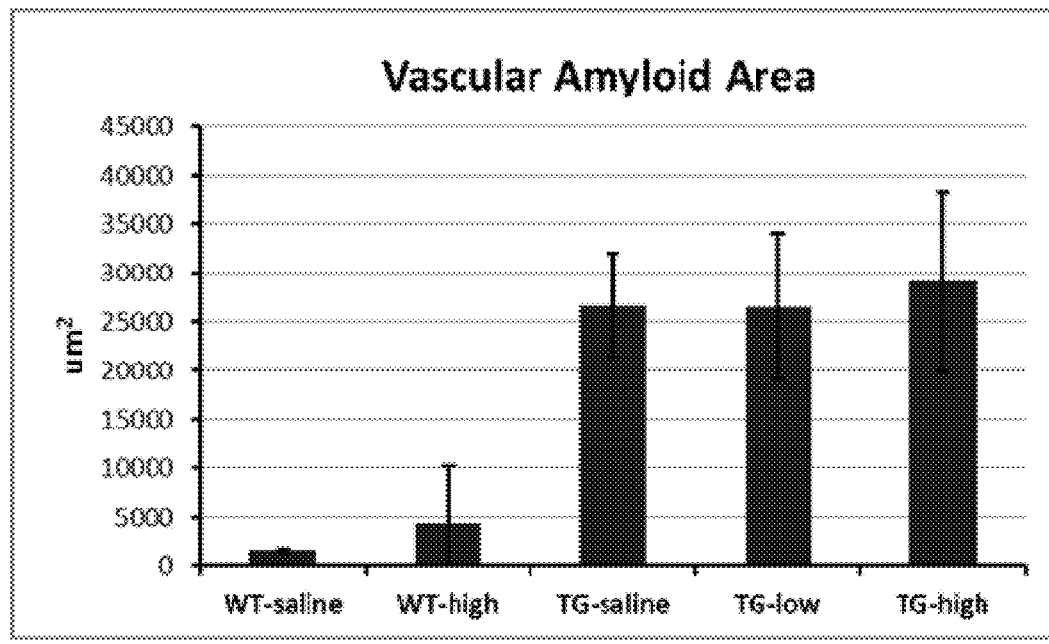
FIGS. 10A-10C illustrate data showing that the vascular component of the amyloid was found to increase slightly when a decrease in amyloid as a result of a decrease in plaque load was observed (FIG. 9).
Figure 10B:
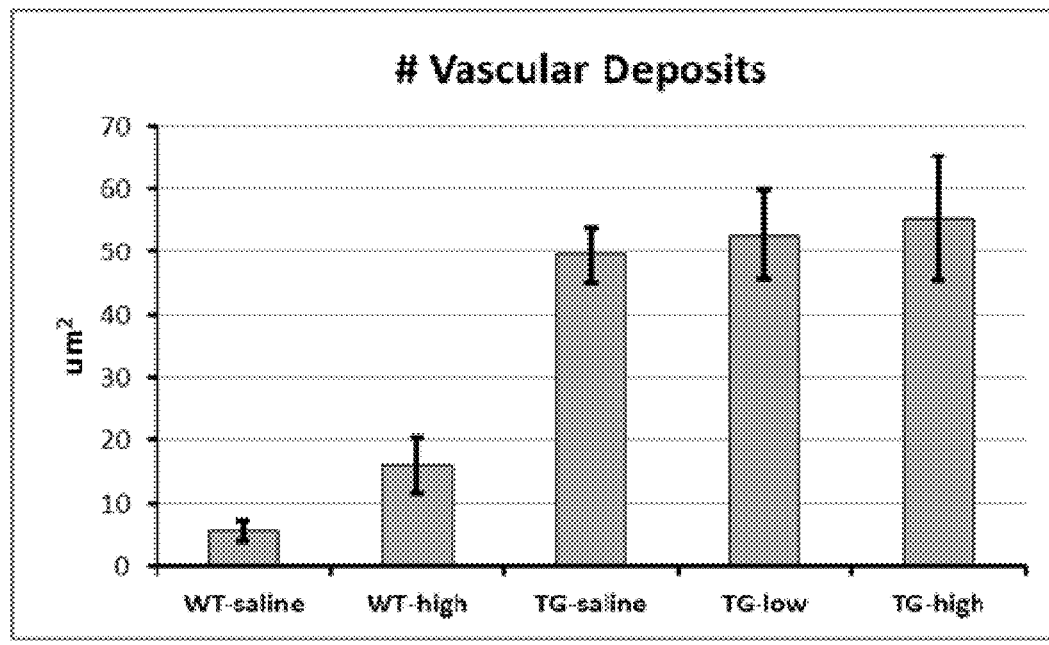
Figure 10C:
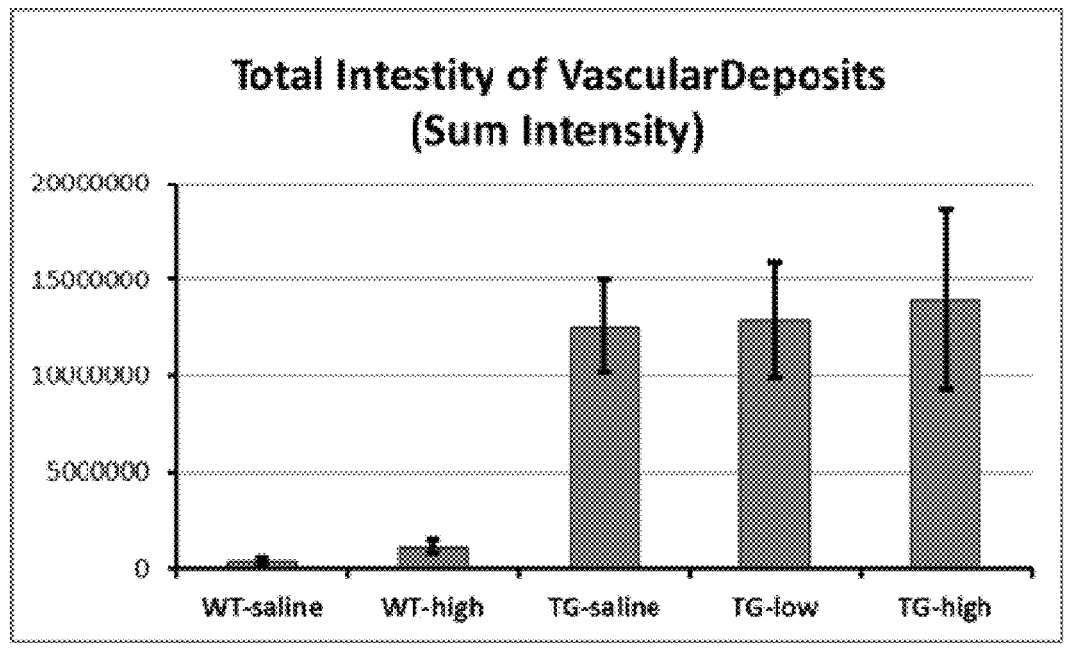

The reduction of amyloid was absent in the vasculature (FIGS. 10A, 10B, and 10C). For the vascular amyloid, each of the three parameters increased in the high IgG intranasal treatment group, whereas this increase was either absent or was present to a lesser degree in the low dose group (FIGS. 10A, 10B, and 10C). The sum intensity of these vascular amyloid deposits increased 3% in the low dose group and 11% in the high dose group (Table 77).

Figure 11A:
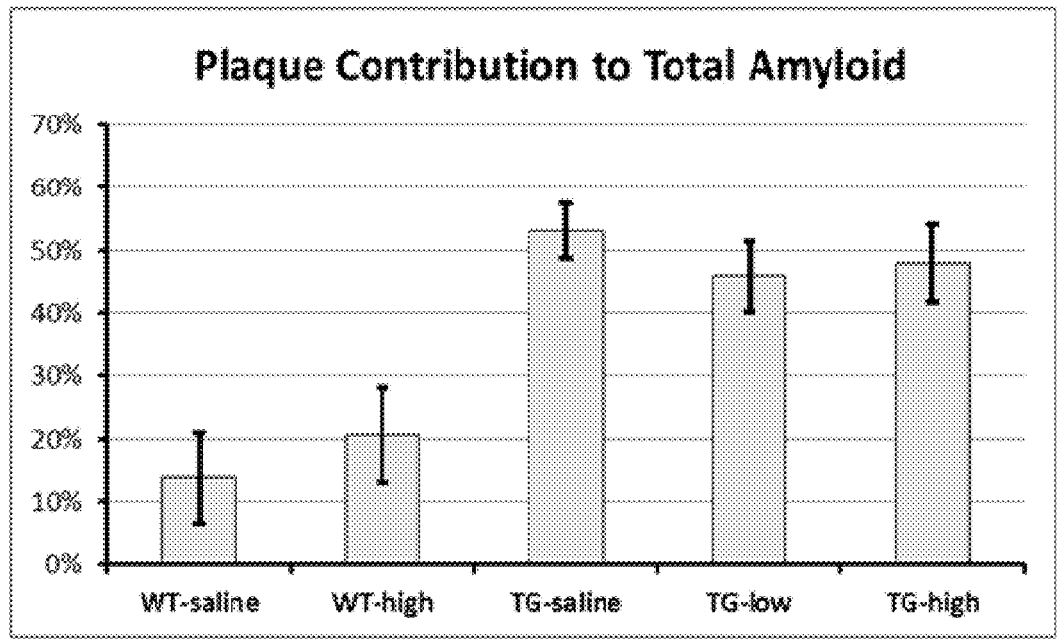
FIGS. 11A-11B illustrate data showing the relative proportions of vascular and plaque amyloid as it contributes to total amyloid.
Figure 11B:
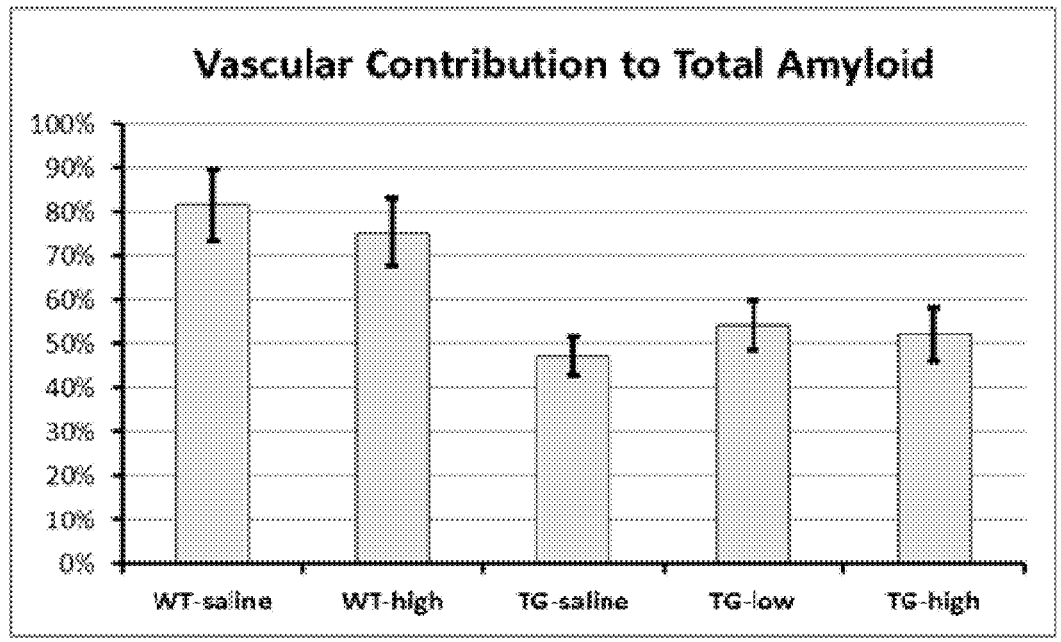

The relative proportions of vascular and plaque amyloid as it contributes to total amyloid is depicted in FIG. 11A and FIG. 11B. The average values from each group, along with standard deviations and percent error are provided in

TABLE 78

Average values of amyloid plaques by treatment group.

| Group | Avg | St. Dev | St. Err | Group | Avg | St. Dev | St. Err | Group | Avg | St. Dev | St. Err |
|---|---|---|---|---|---|---|---|---|---|---|---|
| Total Amyloid Area (Plaque and Vascular) | | | | # Amyloid Deposits (Plaque and Vascular) | | | | Total Intestity of Amyloid Deposits (Sum Intensity) | | | |
| WT-saline | 2329 | 4235 | 1223 | WT-saline | 7 | 2.09 | 0.60 | WT-saline | 891830 | 2038864 | 588569 |
| WT-high | 5039 | 4875 | 1407 | WT-high | 18 | 1.51 | 0.43 | WT-high | 1426429 | 1390829 | 401498 |
| TG-saline | 60930 | 31891 | 9206 | TG-saline | 114 | 34.36 | 9.92 | TG-saline | 35260904 | 19089383 | 5510630 |
| TG-low | 52249 | 31572 | 9114 | TG-low | 104 | 34.60 | 9.99 | TG-low | 31921724 | 23768445 | 6861359 |
| TG-high | 56385 | 54901 | 15849 | TG-high | 113 | 46.17 | 13.33 | TG-high | 31318149 | 30948336 | 8934015 |
| Plaque Amyloid Area | | | | # Amyloid Plaques | | | | Total Intestity of Amyloid Plaques (Sum Intensity) | | | |
| WT-saline | 852 | 2442 | 705 | WT-saline | 1 | 2.09 | 0.60 | WT-saline | 491018 | 1538511 | 444130 |
| WT-high | 647 | 687 | 198 | WT-high | 2 | 1.51 | 0.43 | WT-high | 207397 | 217296 | 62728 |
| TG-saline | 34241 | 19804 | 5717 | TG-saline | 65 | 34.36 | 9.92 | TG-saline | 22685550 | 12752488 | 3681326 |
| TG-low | 26539 | 18268 | 5273 | TG-low | 52 | 34.60 | 9.99 | TG-low | 18985208 | 15068946 | 4350030 |
| TG-high | 27338 | 25815 | 7452 | TG-high | 57 | 46.17 | 13.33 | TG-high | 17345869 | 16402272 | 4734928 |
| Vascular Amyloid Area | | | | # Vascular Deposits | | | | Total Intestity of Vascular Deposits (Sum Intensity) | | | |
| WT-saline | 1477 | 687 | 198 | WT-saline | 6 | 5.33 | 1.54 | WT-saline | 400812 | 550529 | 158924 |
| WT-high | 4391 | 19804 | 5717 | WT-high | 16 | 15.02 | 4.34 | WT-high | 1219032 | 1387106 | 400423 |
| TG-saline | 26688 | 18268 | 5273 | TG-saline | 50 | 15.49 | 4.47 | TG-saline | 12575353 | 8294807 | 2394505 |
| TG-low | 26539 | 25815 | 7452 | TG-low | 53 | 24.61 | 7.10 | TG-low | 12936517 | 10455665 | 3018290 |
| TG-high | 29047 | 31592 | 9120 | TG-high | 55 | 34.12 | 9.85 | TG-high | 13972280 | 16240149 | 4688127 |

TABLE 79

Raw data of the areas and sum intensities for each mouse (identified by ID number).

| ID Number | Group | Area Total | Area Plaques | Area Vascular | SumIntensity Total | SumIntensity Plaques | SumIntensity Vascular |
|---|---|---|---|---|---|---|---|
| 6 | TG-saline | 115,428 | 49,388 | 66,039 | 65,768,632 | 32,797,559 | 32,971,072 |
| 12 | TG-saline | 9,615 | 3,207 | 6,408 | 4,122,348 | 1,775,361 | 2,346,986 |
| 13 | TG-saline | 44,759 | 32,566 | 12,193 | 23,331,489 | 18,754,125 | 4,577,364 |
| 17 | TG-saline | 45,902 | 20,360 | 25,542 | 24,817,330 | 14,365,335 | 10,451,995 |
| 19 | TG-saline | 100,853 | 61,581 | 39,272 | 55,289,299 | 38,307,916 | 16,981,383 |
| 24 | TG-saline | 40,275 | 16,232 | 24,043 | 28,219,039 | 14,592,692 | 13,626,348 |
| 26 | TG-saline | 72,873 | 40,008 | 32,864 | 50,896,735 | 32,669,266 | 18,227,469 |
| 40 | TG-saline | 72,892 | 51,395 | 21,497 | 42,116,237 | 31,329,942 | 10,786,294 |
| 46 | TG-saline | 83,078 | 55,167 | 27,911 | 49,487,815 | 37,301,209 | 12,186,606 |
| 58 | TG-saline | 59,409 | 38,548 | 20,862 | 31,689,695 | 22,410,388 | 9,279,308 |
| 59 | TG-saline | 25,142 | 8,199 | 16,943 | 12,131,324 | 5,237,262 | 6,894,062 |
| 2 | TG-Low | 37,468 | 20,017 | 17,451 | 20,321,550 | 13,258,997 | 7,062,553 |
| 7 | TG-Low | 61,365 | 34,477 | 26,888 | 49,667,940 | 34,128,193 | 15,539,747 |
| 10 | TG-Low | 52,240 | 33,836 | 18,404 | 28,447,707 | 21,346,439 | 7,101,268 |
| 25 | TG-Low | 68,827 | 43,997 | 24,831 | 37,245,908 | 25,626,879 | 11,619,029 |
| 27 | TG-Low | 132,727 | 61,346 | 71,380 | 95,657,774 | 52,780,178 | 42,877,596 |
| 32 | TG-Low | 32,299 | 9,761 | 22,538 | 19,011,353 | 6,252,635 | 12,758,717 |
| 35 | TG-Low | 10,110 | 1,270 | 8,840 | 4,705,869 | 625,181 | 4,080,687 |
| 39 | TG-Low | 14,232 | 3,239 | 10,993 | 6,755,635 | 2,258,758 | 4,496,877 |
| 42 | TG-Low | 50,544 | 38,522 | 12,022 | 29,879,434 | 24,362,743 | 5,516,691 |
| 49 | TG-Low | 68,719 | 39,481 | 29,238 | 38,885,021 | 27,024,755 | 11,860,266 |
| 51 | TG-Low | 49,382 | 18,550 | 30,832 | 27,695,601 | 12,602,421 | 15,093,180 |
| 52 | TG-Low | 49,071 | 13,978 | 35,093 | 24,786,898 | 7,555,312 | 17,231,586 |
| 1 | TG-high | 2,813 | 641 | 2,172 | 1,048,809 | 237,175 | 811,634 |
| 15 | TG-high | 103,101 | 57,180 | 45,921 | 61,230,873 | 37,704,161 | 23,526,712 |
| 16 | TG-high | 53,649 | 34,611 | 19,039 | 31,405,116 | 23,587,366 | 7,817,749 |
| 20 | TG-high | 195,070 | 86,114 | 108,956 | 110,420,271 | 54,319,412 | 56,100,859 |
| 23 | TG-high | 69,989 | 41,806 | 28,184 | 37,222,228 | 26,023,396 | 11,198,831 |
| 34 | TG-high | 7,887 | 1,975 | 5,912 | 3,920,088 | 1,385,403 | 2,534,685 |
| 37 | TG-high | 57,257 | 37,868 | 19,388 | 31,515,587 | 23,230,486 | 8,285,101 |
| 41 | TG-high | 94,661 | 27,898 | 66,763 | 46,735,215 | 14,998,264 | 31,736,951 |
| 44 | TG-high | 23,751 | 4,985 | 18,766 | 13,317,820 | 3,773,642 | 9,544,178 |
| 47 | TG-high | 38,637 | 11,895 | 26,742 | 21,140,702 | 7,803,449 | 13,337,253 |

TABLE 79-continued

Raw data of the areas and sum intensities for each mouse (identified by ID number).

| ID Number | Group | Area Total | Area Plaques | Area Vascular | SumIntensity Total | SumIntensity Plaques | SumIntensity Vascular |
|---|---|---|---|---|---|---|---|
| 53 | TG-high | 10,580 | 8,478 | 2,102 | 6,247,449 | 5,468,454 | 778,995 |
| 55 | TG-high | 19,223 | 14,606 | 4,617 | 11,613,632 | 9,619,224 | 1,994,408 |
| 4 | WT-saline | 775 | — | 775 | 175,280 | — | 175,280 |
| 8 | WT-saline | 203 | — | 203 | 63,844 | — | 63,844 |
| 9 | WT-saline | 2,197 | — | 2,197 | 549,057 | — | 549,057 |
| 14 | WT-saline | 2,274 | — | 2,274 | 537,918 | — | 537,918 |
| 18 | WT-saline | 279 | 191 | 89 | 99,865 | 75,732 | 24,133 |
| 21 | WT-saline | — | — | — | — | — | — |
| 29 | WT-saline | 15,165 | 8,503 | 6,662 | 7,272,935 | 5,363,736 | 1,909,198 |
| 30 | WT-saline | — | — | — | — | — | — |
| 33 | WT-saline | 2,547 | 133 | 2,413 | 806,288 | 64,381 | 741,907 |
| 43 | WT-saline | 3,836 | 1,397 | 2,439 | 1,030,568 | 388,371 | 642,196 |
| 57 | WT-saline | 667 | — | 667 | 166,208 | — | 166,208 |
| 60 | WT-saline | — | — | — | 0 | — | — |
| 5 | WT-high | — | — | — | — | — | — |
| 11 | WT-high | 946 | 546 | 400 | 262,652 | 162,969 | 99,683 |
| 22 | WT-high | 5,233 | 1,035 | 4,198 | 1,418,585 | 303,890 | 1,114,696 |
| 28 | WT-high | 2,826 | 1,988 | 838 | 951,551 | 710,345 | 241,205 |
| 31 | WT-high | 9,405 | 362 | 9,043 | 2,931,770 | 228,181 | 2,703,589 |
| 36 | WT-high | 4,591 | 171 | 4,420 | 1,260,094 | 90,200 | 1,169,894 |
| 38 | WT-high | 15,883 | — | 15,883 | 4,399,983 | — | 4,399,983 |
| 45 | WT-high | — | — | — | — | — | — |
| 48 | WT-high | 11,393 | 1,638 | 9,754 | 3,248,816 | 451,611 | 2,797,205 |
| 50 | WT-high | 1,892 | 1,067 | 826 | 465,341 | 245,731 | 219,610 |
| 54 | WT-high | 4,477 | 959 | 3,518 | 1,191,920 | 295,835 | 896,086 |
| 56 | WT-high | 3,817 | — | 3,817 | 986,431 | — | 986,431 |

Figure 12A:
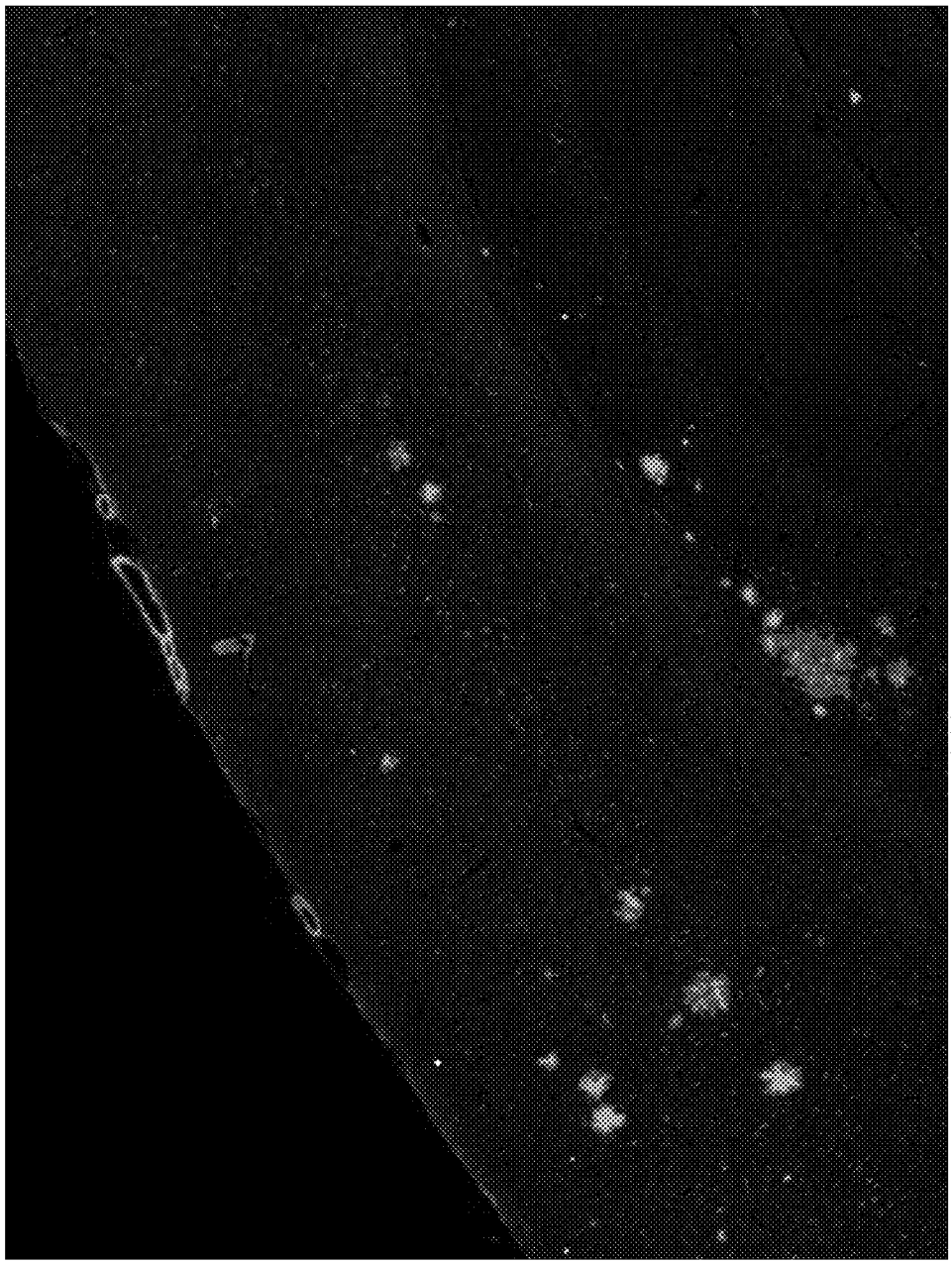
FIGS. 12A-12F show Congo Red stained sagittal sections captured with confocal fluorescent microscopy.
Figure 12B:
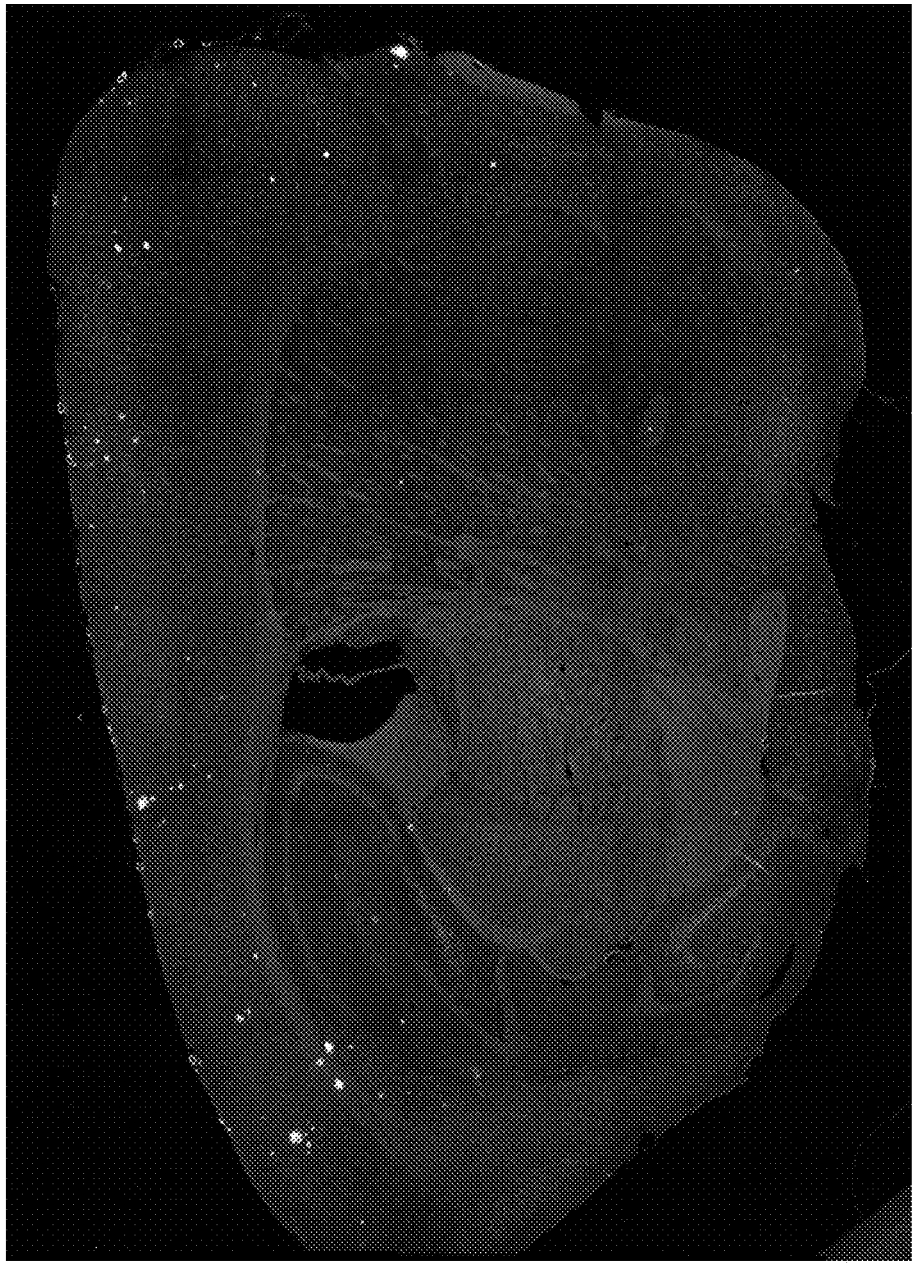
Figure 12C:
Figure 12D:
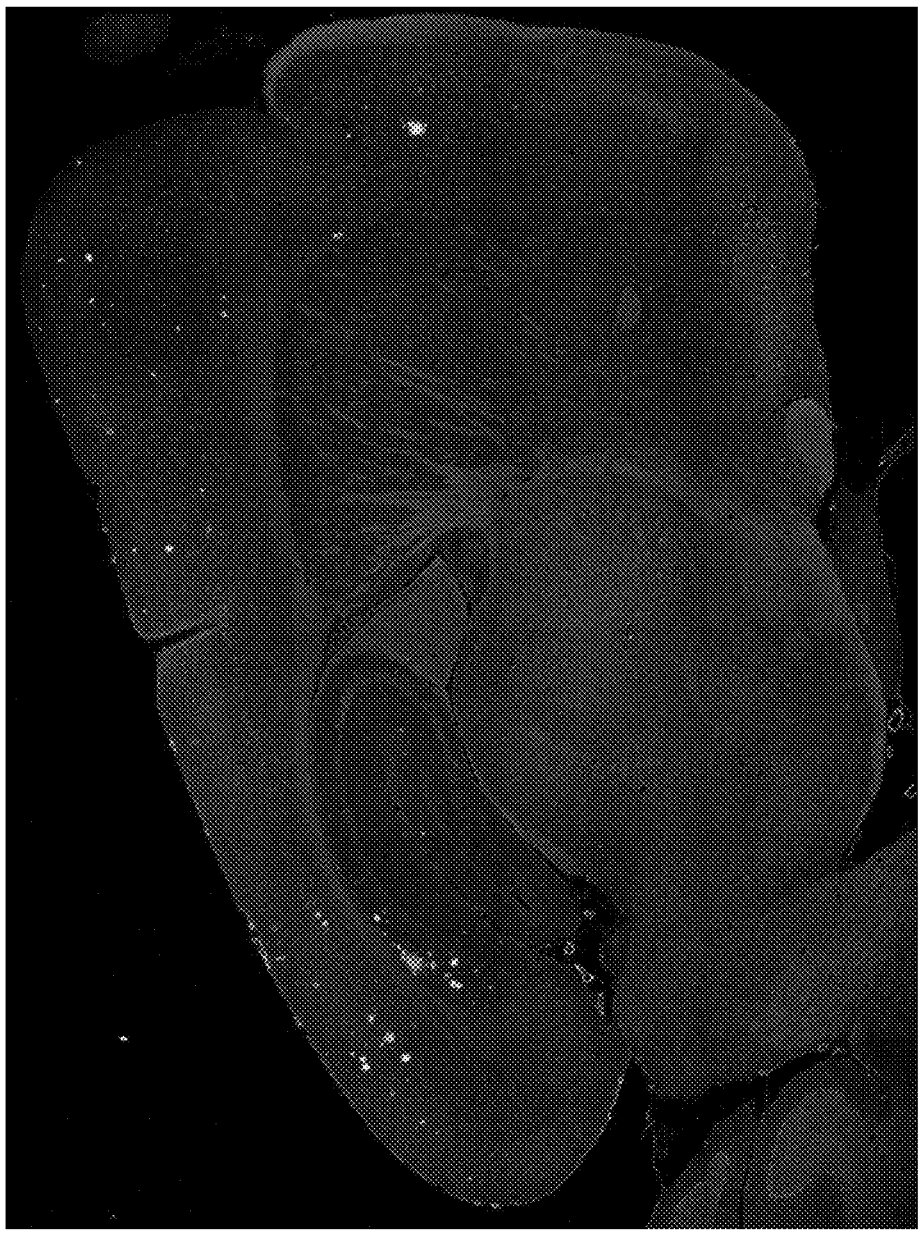
Figure 12E:
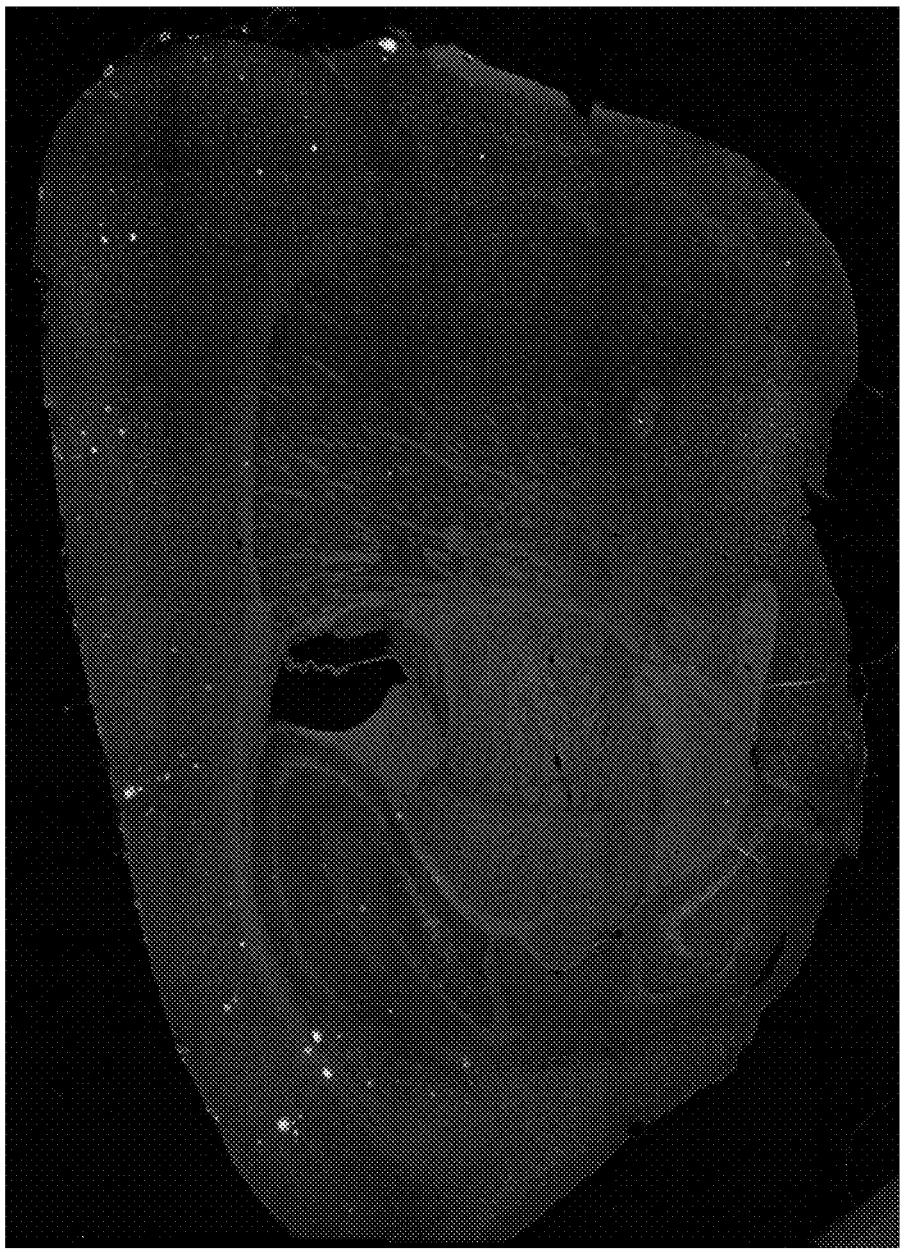
Figure 12F:
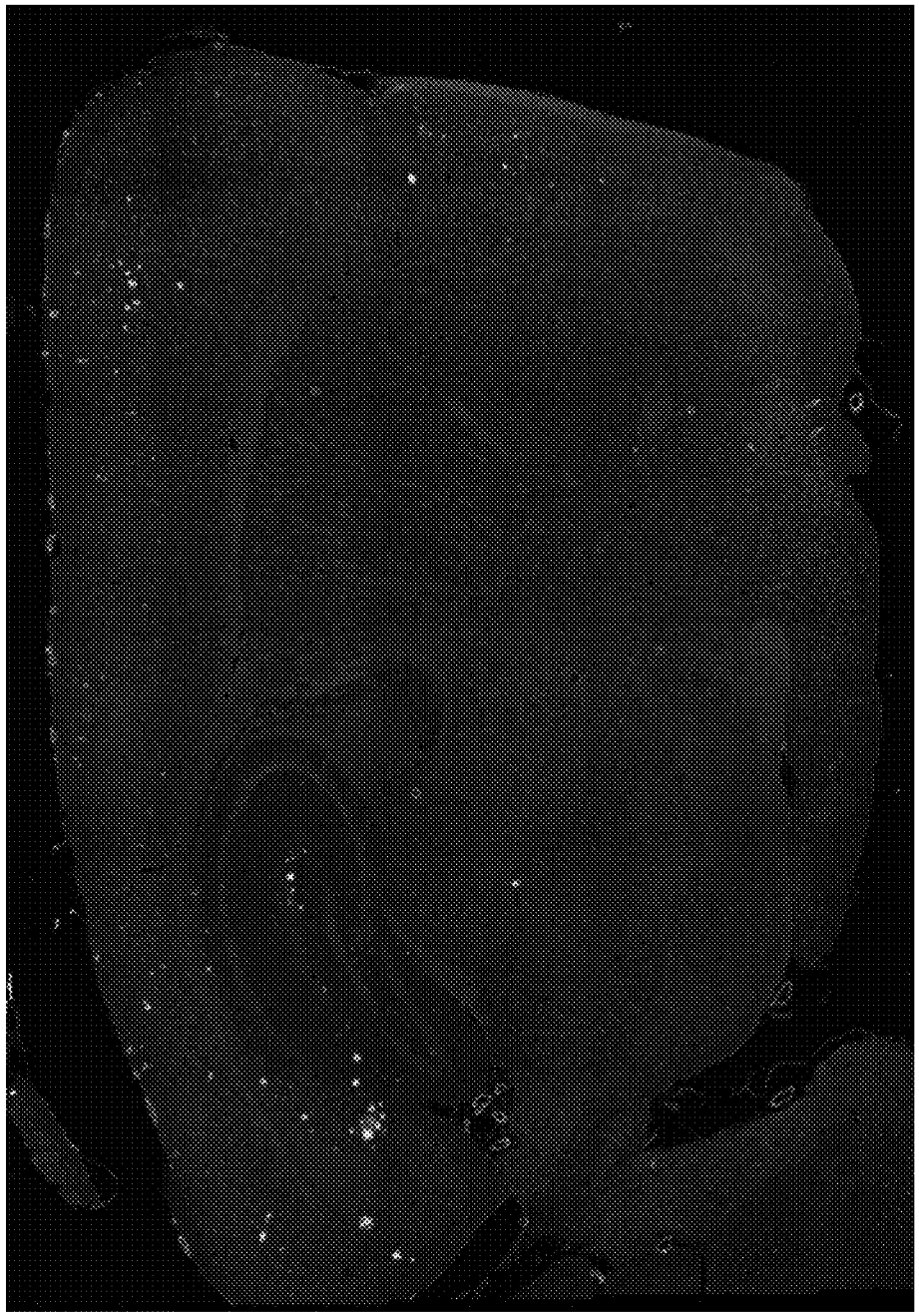

Congo Red stained sagittal sections captured with confocal fluorescent microscopy are shown in FIGS. 12A-12F. Five individual images at 10× with a 512×512 resolution were used to create a z-stack max intensity projection image (FIG. 12A). Thirty of these z-stacks projections, encompassing the whole tissue section were tiled (6×5, 5% overlap) to create a single image for analysis (FIGS. 12B-12F). Laser excitation at 561 nm excited the Congo Red and the spectrum between 570-620 nm was captured for quantification. Selection of the amyloid deposits was conducted with the thresholding function in Nikons Elements AR software. Examples of thresholding are depicted in FIGS. 12A and 12C-12F by highlighting in red. FIG. 12A depicts a portion of the cortex and hippocampus at full resolution, highlighting both amyloid plaques and vascular amyloid. FIG. 12A is an example of a section from a Tg-Low mouse without highlighting. Representative images from the groups, WT-Saline (FIG. 12C), Tg-Saline (FIG. 12D), Tg-Low (FIG. 12E) and Tg-High (FIG. 12F) are shown with thresholding.

Figure 8A:
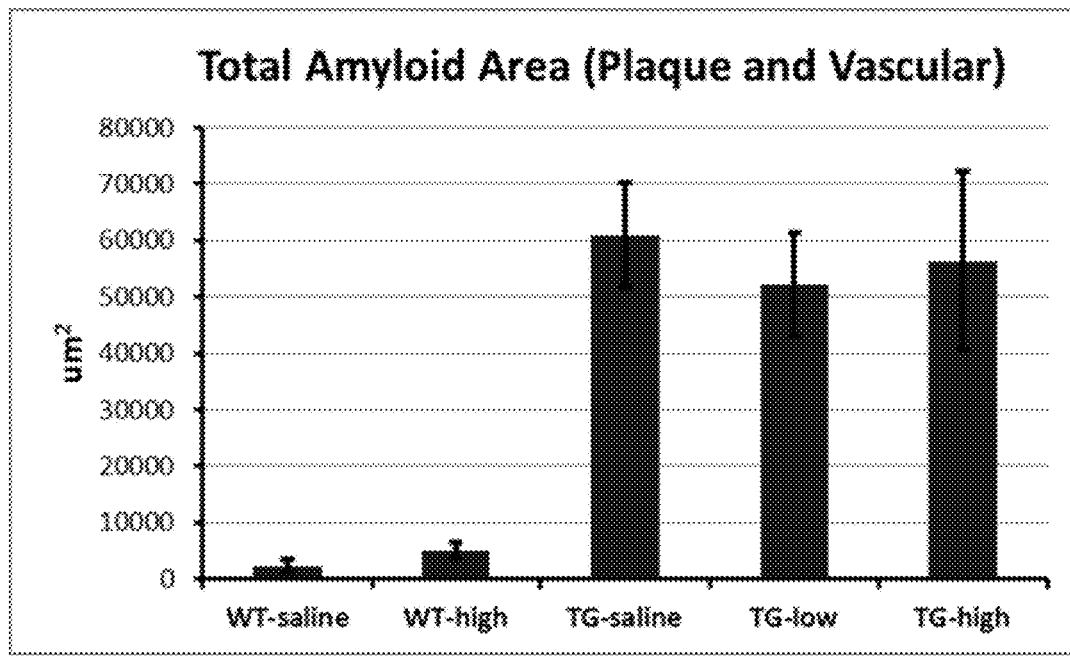
FIGS. 8A-8C illustrate data showing a decrease of amyloid load in the low IgG and high IgG intranasal treatment groups.
Figure 8B:
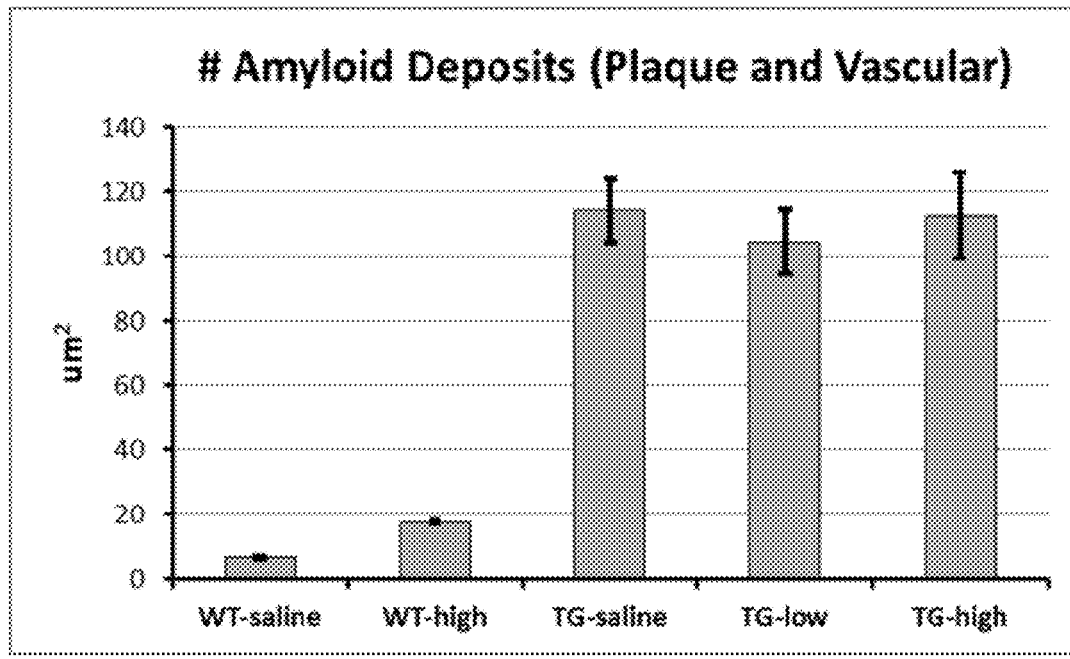
Figure 8C:
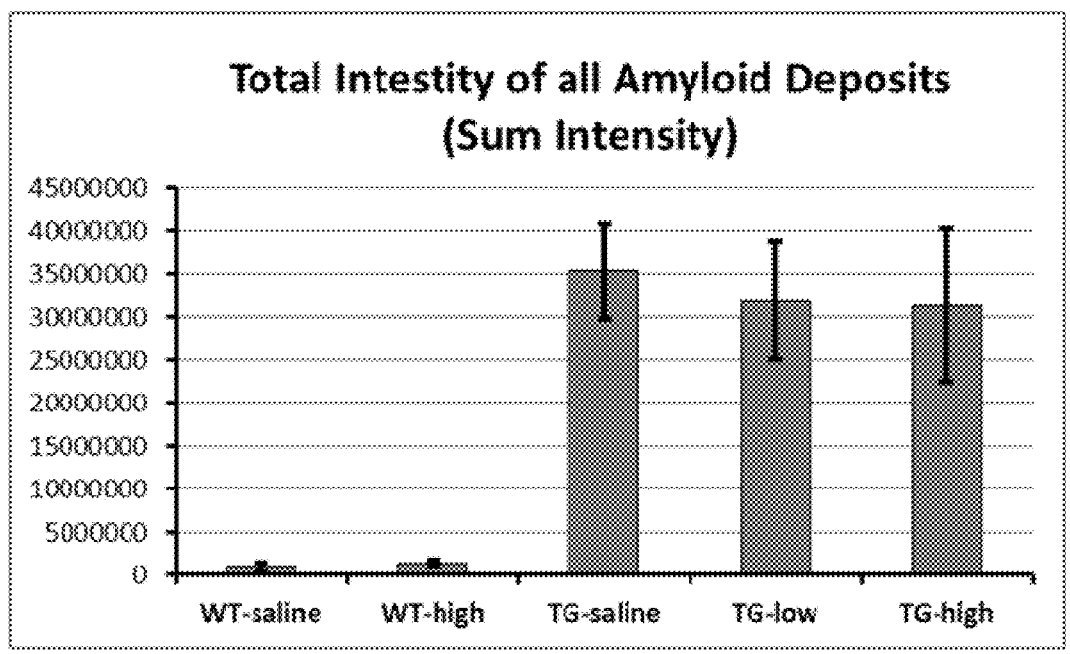
Figure 9A:
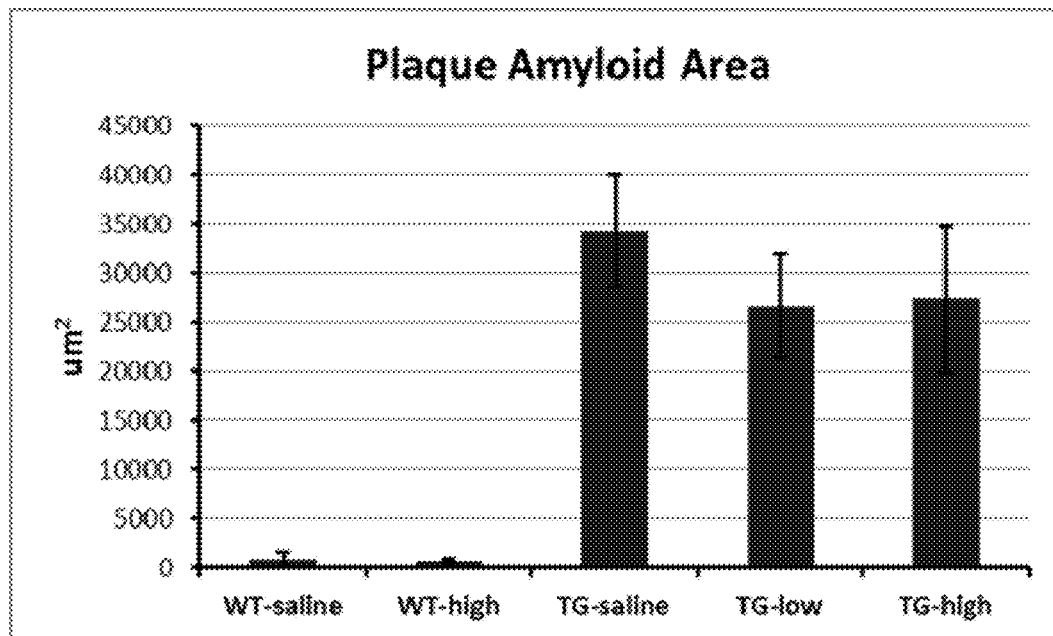
FIGS. 9A-9C illustrate data showing a decrease in amyloid is a result of a decrease in plaque load.
Figure 9B:
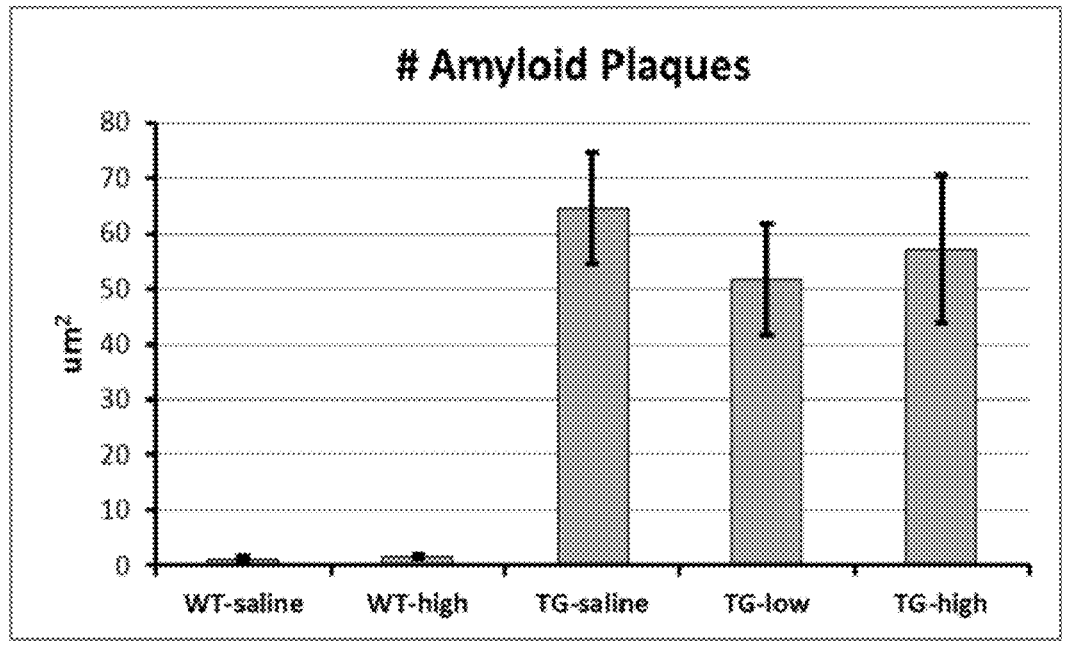
Figure 9C:
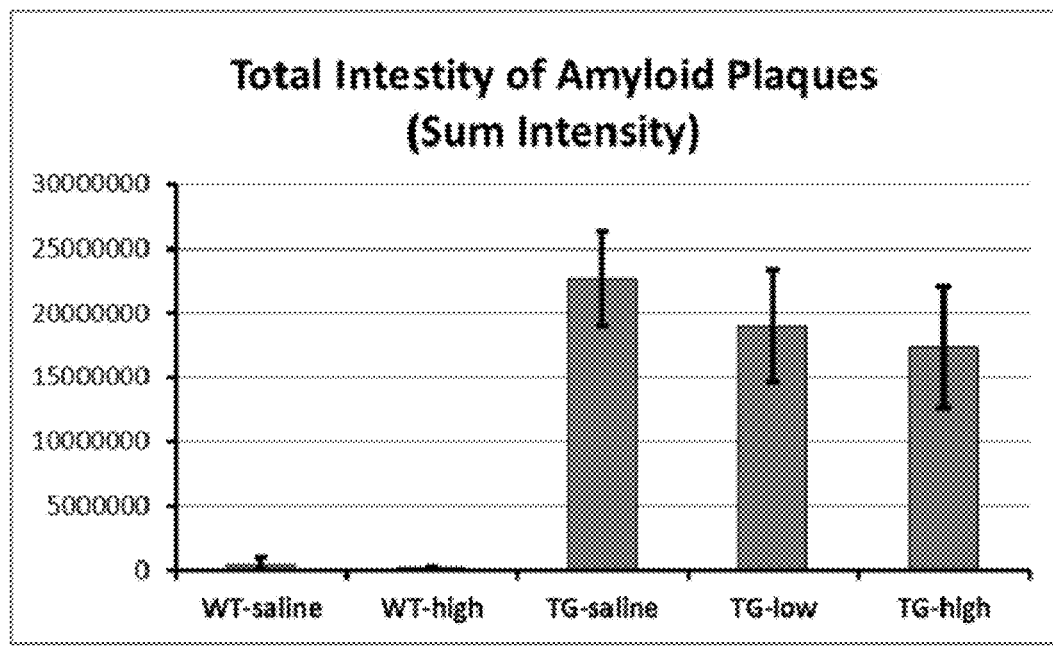

Analysis: Congo Red staining revealed a decrease of amyloid load in both the low IgG and high IgG intranasal treatment groups (FIGS. 8A-8C). This decrease in amyloid was a result of a decrease in plaque load (FIGS. 9A-9C) as the vascular component of the amyloid was found to increase slightly (FIGS. 10A-10C). Although the Congo Red results did not reach statistical significance, the reduction in plaque load is supported by the statistically significant reduction of plaques in the cortex of these mice as determined by the immuno-detection of β-amyloid (IHC study). In that study, using the 4G8 antibody to target β-amyloid, the percent area covered by plaques decreased by 25.7% for the low dose IgG group and 24.3%, for the high dose IgG group, respectively, with p values of 0.014 and 0.037. In the current study using Congo Red fluorescent staining, the area covered by plaques was reduced by 22% for the low dose and 20% for the high dose, respectively, with p values of 0.35 and 0.48. Thus, a similar degree of plaque reduction observed in the IHC analysis was also detected with the Congo Red analysis.

Several experimental parameters may be responsible for the difference of statistical power observed between the IHC and Congo Red analysis. The IHC analysis was limited to either the cortex or hippocampus of the mouse brain and a significant decrease was only observed in the cortex. In the Congo Red analysis, the complete brain section that is anterior to the pons and cerebellum, with the exception of the olfactory bulb was included. Variability and dilution of the plaque load throughout these additional areas of the brain may have contributed to a less significant p value. Additionally, three tissue sections from each mouse were included in the IHC analysis, whereas a single section was analyzed with the Congo Red staining. The difference could also be related to the staining properties of each method. The Congo Red detects the insoluble fibrous protein aggregates of β-sheets of amyloid, whereas the IHC detects all Tg human β-amyloid protein.

Amyloid staining in the vasculature is, for the most part, observed only in the larger vessels of the brain. It has been suggested that this is at least partially due to the absence of the efflux amyloid transporter, LRP1 in these vessels. Consistent with this point, vascular amyloid was observed almost exclusively in the larger vessels in this study and IgG either did not affect the aggregation of vascular amyloid or may have slightly increased it. Although the brain does not have a separate lymphatic system, the perivascular space surrounding the larger cerebral vessels provides a path by which interstitial fluid and extracellular solutes, including β-amyloid can exit the brain.

Example 12

Immunofluorescent Staining of Intranasal IgG Treated Tg2576 Mice Astrocyte (GFAP) and Microglial (CD11b) Quantification Human immunoglobulins are reactive to a wide array of inflammatory proteins and intravenously administered IgG has been shown to induce anti-inflammatory properties under a variety of different conditions (Nimmerjahn F. et al., Annu Rev Immunol, 2008; 26: 513-533). The present study assessed the expression of two inflammatory markers in the brains of Tg2576 mice in response to low and high doses of chronically administered IN IgG.

Figure 14:
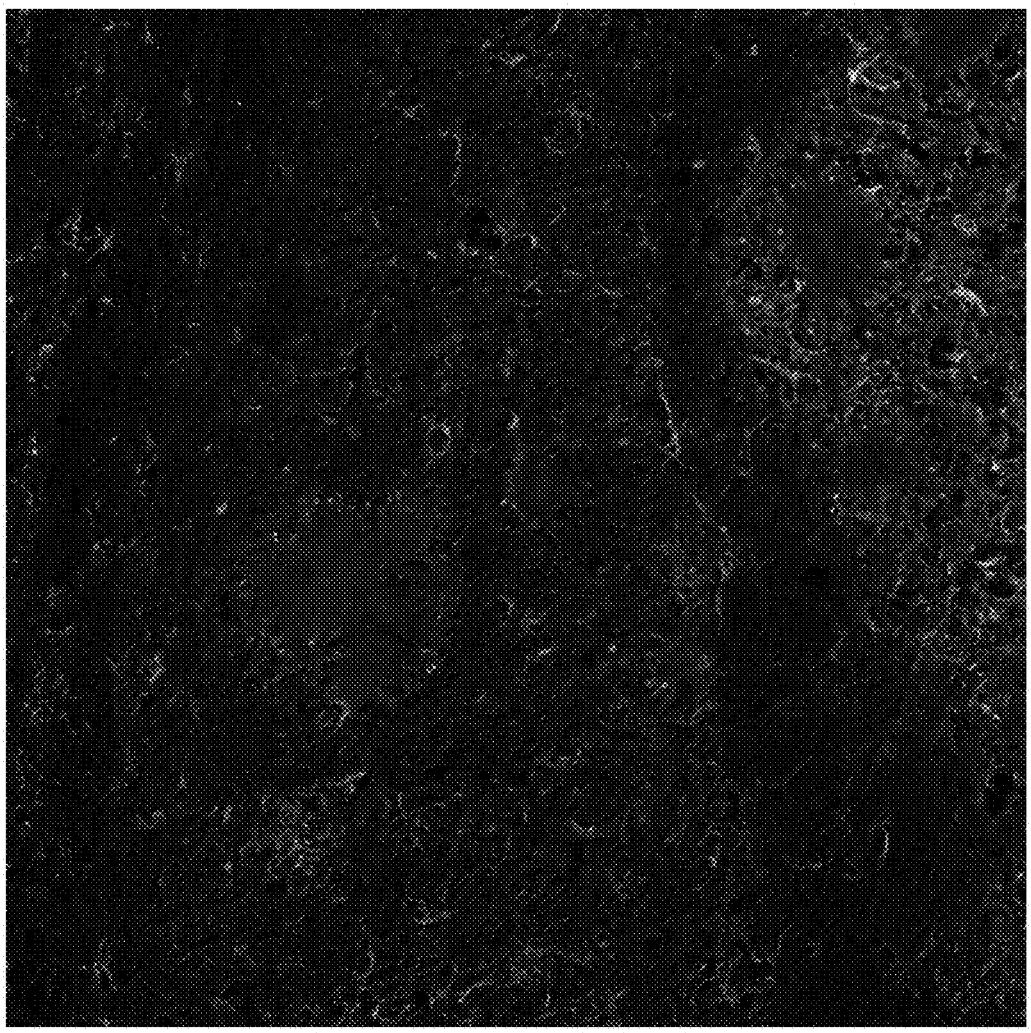
FIG. 14 is an example image of amyloid (blue), GFAP (green) and CD11b (red) staining from a Tg2576 mouse brain that had been treated with a high dose of IN IgG. CD11b staining was often observed surrounding the amyloid plaques.

Brain tissues were analyzed for GFAP and CD11b from the 3 transgenic groups of mice [TG-saline n=2, TG-low (0.4 g/kg/2 wk) n=4, and TG-high (0.8 g/kg/2 wk) n=6] for which frozen samples were available. Quantification of both GFAP and CD11b staining in the brains of the experimental Tg2576 mice were analyzed using fluorescent microscopy. In this procedure fixed frozen brain sections (1 millimeter from the mid-sagittal plane) were triple stained using antibodies for amyloid, a marker for activated astrocytes (GFAP) and a marker for activated microglial (CD11b). Fluorescence was captured with a Nikon A1 Spectral Confocal Microscope. A sagittal section encompassing a portion of the frontal cortex and a portion of the hippocampus was used for quantifying average intensity of GFAP and CD11b staining. An example of the images is shown in FIG. 14.

Briefly, brains were sectioned into 2 mm sagittal sections and placed into 20% sucrose. Sections were then stored at 4° C. until all animals from the study were collected. Once all samples were collected the tissue was mounted in OCT (frozen quickly with dry ice) and sectioned on the Leica CM3050 cryostat at 20 μm. Slide were allowed to dry at room temp overnight and stored in the −20° C. freezer. Prepared sections were then stained according to standard IHC staining protocols.

The fluorescence of stained sections was imaged using three channels corresponding to AlxaFluor405, AlexaFluor488, and AlexaFluor 568 with a Nikon A1 Spectral Confocal Microscope. The system was mounted on a Nikon Ti2000E widefield, inverted, fluorescence microscope. NIS Elements imaging software was used to control acquisition and analysis. An objective with 20× magnification was used for capturing images. Individual 512×512 images that included a portion of the frontal cortex and hippocampus were captured for quantitative analysis. Image quantification was conducted with Nikon's Elements AR software and total and average intensity values (corresponding to GFAP and CD11b) were determined for each image.

Figure 13A:
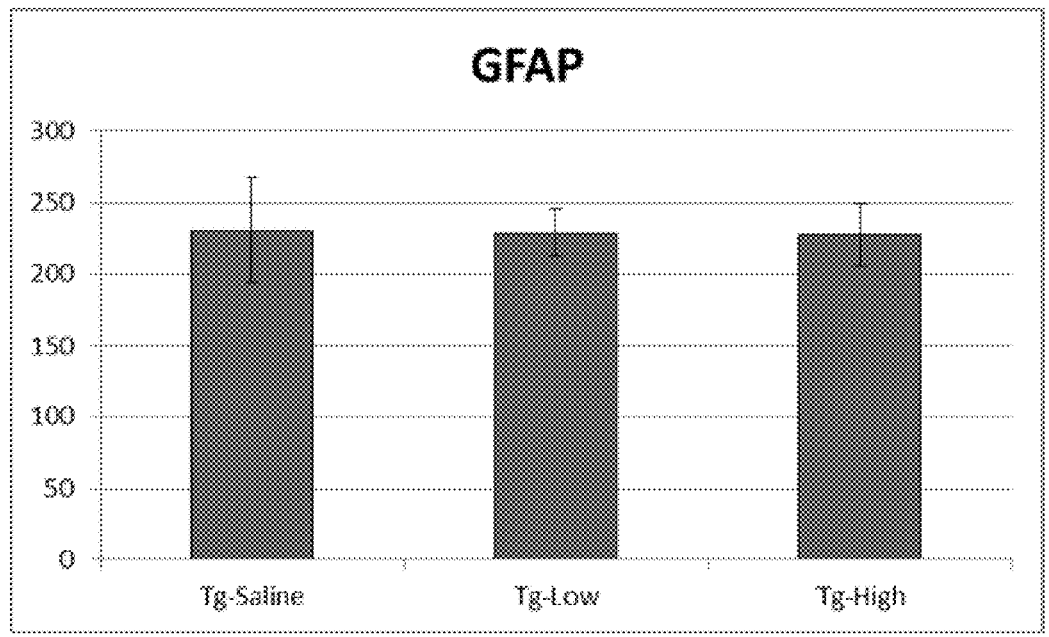
FIGS. 13A-13B illustrate data for the average staining intensity for the Astrocyte marker GFAP (FIG. 13A) and the microglial marker CD11b (FIG. 13B).
Figure 13B:
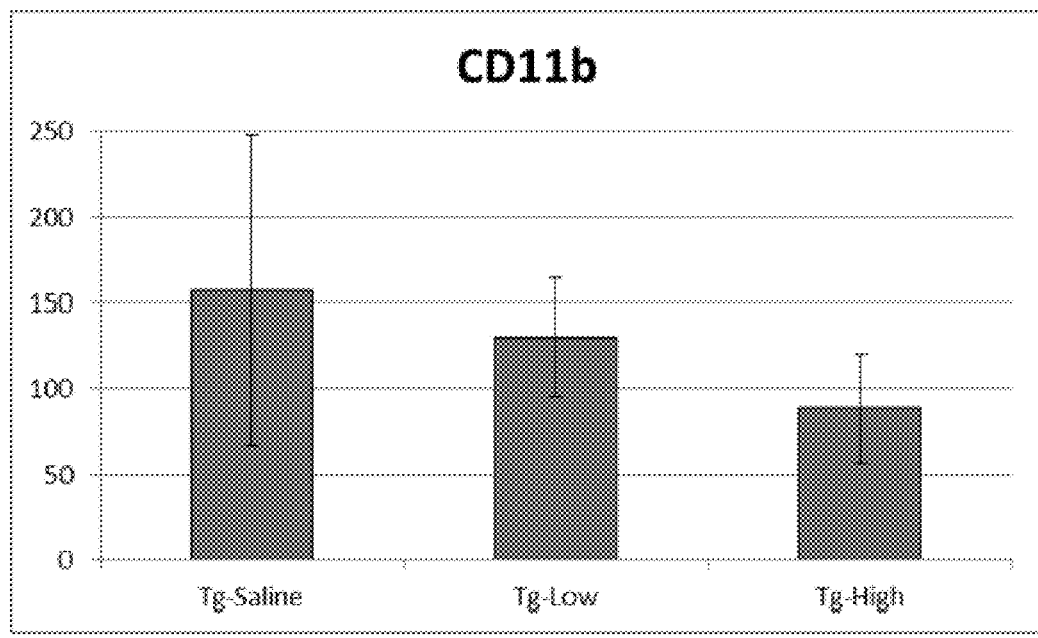

The results show that the Tg-PBS group was not statistically significant from the Tg-low or Tg-high groups for either the GFAP or CD11b comparisons (Table 80). The average intensity of GFAP staining was nearly identical in all three groups, differing by only a few percentage points (Table 80, FIG. 13A). The average intensity of CD11b staining decreased by 17% with the low dose of IN IgG (p=0.741) and the magnitude of this decrease was larger, at 47%, with high dose of IN IgG (p=0.379) (Table 80, FIG. 13B).

TABLE 80

Results of GFAP and CD11b staining.

|  | GFAP | | CD11b | |
| --- | --- | --- | --- | --- |
|  | Ratio | Ttest | Ratio | Ttest |
| Tg-Low vs Tg-Saline | 0.993 | 0.963 | 0.828 | 0.741 |
| Tg-High vs Tg-Saline | 0.987 | 0.946 | 0.565 | 0.379 |
| Tg-Low vs Tg-High | 1.006 | 0.965 | 1.467 | 0.416 |

The immunofluorescent staining of the Tg2576 mouse brains for the markers of inflammation, GFAP and CD11b, did not reveal a significant difference between the saline and the low or high IN IgG treated groups. The statistical power of this analysis was limited by the low number of saline treated Tg mice available. Values obtained for the astrocyte staining using the GFAP antibody revealed practically no change in the quantification with either the low or high IN IgG treatment (Table 80). Although significance was not reached, there was an apparent reduction in microglial staining using an antibody against CD11b. Average intensity of CD11b marker decreased by 17% with the low IN IgG dose and decreased by 47% with the high IN IgG dose (Table 80).

In this study, GFAP, a marker of astrocyte activation, was not altered with either of the two treatment concentrations of IgG. This result is consistent with previous work showing that WIG treatment of APP/PS1 dE9 mice did not significantly affect the expression of GFAP (Puli L. et al., Journal of neuroinflammation, 2012; 9: 105.). In the current study, CD11b, a marker of microglial activation, did show a dose dependent decrease in protein expression. However, neither the low dose nor the high dose values reached statistical significance. In the APP/PS1dE9 study mentioned above, Puli et. al. (Id.) found a significant reduction in the microglia marker CD45 and an elevation of the microglial marker Iba1 with IV IgG treatment. Magga, et. al. (Journal of neuroinflammation, 2010; 7: 90) also found that IVIG functioned in a APP/PS1 mouse model through a mechanism involving microglial, but not through a mechanism involving astrocytes. Although the affects identified in the present study did not reach statistical significance, the results do support a mechanism by which IgG influences the inflammatory state of the CNS through microglial modulation.

What is claimed is:

1. A method for treating Alzheimer's disease in a subject in need thereof, the method comprising:
    delivering a therapeutically effective amount of a composition comprising pooled human immunoglobulin G (IgG) to the brain of the subject,
    wherein delivering the composition to the brain comprises intranasally administering the composition to the upper third of the nasal cavity of the subject,
    wherein at least 40% of the pooled human IgG administered to the subject contacts the nasal epithelium located in the upper third of the nasal cavity of the subject.

2. The method of claim 1, wherein intranasal administration of the composition comprises directed administration of a liquid aerosol of the composition to the nasal epithelium located in the upper third of the nasal cavity of the subject.

3. The method of claim 2, wherein at least 40% of the pooled human IgG administered to the subject contacts the nasal epithelium located in the upper third of the nasal cavity of the subject.

4. The method of claim 2, wherein at least 50% of the pooled human IgG administered to the subject contacts the nasal epithelium located in the upper third of the nasal cavity of the subject.

5. The method of claim 2, wherein at least 60% of the pooled human IgG administered to the subject contacts the nasal epithelium located in the upper third of the nasal cavity of the subject.

6. The method of claim 2, wherein at least 70% of the pooled human IgG administered to the subject contacts the nasal epithelium located in the upper third of the nasal cavity of the subject.

7. The method of claim 1, wherein intranasal administration of the composition comprises directed administration of a powder aerosol of the composition to the nasal epithelium located in the upper third of the nasal cavity of the subject.

8. The method of claim 7, wherein at least 40% of the pooled human IgG administered to the subject contacts the nasal epithelium located in the upper third of the nasal cavity of the subject.

9. The method of claim 7, wherein at least 50% of the pooled human IgG administered to the subject contacts the nasal epithelium located in the upper third of the nasal cavity of the subject.

10. The method of claim 7, wherein at least 60% of the pooled human IgG administered to the subject contacts the nasal epithelium located in the upper third of the nasal cavity of the subject.

11. The method of claim 7, wherein at least 70% of the pooled human IgG administered to the subject contacts the nasal epithelium located in the upper third of the nasal cavity of the subject.

12. The method of claim 1, wherein the composition comprising pooled human IgG consists essentially of pooled human IgG and an amino acid selected from the group consisting of glycine, histidine, and proline.

13. The method of claim 1, wherein the composition comprising pooled human IgG is an aqueous composition comprising:
(a) from 10 mg/mL to 250 mg/mL pooled human IgG; and
(b) from 50 mM to 500 mM glycine.

14. The method of claim 13, wherein the pH of the composition is from 4.0 to 6.0.

15. The method of claim 13, wherein the pH of the composition is from 6.0 to 7.5.

16. The method of claim 1, wherein the composition comprising pooled human IgG is a dry powder composition prepared from an aqueous solution comprising:
(a) from 10 mg/mL to 250 mg/mL pooled human IgG; and
(b) from 50 mM to 500 mM glycine.

17. The method of claim 16, wherein the dry powder composition is prepared from an aqueous solution having a pH of from 4.0 to 6.0.

18. The method of claim 16, wherein the dry powder composition is prepared from an aqueous solution having a pH of from 6.0 to 7.5.

19. The method of claim 1, wherein the method comprises intranasally administering to the subject a dose of from 0.08 mg to 100 mg pooled human IgG per kg body weight of the subject (mg IgG/kg).

20. The method of claim 1, wherein the method comprises intranasally administering to the subject a fixed dose of from 50 mg to 10 g pooled human IgG.

21. The method of claim 1, wherein the method comprises intranasally administering to the subject a dose of pooled human IgG at least twice monthly.

22. The method of claim 1, wherein the composition comprising pooled human IgG comprises at least 0.1% anti-amyloid β IgG.

23. The method of claim 1, further comprising administering a known second therapy for Alzheimer's disease to the subject in need thereof.

24. The method of claim 23, wherein the second therapy for Alzheimer's disease comprises administration of a cholinesterase inhibitor.

25. The method of claim 24, wherein the cholinesterase inhibitor is selected from the group consisting of donepezil, rivastigmine, galantamine, and tacrine.

26. The method of claim 23, wherein the second therapy for Alzheimer's disease comprises administration of an inhibitor of NMDA-type glutamate receptor.

27. The method of claim 26, wherein the inhibitor of NMDA-type glutamate receptor is memantine.

28. The method of claim 1, wherein intranasal administration of the composition comprises directed administration of the composition to the olfactory epithelium of the nasal cavity of the subject.

29. The method of claim 1, wherein at least 50% of the pooled human IgG administered to the subject contacts the nasal epithelium located in the upper third of the nasal cavity of the subject.

30. The method of claim 1, wherein at least 60% of the pooled human IgG administered to the subject contacts the nasal epithelium located in the upper third of the nasal cavity of the subject.

31. The method of claim 1, wherein at least 70% of the pooled human IgG administered to the subject contacts the nasal epithelium located in the upper third of the nasal cavity of the subject.

* * * * *